United States Patent
Kalluri et al.

(10) Patent No.: US 11,926,824 B2
(45) Date of Patent: Mar. 12, 2024

(54) miRNA BIOGENESIS IN EXOSOMES FOR DIAGNOSIS AND THERAPY

(71) Applicants: Board of Regents, The University of Texas System, Austin, TX (US); Beth Israel Deaconess Medical Center, Inc., Boston, MA (US)

(72) Inventors: Raghu Kalluri, Houston, TX (US); Sónia Melo, Oporto (PT)

(73) Assignees: Board of Regents, The University of Texas System, Austin, TX (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 16/827,343

(22) Filed: Mar. 23, 2020

(65) Prior Publication Data

US 2020/0255831 A1   Aug. 13, 2020

Related U.S. Application Data

(63) Continuation of application No. 14/775,716, filed as application No. PCT/US2014/027541 on Mar. 14, 2014, now abandoned.

(60) Provisional application No. 61/791,301, filed on Mar. 15, 2013.

(51) Int. Cl.
| | |
|---|---|
| *C12N 15/113* | (2010.01) |
| *A61K 39/00* | (2006.01) |
| *C07K 14/47* | (2006.01) |
| *C07K 16/40* | (2006.01) |
| *C12Q 1/6886* | (2018.01) |
| *G01N 33/574* | (2006.01) |
| *G16B 20/00* | (2019.01) |

(52) U.S. Cl.
CPC ........ *C12N 15/113* (2013.01); *C07K 14/4703* (2013.01); *C07K 16/40* (2013.01); *C12Q 1/6886* (2013.01); *G01N 33/57488* (2013.01); *G16B 20/00* (2019.02); *A61K 2039/505* (2013.01); *C12N 2310/14* (2013.01); *C12N 2310/141* (2013.01); *C12Q 2600/158* (2013.01); *C12Q 2600/178* (2013.01); *G01N 2333/4704* (2013.01); *Y02A 90/10* (2018.01)

(58) Field of Classification Search
CPC .............. C12N 15/113; C12N 2310/14; C12N 2310/141; C12Q 1/6886; C12Q 2600/178
USPC ..................... 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 9,469,876 B2 | 10/2016 | Kuslich et al. | |
| 2003/0064949 A1 | 4/2003 | Nielsen et al. | |
| 2004/0028692 A1 | 2/2004 | Zitvogel et al. | |
| 2010/0151480 A1 | 6/2010 | Taylor et al. | |
| 2010/0196216 A1 | 8/2010 | Skog et al. | |
| 2010/0279292 A1 | 11/2010 | Marsh et al. | |
| 2011/0054009 A1 | 3/2011 | Croce et al. | |
| 2011/0172295 A1 | 7/2011 | Hammond et al. | |
| 2011/0237450 A1 | 9/2011 | Klass et al. | |
| 2012/0238467 A1 | 9/2012 | Taylor et al. | |
| 2013/0156801 A1 | 6/2013 | Bond et al. | |
| 2015/0038549 A1 | 2/2015 | Smith | |
| 2017/0137892 A1 | 5/2017 | Taylor et al. | |
| 2019/0177729 A1* | 6/2019 | Wang ..................... | A61K 47/60 |
| 2019/0224338 A1* | 7/2019 | Mansour ................. | A61P 43/00 |

FOREIGN PATENT DOCUMENTS

| | | |
|---|---|---|
| CN | 1616476 A | 5/2005 |
| CN | 101755208 A | 6/2010 |
| CN | 102301002 A | 2/2011 |
| JP | 2011/517283 A | 6/2011 |
| JP | 2012/508577 A | 4/2012 |
| WO | WO 2004/014954 | 2/2004 |
| WO | WO 2009/015357 | 1/2009 |
| WO | WO 2009/147519 | 12/2009 |
| WO | WO 2010/056337 | 5/2010 |
| WO | WO 2011/133504 | 10/2011 |
| WO | WO 2012/125471 | 9/2012 |
| WO | WO 2013/022995 | 2/2013 |
| WO | WO 2015/085096 | 6/2015 |

OTHER PUBLICATIONS

Caroleo et al (Fronteirs in Oncology, vol. 10:614541, pp. 1-7 (2016)) (Year: 2016).*
Swahari et al (Molecular & Cell. Oncology, vol. 3, No. 3, e1155006, pp. 1-2 (2016)) (Year: 2016).*
Shan et al (Oncotarget, vol. 7, No. 45, pp. 72,672-72,684 (2016) (Year: 2016).*
Merritt et al (New England J. Med., vol. 359, No. 25, pp. 2641-2650 (2008)). (Year: 2008).*
Al-Nedawi et al., "Intercellular transfer of the oncogenic receptor EGFRvIII by microvesicles derived from tumour cells," *Nature Cell Biology*, 10:619-624, 2008.
Alvarez-Erviti et al., "Delivery of siRNA to the mouse brain by systemic injection of targeted exosomes," *Nature Biotechnology*, 29:341-345, 2011.
Ambros, "The functions of animal microRNAs," *Nature*, 431:350-355, 2004.
Arroyo et al., "Argonaute2 complexes carry a population of circulating microRNAs independent of vesicles in human plasma," *Proceedings of the National Academy of Sciences of the United States of America*, 108:5003-5008, 2011.
Bartel, "MicroRNAs: target recognition and regulatory functions," *Cell*, 136:215-233, 2009.
Bartels and Tsongalis, "MicroRNAs: novel biomarkers for human cancer," *Clinical Chemistry*, 55:623-631, 2009.

(Continued)

*Primary Examiner* — Jane J Zara
(74) *Attorney, Agent, or Firm* — Parker Highlander PLLC

(57) ABSTRACT

Methods for diagnosis and treatment of cancers by use of exosomes comprising miRNAs and precursors thereof. For example, in some aspects, a cancer may be diagnosed or evaluated by determining the miRNA content of exosomes in a sample from a subject or by detecting miRNA processing in exosomes.

10 Claims, 80 Drawing Sheets

Specification includes a Sequence Listing.

(56) References Cited

OTHER PUBLICATIONS

Bernstein et al., "Dicer is essential for mouse development," *Nature Genetics*, 35:215-217, 2003.
Chendrimada et al., "TRBP recruits the Dicer complex to Ago2 for microRNA processing and gene silencing," *Nature*, 436:740-744, 2005.
Cochrane et al., "MicroRNAs link estrogen receptor alpha status and Dicer levels in breast cancer", *Horm. Cancer*, 1(6):306-319, 2010.
Cocucci et al., "Shedding microvesicles: artefacts no more," *Trends Cell Biol*, 19:43-51, 2009.
De Laurentiis et al., "Mass spectrometry-based identification of the tumor antigen UN1 as the transmembrane CD43 sialoglycoprotein," *Mol Cell Proteomics*, 10(5):M111.007898, 2011.
Escola et al., "Selective enrichment of tetraspan proteins on the internal vesicles of multivesicular endosomes and on exosomes secreted by human B-lymphocytes," *The Journal of Biological Chemistry*, 273:20121-20127, 1998.
Escudier et al., "Vaccination of metastatic melanoma patients with autologous dendritic cell (DC) derived-exosomes: results of the first phase I clinical trial," *J Transl Med.*, 3(10), pp. 1-13, 2005.
Extended European Search Report issued in European Application No. 14770497.7, dated Oct. 14, 2016.
Extended European Search Report issued in European Application No. 19151220.1, dated Jul. 16, 2019.
Filipowicz, "RNAi: the nuts and bolts of the RISC machine," *Cell*, 122:17-20, 2005.
Fukagawa et al., "Dicer is essential for formation of the heterochromatin structure in vertebrate cells," *Nature Cell Biology*, 6:784-791, 2004.
Gallo et al., "The majority of microRNAs detectable in serum and saliva is concentrated in exosomes," *PloS One*, 7:e30679, 2012.
Gibbings et al., "Multivesicular bodies associate with components of miRNA effector complexes and modulate miRNA activity," *Nature Cell Biology*, 11:1143-1149, 2009.
Grelier et al., "Prognostic value of Dicer expression in human breast cancers and association with the mesenchymal phenotype," *British Journal of Cancer*, 101:673-683, 2009.
Guermonprez et al., "Antigen presentation and T cell stimulation by dendritic cells," *Annu Rev Immunol*, 20:621-667, 2002.
Guescini et al., "Astrocytes and Glioblastoma cells release exosomes carrying mtDNA," *J Neural Transm*, 117:1-4, 2010.
Gyorgy et al., "Membrane vesicles, current state-of-the-art: emerging role of extracellular vesicles," *Cell Mol Life Sci*, 68:2667-2688, 2011.
Hirata et al., "Oncogenic miRNA-182-5p targets Smad4 and RECK in human bladder cancer," *PloS One*, 7:e51056, 2012.
Hood et al., "Exosomes released by melanoma cells prepare sentinel lymph nodes for tumor metastasis," *Cancer research*, 71:3792-3801, 2011.
Iglehart and Silver, "Synthetic lethality—a new direction in cancer-drug development", *New Engl. J. Med.*, 361(2): 189-191, 2009.
Ismail et al., "Macrophage microvesicles induce macrophage differentiation and miR-223 transfer," *Blood*, 121:984-995, 2013.
Kahlert et al., "Exosomes in tumor microenvironment influence cancer progression and metastasis," *J Mol Med (Berl)*, 91:431-437, 2013.
Karube et al., "Reduced expression of Dicer associated with poor prognosis in lung cancer patients," *Cancer science*, 96:111-115, 2005.
King et al., "Hypoxic enhancement of exosome release by breast cancer cells," *BMC Cancer*, 12:421, 2012.
Kogure et al., "Intercellular nanovesicle-mediated microRNA transfer: a mechanism of environmental modulation of hepatocellular cancer cell growth," *Hepatology*, 54:1237-1248, 2011.
Kosaka et al., "Neutral sphingomyelinase 2 (nSMase2)-dependent exosomal transfer of angiogenic microRNAs regulate cancer cell metastasis," *The Journal of biological chemistry*, 288:10849-10859, 2013.
Kumar et al., "Impaired microRNA processing enhances cellular transformation and tumorigenesis," *Nature genetics*, 39:673-677, 2007.
Lee et al., "Microvesicles as mediators of intercellular communication in cancer—the emerging science of cellular 'debris'," *Semin Immunopathol*, 33:455-467, 2011.
Li et al., "Argonaute 2 complexes selectively protect the circulating microRNAs in cell-secreted microvesicles," *PloS one*, 7:e46957, 2012.
Liu et al., "MicroRNA expression profiling using microarrays," *Nat Protoc*, 3:563-578, 2008.
Logozzi et al., "High levels of exosomes expressing CD63 and caveolin-1 in plasma of melanoma patients," *PloS one*, 4:e5219, 2009.
Lu et al., "MicroRNA expression profiles classify human cancers," *Nature*, 435:834-838, 2005.
Luga et al., "Exosomes Mediate Stromal Mobilization of Autocrine Wnt-PCP Signaling in Breast Cancer Cell Migration," *Cell*, 151:1542-1556, 2012.
Luzio et al., "The delivery of endocytosed cargo to lysosomes," *Biochemical Society transactions*, 37:1019-1021, 2009.
Ma et al., "Tumour invasion and metastasis initiated by microRNA-10b in breast cancer," *Nature*, 449:682-688, 2007.
Macfarlane et al., "MicroRNA: biogenesis, function and role in cancer," *Current Genomics*, 11(7):537-561, 2010.
Maehama, "PTEN: its deregulation and tumorigenesis," *Biological & pharmaceutical bulletin*, 30:1624-1627, 2007.
Maniataki and Mourelatos, "A human, ATP-independent, RISC assembly machine fueled by pre-miRNA," *Genes & development*, 19:2979-2990, 2005.
Mao et al., "Serum miR-21 is a diagnostic and prognostic marker of primary central nervous system lymphoma," *Neurological Sciences*, 35(2):233-238, 2014.
Martello et al., "A MicroRNA targeting dicer for metastasis control," *Cell*, 141:1195-1207, 2010.
Mathivanan et al., "Exosomes: extracellular organelles important in intercellular communication," *Journal of proteomics*, 73:1907-1920, 2010.
Mavel et al., "Synthesis of imidazo[2,1-a]phthalazines, potential inhibitors of p38 MAP kinase. Prediction of binding affinities of protein ligands," *Arch Pharm (Weinheim)*, 335:7-14, 2002.
McCready et al., "Secretion of extracellular hsp90alpha via exosomes increases cancer cell motility: a role for plasminogen activation," *BMC cancer*, 10:294, 2010.
Melo et al., "A genetic defect in exportin-5 traps precursor microRNAs in the nucleus of cancer cells," *Cancer cell*, 18:303-315, 2010.
Melo et al., "A TARBP2 mutation in human cancer impairs microRNA processing and DICER 1 function," *Nature genetics*, 41:365-370, 2009.
Melo et al., "Cancer exosomes perform cell-independent microRNA biogenesis and promote tumorigenesis," *Cancer Cell*, 26(5):707-721, 2014.
Melo et al., "Small molecule enoxacin is a cancer-specific growth inhibitor that acts by enhancing TAR RNA-binding protein 2-mediated microRNA processing," *Proceedings of the National Academy of Sciences of the United States of America*, 108:4394-4399, 2011.
Merritt et al., "Dicer, Drosha, and outcomes in patients with ovarian cancer," *The New England journal of medicine*, 359:2641-2650, 2008.
Mittelbrunn et al., "Unidirectional transfer of microRNA-loaded exosomes from T cells to antigen-presenting cells," *Nature communications*, 2:282, 2011.
Miyata, "Hsp90 inhibitor geldanamycin and its derivatives as novel cancer chemotherapeutic agents," *Current pharmaceutical design*, 11:1131-1138, 2005.
Montecalvo et al., "Mechanism of transfer of functional microRNAs between mouse dendritic cells via exosomes," *Blood*, 119:756-766, 2012.
Narayanan et al., "Exosomes derived from HIV-1-infected cells contain trans-activation response element RNA," *The Journal of biological chemistry*, 288:20014-20033, 2013.

(56) References Cited

OTHER PUBLICATIONS

Nicoloso et al., "MicroRNAs—the micro steering wheel of tumour metastases," *Nature reviews Cancer*, 9:293-302, 2009.
O'Brien and Stokoe, "Converting cancer mutations into therapeutic opportunities", *EMBO Mol. Med.*, 1:297-299, 2009.
Office Action issued in Chinese Application No. 201480022292.7, dated Dec. 4, 2017, and English language translation thereof.
Office Action issued in Chinese Application No. 201480022292.7, dated Jun. 4, 2018, and English language translation thereof.
Office Action issued in European Application No. 14770497.7, dated Oct. 20, 2017.
Office Action issued in European Application No. 14770497.7, dated Jun. 6, 2018.
Office Action issued in Israeli Application No. 241409, dated Aug. 22, 2018 (with concise explanation of relevance).
Office Action issued in Japanese Application No. 2016-502475, dated Mar. 15, 2018, and English language translation thereof.
Office Action issued in Russian Application No. 2018101152/10(001468), dated Jul. 2, 2018, and English language translation thereof.
Ostrowski et al., "Rab27a and Rab27b control different steps of the exosome secretion pathway," *Nature cell biology*, 12:19-30; sup pp. 11-13, 2010.
Ozen et al., "Widespread deregulation of microRNA expression in human prostate cancer," *Oncogene*, 27:1788-1793, 2008.
Pant et al., "The multifaceted exosome: biogenesis, role in normal and aberrant cellular function, and frontiers for pharmacological and biomarker opportunities," *Biochemical pharmacology*, 83:1484-1494, 2012.
Park et al., "Neuroprotective effect of human mesenchymal stem cells in an animal model of double toxin-induced multiple system atrophy parkinsonism," *Cell Transplant*, 20:827-835, 2011.
PCT International Preliminary Report on Patentability issued in International Application No. PCT/US2014/027541, dated Sep. 15, 2015.
PCT International Search Report and Written Opinion issued in International Application No. PCT/US2014/027541, dated Jul. 21, 2014.
International Search Report and Written Opinion issued in International Application No. PCT/US2014/068630, dated Feb. 23, 2015.
Pegtel et al., "Functional delivery of viral miRNAs via exosomes," *Proceedings of the National Academy of Sciences of the United States of America*, 107:6328-6333, 2010.
Peinado et al., "Melanoma exosomes educate bone marrow progenitor cells toward a pro-metastatic phenotype through MET," *Nat Med*, 18:883-891, 2012.
Ramachandran et al., "Horizontal transfer of RNAs: exosomes as mediators of intercellular communication," *Wiley Interdiscip Rev RNA*, 3(2):286-293, 2012.
Razi and Futter, "Distinct roles for Tsg101 and Hrs in multivesicular body formation and inward vesiculation," *Molecular biology of the cell*, 17:3469-3483, 2006.
Roccaro et al., "BM mesenchymal stromal cell-derived exosomes facilitate multiple myeloma progression," *The Journal of clinical investigation*, 123(4):1542-1555, 2013.
Rottiers et al., "MicroRNAs in metabolism and metabolic disorders," *Nat Rev Mol Cell Biol.*, 13(4):239-250, 2012.
Savina et al., "Exosome release is regulated by a calcium-dependent mechanism in K562 cells," *The Journal of biological chemistry*, 278:20083-20090, 2003.
Sen et al., "A brief history of RNAi: the silence of the genes," *The FASEB Journal*, 20(9): 1293-1299, 2006.
Shen et al., "Biogenesis of the posterior pole is mediated by the exosome/microvesicle protein-sorting pathway," *The Journal of biological chemistry*, 286:44162-44176, 2011.
Shen et al., "EGFR modulates microRNA maturation in response to hypoxia through phosphorylation of AGO2," *Nature*, 497:383-387, 2013.

Shen et al., "Protein targeting to exosomes/microvesicles by plasma membrane anchors," *The Journal of biological chemistry*, 286:14383-14395, 2011.
Sherer et al., "Visualization of retroviral replication in living cells reveals budding into multivesicular bodies," *Traffic*, 4:785-801, 2003.
Shin et al., "BIG2, a guanine nucleotide exchange factor for ADP-ribosylation factors: its localization to recycling endosomes and implication in the endosome integrity," *Molecular biology of the cell*, 15:5283-5294, 2004.
Siegel et al., "Cancer treatment and survivorship statistics, 2012," *CA Cancer J. Clin.*, 62:220-241, 2012.
Simons and Raposo, "Exosomes—vesicular carriers for intercellular communication," *Curr Opin Cell Biol*, 21:575-581, 2009.
Simpson et al., "Proteomic profiling of exosomes: current perspectives," *Proteomics*, 8:4083-4099, 2008.
Skog et al., "Glioblastoma microvesicles transport RNA and proteins that promote tumour growth and provide diagnostic biomarkers," *Nature cell biology*, 10:1470-1476, 2008.
Tagami et al., "Argonaute2 is a potential target for siRNA-based cancer therapy for HT1080 human fibrosarcoma," *Drug Deliv and Transl. Res.*, 1:277-288, 2011.
Tang, "siRNA and miRNA: an insight into RISCs," *Trends Biochem Sci*, 30:106-114, 2005.
Taylor and Gercel-Taylor, "Exosomes/microvesicles: mediators of cancer-associated immunosuppressive microenvironments," *Semin Immunopathol*, 33:441-454, 2011.
Taylor and Gercel-Taylor, "MicroRNA signatures of tumor-derived exosomes as diagnostic biomarkers of ovarian cancer," *Gynecologic oncology*, 110:13-21, 2008.
Thery and Casas, "Predator and prey views of spider camouflage," *Nature*, 415:133, 2002.
Thery et al., "Exosomes: composition, biogenesis and function," *Nat Rev Immunol*, 2:569-579, 2002.
Thery et al., "Indirect activation of naive CD4+ T cells by dendritic cell-derived exosomes," *Nat Immunol*, 3:1156-1162, 2002.
Thery et al., "Isolation and characterization of exosomes from cell culture supernatants and biological fluids," *Current protocols in cell biology*, Chapter 3, Unit 3.22, 2006.
Thomson et al., "On measuring miRNAs after transient transfection of mimics or antisense inhibitors," *PloS one*, 8:e55214, 2013.
Tse and Kalluri, "Waking up dormant tumors," *Breast cancer research*, 13:310, 2011.
Turchinovich et al., "Characterization of extracellular circulating microRNA," *Nucleic acids research*, 39:7223-7233, 2011.
Vaishnaw et al., "A status report on RNAi therapeutics", *Silence*, 1:14-26, 2010.
Valadi et al., "Exosome-mediated transfer of mRNAs and microRNAs is a novel mechanism of genetic exchange between cells," *Nature cell biology*, 9:654-659, 2007.
Van Balkom et al., "Endothelial cells require miR-214 to secrete exosomes that suppress senescence and induce angiogenesis in human and mouse endothelial cells," *Blood*, 121:3997-4006, 2013.
Van der Pol et al., "Classification, functions, and clinical relevance of extracellular vesicles", *Pharmacol. Rev.*, 64(3):676-705, 2012.
Vickers et al., "MicroRNAs are transported in plasma and delivered to recipient cells by high-density lipoproteins," *Nature cell biology*, 13:423-433, 2011.
Volinia et al., "A microRNA expression signature of human solid tumors defines cancer gene targets," *Proceedings of the National Academy of Sciences of the United States of America*, 103:2257-2261, 2006.
Wiesen and Tomasi, "Dicer is regulated by cellular stresses and interferons," *Mol Immunol*, 46:1222-1228, 2009.
Yan et al., "Knockdown of miR-21 in human breast cancer cell lines inhibits proliferation, in vitro migration and in vivo tumor growth," *Breast Cancer Research*, 13(1):R2, 2011.
Yan et al., "MicroRNA miR-21 overexpression in human breast cancer is associated with advanced clinical stage, lymph node metastasis and patient poor prognosis," *RNA*, 14:2348-2360, 2008.
Yang and Robbins, "The roles of tumor-derived exosomes in cancer pathogenesis," *Clin Dev Immunol*, 2011:842849, 2011.

(56) References Cited

OTHER PUBLICATIONS

Yang et al., "Exosomes derived from immature bone marrow dendritic cells induce tolerogenicity of intestinal transplantation in rats," *J Surg Res*, 171:826-832, 2011.

Yi et al., "Exportin-5 mediates the nuclear export of pre-microRNAs and short hairpin RNAs," *Genes & Development*, 17:3011-3016, 2003.

Yoo et al., "Increased RNA-induced silencing complex (RISC) activity contributes to hepatocellular carcinoma," *Hepatology*, 53(5):1538-1548, 2011.

Zernecke et al., "Delivery of microRNA-126 by apoptotic bodies induces CXCL12-dependent vascular protection," *Science Signaling*, 2(100):ra81, 2009.

Zhang et al., "Secreted monocytic miR-150 enhances targeted endothelial cell migration," *Molecular Cell*, 39:133-144, 2010.

Christensen et al, "Small interfering RNAs against the TAR RNA binding protein, TRBP, a Dicer cofactor, inhibit human immunodeficiency virus type 1 long terminal repeat expression and viral production," J. Virol., 81:5121-5131, 2007.

Kuang, "Repesssion of Dicer is required to maintain invasive phenotype and chemo-resistance in ovarian cancer," China Doctors' Theses Full-test Database, the volume of medicine and health technology, p. E072-41, Aug. 15, 2012. (English abstract only).

Lin et al., "Effects of Argonaute Subfamily Proteins on Cell Cycle of Human Cancer Cells," Prog. Biochem. Biophys., 35:1394-1402, 2008. (Chinese text with English abstract).

Gregory et al., "Human RISC couples microRNA biogenesis and posttranscriptional gene silencing," *Cell*, 123:631-640, 2005.

Office Action issued in Chinese Application No. 201910120129.9, dated May 16, 2023, and English translation thereof.

\* cited by examiner

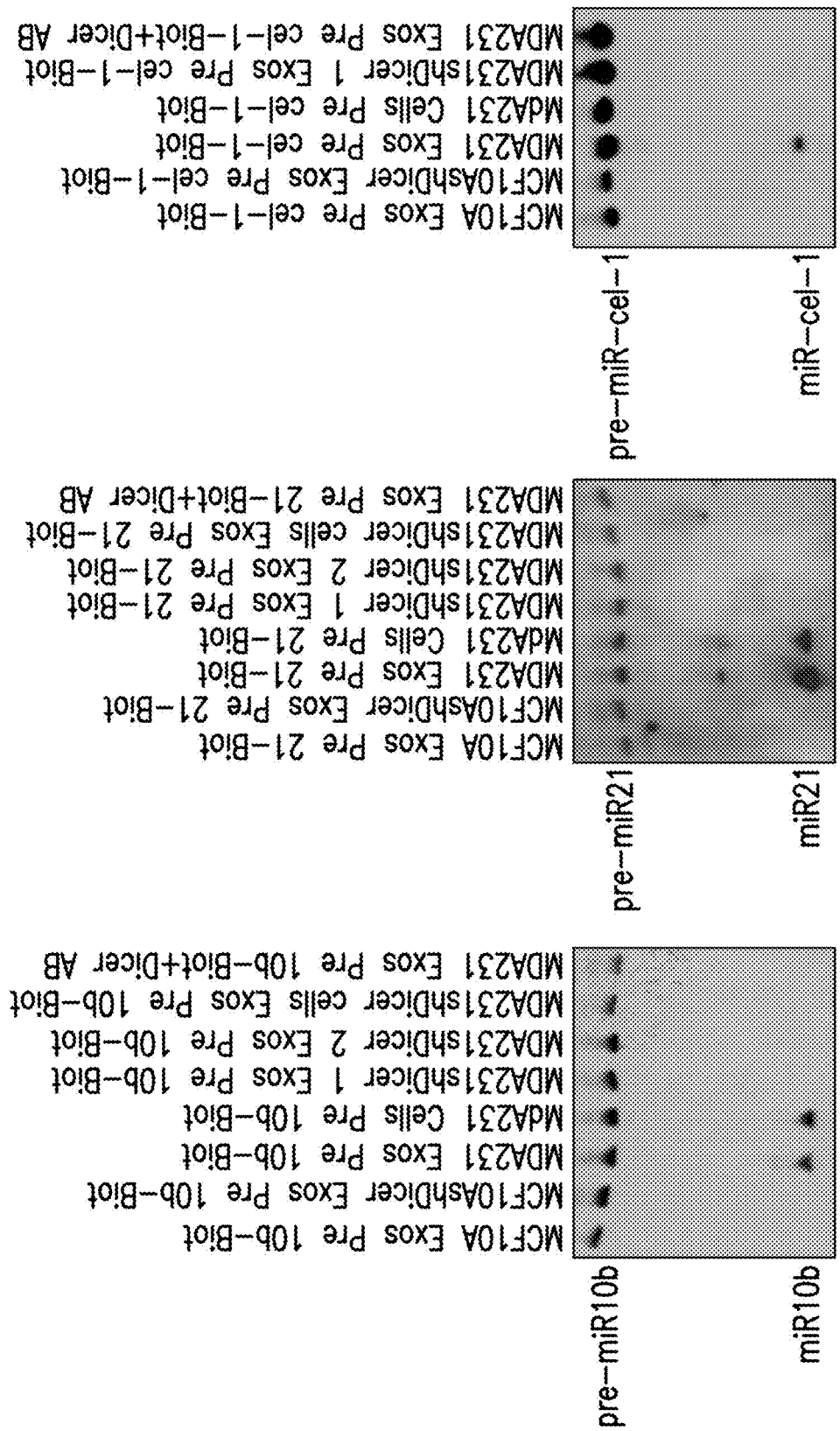

miRNA BIOGENESIS IN EXOSOMES FOR DIAGNOSIS AND THERAPY

The present application is a continuation of U.S. application Ser. No. 14/775,716, filed Sep. 13, 2015, which is a national phase application under 35 U.S.C. § 371 of International Application No. PCT/US2014/027541, filed Mar. 14, 2014, which claims the priority benefit of U.S. provisional application No. 61/791,301, filed Mar. 15, 2013, the entire contents of each of which are incorporated herein by reference.

The invention was made with government support under Grant Nos. EB003472, EB006462, CA135444, CA125550, CA155370, CA151925, DK081576, and DK055001 awarded by the National Institutes of Health and Grant Nos. EFRI-1240410, CBET-0922876, and CBET-1144025 awarded by the National Science Foundation. The government has certain rights in the invention.

BACKGROUND OF THE INVENTION

1. Field of the Invention

The present invention relates generally to the field of molecular biology, oncology and medicine. More particularly, it concerns methods for detecting cancer by their unique exosome content and methods for enhanced inhibitory RNA-based therapies.

2. Description of Related Art

All cells communicate with their surrounding environment via many different pathways, including growth factors, cytokines, hormones, chemokines, membrane-bound proteins and lipids. Exosomes are capable of mediating such communications and achieve this across long distances (Mathivanan et al., 2010; Kahlert and Kalluri, 2013). Communication via exosomes can likely overcome the limitations associated with stability and diffusion of growth factors/cytokines/chemokines/hormones (Mathivanan et al., 2010). Exosomes are nano-vesicles of 30-140 nm in size, which contain proteins, mRNA, and microRNAs (miRNAs) protected by a lipid bilayer (Cocucci et al., 2009; Simons and Raposo, 2009; Simpson et al., 2008; Thery et al., 2002). Several recent studies demonstrated that exosomes are secreted by multiple cell types, including cancer cells, stem cells, immune cells and neurons (Simpson et al., 2008; Thery, 2001). It is noted that cancer cells secrete more exosomes than normal cells (Taylor and Gercel-Taylor, 2011). Moreover, exosomes are increased in the circulation of cancer patients when compared to normal subjects (Logozzi et al., 2009; Taylor and Gercel-Taylor, 2008); however, a functional role remains unknown. Recent evidence suggests that exosomes may play an important role in cancer progression and metastasis (Luga et al., 2012; Peinado et al., 2012; Yang et al., 2011).

The idea that exosomes mediate the transfer of RNAs and miRNAs between cells further increases the complexity of cell-to-cell communications in the body. RNAi is a natural biological process within living cells that participates in the control of gene expression and activity. Extracellular miRNAs were initially only thought to be contained inside exosomes (Valadi et al., 2007). Since then, several reports confirmed the existence of miRNAs in apoptotic bodies (Zernecke et al., 2009), high- and low-density lipoproteins (Vickers et al., 2011) (HDL/LDL), large extracellular vesicles, termed microvesicles, and are associated with AGO2 (Arroyo et al., 2011; Li et al., 2012; Turchinovich et al., 2011). However, a recent report suggests that most miRNAs detected in human serum and saliva are mostly concentrated inside exosomes (Gallo et al., 2012). The presence of miRNAs in exosomes offers the possibility of regulating gene expression of cells at distant sites (Guescini et al., 2010; Valadi et al., 2007; Mittelbrunn et al., 2011; van Balkom et al., 2013). Via their regulation of mRNA translation, miRNAs coordinate the expression of entire sets of genes and shape the organism's transcriptome (Bartel, 2009).

miRNAs are enriched in exosomes derived from many different cell types (Valadi et al., 2007). They are small non-coding RNAs of 18-24 nucleotides (nt) in length that control gene expression post-transcriptionally. They are synthesized via sequential actions of Drosha and Dicer endonucleases and loaded into the RISC (RNA induced silencing complex) to target mRNAs (Bartel, 2009; Maniataki and Mourelatos, 2005). In the Dicer knockout mice, failure of miRNA biosynthesis results in lethality due to defective embryonic stem cell proliferation and differentiation (Bernstein et al., 2003; Fukagawa et al., 2004).

MicroRNAs operate via sequence-specific interaction and pairing of the miRNA-associated RISC (composed of Dicer, TRBP and AGO2 proteins) with the target mRNAs (Bartel, 2009). This action consequently inhibits translation and/or causes mRNA destabilization (Filipowicz, 2005). The degree of complementarity of the miRNA and its mRNA target dictates the process of mRNA silencing, either via mRNA destabilization/degradation or by inhibition of translation (Ambros, 2004; Bartel, 2009). If complete complementation is encountered between the miRNA and target mRNA sequence, the RISC complex acts to cleave the bound mRNA for degradation (Ambros, 2004; Bartel, 2009). If absolute complementation is not encountered, as in most cases of miRNAs in animal cells, translation is prevented to achieve gene silencing (Ambros, 2004; Bartel, 2009).

For a miRNA to be functional and achieve efficient miRNA-mediated gene silencing, it must be complexed with the RLC (RISCloading complex) proteins Dicer, TRBP and AGO2. Within the RLC, Dicer and TRBP are required to process precursor miRNAs (pre-miRNAs), after they emerge from the nucleus via exportin-5, to generate miRNAs and associate with AGO2. AGO2 bound to the mature miRNA constitutes the minimal RISC and may subsequently dissociate from Dicer and TRBP (Chendrimada et al., 2005; Gregory et al., 2005; Haase et al., 2005; MacRae et al., 2008; Maniataki and Mourelatos, 2005; Melo et al., 2009). Single-stranded miRNAs by themselves incorporate into RISC very poorly and therefore cannot be efficiently directed to its target mRNA for post-transcriptional regulation (Tang, 2005; Thomson et al., 2013).

Synthetic siRNAs (double-stranded) cause mRNA decay through perfect base pairing with their target mRNAs (Ambros, 2004; Bartel, 2009). Such siRNAs are loaded directly into the RISC proteins Dicer, TRBP and AGO2 due to its double stranded nature (Tang, 2005). A single-stranded miRNA cannot incorporate into RISC and therefore, cannot be directed to its target mRNA for translation inhibition or degradation (Tang, 2005).

Some reports have suggested that miRNAs contained in exosomes can influence gene expression in target cells (Ismail et al., 2013; Kogure et al., 2011; Kosaka et al., 2013; Narayanan et al., 2013; Pegtel et al., 2010; Valadi et al., 2007; Zhang et al., 2010), but a question remains as to how efficient are these miRNAs in silencing mRNA if they are not incorporated into the RISC as pre-miRNAs for appropriate mRNA recognition and efficient arrest of translation. While mature miRNAs (single-stranded) cannot associate with RISC of target cells, pre-miRNAs of exosomes can to some extent induce gene silencing by co-opting the RISC proteins of the target cells. Nonetheless, such process is highly inefficient and slow due to potential saturated state of proteins involved in the miRNA biogenesis pathway of the target cells. A recent report showed the presence of Drosha and Dicer in exosomes from cell culture supernatants from HIV-1 infected cells and HIV patient sera (Narayanan et al., 2013). Additionally, another study showed co-fractionation of Dicer, TRBP and AGO2 in late endosome/MVB (multi-vesicular body) (Shen et al., 2013).

SUMMARY OF THE INVENTION

Exosomes secreted by cancer cells are unique relative to non-cancer exosomes, the cancer exosomes comprising a unique repertoire of miRNAs as well as active RNA processing RISC complexes. Such encapsulated RNA-RISC complexes could also be used for cell-independent miRNA biogenesis and highly efficient mRNA silencing in target cells.

In one embodiment, the present disclosure provides a method of detecting a cancer biomarker in a subject comprising (a) obtaining a biological sample from the subject; (b) measuring the level of either (i) one or more miRNA(s) selected from the miRNAs provided in Table 5 in an exosome fraction of the sample; (ii) a precursor miRNA; (iii) a RISC protein in an exosome fraction of the sample; or (iv) a miRNA processing activity (e.g., primary miRNA and/or precursor-miRNA processing activity) in an exosome fraction of the sample; and (c) identifying the subject having or not having a cancer biomarker based on the measured level of said miRNA(s), precursor miRNA, RISC protein or miRNA processing activity. In some aspects, the method comprises measuring the level of at least 2, 3, 4, 5, 6, 7, 8, 9, 10 of said miRNAs. In further aspects, the method comprises measuring the level of AGO2, TRBP, or DICER protein.

In some aspects, the biological sample is essentially free of cells. For example, the sample may have less than 10, 9, 8, 7, 6, 5, 4, 3, 2, or 1 cell(s). In one aspect, the biological sample does not contain cells. In certain aspects, the biological sample may be a lymph, saliva, urine or blood (e.g., plasma) sample. In a further aspect, the method my further comprise purifying an exosome fraction of the sample and/or increasing the production of an exosome fraction of the sample.

In certain aspects, the cancer is a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer or skin cancer. In certain aspects, the cancer is a breast cancer. In one aspect, the subject has previously been treated for a cancer or has previously had a tumor surgically removed.

In some aspects, identifying the subject as having or not having a cancer biomarker further comprises correlating the measured miRNA level(s), precursor miRNA level, RISC level or miRNA processing activity with a risk for cancer. In a further aspect, identifying the subject as having or not having a cancer biomarker further comprises analysis of the measured miRNA level(s), precursor miRNA level, RISC level or miRNA processing activity using an algorithm. In some cases, an analysis may be performed by a computer.

In certain aspects, the method of the embodiments further comprises measuring the level of either (i) one or more miRNA(s) selected from the miRNAs provided in Table 5 in an exosome fraction of the sample and a reference sample; (ii) precursor miRNA; (iii) a RISC protein in an exosome fraction of the sample and a reference sample; or (iv) a miRNA processing activity in an exosome fraction of the sample and a reference sample; and (c) identifying the subject as having or not having a cancer biomarker by comparing the level of miRNA(s), a precursor miRNA, RISC or miRNA processing activity in the sample from the subject to the level of miRNA(s), a precursor miRNA, RISC miRNA processing activity in the reference sample.

In some aspects, measuring RISC protein levels comprises performing a Western blot, an ELISA or binding to an antibody array. In other aspects, measuring miRNA levels comprises measuring processed miRNA levels. In some casess, measuring miRNA levels comprises performing RT-PCR, Northern blot or an array hybridization.

In some aspects, the method further comprises reporting whether the subject has or does not have a cancer biomarker. Reporting may comprise preparing a written, oral or electronic report. For example, the report may be provided to the patient, a doctor, a hospital or an insurance company.

In a further embodiment, the present disclosure provides a method of treating a subject comprising selecting a subject identified as having a cancer biomarker in accordance with the embodiments and administering an anti-cancer therapy the subject. For example, the method can comprise (a) obtaining the level of (i) one or more miRNA(s) selected from the miRNAs provided in Table 5; (ii) a precursor miRNA, (ii) a RISC protein; or (iii) a miRNA processing activity, in an exosome fraction of a sample from the subject; (b) selecting a subject having a cancer biomarker based on the level of said miRNA(s), precursor miRNA, RISC protein or miRNA processing activity; and (c) treating the selected subject with an anti-cancer therapy. In certain aspects, the anti-cancer therapy is a chemotherapy, a radiation therapy, a hormonal therapy, a targeted therapy, an immunotherapy or a surgical therapy.

In a further embodiment, the present disclosure provides a method of selecting a subject for a diagnostic procedure comprising (a) obtaining the level of either (i) one or more miRNA(s) selected from the miRNAs provided in Table 5; (ii) precursor miRNA level, (iii) a RISC protein; or (iv) a miRNA processing activity, in an exosome fraction of a sample from the subject; (b) selecting a subject having a cancer biomarker based on the level of said mRNA(s), RISC protein or miRNA processing activity; and (c) performing a diagnostic procedure on the subject. In one aspect, the diagnostic procedure comprises diagnostic imaging. The imaging may be a biopsy, X-ray, CT, MRI or PET imaging.

In still a further embodiment, the present disclosure provides a tangible computer-readable medium comprising computer-readable code that, when executed by a computer, causes the computer to perform operations comprising (a) receiving information corresponding to a level of either (i) one or more miRNA(s) selected from the miRNAs provided in Table 5; (ii) a precursor miRNA, (iii) a RISC protein; or (iv) a miRNA processing activity, in an exosome fraction of a sample from the subject; and (b) determining a relative level of one ore more of said miRNAs, precursor miRNA, RISC proteins or a miRNA processing activity compared to a reference level, wherein altered level compared to a reference level indicates that the subject has a cancer biomarker.

In certain aspects, the operation of the tangible computer-readable medium further comprises receiving information corresponding to a reference level of (i) one or more miRNA(s) selected from the miRNAs provided in Table 5; (ii) a a precursor miRNA; (iii) a RISC protein; or (iv) a miRNA processing activity, in an exosome fraction of a subject no having a cancer.

In certain aspects, the tangible computer-readable medium further comprises computer-readable code that, when executed by a computer, causes the computer to perform one or more additional operations comprising: sending information corresponding to the relative level of miRNA; a precursor miRNA, RISC protein or miRNA processing activity, to a tangible data storage device.

In a further aspect, the reference level is stored in said tangible computer-readable medium. In one aspect, receiving information comprises receiving from a tangible data storage device information corresponding to a level of miRNA; a precursor miRNA level, RISC protein or miRNA processing activity, in a sample from a subject. In some aspects, receiving information further comprises receiving information corresponding to a level of at least 2, 3, 4, 5, 6, 7, 8, 9, or 10 of said miRNAs in a sample from a subject.

In some aspects, the computer-readable code, when executed by a computer, causes the computer to perform operations further comprising (c) calculating a diagnostic score for the sample, wherein the diagnostic score is indicative of the probability that the sample is from a subject having a cancer.

In a further embodiment, the present disclosure provides a method of detecting cancer biomarker in a subject comprising (a) obtaining a biological sample from the subject; (b) measuring the level of one or more miRNA(s) in the sample selected from the miRNAs provided in Table 5 or a precursor miRNA thereof; and (c) identifying the subject having or not having a cancer biomarker based on the measured level of said miRNA(s). In one aspect, the biological sample is essentially free of cells. In certain aspects, the biological sample may be a lymph, saliva, urine or plasma sample. In one aspect, the method my further comprise purifying an exosome fraction of a body fluid.

In still a further embodiment, the present disclosure provides a method for delivery of active inhibitory RNA comprising contacting a cell with an inhibitory RNA that is provided in association with a RISC protein complex. In one aspect, the RISC protein complex comprises TRBP, DICER and AGO2. In some aspects, the inhibitory RNA is a siRNA or shRNA. In one aspect, the inhibitory RNA is a human miRNA.

In certain aspects, the inhibitory RNA and RISC protein complex are comprises in a liposome, a nanoparticle or a microcapsule comprising a lipid bilayer. In one aspect, the microcapsule is an exosome.

In some aspects, a method further comprises transfecting a cell with the inhibitory RNA and RISC protein complex. In another aspect, the method further comprises administering the inhibitory RNA and RISC protein complex to a subject.

In yet a further embodiment, the present disclosure provides a composition comprising a recombinant or synthetic inhibitory RNA in association with a RISC protein complex, said complex comprised in a liposome, a nanoparticle or a microcapsule. In one aspect, the RISC protein complex comprises TRBP, DICER and AGO2. In some aspects, the inhibitory RNA is a siRNA or shRNA. In some aspects, the inhibitory RNA is a human miRNA. In certain aspects, the complex is comprised in a synthetic liposome, a nanoparticle or a microcapsule. In one aspect, the microcapsule is an exosome.

Certain aspects of the embodiments as detailed supra concern measuring a level of one or more miRNA(s) (or miRNA precursor) in an exosome fraction of a sample selected from those provided in Table 5. For example, a method can comprsing measuring a level of one or more miRNA selected from the group consisting of mmu-miR-709, hsa-miR-1308, mmu-miR-615-3p, hsa-miR-1260b, mmu-miR-1937a, mmu-mir-321-A, hsa-miR-615-3p, hsa-miR-1979, mmu-miR-1937b, hsa-mir-373, mmu-miR-1937c, hsa-miR-1273d-P, mmu-miR-720, mmu-miR-1274a, hsa-mir-565-A, mmu-miR-1931, hsa-miR-1246, hsa-mir-594-P, hsa-mir-321-A, mmu-miR-2145-1-P, hsa-mir-639-P, hsa-miR-720, hsa-miR-1280, mmu-miR-3473, hsa-miR-1260, hsa-miR-1281, mmu-miR-1224-P, mmu-miR-690, hsa-miR-375-P, hsa-miR-4301, mmu-miR-700, mmu-miR-125b-5p, mmu-miR-1191-P, hsa-miR-1274a, hsa-miR-3197, mmu-miR-1935, hsa-miR-1975-P, hsa-miR-4324, hsa-miR-886-3p, hsa-miR-1274b, mmu-miR-1957, hsa-miR-933, hsa-mir-675, hsa-miR-595, mmu-miR-2137, hsa-mir-572-P, mmu-miR-1195, hsa-miR-4294-P, mmu-mir-1899-P, mmu-miR-689-P, hsa-miR-199b-3p, hsa-miR-3117-P, mmu-mir-321-P, mmu-miR-1961-P, hsa-mir-10a, mmu-miR-669d-P, mmu-miR-1937b-2-P, hsa-miR-3125-P, mmu-miR-1934-P, hsa-miR-574-3p, hsa-miR-718, mmu-miR-1198, mmu-miR-2182-P, hsa-miR-1273, mmu-miR-2133-P, hsa-miR-92b*, hsa-miR-1290, hsa-miR-448, mmu-miR-689, mmu-miR-449a, mmu-miR-1937b-4-P, hsa-miR-4286, mmu-miR-1947, mmu-miR-342-3p, hsa-miR-1303-P, mmu-miR-2132, hsa-miR-4321-P, hsa-miR-4256-P, hsa-miR-4311, mmu-miR-130a, mmu-miR-1939, hsa-miR-1268-P, mmu-miR-31, mmu-miR-99b, mmu-miR-2141, hsa-miR-1202-P, mmu-miR-466b-3p, mmu-miR-2133, hsa-miR-1268, hsa-miR-466, mmu-miR-494, hsa-miR-1289, hsa-miR-320b, hsa-miR-4254, hsa-mir-7-3-P, hsa-miR-923, hsa-miR-764, mmu-miR-291a-3p, mmu-miR-883b-3p, hsa-mir-594-A, mmu-miR-1948-P, hsa-miR-206, hsa-mir-565-P, mmu-miR-467e*, hsa-miR-1826, mmu-miR-467a*, mmu-miR-1983, hsa-miR-324-5p, mmu-let-7c, mmu-miR-1965, hsa-mir-632-P, hsa-miR-181a*MM2GT/AC, hsa-miR-1265, hsa-miR-323b-5p, hsa-mir-1914, hsa-mir-1910, hsa-miR-21, hsa-miR-431*, hsa-miR-3135-P, mmu-miR-187-P, mmu-miR-126-3p, mmu-miR-669a-P, hsa-miR-367, mmu-mir-320-P, hsa-miR-181a*MM1G/C, mmu-miR-484-P, mmu-miR-467c-P, hsa-miR-3154, mmu-miR-466d-3p, hsa-miR-3162-P, mmu-miR-201, mmu-miR-1946a, hsa-miR-937, hsa-miR-3147, hsa-mir-596-P, hsa-miR-3148, hsa-miR-1304, hsa-miR-222MM2GG/AC, mmu-miR-125a-5p, hsa-miR-1272-P, hsa-miR-638, hsa-mir-320, hsa-miR-545*, hsa-mir-1908-P, hsa-let-7d-v2-P, mmu-mir-30d-P, hsa-miR-4297, mmu-miR-182, hsa-miR-3166-P, hsa-miR-494, mmu-miR-669o-P, hsa-miR-566, mmu-miR-1188, mmu-miR-2134-AP, hsa-miR-4259-P, mmu-miR-152, mmu-miR-2134, hsa-miR-3193-AP, hsa-miR-125b, hsa-miR-3124-P, hsa-miR-10b, hsa-miR-455-5p, mmu-miR-144, hsa-miR-130a, hsa-miR-1285, hsa-miR-516b*, hsa-miR-27a, hsa-miR-138-1*, mmu-miR-471, hsa-miR-4298-P, hsa-miR-301b, hsa-mir-147-P, hsa-miR-362-5p, mmu-mir-471-P, mmu-miR-466a-3p, hsa-miR-561, hsa-miR-486-5p, mmu-miR-2861, hsa-miR-587, mmu-miR-375, hsa-mir-329-2-P, mmu-miR-2861-P, hsa-miR-144*, hsa-miR-1255a-P, hsa-mir-519a-2-P, hsa-miR-34c-5p, mmu-miR-466e-3p, mmu-miR-743b-5p, mmu-mir-350-P, mmu-miR-181d, hsa-miR-376a*, hsa-miR-1308-P, mmu-miR-467g, mmu-miR-1946a-P, hsa-miR-147-P, hsa-miR-923-P, mmu-miR-465c-5p, hsa-miR- 891a, hsa-miR-28-5p, hsa-miR-4292, mmu-miR-677-P, hsa-miR-4257, hsa-miR-4326, hsa-miR-17*MM2GG/AA, hsa-miR-939-P, mmu-miR-2182, hsa-miR-220c-P, hsa-miR-3132-P, hsa-miR-532-5p, mmu-miR-1947-P, mmu-miR-29a, hsa-miR-3162, hsa-miR-375MM1C/G, hsa-miR-768-3p, mmu-miR-182-P, mmu-miR-205-P, hsa-miR-505, hsa-miR-3146-P, mmu-miR-721, mmu-miR-376c, hsa-miR-1179-P, mmu-miR-1970, hsa-miR-3133-P, hsa-miR-200c, hsa-miR-220a, mmu-miR-100, hsa-miR-1255b, hsa-miR-222MM1G/A, hsa-miR-885-3p, hsa-miR-517b, hsa-miR-200a, hsa-miR-3141, mmu-miR-669h-3p, hsa-miR-1301, hsa-miR-877, hsa-mir-941-2, hsa-mir-487b-P, hsa-miR-4302, hsa-miR-99b, hsa-miR-1253, hsa-let-7a*, hsa-miR-34aMM2CT/TC, hsa-miR-3181-P, hsa-miR-3200, hsa-miR-3129-P, hsa-miR-93*, hsa-miR-548q-P, mmu-miR-466g, mmu-miR-155, hsa-miR-2278-P, hsa-miR-3065-5p, hsa-miR-633, hsa-miR-4265, mmu-miR-2135-P, hsa-miR-190, mmu-miR-669f, hsa-miR-1323, hsa-miR-588, mmu-miR-183*, hsa-mir-941-4, hsa-mir-1913, hsa-miR-2116*, hsa-miR-1178, mmu-miR-196a, mmu-miR-574-3p, hsa-miR-346, mmu-miR-1199, mmu-miR-681, hsa-miR-4292-P, hsa-miR-522, hsa-mir-611-P, hsa-miR-3171, hsa-miR-635, hsa-miR-1197-P, hsa-miR-604, mmu-let-7a*, hsa-miR-335, mmu-miR-466c-3p, mmu-miR-466i, hsa-miR-1297, mmu-miR-338-5p, hsa-mir-526a-2-P, hsa-miR-181aMM2GC/AG, hs a-miR-18, hsa-miR-924-P, mmu-miR-190-P, hsa-miR-345, mmu-miR-711, hsa-miR-3116-2-P, hsa-miR-99a, mmu-miR-26a, hsa-miR-1248-P, mmu-miR-721-P, mmu-miR-801-P, hsa-miR-1826-P, hsa-miR-1236, hsa-miR-339-5p, mmu-miR-804, mmu-miR-467d*, mmu-miR-1191, hsa-miR-148a, hsa-miR-141, mmu-miR-1937a-P, mmu-miR-696 and hsa-miR-302a (i.e., those listed in Table 5).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The patent or application file contains at least one drawing executed in color. Copies of this patent or patent application publication with color drawing(s) will be provided by the Office upon request and payment of the necessary fee. The invention may be better understood by reference to one or more of these drawings in combination with the detailed description of specific embodiments presented herein.

FIGS. 6A-F. Oncosomes process pre-miRNAs to generate mature miRNAs. (A) Exosomes from MDA-MB231 cells were harvested and electroporated with Geldanamycin. The samples were left in cell-free culture conditions for 24 and 72 h, after which exosomes were extracted and the 6 miRNAs were quantified by qPCR. The fold-change of each miRNA in exosomes after 72 h cell-free culture was quantified relative to the same miRNA in exosomes after 24 h cell-free culture in each sample. The graphical plots represent the average fold-change for the miRNAs in 72 h exosomes relative to 24 h exosomes and are represented as ±s.d. (B) Synthetic pre-miRNAs-10b, -21 and -cel-1 were electroporated into exosomes harvested from MCF10A (MCF10A electrop.), MCF10AshDicer (MCF10AshDicer electrop.), MDAMB231 (MDA-MB231 electrop.) and MDA-MB231shDicer (MDAMB231shDicer electrop.) cells. Exosomes were recovered after cell-free culture conditions for 72 h. Pre-miR-10b, -21 and -cel-1 were quantified by qPCR before and after 72 h of electroporation and culture. Each bar on the plots show the fold-change of pre-miR-10b, -21 and -cel-1 72 h after electroporation relative to 0 h after electroporation and are represented as ±s.d. MCF10A and MDA-MB231 exosomes electroporated in the absence of pre-miRNAs were used as controls to highlight basal levels. (C) Synthetic pre-miRNAs-10b, -21 and -cel-1 were electroporated into exosomes harvested from MCF10A (MCF10A electrop.), MCF10AshDicer (MCF10AshDicer electrop.), MDA-MB231 (MDA-MB231 electrop.) and MDAMB231shDicer (MDA-MB231shDicer electrop.) cells. Exosomes were recovered after cell-free culture conditions for 72 h. MiR-10b, -21 and -cel-1 were quantified by qPCR before and after 72 h of electroporation and culture. Each bar on the plots show the fold-change of miR-10b, -21 and -cel-1 72 h after electroporation relative to 0 h (top graphs) or 24 h (bottom graph) after electroporation and are represented as ±s.d. MCF10A and MDA-MB231 exosomes electroporated in the absence of pre-miRNAs were used as controls to determined basal levels. (D) Northern blot without detection probe, using samples from dicing assay. Different exosomal protein extracts and synthetic pre-miR-10b internally labeled with biotin were used for the dicing assay. Samples used were MCF10A, MCF10AshDicer, MDA-MB231 exosomes (MDA231 Exos), exosomes from MDA-MB231shDicer clone1 and clone2 (MDA231shDicer 1 exos and MDA231shDicer 2 exos, respectively), MDA-MB231shDicer cells and MDA-MB231 exosomes electroporated with Dicer antibody (MDA231 exos+Dicer AB). (E) Northern blot without detection probe, using samples from dicing assay. Different exosomal protein extracts and synthetic pre-miR-21 internally labeled with biotin was used for the dicing assay. Samples used were MCF10A, MCF10AshDicer, MDA-MB231 exosomes (MDA231 Exos), exosomes from MDA-MB231shDicer clone1 and clone2 (MDA231shDicer 1 exos and MDA231shDicer 2 exos, respectively), MDA-MB231shDicer cells and MDA-MB231 exosomes electroporated with Dicer antibody (MDA231 exos+Dicer AB). (F) Northern blot without detection probe using samples from dicing assay. Different exosomal protein extracts and synthetic pre-cel-miR-1 internally labeled with biotin was used for the dicing assay. Samples used were MCF10A, MCF10AshDicer, MDA-MB231 exosomes (MDA231 Exos), MDA-MB231shDicer exosomes (MDA231shDicer exos) and MDAMB231 exosomes electroporated with Dicer antibody (MDA231 exos+Dicer AB). Data are the result of three biological replicates and are represented as SD.

Figure 1A:
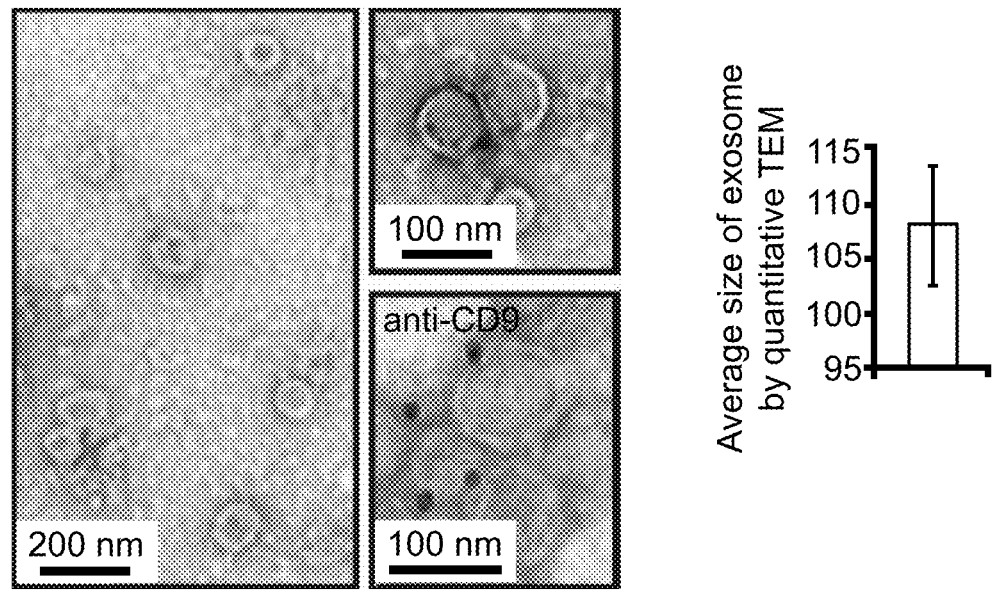
FIGS. 1A-F. Characterization of Exosomes—Oncosomes are enriched in oncogenic miRNAs compared to normosomes. (A) Transmission electron micrograph of oncosomes (upper left photo and lower left photo and inset zoom; doted lines depict the zoom area). Lower right images produced by immunogold labeling using anti-CD9 antibody and transmission electron microscopy. Gold particles are depicted as black dots. Graph represents the average size of exosomes preparations analyzed from 112 TEM pictures. (B) Atomic Force Microscopy image of exosomes from breast cancer cells. Middle graph represents dispersion of particles in the coverslip with size range of exosomes. Right graph represents average size of exosomes preparations analyzed from 26 AFM pictures. (C) Immunoblot using anti-Dicer antibody in exosomes harvested from: non-tumorigenic mouse (NMuMG) and human (MCF10A) cell lines (left blot, first panel); mouse cancer cell lines, 67NR and 4T1 (middle blot, first panel); human cancer cell lines MCF7 and MDA-MB231 (right blot, first panel). Controls used were: exosomes treated with TritonX followed by proteinase K (Triton+PK), to induce lysis of exosomes and subsequent degradation of exosomal proteins; exosomes treated with proteinase K to degrade extra-exosomal proteins (PK); supernatant after ultracentrifugation to harvest exosomes (Supernatant). TSG101 (second row) and CD9 (third row) immunoblots were used to confirm presence of exosomes. (D) Flow cytometry analysis using exosomes markers TSG101, CD9, flotillin-1 and CD63 antibodies of MDA-MB231-derived exosomes coupled to 0.4 μm beads. (E) Sizing exosomes with Light Scattering Spectroscopy (LSS). Calibration of the system was done using signals from phosphate buffered saline (PBS) suspensions of glass microspheres with nominal diameters of 24 nm and 100 nm and polystyrene microspheres with nominal diameters of 119 nm, 175 nm, 356 nm and 457 nm. The experimental spectra and resulting fits are shown in the left graph for glass microspheres with nominal diameter of 100 nm and polystyrene microspheres with nominal diameter of 356 nm. Right graph represents the size measurement of a PBS suspension of cancer exosomes. Inset shows same graph with a scale up to 10 μm to exclude potential contamination of our exosomes preparations with cells and cellular debris. (F) Exosomes size distribution using NanoSight. Left graph represents the size distribution of particles in solution showing a mean size of 105 nm and also showing no peaks at larger sizes. Right graph represents distribution by size and concentration of particles in solution by NanoSight. Data represented in this figure are the result of three independent experiments each with three replicates and are represented as ±s.d.
Figure 1A:
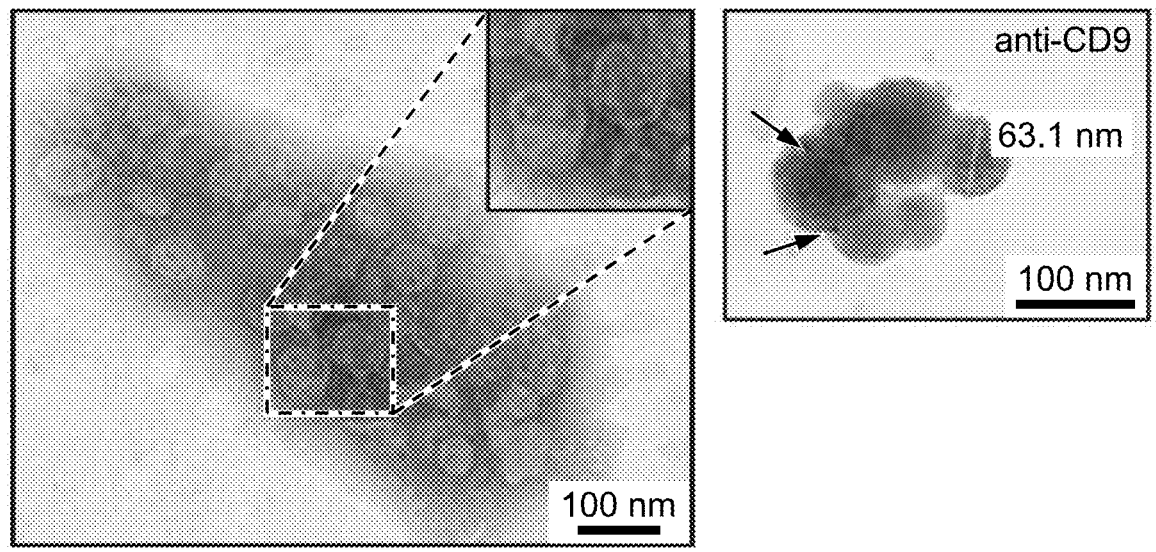

(E) Immunoblot analysis of cytochrome C in exosomes using MDA-MB231 cells as a positive control and TSG101 as a loading control for exosomes. The data presented in this figure are the result of three independent experiments each with three replicates, and are represented as ±s.d.

FIGS. 11A-E. Oncosomes are enriched in miRNAs compared to normosomes. (A) Bioanalyzer graphical representation depicted in fluorescence units (FU) per nucleotides (nt) (graphs) and gel images (right image) of the RNA content of human mammary MCF10A (non-tumorigenic) and MDA-MB231 (breast cancer) cell lines. (B) Exosomes harvested from 4T1, MCF10A and MDA-MB231 cells were resuspended in DMEM media and maintained in cell-free culture conditions for 24 and 72 h. After 24 and 72 h exosomes were recovered and 15 miRNAs (see Table 4) were quantified by qPCR. Graphs show fold change of each miRNA in oncosomes after cell-free culture for 24 h (upper graphs) and 72 h (lower graphs) relative to normosomes after 24 and 72 h of cell-free culture, respectively. Data represented are the result of three biological replicates and are represented as SD. (C) Fifteen mature miRNAs (see Table 4) were quantified by qPCR in MCF10A (left graph), MDA-MB231 (middle graph) and 4T1 (right graph) cells and their respective exosomes. The fold change of each miRNA in exosomes was quantified relative to the same miRNA in cells. TS: tumor suppressor miRNAs; ONC: oncogenic miRNAs. Data are the result of three biological replicates and are represented as SD. (D) Exosomes harvested from MCF10A, MDA-MB231 and 4T1 cells, were resuspended in DMEM media and maintained for 24 and 72 h in cell-free culture conditions. After 24 and 72 h exosomes were extracted once again and 15 miRNAs (see Table 4) were quantified by qPCR. The fold change of each miRNA in exosomes after 72 h cell-free culture was quantified relative to the same miRNA in exosomes after 24 h cell-free culture. Data corresponds to detailed graphs of the fold change average graphs in FIG. 2C. The data presented in this figure are the result of three independent experiments each with three replicates, and are represented as ±s.d. (E) Correlation plots between the 15 quantified miRNAs in MCF7 and 67NR cells and their respective exosomes after 72 h of cell free culture.

FIGS. 12A-E. Exosomes contain pre-miRNAs. (A) Fifteen pre-miRNAs corresponding to the mature miRNAs previously quantified (see Table 4) were quantified by qPCR in NMuMG and 4T1 exosomes. The inverse of the ΔCt value for each pre-miRNA was plotted to reflect their abundance. Data are the result of three biological replicates and are represented as ±s.d. (B) Exosomes harvested from NMuMG and 4T1 cells were resuspended in DMEM media and maintained for 24 and 72 h in cell-free culture conditions. After 24 and 72 h exosomes were extracted once again and 15 pre-miRNAs were quantified by qPCR. Graphs show fold change of each pre-miRNA in NMuMG and 4T1 exosomes after 72 h of cell-free culture relative to 24 h cell-free culture. Data are the result of three biological replicates and are represented as SD. (C) XPOS mRNA expression in MDAMB231 cells with two transiently transfected siRNAs targeting XPOS compared as a fold change to control cells. (D) MDA-MB231 cells were transfected with XPOS siRNA constructs and miR-21 expression was assessed at several time points 12 h post-transfection (0 h, 6 h, 12 h, 24 h, 36 h, 48 h, 72 h and 96 h). As a comparison to show the effect of long centrifugation time periods MDA-MB231 cells transfected with XPOS siRNA constructs were centrifuged at 4° C. for 3 h and put back in culture. MiR-21 expression was assessed at several time points postcentrifugation (0 h, 6 h, 12 h, 24 h, 36 h, 48 h, 72 h and 96 h). Processing of premiR21 to miR-21 is delayed in centrifuged cells (green bar). The presented data in this figure are the result of three independent experiments, each with three replicates and are represented as ±s.d. (E) Exosomes harvested from NMuMG and 4T1 cells were resuspended in DMEM media and maintained for 0, 24, 72 and 96 h in cell-free culture conditions. Exosomes were extracted from the different time points and pre-miRNAs were quantified by qPCR. The inverse of the ΔCt value for each pre-miRNA in the different time points was plotted to reflect their abundance. Data are the result of three biological replicates and are represented as SD.

FIGS. 13A-H. Oncosomes contain Dicer. (A) Transmission electron micrograph image produced by immunogold labeling using anti-Dicer antibody (right photso) and negative control (left photots) in MCF10A cells-derived exosomes. Compare with FIG. 4B for positive immunogold labeling of MDA-MB231 exosomes. (B) Transmission electron micrograph image produced by immunogold labeling using anti-GFP antibody MDA-MB231-derived exosomes. (C) Immunoblot using anti-flag antibody (upper panel) in MCF10A and MDAMB231 cells transfected with empty vector (pCMV-Tag4B; first and third lanes respectively) and Flag-Dicer vector (second and fourth lanes). Beta actin immunoblot was used as a loading control (lower panel). (D) Immunoblot using anti-Dicer antibody (upper panel) in MCF10A, MCF10AshScramble and MCF10AshDicer clones 1 and 2, respectively (MCF10AshDicer clone1 and MCF10AshDicer clone2) cells. Beta actin immunoblot was used as a loading control (lower panel). (E) Immunoblot using anti-Dicer antibody (upper panel) in MDA-MB231, MDA-MB231shScramble and MDA-MB231shDicer clones 1 and 2, respectively (MDA-MB231shDicer clone1 and MDA-MB231shDicer clone2) cells. Beta actin immunoblot was used as a loading control (lower panel). Immunoblots quantification was done using Image J software. (F) Immunoblot using AGO2 antibody in exosomal proteins extracted from MCF10A and MDA-MB231 cells immunoprecipitated with Dicer antibody or IgG (upper panel). 5% of the lysate input of exosomes extracted from MDA-MB231 cells was used as control Immunoblot of Dicer was used as control for immunoprecipitation (lower panel). (G) Immunoblot using anti-TRBP antibody in exosomal proteins extracted from MCF10A and MDA-MB231 cells immunoprecipitated with Dicer antibody or IgG (upper panel). Lysate input of exosomes (5%) extracted from MDA-MB231 cells was used as control Immunoblot of Dicer was used as control for immunoprecipitation (lower panel). (H) Immunoblot of Dicer in oncosomes from A549 (human lung cancer), SW480 (human colon cancer), HeLa (human cervical cancer) and 4T07 (murine breast cancer) cell lines (upper blot). TSG101 immunoblot was used to confirm presence of exosomes and loading (lower blot).

FIGS. 14A-F. Dicer detection in exosomes. (A) Immunoblot using anti-Dicer antibody in 4T1, 4T1shScramble and 4T1shDicer cells and exosomes harvested from 4T1 (4T1 exos) and 4T1shDicer (4T1shDicer exos) cells (upper blot). GADPH immunoblot was used as loading control (lower blot). Quantification was done using Image J software. (B) Exosomes were harvested from 4T1, 4T1shScramble and 4T1shDicer cells and maintained under cell-free culture conditions for 24 and 72 h. After 24 and 72 h exosomes were extracted once again and 15 pre-miRNAs were quantified by qPCR. Graphs show fold change of each pre-miRNA in the different exosomes after 72 h of cell-free culture relative to 24 h cell-free culture. Data are the result of three biological replicates and are represented as SD. (C) Exosomes were harvested from 4T1, 4T1shScramble and 4T1shDicer cells and maintained under cell-free culture conditions for 24 and 72 h. After 24 and 72 h exosomes were extracted once again and 15 miRNAs were quantified by qPCR. Graphs show fold change of each miRNA in the different exosomes after 72 h of cell-free culture relative to 24 h cell-free culture. Data are the result of three biological replicates and are represented as SD. (D) Exosomes were harvested from MDA-MB231 cells in duplicate. One of the samples was electroporated with anti-Dicer antibody. Both samples were left in cell-free culture conditions for 24 and 72 h. After 24 and 72 h exosomes were extracted once again and 15 pre-miRNAs (see Table 4) were quantified by qPCR. The fold change of each pre-miRNA in exosomes after 72 h cell-free culture was quantified relative to the same pre-miRNA in exosomes after 24 h cell-free culture in each sample. The graphical plots represent fold change of pre-miRNAs in 72 h exosomes relative to 24 h exosomes and are a detailed analysis of graph represented in FIG. 5D. Data are the result of three biological replicates and are represented as SD. (E) Exosomes were harvested from MDA-MB231 cells in duplicate. One of the samples was electroporated with anti-Dicer antibody. Both samples were left in cell-free culture conditions for 24 and 72 h. After 24 and 72 h exosomes were extracted once again and 15 miRNAs (see Table 4) were quantified by qPCR. The fold change of each miRNA in exosomes after 72 h cell-free culture was quantified relative to the same miRNA in exosomes after 24 h cell-free culture in each sample. The graphical plots represent fold change of miRNAs in 72 h exosomes relative to 24 h exosomes and are a detailed analysis of graph represented in FIG. 5E. Data are the result of three biological replicates and are represented as SD. (F) Graphical representation of the categories (Oncogenic, Tumor Suppressor and Non-determined related to Cancer) of the down regulated miRNAs in MDA-MB231 exosomes electroporated with Dicer (MDA-MB231 exos Dicer AB) compared to MDA-MB231 exosomes (MDA-MB231 exos). MicroRNAs were attributed to each category based on literature. The presented data in this figure are the result of three independent experiments each with three replicates and are represented as ±s.d.

Figure 15A:
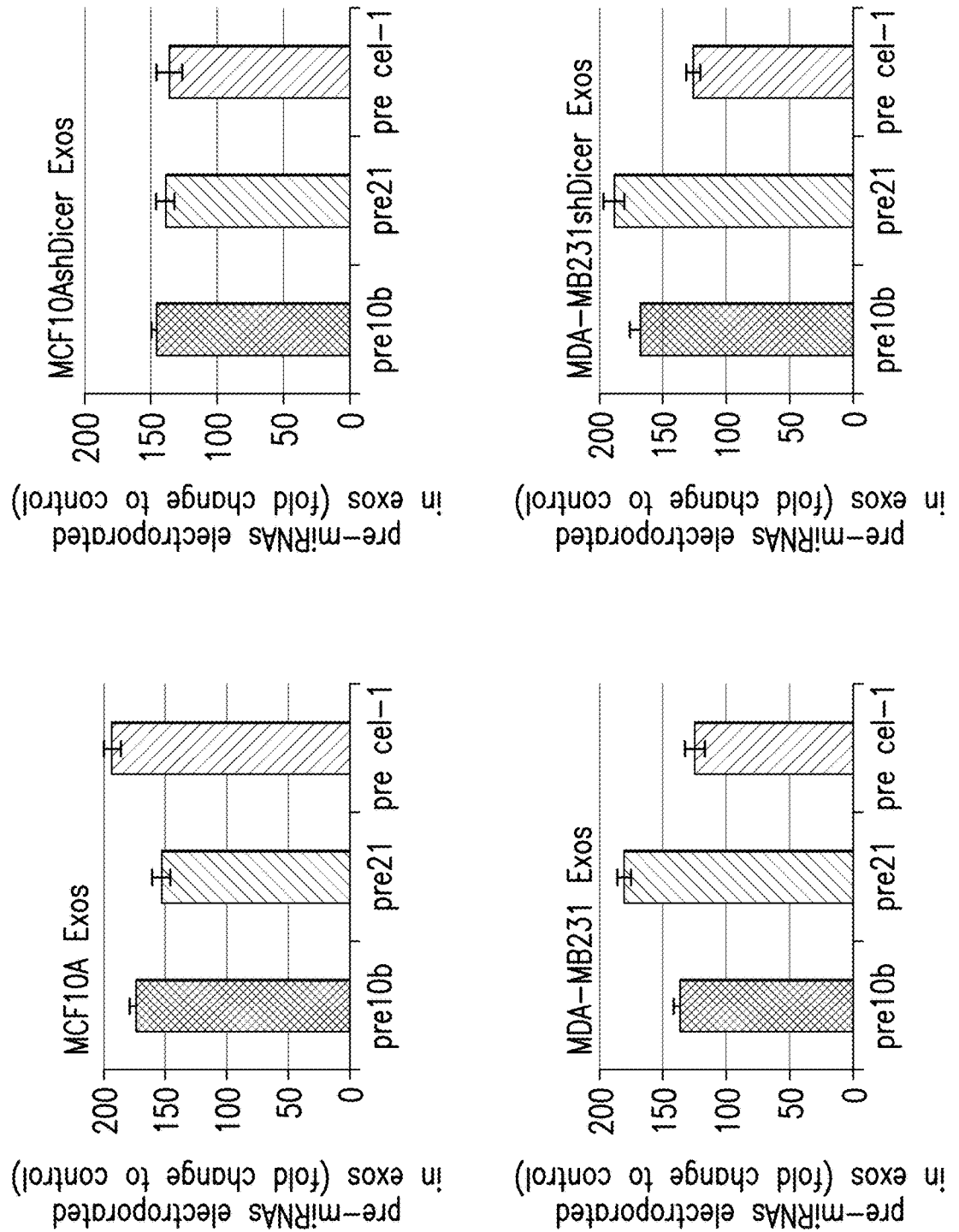
Figure 15B:
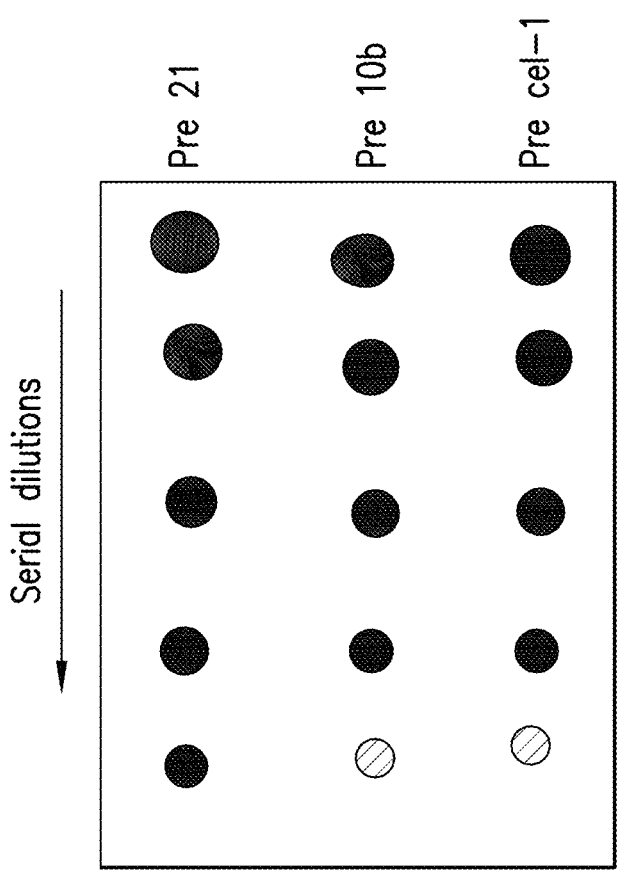
Figure 15C:
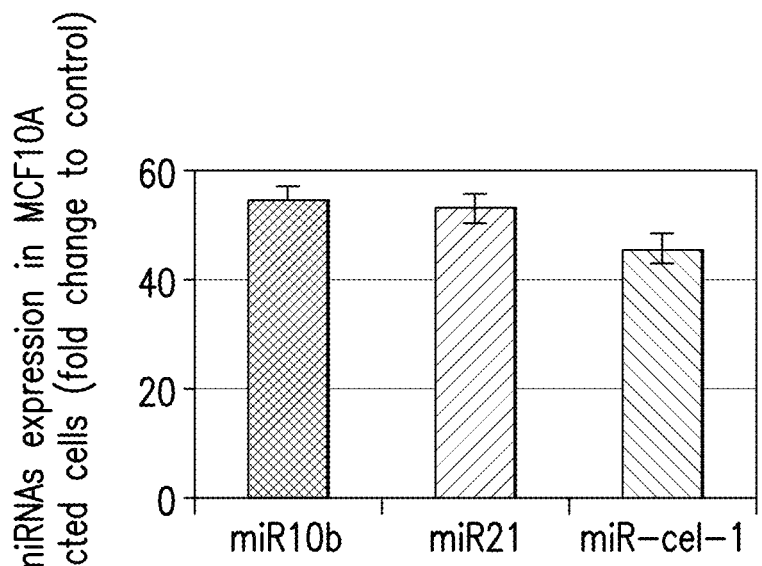

FIGS. 15A-C. Dicer detection in exosomes. (A) Exosomes were harvested from MCF10, MCF10AshDicer, MDA-MB231 and MDA-MB231shDicer cells and electroporated with synthetic pre-miRNA-10b, -21 and -cel-1. Each pre-miRNA was quantified by qPCR in the electroporated exosomes and represented as a fold change relative to exosomes that were electroporated with electroporation buffer only. (B) Dot blot of biotin internally labeled pre-miR-21, -10b and -cel-1. (C) miR-10b, -21 and -cel-1 expression analysis of MCF10A cells transfected with pre-miR-10b, -21 and -cel-1. Each bar represents the fold change of the transfected cells compared to nontransfected. The presented data in this figure are the result of three independent experiments each with three replicates and are represented as ±s.d.

FIGS. 16A-I. Dicer is present in multivesicular bodies and cytoplasmic CD43 mobilizes Dicer into exosomes. (A) Graph represents the percentage of colocalization in the confocal images as quantified using image J software. (B) Hrs, TSG101 and BiG2 mRNA expression after down regulation using two different siRNAs for Hrs and TSG101 and two different sh clones for BiG2. Non-transfected and shScramble transfected cells were used as control. (C) Protein quantification by Bradford assay of exosomes extracted from MCF10A, MCF10AsiHrs, MDA-MB231 and MDA-MB231siHrs (left graph), MCF10shScramble, MCF10AshBiG2, MDA-MB231shScramble, MDA-MB231shBiG2 (middle graph) and MCF10AsiTSG101 and MDA-MB231siTSG101 (right graph). Parental non-transfected cells were used as relative controls for fold change analysis. Data was normalized by cell number and is the result of three biological replicates represented as SD. (D) Immunoblot of CD9 in exosomal protein extracts of MCF10A, MCF10AsiTSG101 (siTSG101), MCF10AsiHrs (siHrs) and MCF10AshBiG2 (shBiG2) cells (upper blot); immunoblot of CD9 in exosomal protein extracts of MDA-MB231, MDA-MB231siTSG101 (siTSG101), MDA-MB231siHrs (siHrs) and MDA-MB231shBiG2 (shBiG2) cells (lower blot). (E) NanoSight particle tracking analysis of MDA-MB231, MDA-MB-231siTSG101, -siHrs and shBiG2-derived exosomes showing down regulation of exosomes number in Hrs, TSG101 and BiG2 down regulated cells and the exosomes expected size distribution. (F) mRNA expression of Dicer in MCF10A, MCF10AshScramble, MCF10AsiHrs, MCF10AshBiG2, MCF10AsiTSG101, MDA-MB231, MDA-MB231shScramble, MDA-MB231siHrs, MDA-MB231shBiG2, MDA-MB231siTSG101, 4T1, 4T1siHrs, 4T1shBiG2 and 4T1siTSG101 cells. Parental cells were used as relative control for fold change comparison. Data are the result of three biological replicates and are represented as SD. (G) Immunoblot of Dicer in protein extracts of MDA-MB231 and 4T1 cancer cells immunoprecipitated with anti-Dicer antibody (upper blot, two left lanes) together with 5% of the input that corresponds to the protein lysate used for immunoprecipitation (upper blot, two right lanes) Immunoblot of poli-ubiquitin in protein extracts of MDA-MB231 and 4T1 cells immunoprecipitated with anti-Dicer antibody (lower blot, two left lanes) together with 5% of the input that corresponds to the protein lysate used for immunoprecipitation (lower blot, two right lanes). (H) mRNA expression of CD43 in MCF10A, MCF10AsiCD43, MDA-MB231 and MDA-MB231siCD43 cells. MCF10A and MDA-MB231 parental cells were used as relative control for fold change comparison. Data are the result of three biological replicates and are represented as SD. (I) mRNA expression of Dicer in MCF10A, MCF10AsiCD43, MDA-MB231 and MDA-MB231siCD43 cells. MCF10A and MDA-MB231 parental cells were used as relative control for fold change comparison. Data are the result of three biological replicates and are represented as SD FIGS. 17A-G. Oncosomes induce transcriptome alterations inreceiving cells and tumor formation in a Dicer-dependent manner (A) NanoSight particle tracking analysis of exosomes derived from MDA-MB231 CD63-GFP cells. Black line represents a measure of total exosomes population and green line depicts the population of exosomes that is labeled with CD63-GFP using the NanoSight equipped with a 488 nm laser beam. Light gray and light green represent the error bars of each measure. (B) Immunoblot using anti-PTEN antibody and protein extracts of MCF10A cells treated for 0, 30 min, 1h, 12 h and 24 h with MDA-MB231 oncosomes freshly extracted. Beta actin was used as a loading control. (C) Immunoblot using anti-HOXD10 antibody and protein extracts of MCF10A cells treated for 0, 30 min, 1h, 12 h and 24 h with MDA-MB231 oncosomes freshly extracted. Beta actin was used as a loading control. (D) MCF10A cells were transfected with siRNA for XPOS to down regulate the flow of pre-miRNAs into the cytoplasm from the nucleus. The processing of pre-miR15 was assessed measuring the levels of miR-15 over time (6 h, 12 h, 24 h, 36 h and 48 h) in MCF10AsiXPO5 cells and MCF10AsiXPO5 cells treated with MDA-MB231 exosomes with and without Dicer antibody. No significant changes were denoted. (E) miR182-5p expression was monitored in MDA-MB231 derived exosomes over time (0 h, 6 h, 12 h, 24 h, 36 h, 48 h, 72 h and 96 h). Each bar represents the fold change of each time point compared to 0 h. No significant differences were noted. (F) Graph provides colony number quantification of FIG. 7G. *p=0.0006. (G) Immunoblot using anti-Dicer antibody and protein extracts of MCF10A cells treated for 0, 30 min, 1, 12 and 24 h with MDA-MB231 oncosomes electroporated with Dicer antibody after cell-free culture conditions. Alpha tubulin was used as loading control.

FIGS. 18A-D. Breast cancer patient-exosomes contain Dicer, process pre-miRNAs and enter cells in different organs. (A) Representative photos from orthotopic xenografts derived from fragments of fresh primary human ovary, endometrial and breast tumors in nude mice. (B) Hematoxylin-eosin (HE) staining of ovary, endometrial and breast cancer orthotopic xenografts. (C) Transmission electron micrograph of serum exosomes harvested from mice with orthotopic tumor xenografts. (D) Comassie staining of membranes of immunoblots depicted in FIG. 8A.

DESCRIPTION OF ILLUSTRATIVE EMBODIMENTS

Cancer progression is dependent on effective communication between cells in the tumor. Exosomes are nanovesicles secreted by all cell types and contain proteins and nucleic acids. Exosomes secreted by cancer cells specifically contain microRNAs (miRNAs) associated with the RNA Induced Silencing Complex (RISC; Dicer/TRBP/AGO2) and possess cell autonomous capacity to process precursor microRNAs (pre-miRNAs) into mature miRNAs. The existence of RISC-associated miRNAs, instead of naked miRNAs, allows for a highly efficient and rapid silencing of mRNAs in target cells, effectively altering their transcriptome. The RISC proteins in cancer cells are specifically directed into multivesicular bodies (MVBs) and subsequently into exosomes in a CD43-dependent manner RISC-incorporated miRNAs of exosomes stimulate non-tumorigenic epithelial cells to form tumors via specific induction of oncogenic pathways and activate stromal fibroblasts. This study unravels the possible role of cancer exosomes in inducing oncogenic "field effect" that further subjugates normal cells to participate in cancer development and progression. Moreover, miRNA biogenesis can occur in a cell-independent manner in exosomes, which offers new opportunities to engineer efficient miRNA-mediated targeted therapy for a myriad of diseases.

I. CANCER DERIVED EXOSOMES

Tumors contain cancer cells and stromal elements (Tse and Kalluri, 2011). Emerging evidence suggests that communication between cells of the tumors and their surroundings also determine the rate and intensity of systemic spread in cancer (Luga et al., 2012). Some studies suggest that primary tumors can educate and prepare secondary tumor sites for future metastasis via cancer cell secreted factors (Hood et al., 2011; Peinado et al., 2012). Several such mediators have been identified, which include soluble growth factors, glucose metabolites, chemokines, enzymes, microparticles, microvesicles, exosomes and free nucleic acids (Guermonprez et al., 2002; Luga et al., 2012; Peinado et al., 2012; Simons and Raposo, 2009; Thery and Casas, 2002).

Recent years have seen a plethora of publications related to exosomes and their association with cancer (Yang and Robbins, 2011). Most studies show that cancer cells secrete higher number of exosomes when compared to normal cells (Yang and Robbins, 2011). Hypoxic cancer cells shed more exosomes than normoxic cancer cells (King et al., 2012). Cancer derived exosomes are speculated to carry specific payloads of proteins and nucleic acids, including miRNAs (Valadi et al., 2007). While provocative, such studies fall short of explaining how proteins and miRNAs can induce significant functional changes in target cells, near or far. Most studies have identified mature miRNAs in exosomes but their function is largely unknown. Moreover, single-stranded miRNAs are highly inefficient in silencing target mRNAs without RISC incorporation to facilitate mRNA recognition. Proteins of the RLC recognize the pre-miRNA and process it into a 22-nucleotide RNA duplex. AGO2 selects one strand for subsequent gene silencing while the other strand is often degraded. The overall reaction is spontaneous and does not require any factors beyond the three proteins and the incorporated pre-miRNA (Maniataki and Mourelatos, 2005). Therefore, for a miRNA to be fully functional it needs RLC-incorporated processing of its pre-miRNA and AGO-mediated mRNA recognition and silencing.

Herein, the miRNA profiles of exosomes from cancer cells (oncosomes) and control cells (normosomes) were probed and the functional capabilities of exosomal miRNAs were evaluated in achieving gene silencing and alteration of target cell transcriptome. Oncosomes specifically contain Dicer, TRBP and AGO2 as a functional complex with an ability to process pre-miRNAs to miRNAs. The pre-miRNAs were present in all exosomes but only processed in the oncosomes due to the presence of RLC. Interestingly there was preference for accumulation of oncogenic pre-miRNAs/miRNAs in the oncosomes and this could be mere reflection of the pre-miRNA content of cancer cells, which were generally enriched in oncogenic miRNAs/pre-miRNAs (Bartels and Tsongalis, 2009; Nicoloso et al., 2009).

Previous reports suggested the presence of miRNA in exosomes and speculated on their function (Valadi et al., 2007; Zhang et al., 2010). Given that miRNAs need to be present in a stoichiometric concentration for appropriate silencing of mRNA targets, it seems unlikely that exosomes in circulation would provide sufficient concentrations of mature miRNAs to repress target transcriptome. The processing of the pre-miRNAs originated from exosomes in the recipient cells is an unlikely event because miRNA biogenesis in recipient cells is rate-limiting not only due to the total amount of pre-miRNAs available for processing that exist inside the cell already, but also due to rate-limiting amounts of required enzymes. Therefore, it is more efficient to have mature miRNAs entering recipient cells for direct alteration of gene expression post-transcriptionally without having to go through a processing pathway, as it would happen in the case that pre-miRNAs are transferred to recipient cells and not the respective mature miRNAs. Specific miRNA biogenesis in exosomes solves this conundrum for cancer cells. Oncosomes get highly enriched in a subset of mature miRNAs that are RISC-associated and can play an important biological role in shaping the phenotype of target cells.

Moreover, cancer cells overexpress miRNAs with oncogenic potential, such as miR-21 and miR-155, which provide them with a proliferative and survival advantage and are associated with advanced clinical stage, metastasis and poor prognosis (Yan et al., 2008). It has also been previously reported that these miRNAs are overexpressed in the circulation of cancer patients (Mao et al., 2013). The synthesis of miRNAs in cells is an enzymatic reaction and therefore depends on the amount of key enzymes, such as Dicer, present in their cytoplasm. Dicer has been described as down regulated in breast cancer cells and tumors (Grelier et al., 2009; Martello et al., 2010). Therefore, the quantity of miRNAs these cancer cells can synthesize is limited. Because exosomes production is a continuous process, it is hypothesized that cancer cells pack specific pre-miRNAs with RLC proteins to allow enrichment of the mature miRNA in exosomes and at the same time, keep these miRNAs up-regulated in the cells of origin. Oncosomes are highly enriched in mature miRNAs that are RISC-associated and can play an important biological role in shaping the phenotype of target cells. At the same time, the cells of origin maintain their overexpression of advantageous oncogenic miRNAs while the recipient cells do not see their biogenesis pathway oversaturated with the entrance of pre-miRNAs through exosomes.

The present studies unveil the RISC-dependent mechanism by which cancer exosomes get enriched in a subset of miRNAs. Using siRNA/shRNA against Dicer in cancer cells was not a viable option to probe the content of miRNA in exosomes, as any decrease in exosomal miRNA could be a mere reflection of low level of miRNAs due to Dicer suppression. Therefore, an electroporation method was developed to deliver neutralizing antibodies directly to exosomes. This method worked efficiently to inhibit Dicer activity in exosomes and prevent processing of pre-miRNAs.

While certain miRNAs are up regulated in specific tumors (Volinia et al., 2006), a global reduction of miRNA is also reported to occur in human cancers (Kumar et al., 2007; Lu et al., 2005; Melo et al., 2011; Melo et al., 2010; Melo et al., 2009; Ozen et al., 2008). Dicer is described as suppressed in cancer cells but low levels are sufficient to sustain tumor growth (Kumar et al., 2009). Partial Dicer down regulation via miR-103/107 enhances cancer cell invasiveness without affecting cell proliferation (Martello et al., 2010). Complete loss of Dicer is detrimental for cell survival (Fukagawa et al., 2004). While low levels of Dicer are associated with poor survival in lung and ovarian cancer patients (Karube et al., 2005; Merritt et al., 2008). Likewise, heterozygous loss of Dicer correlates with metastasis in breast cancer patients (Martello et al., 2010). Down regulation of Dicer in breast cancer also occurs post-transcriptionally because mRNA levels remain unchanged (Grelier et al., 2009; Wiesen and Tomasi, 2009). In cancer cells, a fraction of Dicer is targeted to endosomes/MVBs in a CD43-dependent manner Eventually Dicer is secreted via exosomes. Down regulation of Hrs, BiG2 and TSG101, components of the exosomal biogenesis pathway, led to dramatic changes in the cellular localization of Dicer protein. One possible explanation for suppressed Dicer levels in cancer cells may be due to active export via exosomes. If exosomes secretion pathway is shut down, cancer cells sense the increase in Dicer protein and down regulate their mRNA expression. In addition, they shuttle the protein into the nuclear compartment, were it can no longer aid in the production of mature miRNAs. In this regard, Dicer up-regulation in aggressive cancer cells makes them more indolent (Park et al., 2011).

CD43 is transmembrane protein that is predominantly present in leukocytes. In some cancer cells, a truncated CD43 is observed in the cytoplasm and nucleus (Shelley at al. 2012). It has been previously shown that CD43 could target certain membrane proteins to exosomes (Shen et al., 2011a). Suppression of CD43 in a mouse model of orthotopic breast cancer reduces tumor burden by 76% (Shelley et al., 2012). Clinical studies suggest that CD43 expression correlates with poor survival of breast cancer patients (de Laurentiis et al., 2011). This report identifies that CD43 is functionally involved in directing Dicer into oncosomes.

Recent studies show that melanoma-derived exosomes play a role in metastasis and exosomes derived from fibroblasts play a role in migration of breast cancer cells (Luga et al., 2012; Peinado et al., 2012). Exosomes derived from cancer cells have a pro-tumorigenic role associated with the transfer of mRNA and pro-angiogenic proteins (Luga et al., 2012; Peinado et al., 2012; Skog et al., 2008). Exosomes derived from cancer cells can also contribute to a horizontal transfer of oncogenes, such as EGFRvIII (Skog et al., 2008). Oncosomes mediate significant transcriptome alterations in target cells via RISC-associated miRNAs. A myriad of biological process are affected in the target cells, inducing proliferation and converting non-tumorigenic cell into tumor-forming cells. Nonetheless, the potential in vivo effect of oncosomes on recipient cells likely depends on several other environmental parameters and accessibility barriers.

Oncosomes also activate stromal fibroblasts to acquire a myofibroblasts phenotype. As an example, the capacity of oncosomes to silence tumor suppressors PTEN and HOXD10 via oncosomes derived miR-21 and miR-10b, respectively, were illustrated (Ma et al., 2007; Maehama, 2007). These results highlight the complex nature of communication adopted by cancer cells to achieve malignancy. These data illustrate that cancer cells can use exosomes to manipulate surrounding normal cells to accelerate cancer progression and recruit reactive stroma.

Many studies have show that fibroblasts and normal epithelial cells, also exhibit down regulation of tumor suppressors and activation of oncogenes without obvious mutations. Collectively, this study unravels the possible role cancer exosomes play in inducing an oncogenic "field effect" that further subjugates adjacent normal cells to participate in cancer development and progression. Oncosomes can convert non-tumorigenic cells into tumor forming cells via activation of oncogenic pathways. Additionally, oncosomes can also participate in generating reactive stroma. This is likely achieved without the need for defined genetic mutations and explains the complex nature of how mutated cancer cells extend their agenda to recruit support from their micro- and macro-environment.

II. BIOMARKER DETECTION

The expression of biomarkers or genes may be measured by a variety of techniques that are well known in the art. Quantifying the levels of the messenger RNA (mRNA) of a biomarker may be used to measure the expression of the biomarker. Alternatively, quantifying the levels of the protein product of a biomarker may be used to measure the expression of the biomarker. Additional information regarding the methods discussed below may be found in Ausubel et al. (2003) or Sambrook et al. (1989). One skilled in the art will know which parameters may be manipulated to optimize detection of the mRNA or protein of interest.

In some embodiments, said obtaining expression information may comprise RNA quantification, e.g., cDNA microarray, quantitative RT-PCR, in situ hybridization, Northern blotting or nuclease protection. Said obtaining expression information may comprise protein quantification, e.g., protein quantification comprises immunohistochemistry, an ELISA, a radioimmunoassay (RIA), an immunoradiometric assay, a fluoroimmunoassay, a chemiluminescent assay, a bioluminescent assay, a gel electrophoresis, a Western blot analysis, a mass spectrometry analysis, or a protein microarray.

A nucleic acid microarray may be used to quantify the differential expression of a plurality of biomarkers. Microarray analysis may be performed using commercially available equipment, following manufacturer's protocols, such as by using the Affymetrix GeneChip® technology (Santa Clara, CA) or the Microarray System from Incyte (Fremont, CA). For example, single-stranded nucleic acids (e.g., cDNAs or oligonucleotides) may be plated, or arrayed, on a microchip substrate. The arrayed sequences are then hybridized with specific nucleic acid probes from the cells of interest. Fluorescently labeled cDNA probes may be generated through incorporation of fluorescently labeled deoxynucleotides by reverse transcription of RNA extracted from the cells of interest. Alternatively, the RNA may be amplified by in vitro transcription and labeled with a marker, such as biotin. The labeled probes are then hybridized to the immobilized nucleic acids on the microchip under highly stringent conditions. After stringent washing to remove the non-specifically bound probes, the chip is scanned by confocal laser microscopy or by another detection method, such as a CCD camera. The raw fluorescence intensity data in the hybridization files are generally preprocessed with the robust multichip average (RMA) algorithm to generate expression values.

Quantitative real-time PCR (qRT-PCR) may also be used to measure the differential expression of a plurality of biomarkers. In qRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified.

A non-limiting example of a fluorescent reporter probe is a TaqMan® probe (Applied Biosystems, Foster City, CA). The fluorescent reporter probe fluoresces when the quencher is removed during the PCR extension cycle. Multiplex qRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, qRT-PCR may be performed using a reference standard. The ideal reference standard is expressed at a constant level among different tissues, and is unaffected by the experimental treatment. Suitable reference standards include, but are not limited to, mRNAs for the housekeeping genes glyceraldehyde-3-phosphate-dehydrogenase (GAPDH) and β-actin. The level of mRNA in the original sample or the fold change in expression of each biomarker may be determined using calculations well known in the art.

Immunohistochemical staining may also be used to measure the differential expression of a plurality of biomarkers. This method enables the localization of a protein in the cells of a tissue section by interaction of the protein with a specific antibody. For this, the tissue may be fixed in formaldehyde or another suitable fixative, embedded in wax or plastic, and cut into thin sections (from about 0.1 mm to several mm thick) using a microtome. Alternatively, the tissue may be frozen and cut into thin sections using a cryostat. The sections of tissue may be arrayed onto and affixed to a solid surface (i.e., a tissue microarray). The sections of tissue are incubated with a primary antibody against the antigen of interest, followed by washes to remove the unbound antibodies. The primary antibody may be coupled to a detection system, or the primary antibody may be detected with a secondary antibody that is coupled to a detection system. The detection system may be a fluorophore or it may be an enzyme, such as horseradish peroxidase or alkaline phosphatase, which can convert a substrate into a colorimetric, fluorescent, or chemiluminescent product. The stained tissue sections are generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for the biomarker.

An enzyme-linked immunosorbent assay, or ELISA, may be used to measure the differential expression of a plurality of biomarkers. There are many variations of an ELISA assay. All are based on the immobilization of an antigen or antibody on a solid surface, generally a microtiter plate. The original ELISA method comprises preparing a sample containing the biomarker proteins of interest, coating the wells of a microtiter plate with the sample, incubating each well with a primary antibody that recognizes a specific antigen, washing away the unbound antibody, and then detecting the antibody-antigen complexes. The antibody-antibody complexes may be detected directly. For this, the primary antibodies are conjugated to a detection system, such as an enzyme that produces a detectable product. The antibody-antibody complexes may be detected indirectly. For this, the primary antibody is detected by a secondary antibody that is conjugated to a detection system, as described above. The microtiter plate is then scanned and the raw intensity data may be converted into expression values using means known in the art.

An antibody microarray may also be used to measure the differential expression of a plurality of biomarkers. For this, a plurality of antibodies is arrayed and covalently attached to the surface of the microarray or biochip. A protein extract containing the biomarker proteins of interest is generally labeled with a fluorescent dye or biotin. The labeled biomarker proteins are incubated with the antibody microarray. After washes to remove the unbound proteins, the microarray is scanned. The raw fluorescent intensity data may be converted into expression values using means known in the art.

Luminex multiplexing microspheres may also be used to measure the differential expression of a plurality of biomarkers. These microscopic polystyrene beads are internally color-coded with fluorescent dyes, such that each bead has a unique spectral signature (of which there are up to 100). Beads with the same signature are tagged with a specific oligonucleotide or specific antibody that will bind the target of interest (i.e., biomarker mRNA or protein, respectively). The target, in turn, is also tagged with a fluorescent reporter. Hence, there are two sources of color, one from the bead and the other from the reporter molecule on the target. The beads are then incubated with the sample containing the targets, of which up to 100 may be detected in one well. The small size/surface area of the beads and the three dimensional exposure of the beads to the targets allows for nearly solution-phase kinetics during the binding reaction. The captured targets are detected by high-tech fluidics based upon flow cytometry in which lasers excite the internal dyes that identify each bead and also any reporter dye captured during the assay. The data from the acquisition files may be converted into expression values using means known in the art.

In situ hybridization may also be used to measure the differential expression of a plurality of biomarkers. This method permits the localization of mRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an mRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each biomarker.

In a further embodiment, the marker level may be compared to the level of the marker from a control, wherein the control may comprise one or more tumor samples taken from one or more patients determined as having a certain metastatic tumor or not having a certain metastatic tumor, or both.

The control may comprise data obtained at the same time (e.g., in the same hybridization experiment) as the patient's individual data, or may be a stored value or set of values, e.g., stored on a computer, or on computer-readable media. If the latter is used, new patient data for the selected marker(s), obtained from initial or follow-up samples, can be compared to the stored data for the same marker(s) without the need for additional control experiments.

III. DEFINITIONS

As used herein, "obtaining a biological sample" or "obtaining a blood sample" refer to receiving a biological or blood sample, e.g., either directly or indirectly. For example, in some embodiments, the biological sample, such as a blood sample or a sample containing peripheral blood mononuclear cells (PBMC), is directly obtained from a subject at or near the laboratory or location where the biological sample will be analyzed. In other embodiments, the biological sample may be drawn or taken by a third party and then transferred, e.g., to a separate entity or location for analysis. In other embodiments, the sample may be obtained and tested in the same location using a point-of care test. In these embodiments, said obtaining refers to receiving the sample, e.g., from the patient, from a laboratory, from a doctor's office, from the mail, courier, or post office, etc. In some further aspects, the method may further comprise reporting the determination to the subject, a health care payer, an attending clinician, a pharmacist, a pharmacy benefits manager, or any person that the determination may be of interest.

By "subject" or "patient" is meant any single subject for which therapy or diagnostic test is desired. This case the subjects or patients generally refer to humans. Also intended to be included as a subject are any subjects involved in clinical research trials not showing any clinical sign of disease, or subjects involved in epidemiological studies, or subjects used as controls.

As used herein, "increased expression" refers to an elevated or increased level of expression in a cancer sample relative to a suitable control (e.g., a non-cancerous tissue or cell sample, a reference standard), wherein the elevation or increase in the level of gene expression is statistically significant ($p<0.05$). Whether an increase in the expression of a gene in a cancer sample relative to a control is statistically significant can be determined using an appropriate t-test (e.g., one-sample t-test, two-sample t-test, Welch's t-test) or other statistical test known to those of skill in the art. Genes that are overexpressed in a cancer can be, for example, genes that are known, or have been previously determined, to be overexpressed in a cancer.

As used herein, "decreased expression" refers to a reduced or decreased level of expression in a cancer sample relative to a suitable control (e.g., a non-cancerous tissue or cell sample, a reference standard), wherein the reduction or decrease in the level of gene expression is statistically significant ($p<0.05$). In some embodiments, the reduced or decreased level of gene expression can be a complete absence of gene expression, or an expression level of zero. Whether a decrease in the expression of a gene in a cancer sample relative to a control is statistically significant can be determined using an appropriate t-test (e.g., one-sample t-test, two-sample t-test, Welch's t-test) or other statistical test known to those of skill in the art. Genes that are underexpressed in a cancer can be, for example, genes that are known, or have been previously determined, to be underexpressed in a cancer.

The term "antigen binding fragment" herein is used in the broadest sense and specifically covers intact monoclonal antibodies, polyclonal antibodies, multispecific antibodies (e.g., bispecific antibodies) formed from at least two intact antibodies, and antibody fragments.

The term "primer," as used herein, is meant to encompass any nucleic acid that is capable of priming the synthesis of a nascent nucleic acid in a template-dependent process. Primers may be oligonucleotides from ten to twenty and/or thirty base pairs in length, but longer sequences can be employed. Primers may be provided in double-stranded and/or single-stranded form, although the single-stranded form is preferred.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Experimental Procedures

Exosome isolation and purification. Exosomes were purified by differential centrifugation as described previously (Thery et al., 2006; Luga et al., 2012). In short, supernatant from cells cultured for 24 hr were subjected to sequential centrifugation steps of 800 g and 2000 g and supernatant was filtered using 0.2 μm filter in culture bottles. Exosomes were pelleted at 100,000 g in an SW40Ti swinging bucket rotor for 2 hr (Beckman). Supernatant was discarded and PBS was added for a 1 hr-washing step. The pellet was analyzed for exosome. Exosomes for RNA extraction were resuspended in 500 ul of Trizol; exosomes for protein extraction were resuspended in 250 ul of lysis buffer (8M Urea/2.5% SDS, 5 μg/ml leupeptin, 1 μg/ml pepstatin and 1 mM phenylmethylsulphonyl fluoride); and exosomes for treatments were resuspended in PBS. Frozen serum samples were thawed on ice and 500 μl were added to 12 mL PBS and the same aforementioned procedure was followed. Exosomes purified by centrifugation were treated (37° C., 60 minutes) with 500 g/mL proteinase K (Sigma-Aldrich) dissolved in RNase-free water, followed by heat inactivation of the protease (60° C., 10 minutes) and incubation (37° C., 15 minutes) with 2 g/mL protease-free RNaseA (Sigma-Aldrich) followed by addition of 10× concentrated RNase inhibitor (Ambion). For exosomes treatment, exosomes were purified in duplicate and one of the pellets was used for protein quantification.

Flow Cytometry Analysis of Exosomes.

Exosomes preparations (5-10 μg) were incubated with 5 μl of 4-μm-diameter aldehyde/sulfate latex beads (Interfacial Dynamics, Portland, OR) and resuspended into 400 μl PBS containing 2% BSA. Exosomes-coated beads (20 μl) were incubated with the following antibodies: anti-CD63 (Santa Cruz), anti-CD9 (abcam), anti-TSG101 (abcam), anti-flotillin-1 (Santa Cruz) for 30 minutes at 4° C. followed, when needed, by incubation with FITC-conjugated secondary antibody and analyzed on a FACS Calibur flow cytometer (BD Biosciences).

Exosome Electroporation.

Exosomes at a total protein concentration of 100 μg (measured by Bradford Assay) and 5 μg of Dicer antibody (polyclonal SC-30226, Santa Cruz, CA), 5 ug of Actin antibody, or 10 μg of pre-miRNA-21, -10b and -cell were mixed in 400 μl of electroporation buffer (1.15 mM potassium phosphate pH 7.2, 25 mM potassium chloride, 21% Optiprep) and electroporated in a 4 mm cuvette using a Gene Pulser Xcell Electorporation System (Biorad) as described previously (Alvarez-Erviti et al., 2011). After electroporation, exosome were treated with proteinase K and/or RNAse when appropriate.

Light Scattering Spectroscopy (LSS).

Figure 10A:
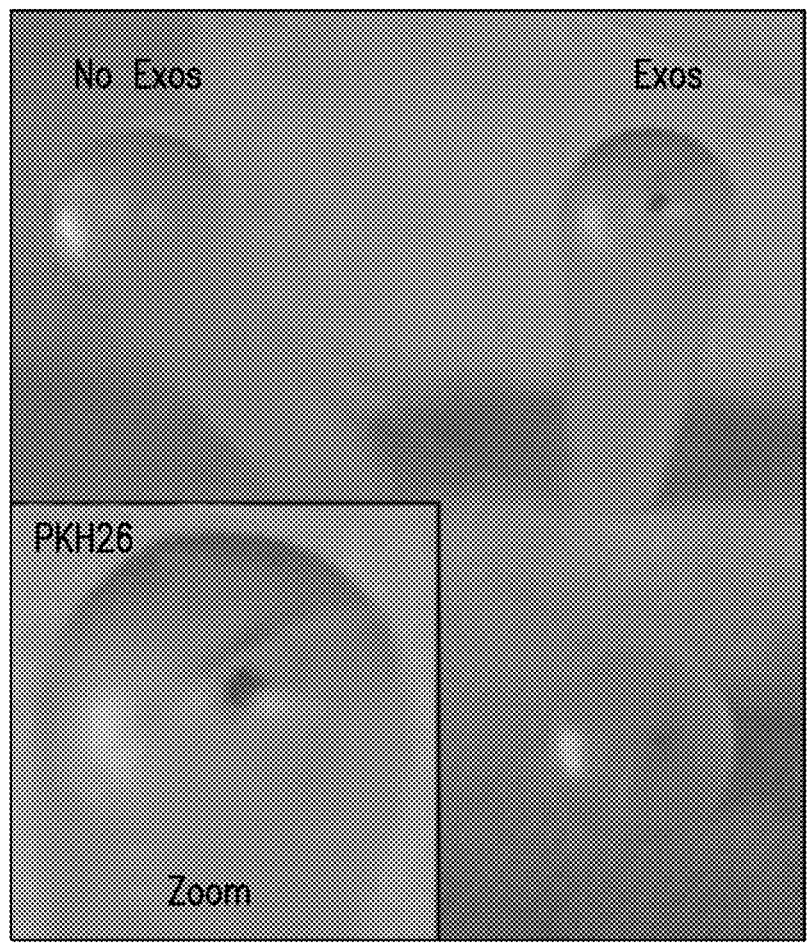
FIGS. 10A-E. Exosomes characterization. (A) Photograph of PKH26 stained exosomes, at the bottom of the ultracentrifugation tube. Inset represents digital zoom image of the exosomes. (B) Schematic representation of experimental system used to collect LSS spectra. (C) Cell viability measured by MTT assay during 5 days of culture of MCF10A, NMuMG, MDA-MB231 and 4T1 cells. (D) Flow cytometry analysis for propidium iodide (PI) and Anexin V of MDA-MB231 and 4T1 cells. MDA-MB231 cells treated with etoposide were used as a positive control for apoptosis.
Figure 10B:
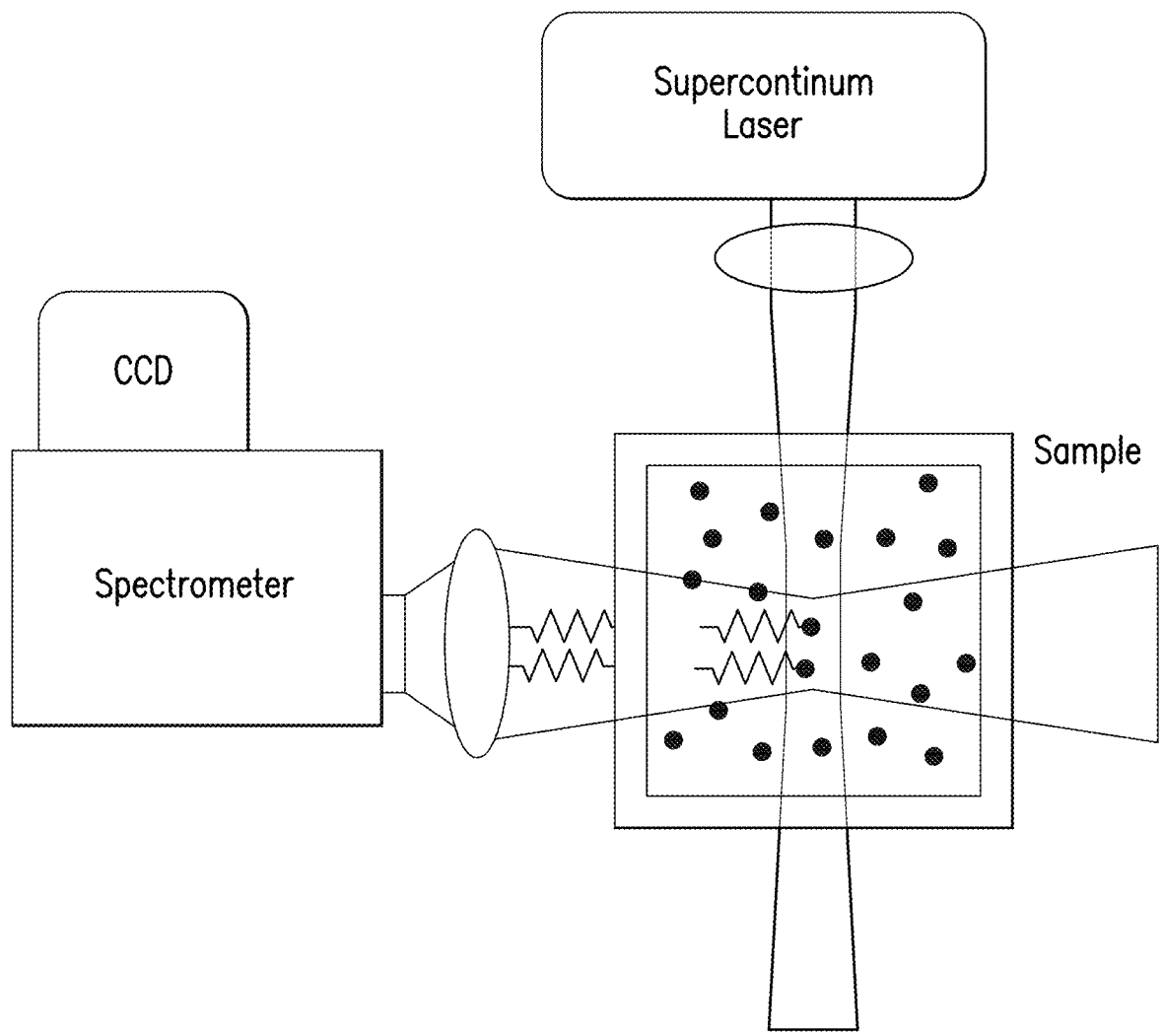

LSS spectra were collected using the experimental system described in FIG. 10B. The Fianium SC-450-2 broadband supercontinuum laser was used as a source of white light. The light from the supercontinuum laser was focused into the sample with a long focus length lens. The samples consisting of liquid suspensions of either exosomes or microspheres were placed in a custom cubic-shaped quartz sample holder. The background signals were collected from the solvent samples with no exosomes or microspheres. The light scattered by exosomes or microspheres at 90° to the incident beam was collected with the other long focus length lens and delivered to the Princiton Instrument Acton 2300i imaging spectrograph coupled with a high efficiency Andor Technology iXon DV885 EMCCD detector. The detection was performed in the 470-870-nm wavelength range. The detector was controlled by a computer, into which the data were transferred, stored, and processed.

Figure 1B:
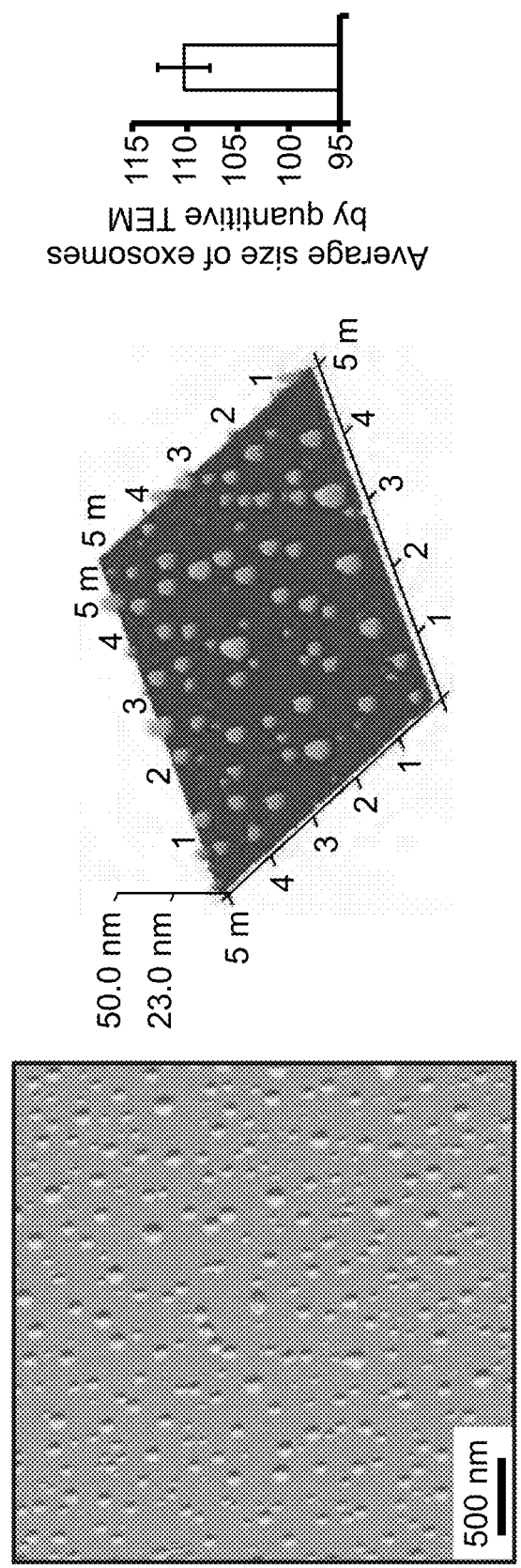
Figure 1C:
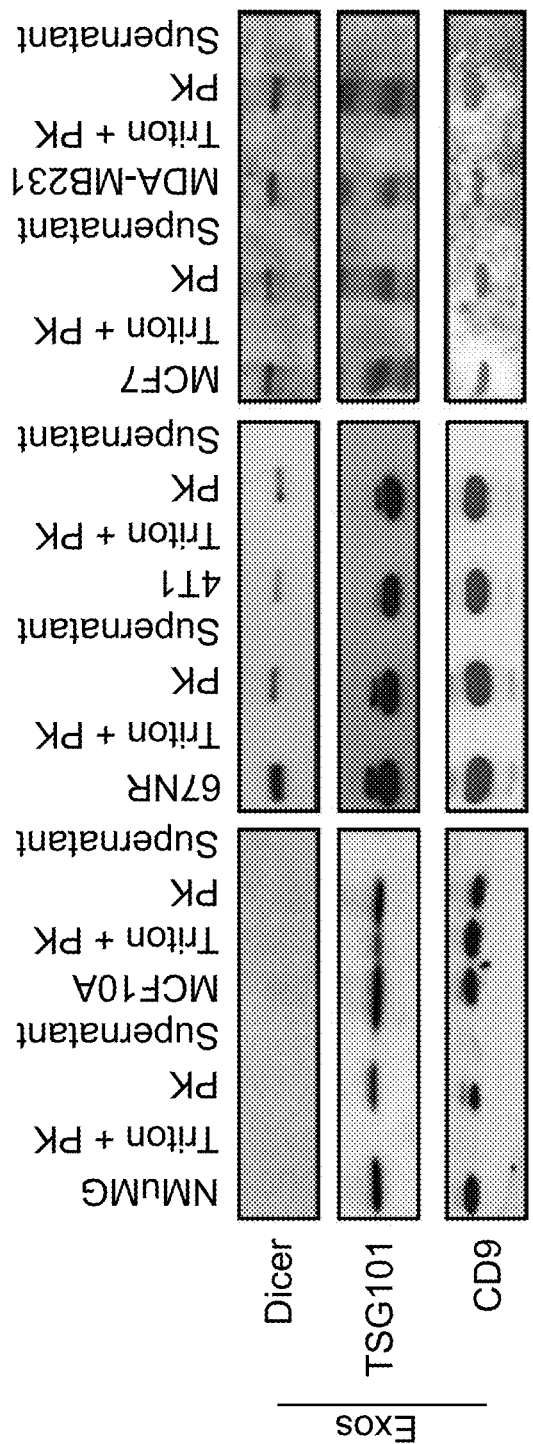
Figure 1D:
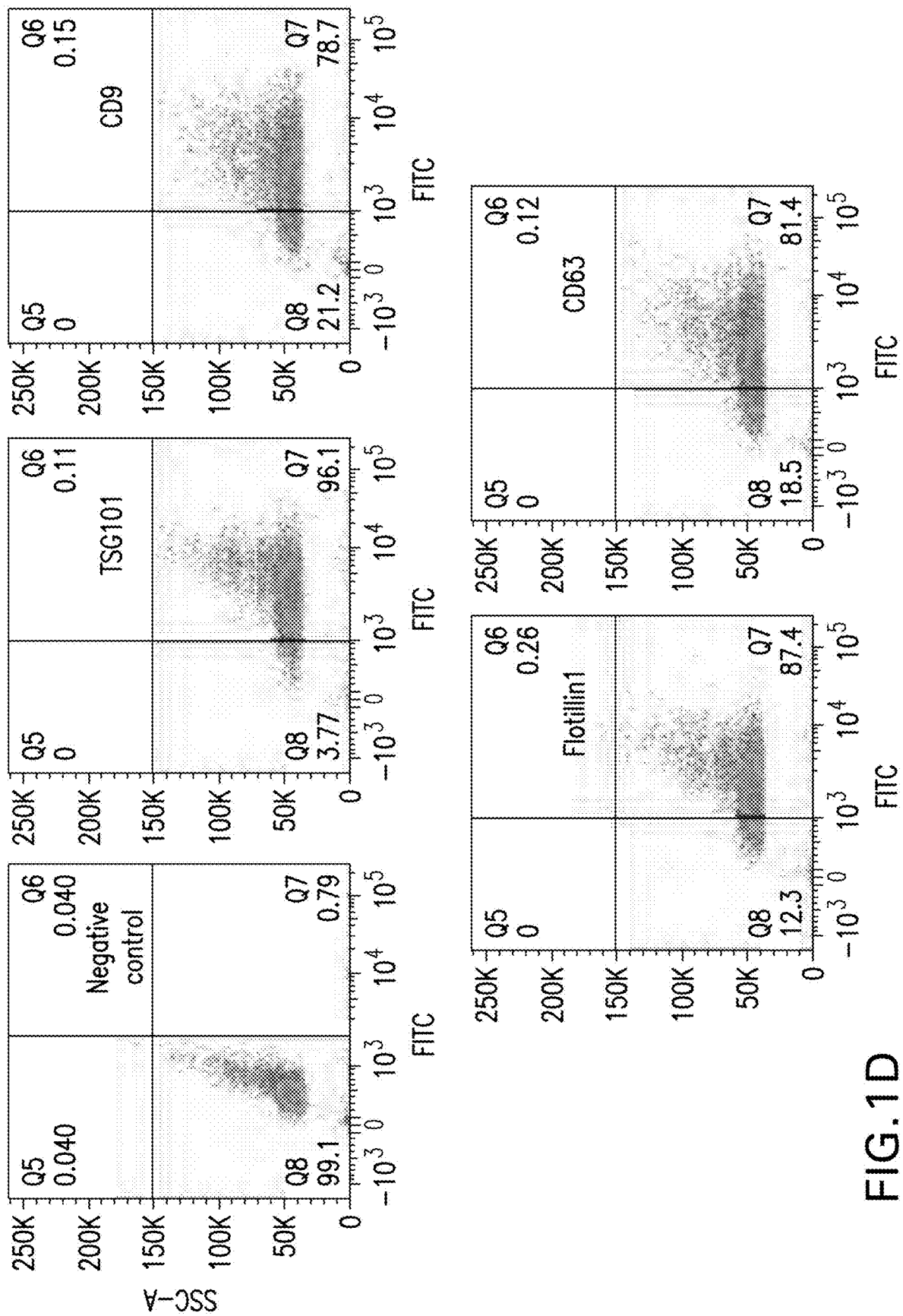
Figure 1E:
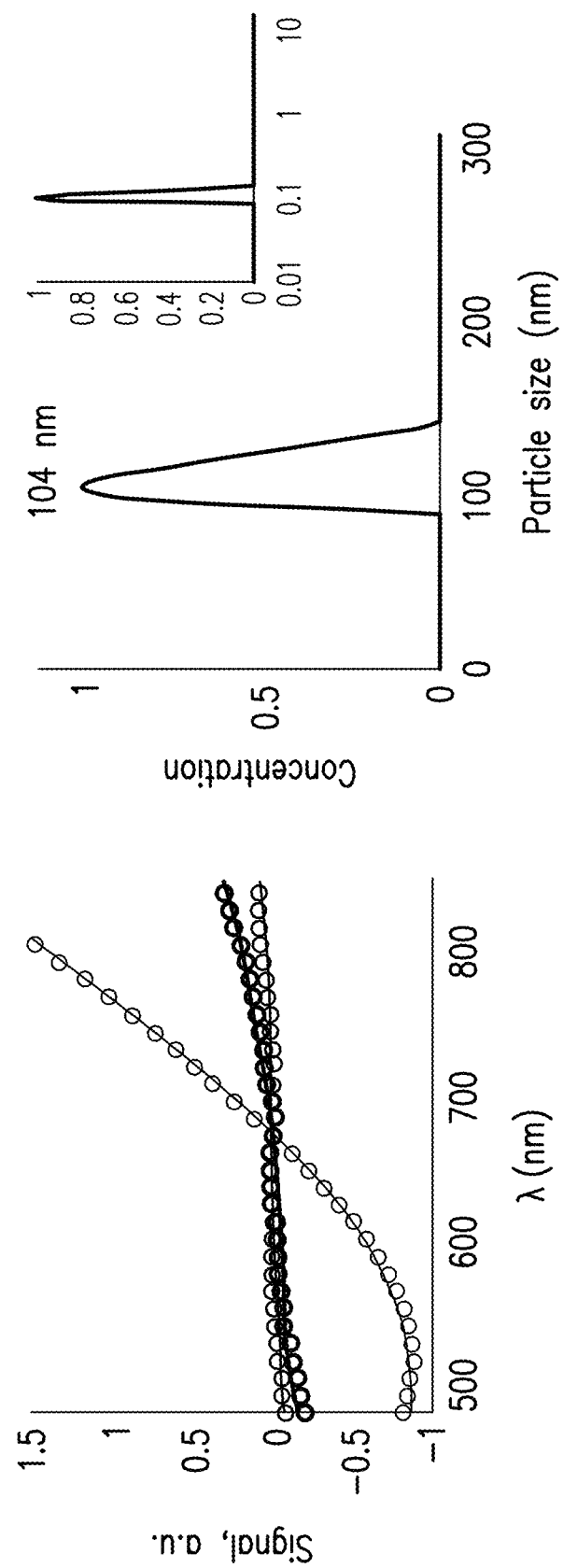

To calibrate the system and establish its ability to accurately detect sizes of the particles, which can be smaller than the wavelength, the signals from from phosphate buffered saline (PBS) suspensions of glass microspheres with nominal diameters of 24 nm and 100 nm and polystyrene microspheres with nominal diameters of 119 nm, 175 nm, 356 nm and 457 nm were measured. The spectra predicted by Mie theory were fitted to the data using the previously developed least-squares minimization method (Fang et al., 2003). The experimental spectra and resulting fits are shown in FIG. 1E for glass microspheres with nominal diameter of 100 nm and polystyrene microspheres with nominal diameter of 356 nm. Here the deviation from the Rayleigh scattering multiplied by the forth power of the wavelength is shown to emphasize the non-Rayleigh behavior of the LSS spectra. By comparing LSS yielded size distributions for microspheres with the manufacturer provided specifications, it was concluded that the accuracy of the LSS method is estimated to be 10 nm. It was also established that the reconstructed size distributions are insensitive to the refractive indices of the microspheres and the solvent. It should be pointed out here that since light scattering of small particles is proportional to the six power of their size, detection of particles smaller than 50 nm in the presence of larger particles would require substantial increase in the signal-to-noise ratio of the experimental system.

LSS experiments with the PBS suspension of exosomes were then performed. The experimental LSS spectrum of the exosomes and the corresponding Mie fit are presented in FIG. 1B. The fit of the reconstructed spectrum is excellent. Using the mentioned above reconstruction technique (Fang et al. 2003; Itzkan et al. 2007; Fang et al. 2007) the size distribution of exosomes (see FIG. 1R right graph and insert), which peaked at 104 nm was found. This extracted size distribution was compared with the morphometric measurements performed on the TEM photographs of the similar exosome samples (FIG. 1A). Since number of particles on the TEM photographs was not large enough to plot statistically meaningful distribution, the mean size of the particles larger than 50 nm was calculated from the TEM photograph and found to be equal 95 nm. Thus, the LSS reconstructed size distribution and morphometric measurements performed on the TEM photographs of exosomes agree with all the data.

N—Rh-PE Treatments.

Cells were labeled with N—Rh-PE by incubating with 8 μM N—Rh-PE (Avanti Polar Lipids, Alabaster, AL) diluted in ice-cold 1× Hanks buffer (Invitrogen, Carlsbad, CA) for 1 hr on ice. Cells were then washed 3 times with ice-cold Hanks buffer before plating them back in DMEM medium. N—Rh-PE cells were used for confocal imaging approximately 24 hr after labeling.

Immunogold Labeling and Electron Microscopy.

Fixed specimens at an optimal concentration were dropped onto a 300 mesh carbon/formvar coated grids and allowed to absorb to the formvar for a minimum of 1 minute. For immunogold staining the grids were placed into a blocking buffer for a block/permeablization step for 1 hr. Without rinsing, the grids were immediately placed into the primary antibody at the appropriate dilution overnight at 4° C. (polyclonal anti-Dicer 1:10 SC-30226, Santa Cruz; monoclonal anti-CD9 1:10, Abcam). As controls, some grids were not exposed to the primary antibody. The next day all of the grids were rinsed with PBS and then floated on drops of the appropriate secondary antibody attached with 10 nm gold particles (AURION, Hatfield, PA) for 2 hours at room temperature. Grids were rinsed with PBS and were placed in 2.5% Glutaraldehyde in 0.1M Phosphate buffer for 15 minutes. After rinsing in PBS and distilled water the grids were allowed to dry and stained for contrast with uranyl acetate. The samples were viewed with a Tecnai Bio Twin transmission electron microscope (FEI, Hillsboro, OR) and images taken with an AMT CCD Camera (Advanced Microscopy Techniques, Danvers, MA).

Protein Blot and Antibodies.

To monitor endogenous gene responses, cells were harvested in RIPA buffer and exosomes in 8M Urea/2.5% SDS, 5 µg/ml leupeptin, 1 µg/ml pepstatin and 1 mM phenylmethylsulphonyl fluoride buffer. Proteins were loaded according to Bradford quantification onto acrylamide gels and transferred onto PVDF membranes (ImmobilonP) by wet electrophoretic transfer. For protein samples of serum exosomes collected from the orthotopic xenograft models, a 4% acrylamide gel with 15 cm height was used to resolve human and mouse Dicer bands. In general, blots were blocked for 1hr at RT with 5% non-fat dry milk in PBS/0.05% Tween and incubated overnight at 4° C. with the following primary antibodies: 1:500 anti-Dicer (SC-30226) Santa Cruz; 1:1000 anti-Ubiquitinylated proteins, clone FK2 Millipore; 1:500 anti-Flag M2-Peroxidase Clone M2 Sigma; 1:500 anti-CD43 ab9088 Abcam; 1:500 anti-PTEN, ab32199, Abcam; 1:300 anti-CD9 ab92726, Abcam; 1:500 anti-GADPH ab9483, Abcam; 1:250 anti-TRBP ab72110, Abcam; 1:300 anti-TSG101 ab83, Abcam; 1:400 anti-AGO2 ab32381, Abcam; 1:4000 anti-β-actin Peroxidase Clone AC-15, Sigma; 1:500 anti-GFP ab6556, Abcam; 1:500 anti-HOXD10 ab76897 Abcam. Secondary antibodies were incubated 1hr at RT. Washes after antibody incubations were done on an orbital shaker, four times at 10 min intervals, with 1×PBS 0.05% Tween20. Blots were developed with chemiluminescent reagents from Pierce.

Real-Time PCR Analysis.

DNase treated RNA was retro-transcribed with Multi-Scribe Reverse Transcriptase (Applied Biosystems) and oligo-d(T) primers following total RNA purification with Trizol (Invitrogen). Real-time PCR for mRNAs was performed on an ABI PRISM 7300HT Sequence Detection System Instrument using SYBR Green Master Mix (Applied Biosystems) and β-actin as the control. The primers are listed in Table 1.

Pre-miRNAs were quantified using 150 ng of DNase treated RNA and the SuperScript III Platinum One-Step RT-qPCR kit (Invitrogen) (Schmittgen et al., 2004). The primers are listed in Table 1.

For miRNA expression analysis, 10 ng of RNA was mixed with TaqMan MicroRNA Reverse Transcription Kit reagent containing specific miRNA primers and reverse-transcribed according to the manufacturer's instructions (Applied Biosystems). Reaction mixes were incubated at 16° C. for 30 minutes, 42° C. for 30 minutes and 85° C. for 5 minutes. Real-time PCR was performed using ABI PRISM 7300HT Sequence Detection System Instrument (Applied Biosystems) using commercially available Assay-on-Demand for each miRNA studied (Applied Biosystems). Expression of miRNAs was normalized to the expression of 18S rRNA (TaqMan Pre-Developed Assay Reagent; Applied Biosystems) that served as internal control for the RNA amount and integrity. Each measurement was performed in triplicate. Threshold cycle (Ct), the fractional cycle number at which the amount of amplified target reached a fixed threshold, was determined and expression was measured using the $2^{-\Delta Ct}$ formula, as previously reported (Livak and Schmittgen, 2001).

TABLE 1 qPCR Primer Sequences.

| Primer Name | Primer Sequence | SEQ ID NO: |
|---|---|---|
| BiG2 F | 5' CAGGAGGTGGTGAAGGACAT3' | 1 |
| BiG2 R | 5' CCCGTTGGTCTGTGAGTTT3' | 2 |
| TSG101 F | 5' GATACCCTCCCAATCCCAGT3' | 3 |
| TSG101 R | 5' GTCACTGACCGCAGAGATGA3' | 4 |
| Hrs F | 5'AGTGGCTGTCGGGTATTCATC3' | 5 |
| Hrs R | 5'CCGTCCATATCCCTTGAAGAATC3' | 6 |
| CD43 F | 5'GCTGGTGGTAAGCCCAGAC3' | 7 |
| CD43 R | 5'GGCTCGCTAGTAGAGACCAAA3' | 8 |
| hsa-Actin F | 5'CATGTACGTTGCTATCCAGGC3' | 9 |
| hsa-Actin R | 5'CTCCTTAATGTCACGCACGAT3' | 10 |
| mmu-Actin F | 5'GGCTGTATTCCCCTCCATCG3' | 11 |
| mmu-Actin R | 5'CCAGTTGGTAACAATGCCATGT3' | 12 |
| Pre-miR-let7-a F | 5'AGGTAGTAGGTTGTATAGTTTTAG G3' | 13 |
| Pre-miR-let7-a R | 5'TAGGAAAGACAGTAGATTGTATAG T3' | 14 |
| Pre-miR-15b F | 5'AGCACATCATGGTTTACATGC3' | 15 |
| Pre-miR-15b R | 5'CTAGAGCAGCAAATAATGATTGG3' | 16 |
| Pre-miR-26a F | 5'TTCAAGTAATCCAGGATAGGCTGT3' | 17 |
| Pre-miR-26a R | 5'TGCAAGTAACCAAGAATAGGCC3' | 18 |
| Pre-miR-31 F | 5'TGAGTGTGTTTTCCCTCCCT3' | 19 |
| Pre-miR-31 R | 5'GCCATGGCTGCTGTCAG3' | 20 |
| Pre-miR-125a F | 5'GTCCCTGAGACCCTTTAACC3' | 21 |
| Pre-miR-125a R | 5'AACCTCACCTGTGACCCTG3' | 22 |
| Pre-miR-125b F | 5'GTCCCTGAGACCCTAACTTG3' | 23 |
| Pre-miR125b R | 5'AGCCTAACCCGTGGATTT3' | 24 |
| Pre-miR-200a F | 5'TTCCACAGCAGCCCCTG3' | 25 |
| Pre-miR-200a R | 5'GATGTGCCTCGGTGGTGT3' | 26 |
| Pre-miR-200c F | 5'CTCGTCTTACCCAGCAGTGT3' | 27 |
| Pre-miR-200c R | 5'GTCATCATTACCAGGCAGTATTAG3' | 28 |
| Pre-miR-335 F | 5'GTCAAGAGCAATAACGAAAAATG3' | 29 |
| Pre-miR-335 R | 5'GAGGTCAGGAGCAATAATGAA3' | 30 |
| Pre-miR-10a,b F | 5'TACCCTGTAGATCCGAATTTGTG3' | 31 |
| Pre-miR-10a,b R | 5'ATTCCCCTAGATACGAATTTGTGA3' | 32 |
| Pre-miR-21 F | 5'GCTTATCAGACTGATGTTGACTG3' | 33 |
| Pre-miR-21 R | 5'CAGCCCATCGACTGGTG3' | 34 |
| Pre-miR-27a F | 5'GCAGGGCTTAGCTGCTTG3' | 35 |
| Pre-miR-27a R | 5'GGCGGAACTTAGCCACTGT3' | 36 |

TABLE 1-continued qPCR Primer Sequences.

| Primer Name | Primer Sequence | SEQ ID NO: |
|---|---|---|
| Pre-miR-155 F | 5'GTTAATGCTAATCGTGATAGGG3' | 37 |
| Pre-miR-155 R | 5'GCTAATATGTAGGAGTCAGTTGGA3' | 38 |
| Pre-miR-373 F | 5'CTCAAAATGGGGCGCTTT3' | 39 |
| Pre-miR-373 R | 5'CACCCCAAAATCGAAGCACT3' | 40 |
| Pre-cel-1 F | 5'CCACCCCGTTCTACATACTTC3' | 41 |
| Pre-cel-1 R | 5'ACCGTACCGAGCTGCATACT3' | 42 |

Northern Blot.

Northern blot was performed using 3' Bio[TEG] DNA oligonucleotides of the reverse compliment to the mature miRNA as probes (see Table 2). Urea/acrylamide 15% gels were used to load 40 μg of exosomal RNA (DNase treated) together with 1×RNA loading dye after 2 minutes at 95° C. followed by a 2 minutes period on ice. MicroRNA marker was used according to manufacturer's instructions (N2102, New England BioLabs). Electrophoresis was done at 4° C. during 3 hr using TBE 1×. Transfer was done using Whatman blotting papers and the BrightStar-Plus Positively Charged Nylon Membrane (Ambion) during 2 hr at 4° C. with TBE 0.5×. The RNA was cross-linked to the membrane using a UV transilluminator for 20 minutes. Membranes were pre-hybridized by rotating for 1 hr at 42° C. in Ambion's ULTRAhyb®-Oligo hybridization solution (Ambion). The probes were thawed on ice and 150 ng were added per mL of hybridization buffer after 5 minutes incubation at 95° C., after which membranes were left in rotation overnight at 42° C. The following washes were done: 2×SSPE/0.5% SDS—twice for 15 minutes; 0.2 SSPE/0.5% SDS—twice for 30 minutes and 2×SSPE—5 minutes. These initial washing steps were followed by more washes and then the blots were developed using the BrightStar BioDetect Kit according to the manufacturer's instructions (Ambion). The blots were exposed overnight with two stacked films. Blots were successfully stripped and re-probed twice more.

TABLE 2

Northern Probe Sequences.

| Probe Name | Probe Sequence | SEQ ID NO: |
|---|---|---|
| miR-10b | 5'CACAAATTCGGTTCTACAGGG3' | 43 |
| miR-21 | 5'TCAACATCAGTCTGATAAGCTA3' | 44 |
| miR-cel-1 | 5'AGTATGCAGCTCGGTACGGT3' | 45 |
| pre-miR-10b | 5'TGAAGTTTTTGCATCGACCATATATTCCCCTAGAATCGAA3' | 46 |
| pre-miR-21 | 5'TGTCAGACAGCCCATCGACTGGTGTTGCCATGAGAT3' | 47 |
| tRNAMet | 5'CAGCACGCTTCCGCTGCGCCACTCT3' | 48 |

Cell Culture, Plasmids, Pre-miRNAs and siRNAs.

MCF10A, MCF7, MDA-MB231, A549, SW480 and HeLa human cell lines as well as NMuMG, 67NR and 4T1 mouse mammary cell lines were cultured in DMEM 10% FBS (all cells are originated from the American Type Culture Collection—ATCC). Transfections were performed using Lipofectamine 2000 reagent (Invitrogen) for siRNA. For synthetic pre-miRNA transfections RNAiFect (Qiagen) was used in all cell lines. Sequences of siRNAs are listed in Table 3.

TABLE 3 siRNA Sequences.

| siRNA Name | siRNA Sequence | SEQ ID NO: |
|---|---|---|
| Hrs | 5'GGAACGAGCCCAAGUACAATT3' | 49 |
| Hrs | 5'UUGUACUUGGGCUCGUUCCGG3' | 50 |
| TSG101 | 5'GUUUAUCAUUCAAGUGUAATT3' | 51 |
| TSG101 | 5'UUACACUUGAAUGAUAAACTG3' | 52 |
| CD43 | 5'GGAGAGCCUUUGGUCUCUAUT3' | 53 |
| CD43 | 5'UAGAGACCAAAGGCUCUCCGG3' | 54 |
| AGO2 | 5'GGCGUUACACGAUGCACUUTT3' | 55 |
| AGO2 | 5'AAGUGCAUCGUGUAACGCCTG3' | 56 |

Plasmids.

p-CMV-Tag4B-Dicer (Melo et al., 2009); p-CMV6-CD63-GFP from Origene (RG217238); GFP-hAGO2 from Addgene (plasmid 11590); pGFP-shBiG2 from Origene (TG314697); pGFP-shDicer from Origene (TG304991); synthetic pre-miR-10b, -21 and -cel-1 were purchased from Ambion; 3'UTR-WTPTEN, 3'UTR-Mutant-PTEN (Dr. Joshua Mendell laboratory), 3' UTR-WTHOXD10 and 3'UTR-Mutant-HOXD10 (Dr. Robert Weinberg laboratory) are from Addgene.

Immunocytochemistry and Confocal Microscopy.

Cells were plated at appropriate confluency in 12 well plates on inserted coverslips and cultured overnight. The next day cells were washed with cold PBS 1× and fixed for 20 min at RT with 4% PFA/PBS. Slides were permeabilized for 10 min at RT with PBS 0.5% Triton X-100, blocked 1 hr at RT with BSA 5%, and incubated overnight at 4° C. with primary antibodies in PBST (PBS, 0.1% Triton) 2% BSA: 1:100 anti-Dicer (SC-30226) Santa Cruz; 1:500 anti-Flag Sigma; 1:50 anti-CD43 ab9088 (Abcam); 1:100 anti-TSG101 ab83 (Abcam); 1:500 anti-GFP ab6556 (Abcam); 1:100 anti-LAPM-1 ab25630 (Abcam); 1:100 anti-Hrs ab56468 (Abcam); 1:100 anti-BiG2 ab75001 (Abcam); 1:500 anti-biotin ab66233 (Abcam). Secondary antibodies goat anti-rabbit Alexa 543 or goat anti-mouse Alexa-488 were incubated 1 hr at RT diluted 1:200 in PBST 2% BSA. DAPI was used to stain the nuclei. For exosomes analysis, harvested exosomes were incubated with Triton X-0.05% for 15 min and subsequently with 5% BSA for 1 hr at RT. The first primary antibody (anti-CD9, 1:50) was incubated overnight in 100 ul PBST at 4° C. and the second primary antibody, anti-flag (1:50), was added the next day and incubated for 1 hr at RT. Secondary antibodies were added consecutively and incubated also 1 hr at RT. Exosomes were plated on top of coverslips in 12 well plates in 4% PFA for 45 min and washed with cold PBS. Images were obtained with a Zeiss LSM510 Upright Confocal System using the recycle tool to maintain identical settings. Aggregated exosomes lead to structures larger than 200 nm visible in confocal microscopy. For data analysis, images were selected from a pool drawn from at least two independent experiments. Figures show representative fields.

In Vitro Dicing Assays.

Exosomal protein extracts (10 µg) were incubated at 37° C. with 3 pmol of pre-miR-10b, -21 and -cel-1 biotin-internally labeled hairpins in the presence of 3 mM $MgCl_2$, 30 mM NaCl and 100 mM Hepes, pH 7.5. The final volume of each reaction was 10 µl. Reactions were stopped by the addition of 10 µl of formamide gel loading buffer. RNA was resolved using denaturating polyacrylamide gel electrophoresis and developed with the BrightStar BioDetect Kit according to the manufacturer's instructions (Ambion).

Cell Viability and Colony Formation Assays.

Cells were plated in 96 well plates and harvested exosomes were added at day 1 at a concentration of 100 µg/mL. Cell viability was determined by the 3-(4,5-dimethyl-2-thiazolyl)-2,5-diphenyl-2H-tetrazolium bromide (MTT) assay. For colony formation experiments, cells were plated in 12 well plates and exosomes were added at day 1 and day 5 of culture at a concentration of 100 µg/mL. After 8 days colonies were fixed and stained with MTT reagent.

Illumina Human-HT12 mRNA Expression Array.

RNA was hybridized in an Illumina Human-HT12 mRNA expression array. Data was normalized using the neqc routine offered by the R package "limma" (Shi et al., 2010). Gene abundances were determined by the median of the probes per gene. Clustering is done by arithmetic mean of euclidean distances of genes (rows) and samples (columns).

miRNA Expression Array.

A custom miRNA array was used as described in9. The array contains 1833 human microRNA probes, 1084 mouse microRNA probes and other 78 noncoding RNAs probes. The probes are printed in duplicate. The GenBank accession ID associated with each probe is included. Bioinformatic analysis was performed using R (version 2.14.2) (on the world wide web at r-project.org) and Bioconductor (on the world wide web at bioconductor.org/). The raw intensity for each probe is the median feature pixel intensity with the median background subtracted. Setting an offset 1 ensures that there will be no negative values after log-transforming data. Data was quantile normalized followed by log 2 transform. Signals from probes measuring same miRNA were averaged. The analysis was performed using the functions of LIMMA library. The heatmaps were generated using the heatplot function of made4 library. When technical replicates were performed, the heatmap represented the average expression values obtained from replicate measurements.

Orthotopic Xenografts of Ovary, Endometrium and Breast Tumors.

Female athymic nu/nu mice (Harlan) between 4 to 6 weeks of age were housed in individually ventilated cages on a 12-hour light-dark cycle at 21 to 23° C. and 40% to 60% humidity. Mice were allowed free access to an irradiated diet and sterilized water. All animal protocols were reviewed and approved according to the Spanish Institutional Animal Care and Use Committees.

The primary tumor specimens were obtained at Hospital Universitari de Bellvitge (L'Hospitalet de Llobregat, Barcelona, Spain). The Institutional Review Board approved the study. Written informed consent was collected from patients. Non-necrotic tissue pieces (ca. 2-3 $mm^3$) from five representative resected human epithelial ovarian tumor (EOCs): serous, endometrioid, clear cell tumor and mucinous, were selected and placed in DMEM (BioWhittaker) supplemented with 10% FBS and penicillin/streptomycin at room temperature. Under isofluorane-induced anesthesia, animals were subjected to a lateral laparotomy, their ovaries exposed and tumor pieces anchored to the ovary surface with prolene 7.0 sutures. Additionally, pieces of human breast and endometrial tumors were implanted in the mammary fat pads and the endometrial wall, respectively.

Orthotopically engrafted tumors were allowed to grow and at the time of sacrifice 2 ml of blood were obtained from anesthesized mice by cardiac punction. Samples were centrifugated at 14,000 rpm and frozen at −80° C.

Immunoprecipitation.

Cells and exosomes where harvested, washed in PBS and centrifuged or ultracentrifuged, respectively, to collect pellets. Ice-cold RIPA buffer or 8 M Urea/SDS buffer were added to cells and exosomes, respectively. Suspensions were gently rocked at 4° C., 15 min for cells and 2 hr for exosomes. The lysates were centrifuged at 14,000 g in a pre-cooled centrifuge for 15 minutes and the pellet was discarded. Protein A or G agarose/sepharose beads were washed twice with PBS and restored with 50% slurry with PBS. A bead/slurry mix (100 µl) was added to 1 mL of cell lysate and 500 µl of exosomal lysate and incubated at 4° C. for 10 min. Beads were removed by centrifugation at 14,000×g at 4° C. for 10 minutes and pellets discarded. Dicer antibody (5 µg for cells and 10 µg for exosomes) was added to 500 µl of cell lysate or 250 µl of exosomal lysate (1 µg/µl cells, 10 µg/µl exosomes) and incubated overnight at 4° C. on an orbital shaker. 100 µl of Protein A or G agarose/sepharose bead slurry were added and left at 4° C. overnight. After centrifugation the supernatant was discarded and beads washed 3 times with ice-cold RIPA buffer for cells or Urea/SDS buffer for exosomes. The agarose/sepharose beads were boiled for 5 minutes to dissociate the immunocomplexes from the beads. The beads were collected by centrifugation and protein blot was performed with the supernatant.

Culture Conditions in the Presence of $Ca^{2+}$ Ionophore A23187.

Cells ($8 \times 10^7$ cells) were seeded at $5 \times 10^5$ cells/ml in DMEM. To treat the cells, A23187 (200 nM final concentration, Calbiochem, La Jolla, CA) was added to the cultures four hours later. Media from treated and non-treated cells was harvested and exosomes collected.

Orthotopic Injection of Cells in Nude Mice.

Orthotopic tumor growth was measured by injecting MCF10A non-tumorigenic breast epithelial cells, MCF10A non-tumorigenic breast epithelial cells exposed to MDA-MB231-derived exosomes and MDA-MB-231 breast cancer cells ($1 \times 10^5$ cells in 0.2 ml PBS) into the mammary fat pad of 3-week-old female athymic nude mice, as described previously (Welch, 1997). Tumor growth was monitored weekly by measuring the tumor length and width with a caliper and was reported as the mean tumor diameter as previously described (Welch, 1997). All animals were euthanized 21 days post tumor cell injection.

Statistics.

Error bars indicate S.D. between biological replicates. Technical as well as biological triplicates of each experiment were performed. Statistical significance was calculated by Student's t-test.

Example 2—Results

Isolation and Identification of Exosomes.

Figure 1F:
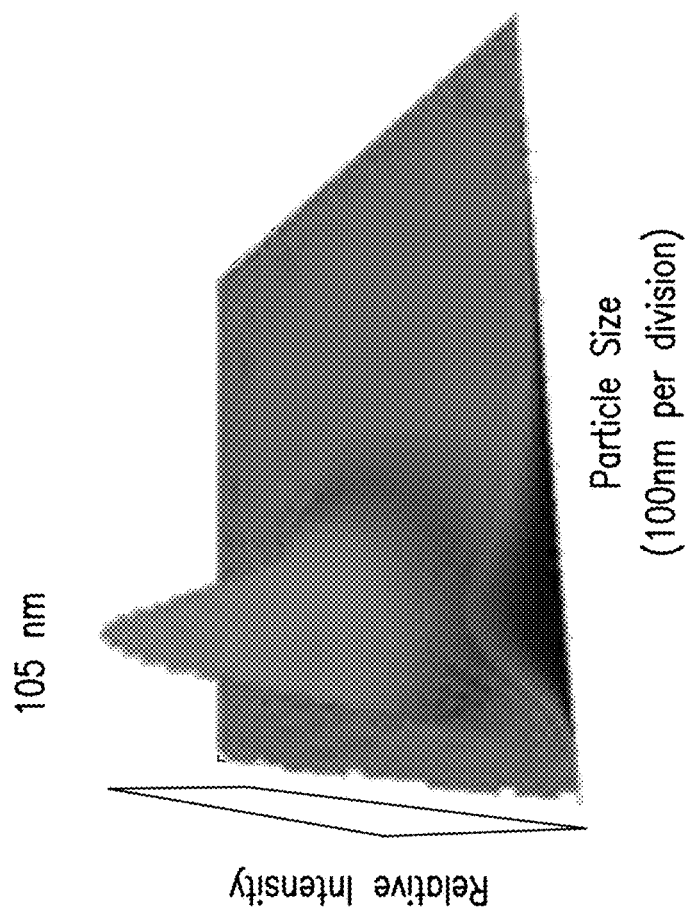
Figure 1F:
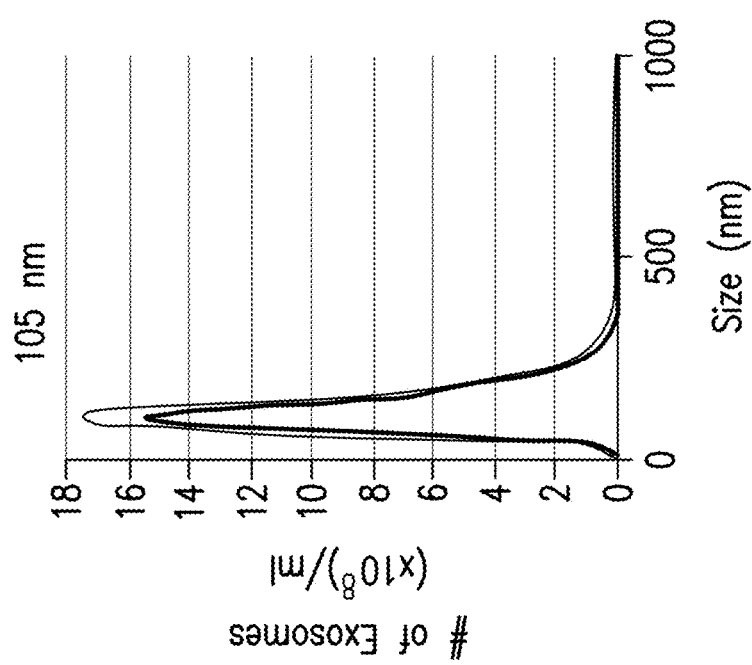
Figure 10C:
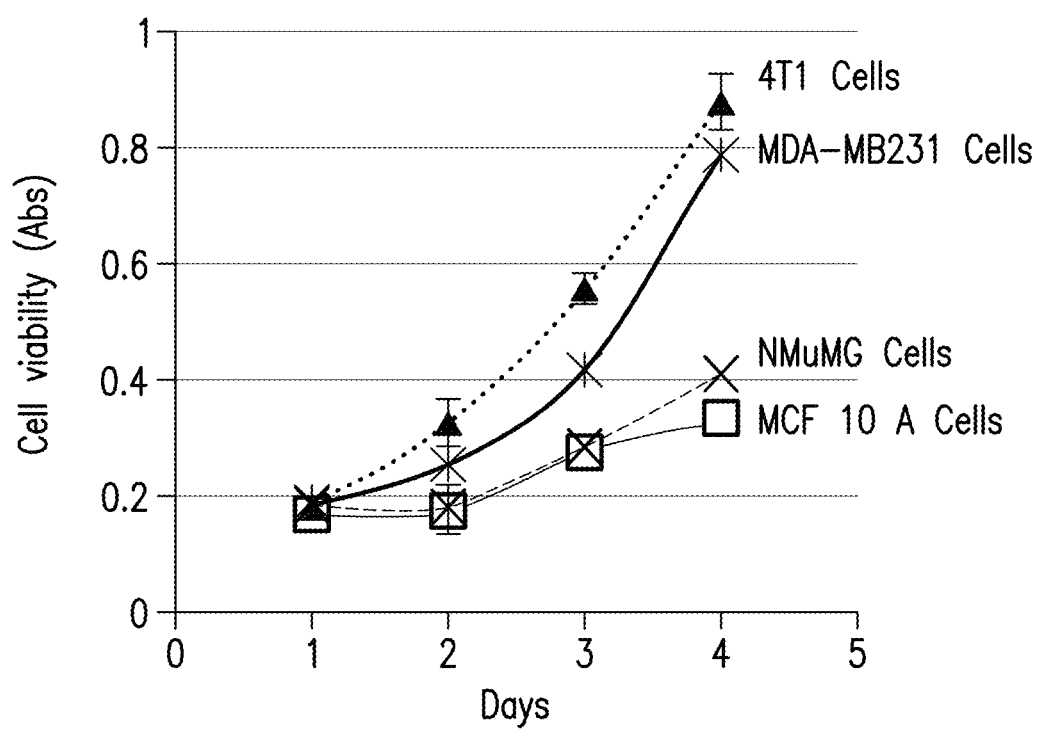
Figure 10D:
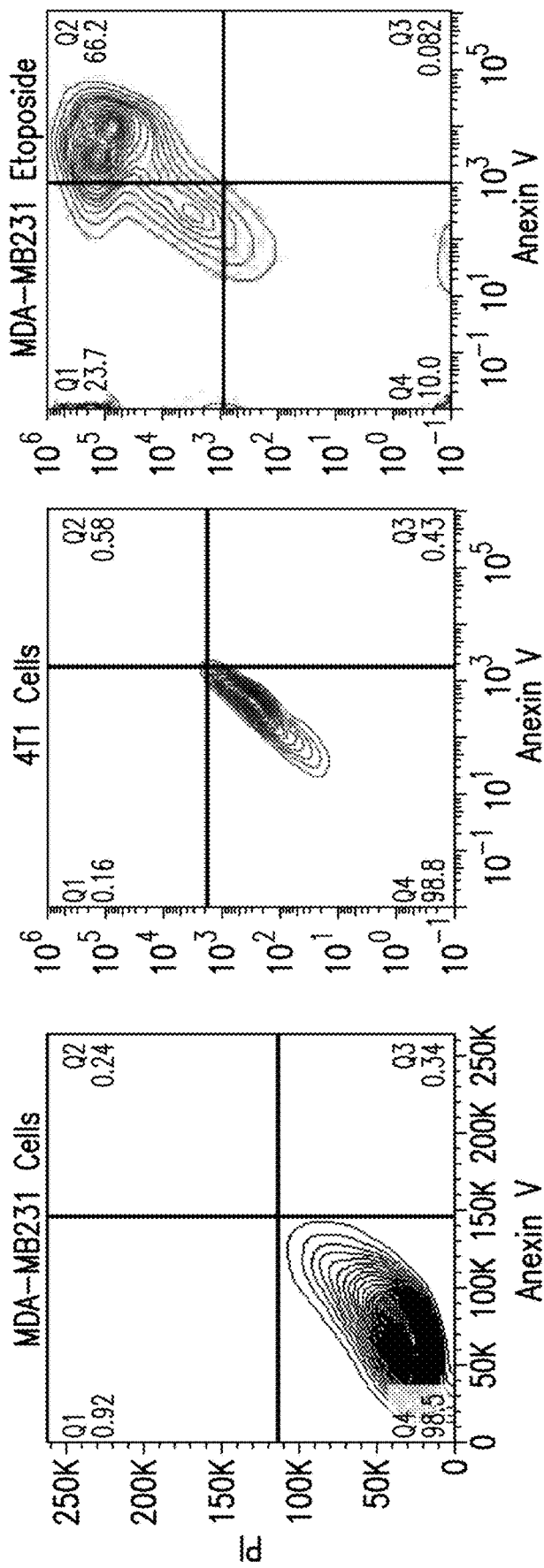
Figure 10E:
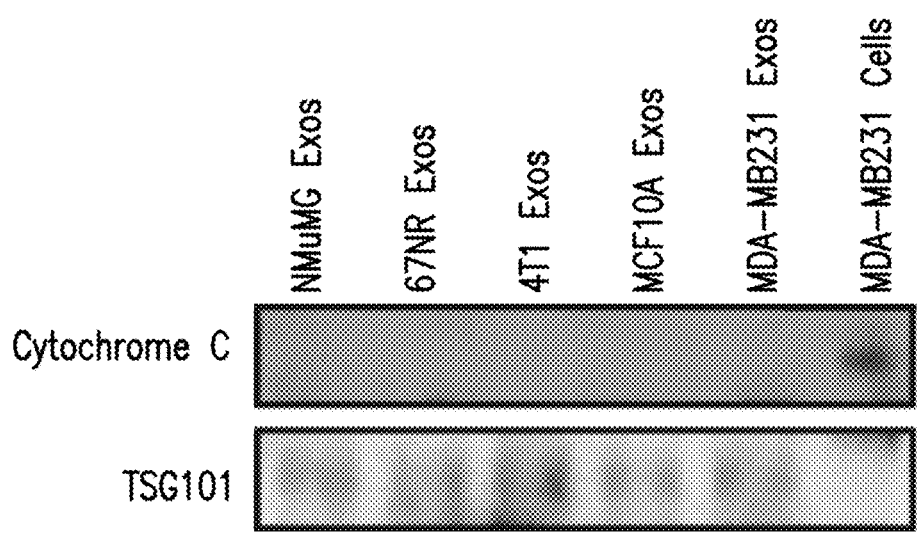

Exosomes from cancer cells (MDA-MB231 triple negative human metastatic breast carcinoma, MCF7 human breast adenocarcinoma, 67NR mouse non-metastatic breast carcinoma and 4T1 mouse metastatic breast carcinoma) and control cells (MCF10A non-tumorigenic human epithelial breast and NMuMG non-tumorigenic mouse epithelial breast) were isolated using established ultracentrifugation methods (FIG. 10A) (Luga et al., 2012; Thery et al., 2006). The harvested exosomes were analyzed by transmission electron microscopy (TEM) and atomic force microscopy (AFM). Particles between 40-140 nm in size were identified (FIGS. 1A-B) (Thery et al., 2002). Further, the identity of the exosomes was confirmed by detecting TSG101 and CD9, two exosomes markers (FIG. 1C) (Ostrowski et al., 2010). The isolated exosomes were also positive for the CD9 marker when analyzed by immunogold-labeling electron microscopy (FIG. 1A). Exosome coupled to latex beads were also analyzed by flow cytometry, showing surface expression of the tetraspanins CD9, CD63, TSG101 and flotillinl, which are commonly-used exosomes markers (FIG. 1D). Additionally, Light Scattering Spectroscopy (LSS) (Fang et al., 2007; Itzkan et al., 2007; Bang and Setabutr, 2010; Benitez-vieyra et al., 2009; Khairkar et al., 2010; Min et al., 2010) was used to show that the isolated samples reveal a tight size distribution peaking at 104 nm in diameter (FIG. 1E, right panel). The LSS system allowed for accurate detection of all sizes of particles in exosomes extracts by using glass microspheres of different diameters as internal controls. LS S also excluded potential microvesicles and bacterial or cellular debris contamination in these isolates (FIG. 1E, see inset on right graph). Furthermore, and in agreement with LSS data, the NanoSight nanoparticle tracking analysis revealed particles with a size distribution peaking at 105±1.0 nm in diameter (FIG. 1F) further excluding the existence of potential contaminants of different size ranges that exist in solution when it is not filtered (FIG. 1F, right graph). Colorimetric cell viability assay (MTT), terminal deoxynucleotidyl transferase dUTP nick end labeling (TUNEL) assay, flow cytometry analysis for Anexin V and propidium iodide, and cytochrome C immunoblots of exosomes (FIGS. 10C-E) were used to demonstrate the viability of cells before exosomes extraction in order to exclude the possibility of contamination of the isolates with apoptotic bodies or random cell debris. Exosomes isolated from cancer cells are collectively termed as oncosomes, as defined previously (Lee et al., 2011). Exosomes isolated from control cells are collectively termed as normosomes.

Oncosomes are Specifically Enriched in Oncogenic miRNAs when Compared to Normosomes.

Figure 2A:
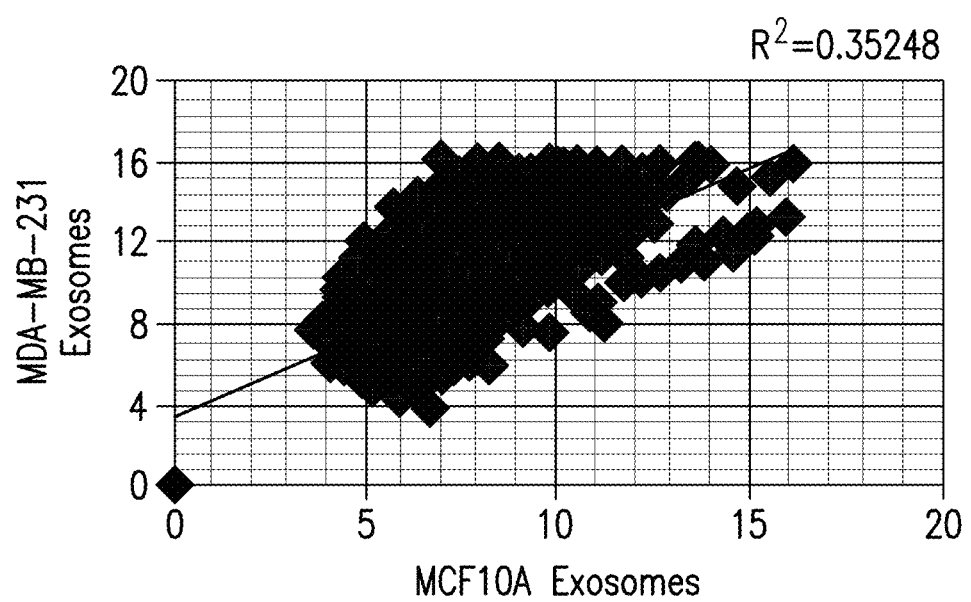
FIGS. 2A-F. Oncosomes become enriched in miRNAs. (A) Correlation graph of expressed miRNAs in MDA-MB231 exosomes and MCF10A exosomes. (B) Correlation graphs between miRNAs in cells and respective exosomes using 6 of the differentially expressed miRNAs between normosomes and oncosomes (miR-10a, miR-10b, miR-21, miR-27a, miR-155, and miR-373) after 72 h of cell-free culture. (C) Normosomes and oncosomes were resuspended in DMEM media and maintained in cell-free culture for 24 and 72 h. After 24 and 72 h, exosomes were recovered and 15 miRNAs (see Table 4) were quantified by qPCR. The fold-change of each miRNA in exosomes after 72 h cell-free culture was quantified relative to the same miRNA in exosomes after 24 h cell-free culture. The graphical plots represent an average of fold-change for the tumor suppressor (TS) and oncogenic (ONC) miRNAs in exosomes harvested after 72 h compared to those harvested after 24 h. (D) Northern blots of miR-10b and miR-21 from normosomes after 24 and 72 h of cell-free culture and oncosomes without culture and with 24 h, 72 h and 96 h of cell-free culture. The tRNAMet was used as a loading control. Quantification was done using Image J software. (E) Correlation plots between the 15 quantified miRNAs in MCF10A, MDA-MB231 and 4T1 cells and their respective exosomes after 72 h of cell-free culture. Oncosomes present low correlation values with their cell of origin (middle and right graphs) when compared to normosomes (left graph). (F) Bioanalyzer graph representation depicted in fluorescence units (FU) per seconds (s) and gel images of exosomes RNA content of normosomes and oncosomes.
Figure 2B:
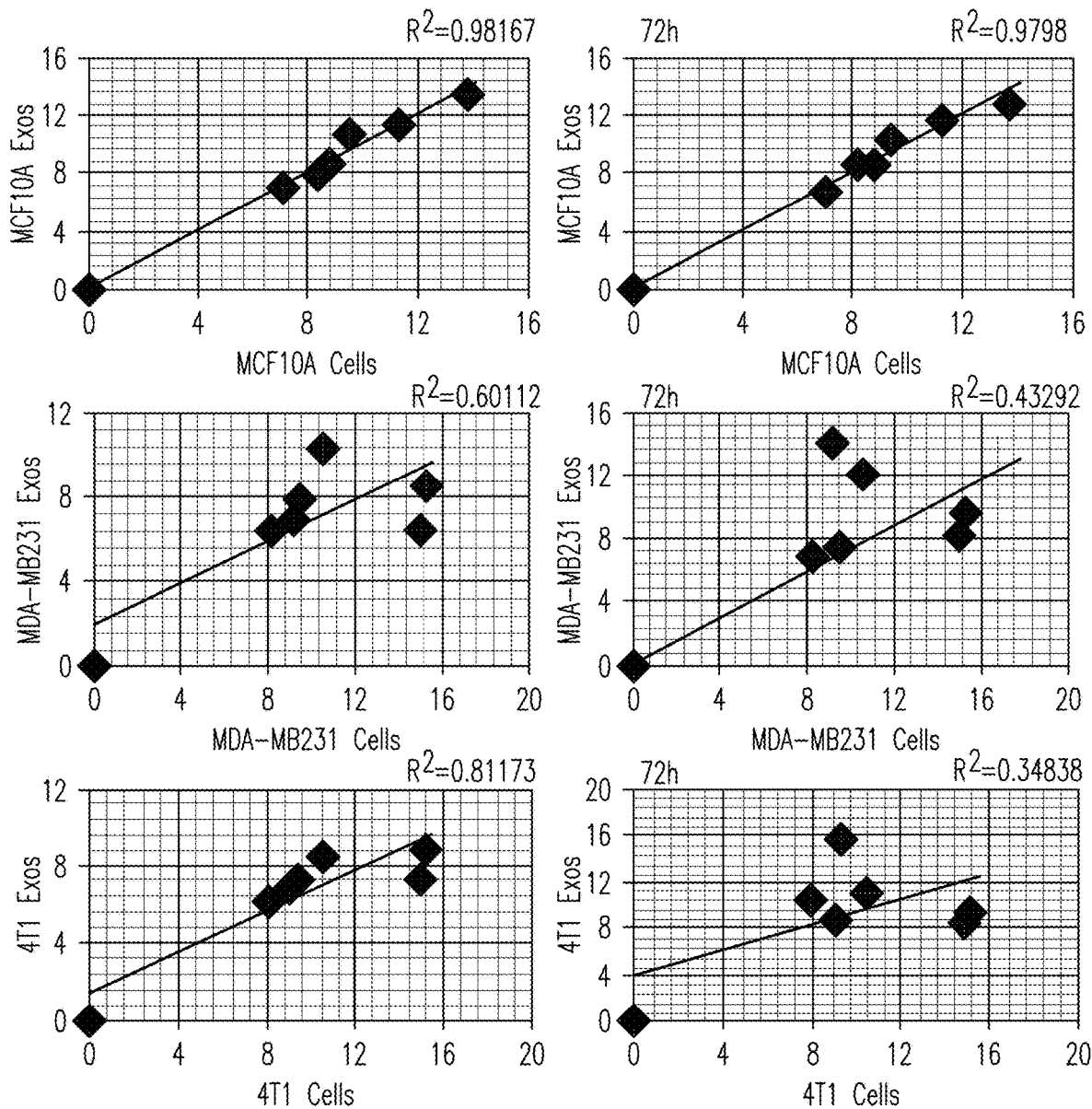
Figure 2C:
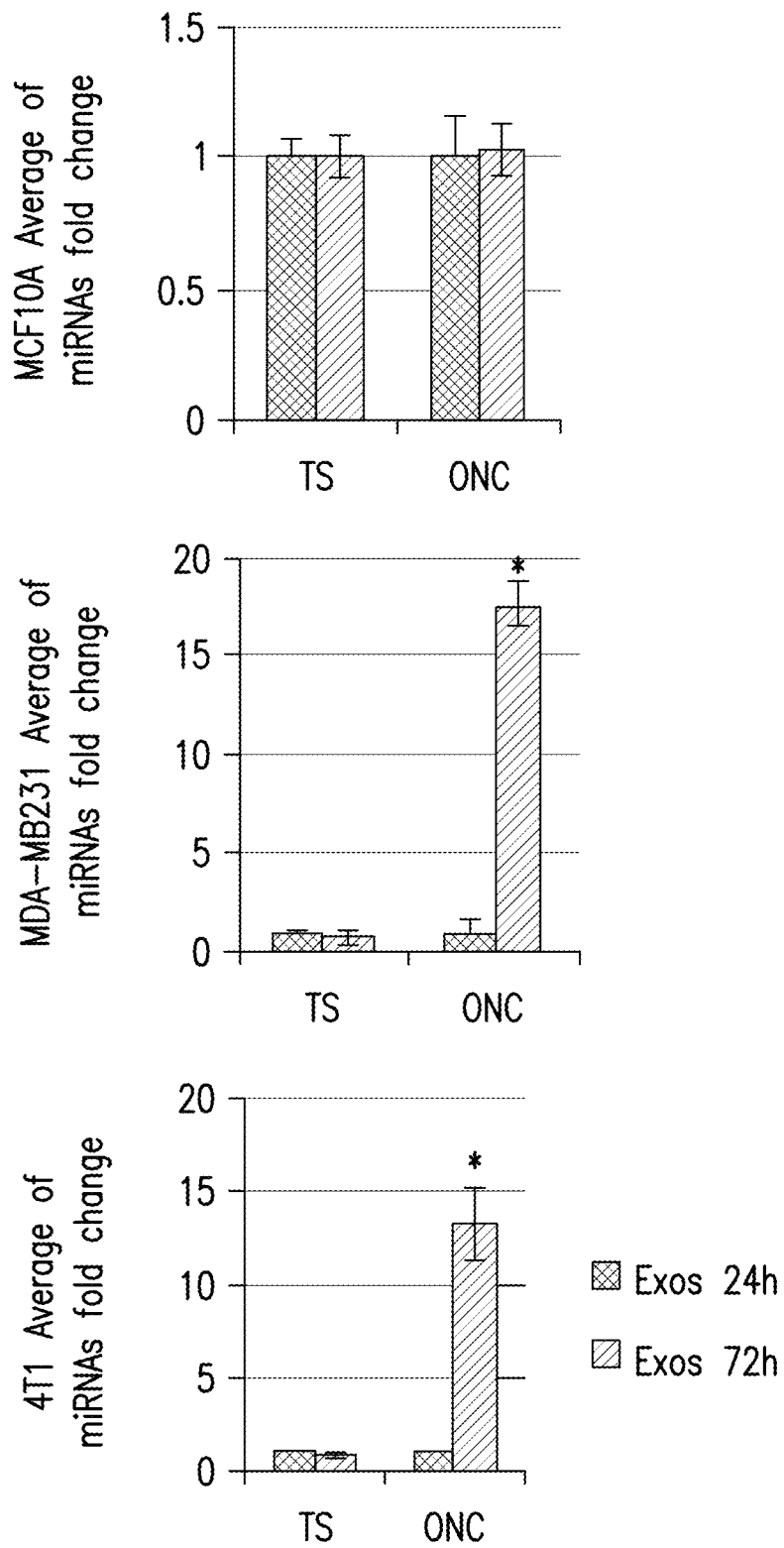
Figure 2D:
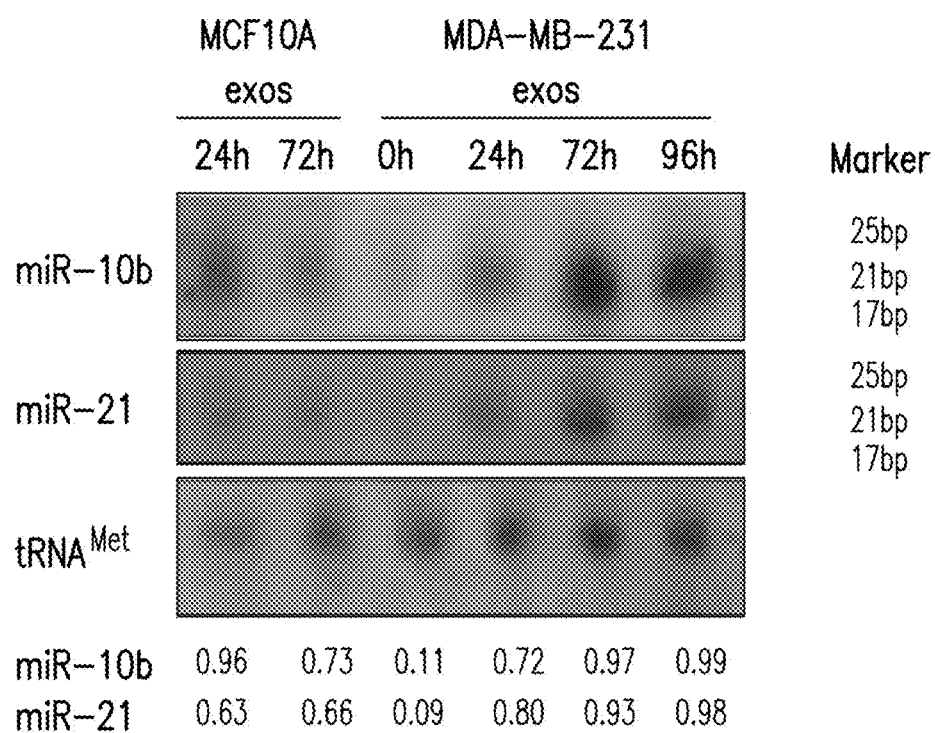
Figure 2E:
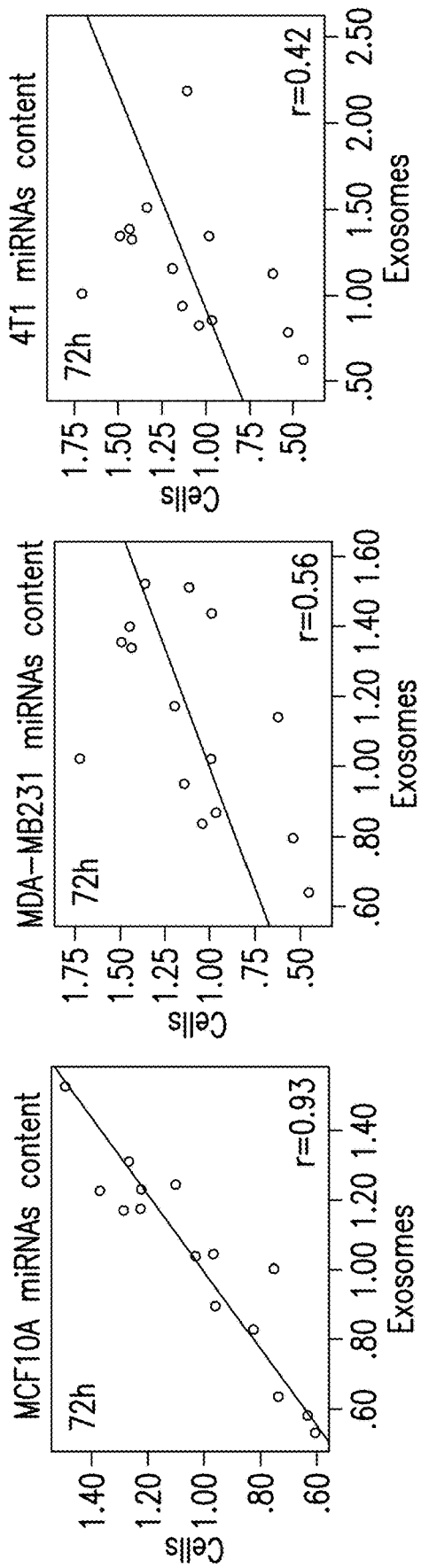
Figure 2F:
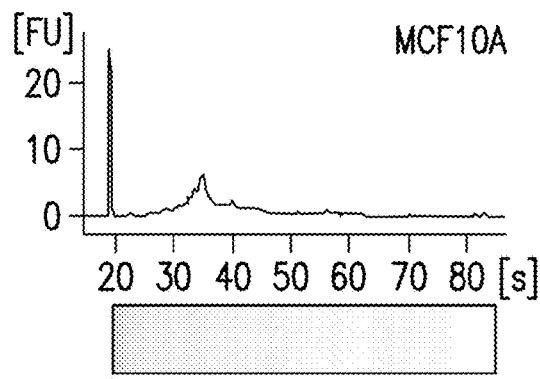
Figure 2F:
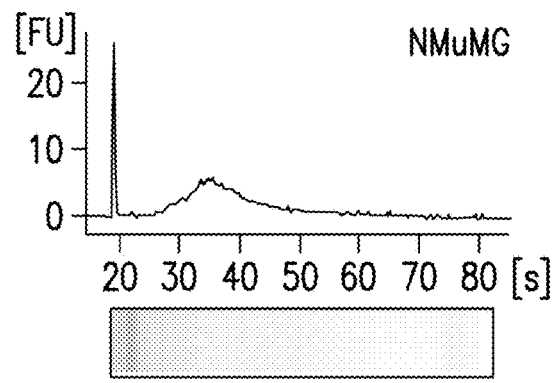
Figure 2F:
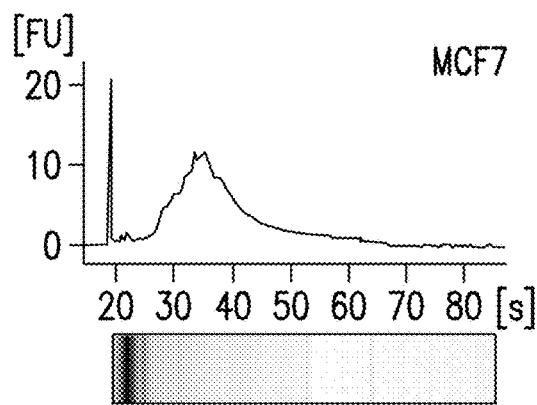
Figure 2F:
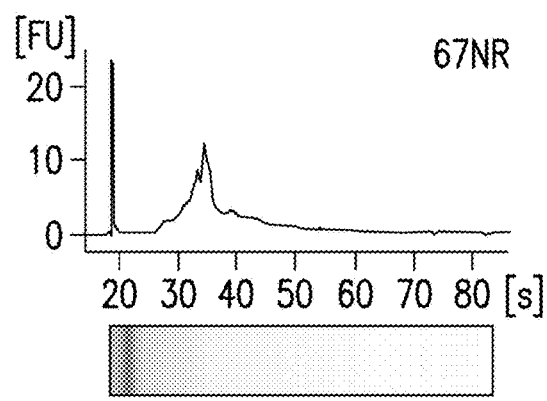
Figure 2F:
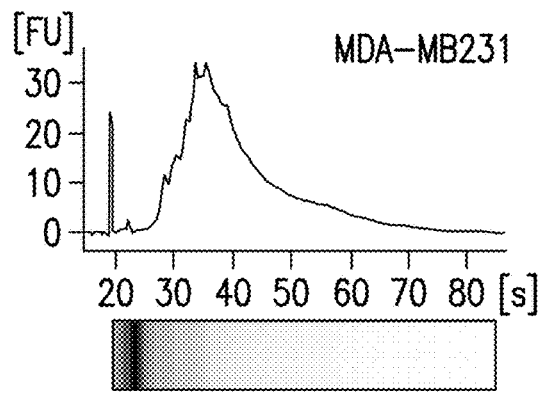
Figure 2F:
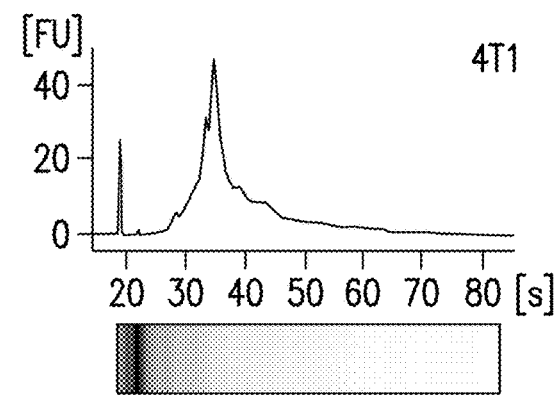
Figure 11A:
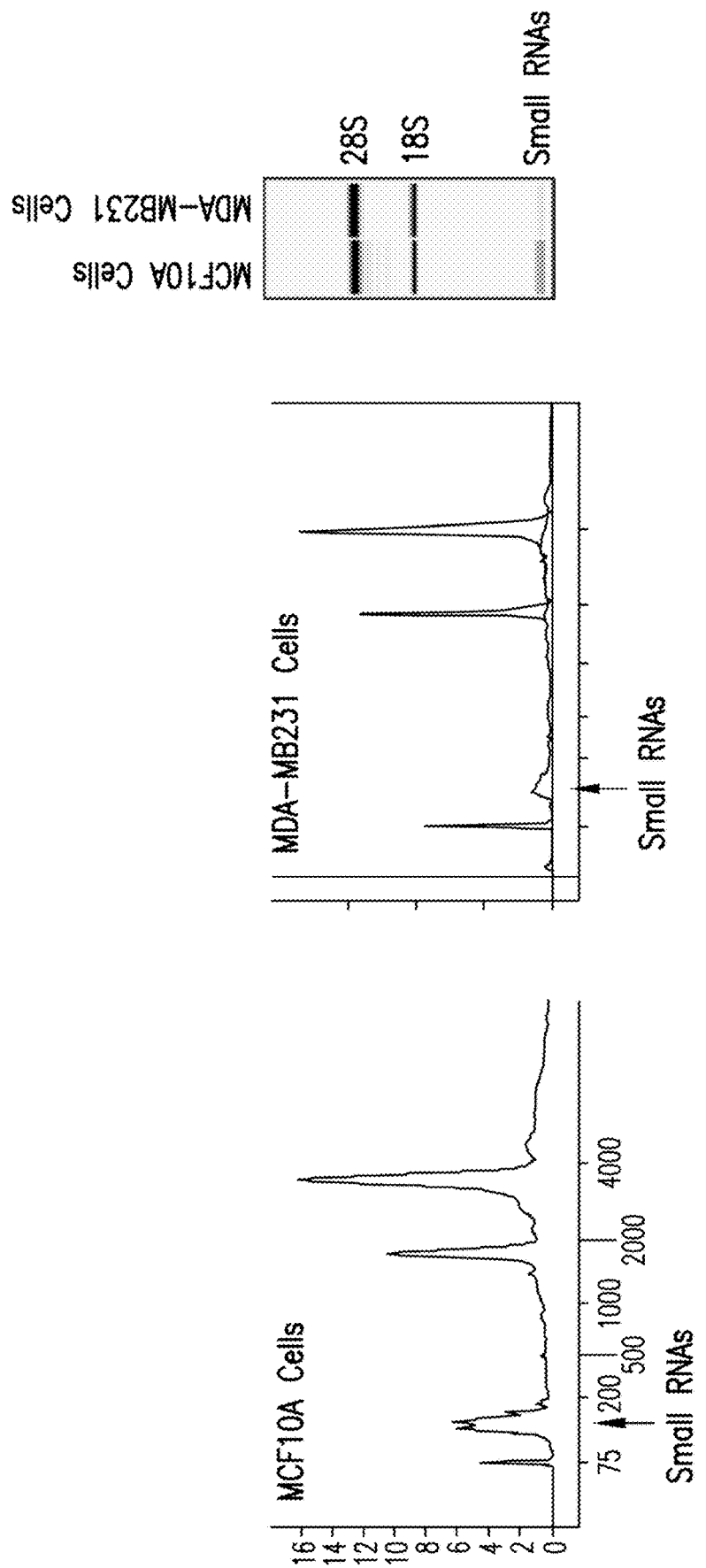

The global miRNA content of oncosomes and normosomes were investigated. Microfluidics analysis of RNA isolated from exosomes revealed an increase in the small RNA content of oncosomes when compared to normosomes (FIG. 2F). Furthermore, a low correlation between the levels of miRNAs in normosomes (MCF10A-derived) and oncosomes (MDA-MB-231-derived) was observed, with an $R^2$ value of 0.35 (FIG. 2A). Global miRNA array analysis showed an enrichment of miRNAs content in oncosomes when compared with normosomes. This analysis also revealed a very distinct miRNA expression profile in oncosomes when compared to normosomes. The miRNA array data showed 305 differentially expressed miRNAs between oncosomes and normosomes (Table 5), with an overall enrichment of miRNA content in oncosomes when compared with normosomes. Enrichment of miRNAs in oncosomes was not a mere reflection of an increase in miRNAs in the cancer cells because the cancer cells showed a decrease in the overall amount of total small RNAs when compared to non-tumorigenic cells (FIG. 11A). Therefore, accumulation of miRNAs in exosomes appeared to be specific and targeted.

Figure 11B:
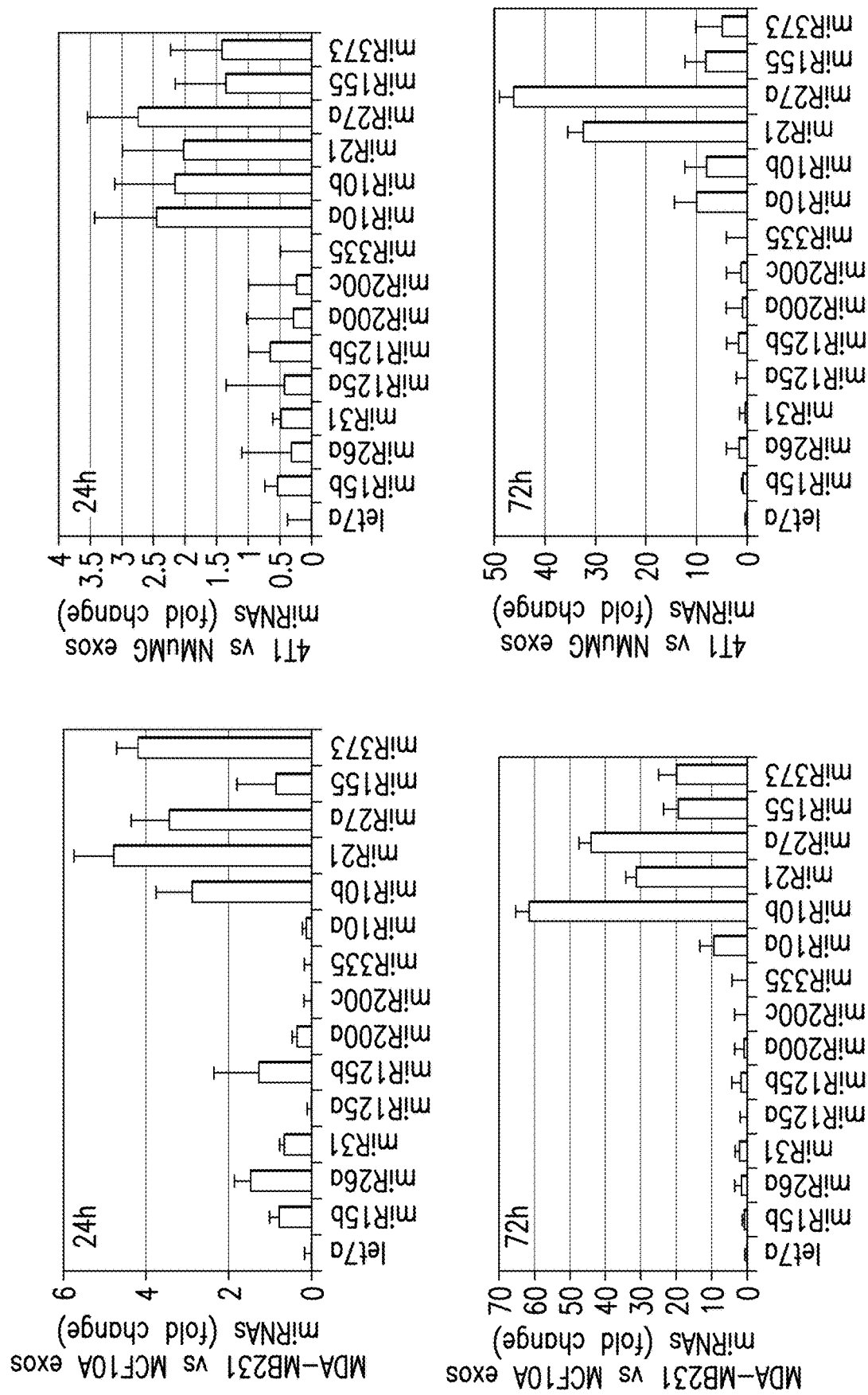
Figure 11C:
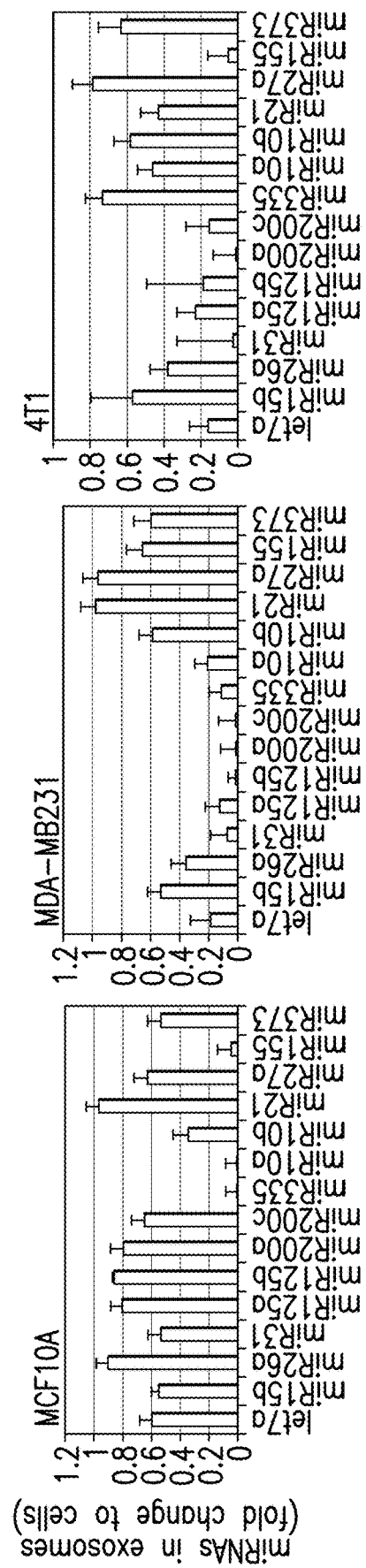
Figure 11D:
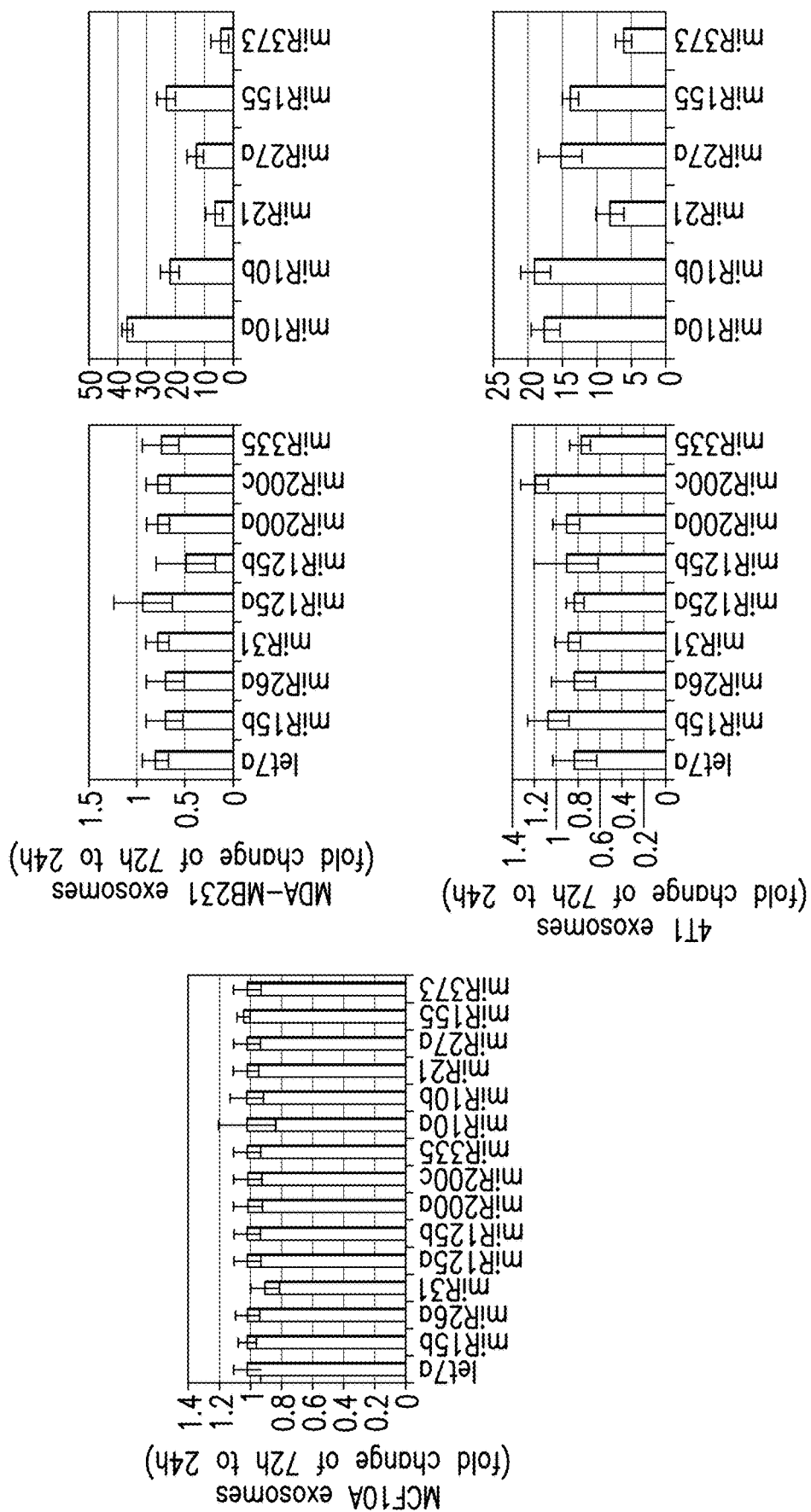
Figure 11E:
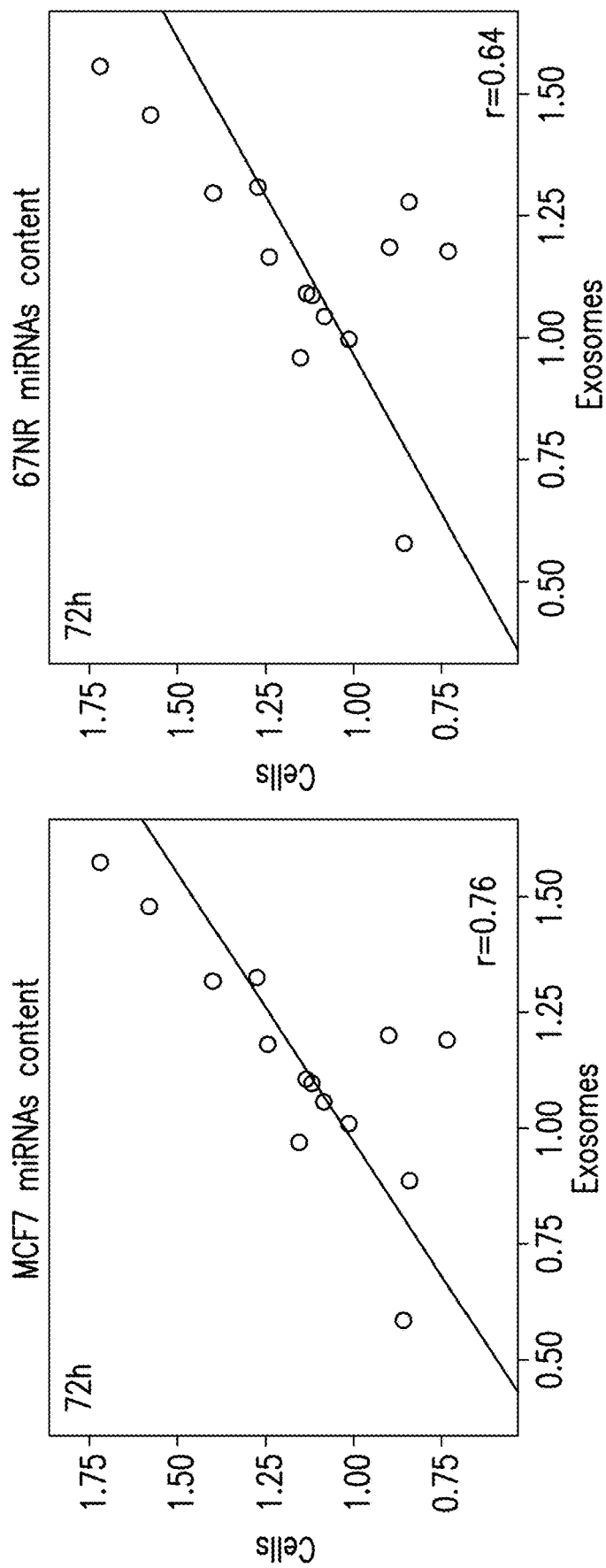

The expression of 15 miRNAs in the cancer cells and exosomes derived from these cells that were found to be differentially expressed in the miRNA array between oncosomes and normosomes were further evaluated (Tables 4 and 5). Six miRNAs from this collection have been implicated in cancer progression (oncogenic miRNAs: miR-10a, miR-10b, miR-21, miR-27a, miR-155 and miR-373) and nine miRNAs were reported to possess tumor suppressive functions (tumor suppressor miRNAs: let7a, miR15b, miR26a, miR31, miR125a, miR125b, miR200a, miR200c, miR335) and are expressed in cells and exosomes derived from those cells (FIGS. 11B-C and Table 4). To determine the half-life of miRNAs in exosomes, a cell-free system was developed to study them in isolated exosomes. Purified exosomes, free from cells, were placed in culture media and incubated for either 24 h or 72 h at 37° C. After the incubation period, the exosomes were analyzed for their miRNA content and compared to the cells from which they originated. There was a decrease in the correlation values of these miRNAs in the oncosomes compared to the cells at 72 h when compared to 24 h ($R^2$=0.60 to $R^2$=0.43), while a high correlation was maintained between normosomes and MCF10A cells (cells used to derive the normosomes; $R^2$=0.98 to $R^2$=0.98) (FIG. 2B). A striking up-regulation of the six analyzed oncogenic miRNAs was observed exclusively in oncosomes cultured for 72 h when compared to oncosomes cultured for 24 h, with an average fold-change of 17.6 and 13.2 for MDA-MB231 and 4T1 derived oncosomes, respectively, further supporting a specific increase in miRNA content in oncosomes with time (FIG. 2C middle and lower graphs and FIG. 11D right, up and lower graphs). Insignificant differences are noted for tumor suppressive miRNAs when oncosomes were cultured for either 24 h or 72 h (FIG. 2C and FIG. 11D). Normosomes did not reveal any differences in their miRNA content irrespective of the culture time (FIG. 2C and FIG. 11D). The presence of all 15 miRNAs were identical in 72 h cultured normosomes and cells they were derived from, with a correlation coefficient of 0.93 (FIG. 2E, left). The correlation coefficients of MDA-MB231 and 4T1 exosomes were significantly lower ($r^2$=0.56 and 0.42, respectively), further supporting a specific alteration in miRNA levels of oncosomes with time (FIG. 2E, middle and right). Additionally, the correlation levels decrease with increasing malignancy of the cells lines when oncosomes are compared from MCF7 ($r^2$=0.76), MDA-MB231 ($r^2$=0.56), 67NR ($r^2$=0.64) and 4T1 ($r^2$=0.42) (FIG. 2E and FIG. 11E). Therefore, the miRNA content of normosomes was a reflection of their cell-of-origin at all times, while oncosomes altered their miRNAs content with time in a cell-independent manner.

When miRNA content of MDA-MB231 and 4T1 oncosomes were compared to that of normosomes from MCF10A and NMuMG cells, an enrichment was observed of oncogenic miRNAs in oncosomes cultured for 24 h with an average fold change of 2.7 and 2.0 respectively (FIG. 11B). At the 72 h time point, an average fold-change of 30 and 18.2 was detected in oncogenic miRNAs in MDA-MB231 and 4T1 derived oncosomes, respectively, when compared to MCF10A and NMuMG derived normosomes (FIG. 11B). Northern blots confirmed the up-regulation of oncogenic miR-10b and miR-21 exclusively in oncosomes, supporting both the miRNA array as well as the qPCR analysis (FIG. 2D).

Oncosomes Contain Pre-miRNAs and the Core RLC Proteins.

Cell-free culture of freshly isolated oncosomes resulted in an increase in miRNA content, suggesting active biogenesis in exosomes. Additionally, microfluidics analysis also suggested the presence of larger RNA molecules (FIG. 2F). Therefore, the potential presence of pre-miRNAs in normosome and oncosome preparations was explored. Cell-free culture of exosomes for 24 h or 72 h after their isolation was performed and subjected to RNAse treatment for depletion of any possible extra-exosomal RNA. This was followed by detection of pre-miRNAs in exosomes. The analyzed pre-miRNAs were the ones that corresponded to the 15 mature miRNAs previously evaluated (Table 4).

TABLE 4

The 15 miRNAs differentially expressed between oncosomes and normosomes.

| MicroRNA ID | References |
| --- | --- |
| miR-let7-a | Kim et al., 2012; Spizzo et al., 2009 |
| miR-15b | Cimmino et al., 2005; Palamarchuk et al., 2010 |
| miR-26a | Kota et al., 2009 |
| miR-31 | Valastyan et al., 2009 |
| miR-125a | Guo et al., 2009; Spizzo et al., 2009 |
| miR-125b | Spizzo et al., 2009; Zhang et al., 2011 |
| miR-200a | Park et al., 2008; Spizzo et al., 2009 |
| miR-200c | Park et al., 2008; Spizzo et al., 2009 |
| miR-335 | Heyn et al., 2011; Scarola et al., 2010; Tavazoie et al., 2008 |
| miR-10a | Tan et al., 2009 |
| miR-10b | Spizzo et al., 2009; Yigit et al., 2012 |
| miR-21 | Spizzo et al., 2009; Yan et al., 2008 |
| miR-27a | Guttilla and White, 2009; Mertens-Talcott et al., 2007 |
| miR-155 | Mattiske et al., 2012 |
| miR-373 | Spizzo et al., 2009; Voorhoeve et al., 2006 |

Figures 3A, 3B:
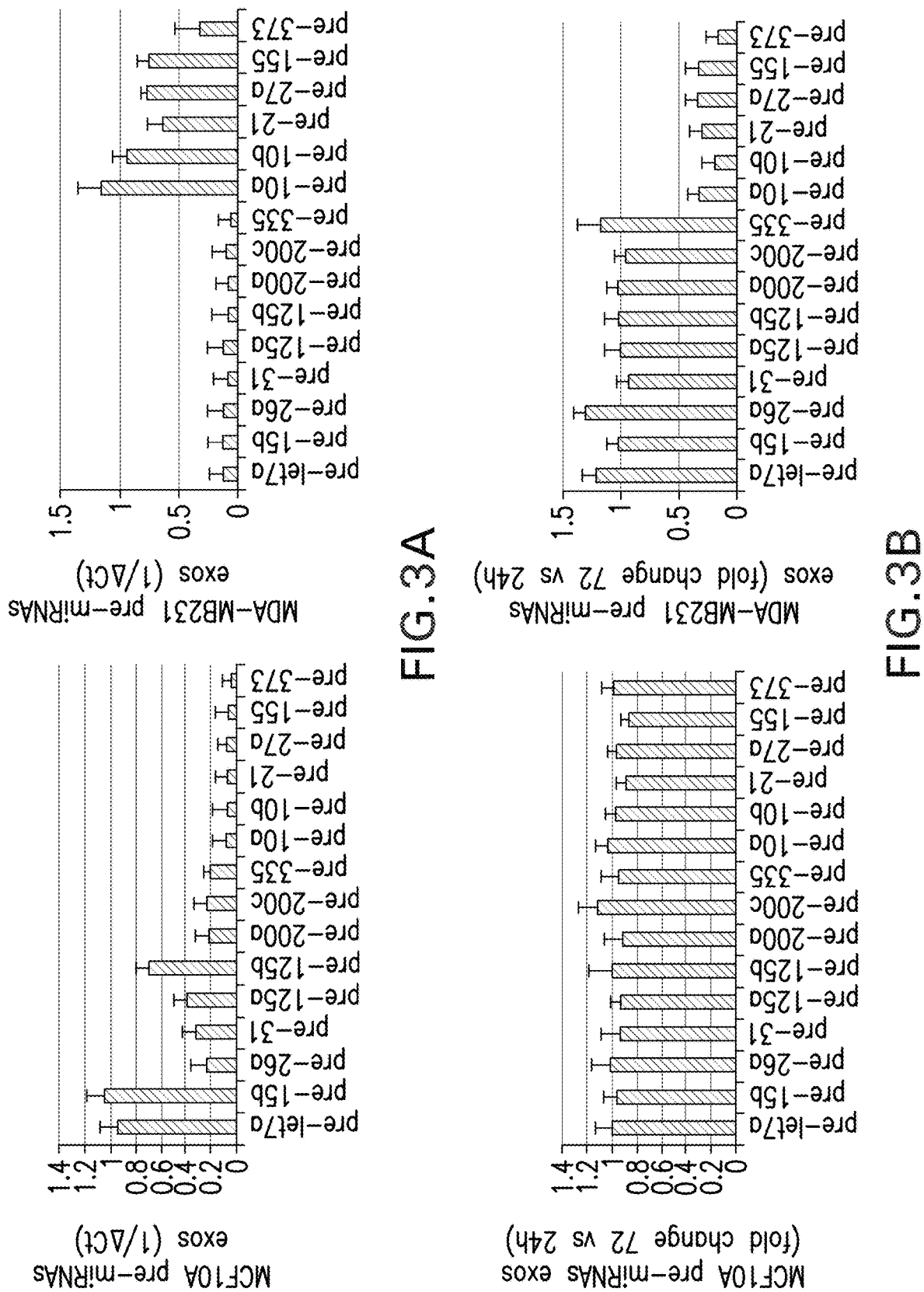
FIGS. 3A-E. Exosomes contain pre-miRNAs. (A) Fifteen pre-miRNAs corresponding to the mature miRNAs studied were quantified using qPCR of MCF10A and MDA-MB231 exosomes. The inverse of the $\Delta$Ct value for each pre-miRNA was plotted to reflect their abundance and values are represented as ±s.d. (B) Oncosomes and normosomes were resuspended in DMEM media and maintained for 24 and 72 h in cell-free culture conditions. After 24 and 72 h exosomes were extracted once again and 15 pre-miRNAs were quantified by qPCR. Graphs show fold-change of each pre-miRNA in MCF10A and MDA-MB231 exosomes after 72 h of cell-free culture relative to 24 h cell-free culture and are represented as ±s.d. (C) Northern blots of premiR-10b and pre-miR-21 using MCF10A normosomes after 24 h and 72 h of cell-free culture, and MDA-MB231 oncosomes with 0 h, 24 h, 72 h and 96 h of cell-free culture. The tRNAMet was used as a loading control. Quantification was done using Image J software. (D) Top graphs: Oncogenic pre-miRNAs (left graph) and oncogenic miRNAs (right graph) of oncosomes (MDA-MB231) were quantified after 24 h and 72 h cell-free culture conditions. The inverse of the $\Delta$Ct value for each pre-miRNA (left graph) and miRNA (right graph) at different time points was plotted to reflect their abundance and an exponential trend was noted. The presented data are the result of three biological replicates and are represented as SD. Bottom graphs: Pre-miRNAs (left graph) and mature miRNAs (right graph) of oncosomes (MDA-MB231) were quantified after 6 h, 12 h, 24 h, 36 h, 48 h, 72 h and 96 h of cell-free culture conditions. The inverse of the $\Delta$Ct value for each pre-miRNA (left graph) and miRNA (right graph) at different time points was plotted and an exponential trend was noted. The data presented in this figure are the result of three independent experiments each with three replicates and are represented as ±s.d. (E) Oncosomes and normosomes were resuspended in DMEM media and maintained for 0 h, 24 h, 72 h and 96 h in cell-free culture conditions. Exosomes were extracted from the different time points and pre-miRNAs were quantified by qPCR. The inverse of the $\Delta$Ct value for each pre-miRNA in the different time points was plotted to reflect their abundance.
Figure 3C:
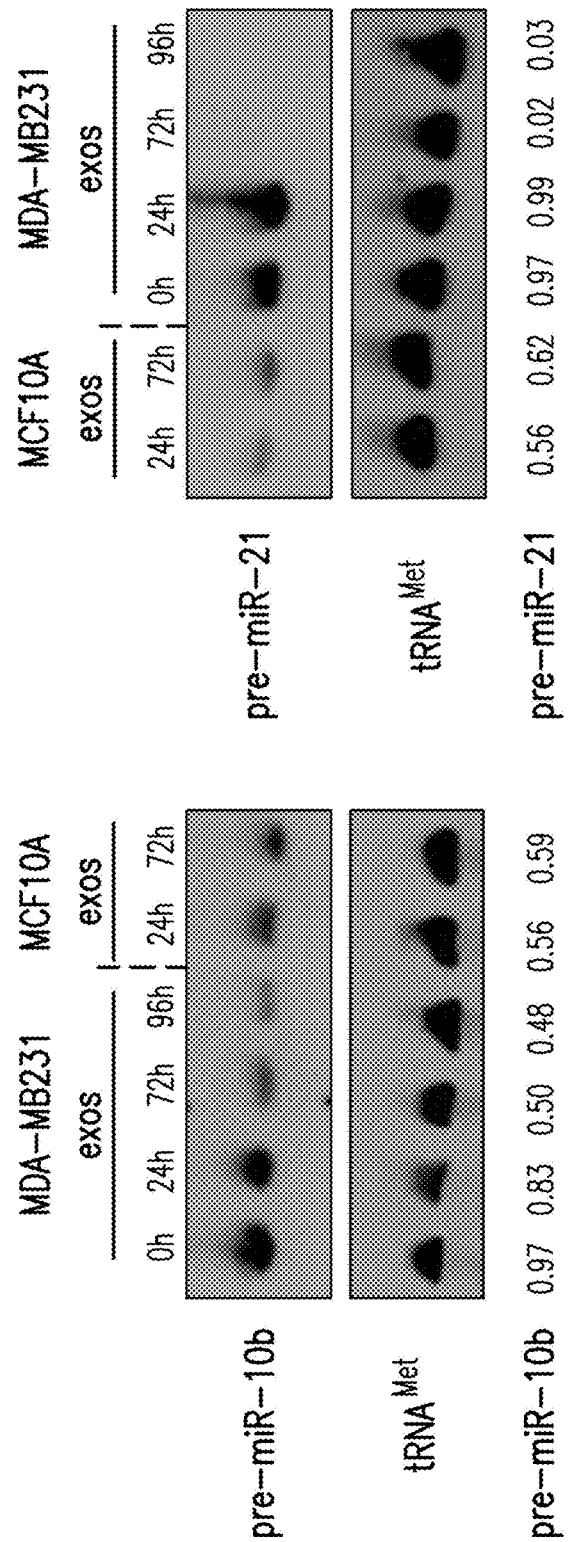
Figure 3D:
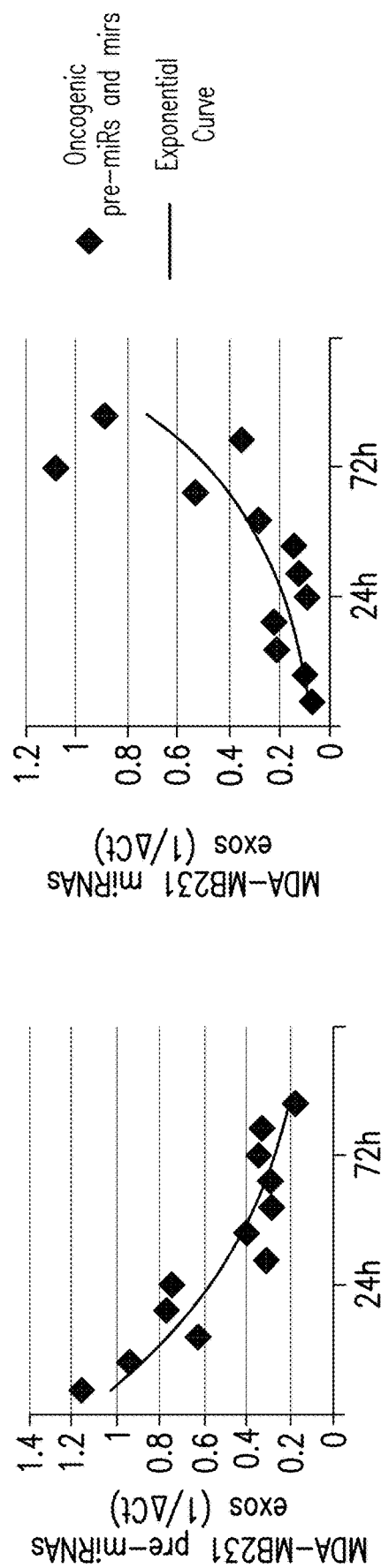
Figure 3D:
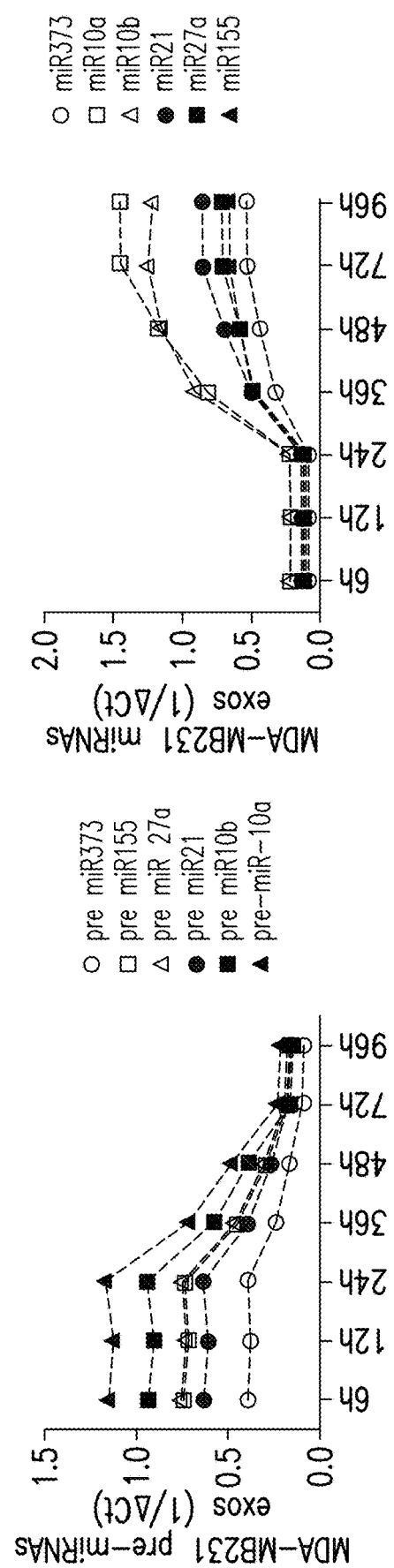
Figure 3E:
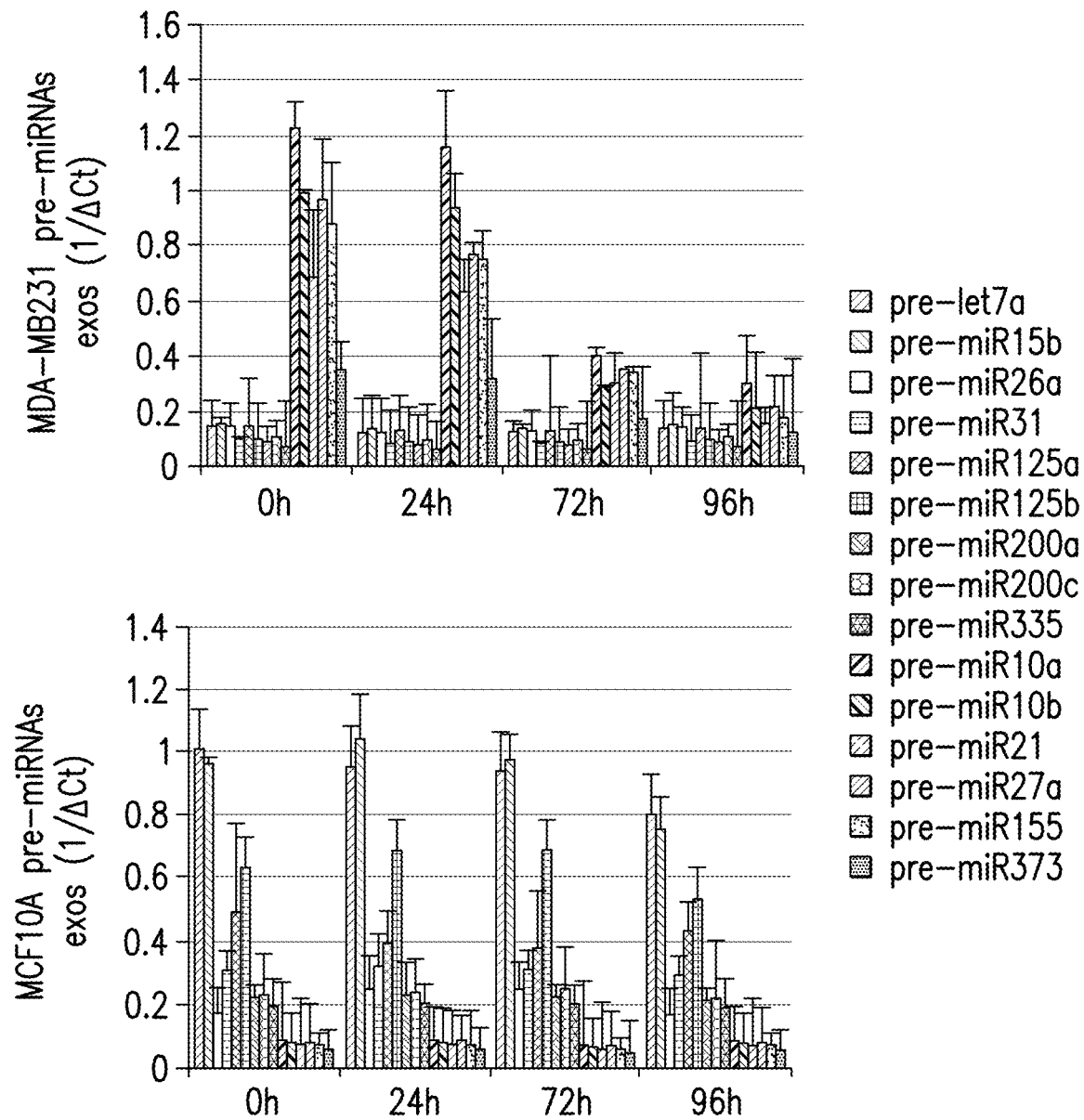
Figure 12A:
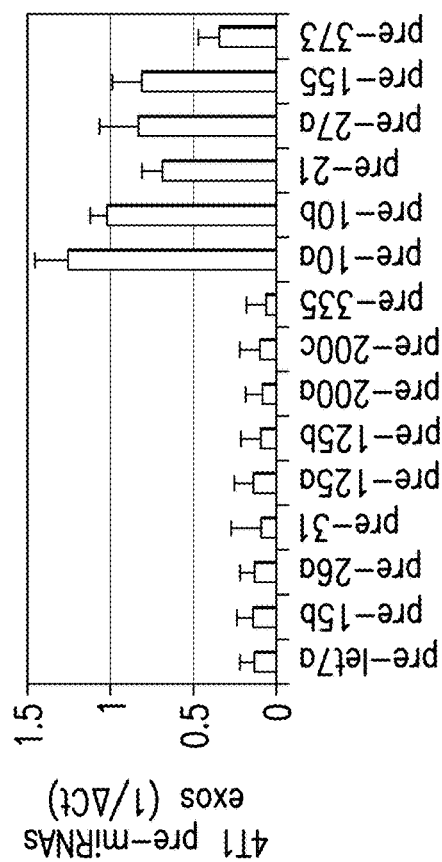
Figure 12A:
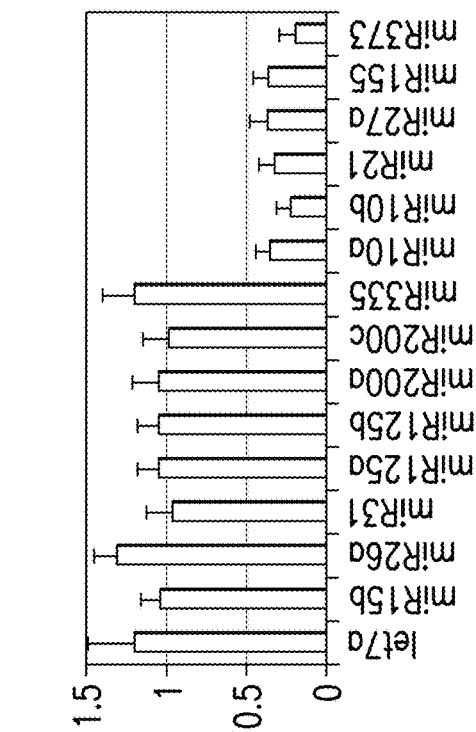
Figure 12B:
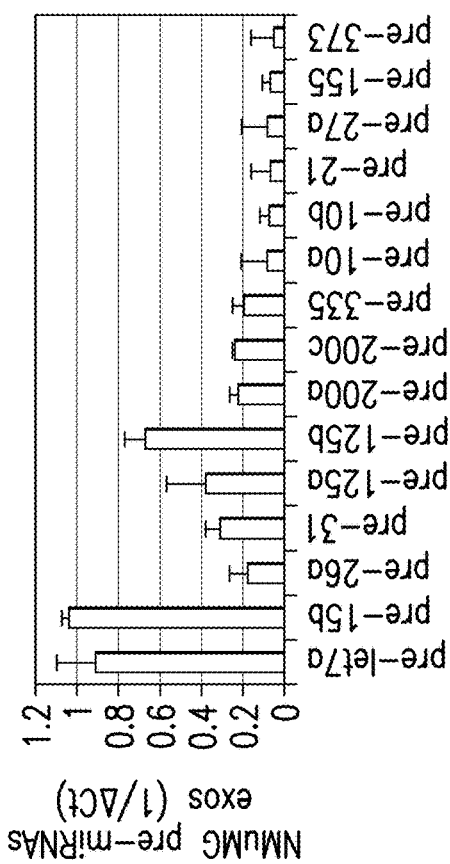
Figure 12B:
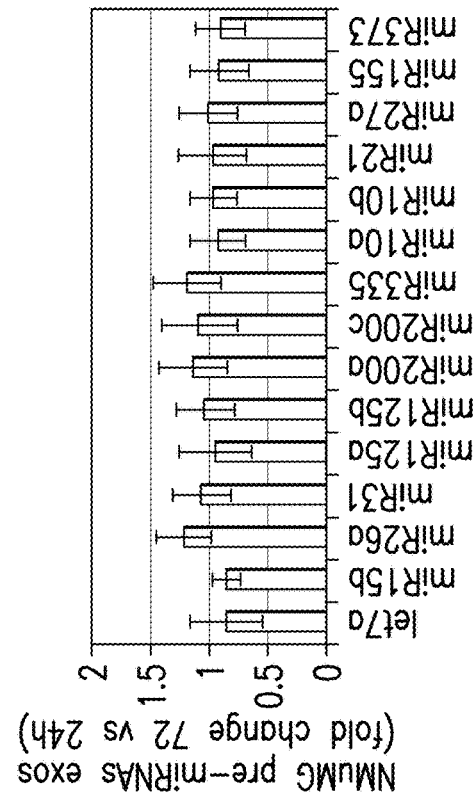

All 15 pre-miRNAs analyzed were present in exosomes (normosomes and oncosomes) (FIG. 3A and FIG. 12A). As observed with miRNAs, oncosomes were highly enriched in oncogenic pre-miRNAs, while tumor-suppressive pre-miRNAs were underrepresented (FIG. 3A and FIG. 12A). When exosomes were cultured for 24 h or 72 h, a significant down regulation of oncogenic pre-miRNAs was observed in oncosomes cultured for 72 h when compared to oncosomes cultured for 24 h. Such variation was not found in normosomes (FIG. 3B and FIG. 12B). The tumor-suppressive pre-miRNAs did not show any difference in oncosomes or normosomes (FIG. 3B and FIG. 12B). Moreover, decreasing amounts of oncogenic pre-miRNAs in oncosomes, but not in normosomes, was noted after 96 h of culture, at which point the oncogenic pre-miRNA levels reached the levels of tumor-suppressive pre-miRNAs (FIG. 3E and FIG. 12E). Down regulation of oncogenic pre-miRNAs in oncosomes was confirmed by Northern blotting for pre-miR10b and pre-miR21 (FIG. 3C). Next, a time-course analysis of pre-miRNAs and miRNAs in exosomes was performed. By culturing isolated oncosomes for 6 h, 12 h, 24 h, 36 h, 48 h, 72 h and 96 h, it was observed that the levels of the 6 analyzed pre-miRNAs were inversely proportional to their respective miRNAs with increased culture time (FIG. 3D). Mature miRNAs increased in quantity between 24 and 72 h of culture, after which they reached a plateau (FIG. 3D). Therefore, oncosomes deplete their premiRNAs content with a concomitant increase in their respective mature miRNAs with time. This observation led to the hypothesis that oncosomes have the ability for miRNA biogenesis.

Figure 12C:
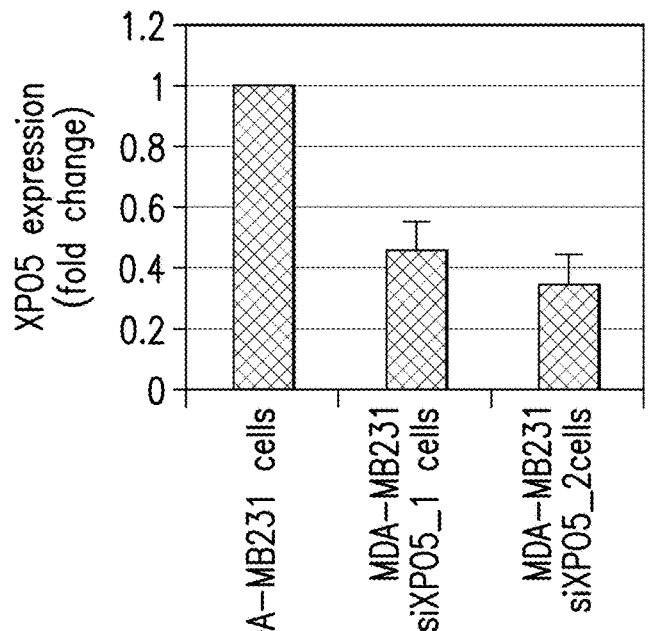
Figure 12D:
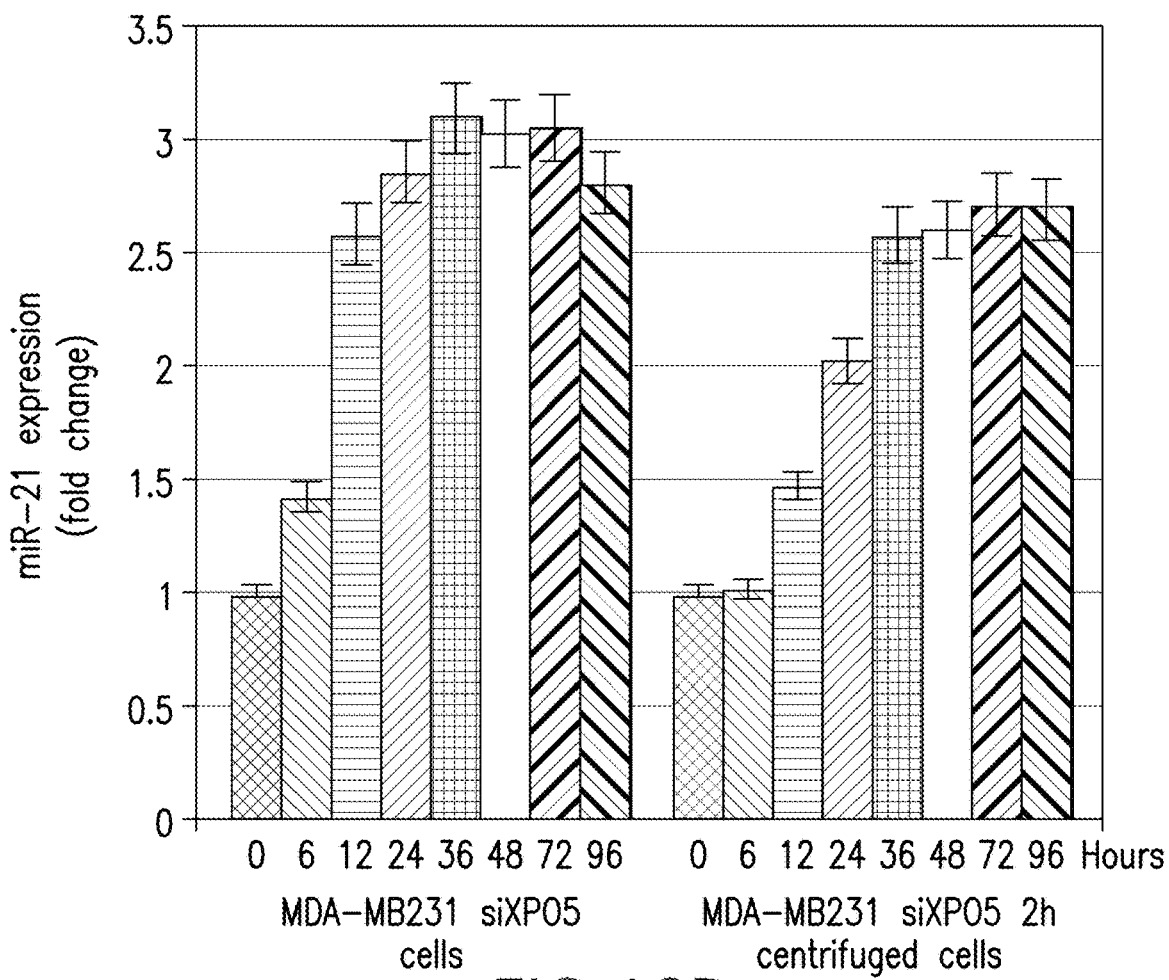
Figure 12E:
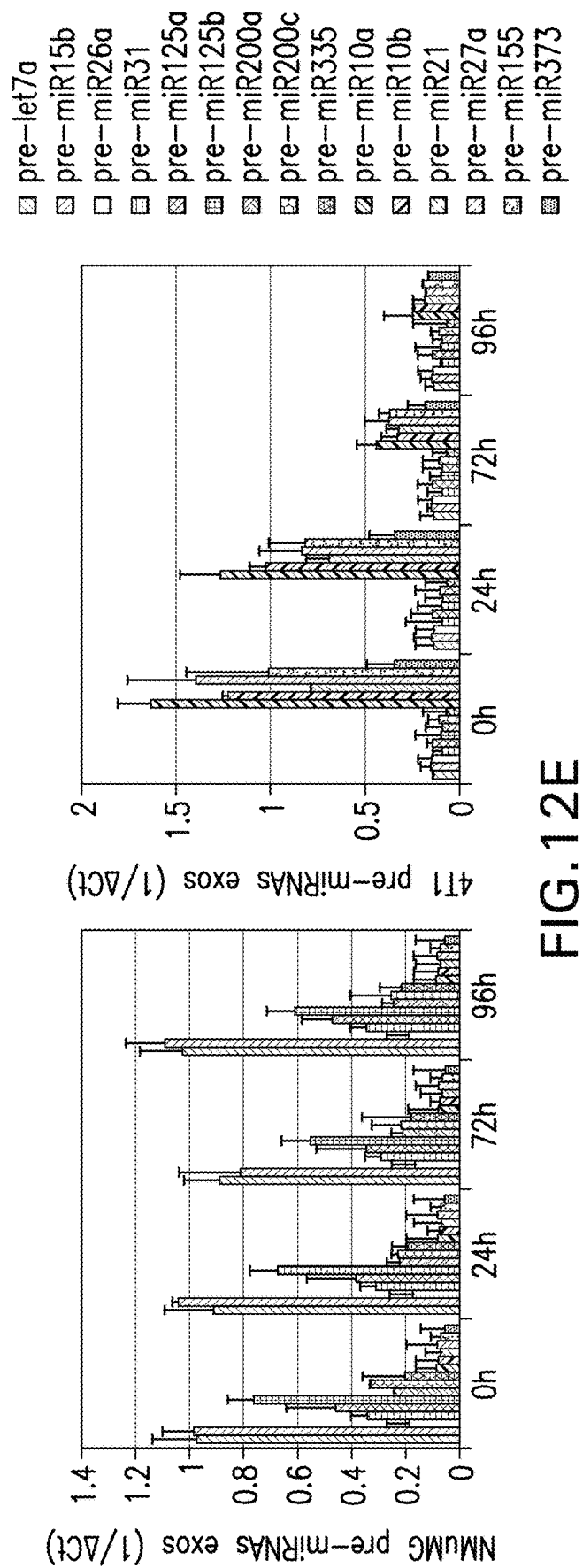

To understand why the processing of pre-miRNAs in cultured exosomes starts after 24 h and not immediately, all six miRNAs in MDA-MB-231 cells silenced for exportin-5 (XPOS) were monitored (FIGS. 12C and D). XPOS is responsible for the transport of pre-miRNAs from the nucleus to the cytoplasm (Yi et al., 2003). Silencing XPOS prevents the flow of pre-miRNAs from the nucleus to the cytoplasm and allows for an evaluation of cytoplasmic premiRNA processing without the introduction of new cytoplasmic pre-miRNA from the nucleus. MicroRNA-21 was monitored in MDA-MB-23 lsiXPO5 cells before and after centrifugation (FIGS. 12C and D), which occurred at 4° C. for 3 hours to mimic the conditions of exosomes isolation. A significant up-regulation of the miR-21 was not observed at the same time points between centrifuged versus non-centrifuged cells, where the previous cells suffer a lag period of 24 h (FIGS. 12C and D). Therefore, both cells and exosomes require a period of time to recover from the stress of centrifugation at 4° C. to initiate the processing of pre-miRNAs. Such acclimatization is expected for enzymatic activities in cultured cells after tissue culture passage.

Oncosomes Contain the Core RISC (RLC) Proteins.

Figure 4A:
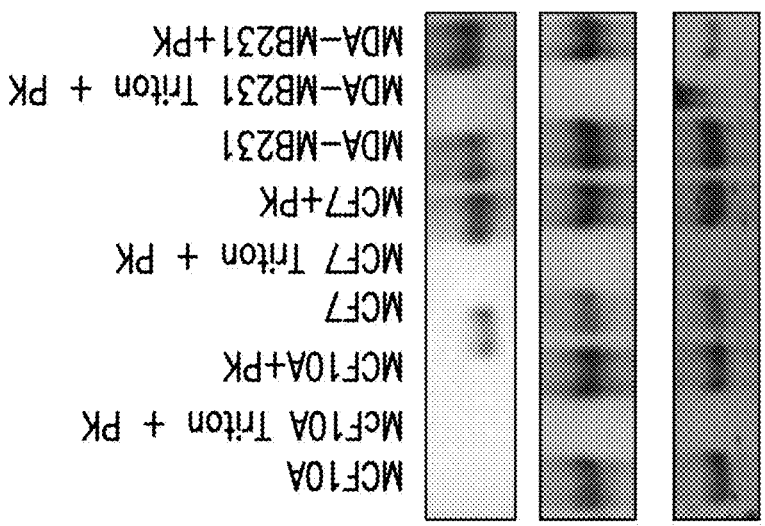
FIGS. 4A-N. Oncosomes contain RLC proteins. (A) Immunoblot using anti-Dicer antibody in exosomes harvested from: nontumorigenic mouse (NMuMG) and human (MCF10A) cell lines; mouse cancer cell lines, 67NR and 4T1; and human cancer cell lines MCF7 and MDAMB231. Controls used were: exosomes treated with TritonX followed by proteinase K treatment (Triton+PK) to induce lysis of exosomes and subsequent degradation of exosomal proteins; and exosomes treated with proteinase K to degrade extra-exosomal proteins (PK). TSG101 (second row) and CD9 (third row) immunoblots were used to confirm presence of exosomes. (B) Transmission electron micrographs of immunogold labeling using anti-Dicer antibody in oncosomes (MDA-MB231). Right upper image is digitally zoomed from a new independent image of the extraction. Negative control refers to IgG. Gold particles are depicted as black dots and are indicated by black arrows in the bottom image. Graph represents quantification of the two upper images on the left. (C) Immunoblot using anti-flag antibody (upper panel) in MCF10A and MDA-MB231 exosomes harvested from cells transfected with empty vector (pCMV-Tag4B; first and third lanes respectively) and Flag-Dicer vector (second and fourth lanes). CD9 immunoblot was used to confirm the presence of exosomes and as a loading control (lower panel). (D) Immunoblot for Dicer in exosomes harvested from MCF10A and MDA-MB231 cells treated with the calcium ionophore A23187 (upper panel). Exosomes extracted from untreated cells were used as control. CD9 immunoblot (lower panel) was used as control to show increased exosomes secretion. (E) Immunoblot for Dicer in exosomes extracted from MCF10A and MDA-MB231 parental cells and cells transfected with shScramble and shDicer plasmids (upper blot). CD9 immunoblot was used to show exosomes presence and as a loading control (lower blot). Immunoblot quantification was done using Image J software. (F) Transmission electron micrographs of immunogold labeling using anti-Dicer antibody in oncosomes derived from MDAMB231shDicer cells. Gold particles are depicted as black dots. Right graph depicts quantification of gold particles in EM pictures. (G) Immunoblot using anti-AGO2 antibody in exosomes harvested from oncosomes (MCF7 and MDA-MB231) and normosomes (MCF10A). Controls used were: exosomes treated with Triton X followed by proteinase K (Triton X+PK) to induce lysis of exosomes and subsequent degradation of exosomal proteins; exosomes treated with proteinase K to degrade extra-exosomal proteins (PK); and supernatant after ultracentrifugation to harvest exosomes (Supernatant). TSG101 (second row) and CD9 (third row) immunoblots were used to confirm the presence of exosomes. (H) Immunoblot using anti-TRBP antibody in exosomes harvested from oncosomes (MCF7 and MDA-MB231) and normosomes (MCF10A). The controls used were: exosomes treated with Triton X followed by proteinase K (Triton X+PK) to induce lysis of exosomes and subsequent degradation of exosomal proteins; exosomes treated with proteinase K to degrade extra-exosomal proteins (PK); and supernatant after ultracentrifugation to harvest exosomes (Supernatant). TSG101 (second row) and CD9 (third row) immunoblots were used as exosomes markers. (I) Immunoblot using anti-GFP antibody in MCF10A and MDA-MB231 cells transfected with GFP-AGO2 plasmid (upper panel). Beta actin was used as loading control (lower panel). (J) Immunoblot using anti-GFP antibody in exosomes extracted from MCF10A and MDA-MB231 cells transfected with GFP-AGO2 plasmid (upper panel). TSG101 (middle panel) and CD9 (lower panel) were used as exosomes markers and loading controls. (K) AGO2 mRNA expression in MCF10A and MDA-MB231 cells transfected with siAGO2. MCF10A and MDA-MB231 parental cells were used as relative controls for fold change comparison. Data are the result of three biological replicates and are represented as SD. (L) Immunoblot using AGO2 antibody in exosomes extracted from MCF10A and MDA-MB231 parental cells or cells transfected with sicontrol or siAGO2 (upper panel). TSG101 (middle blot) and CD9 (lower blot) were used as exosomes markers and loading controls. Quantification was done using Image J software. (M) Immunoblot using AGO2 antibody in exosomal proteins extracted from MCF10A and MDA-MB231 cells immunoprecipitated with Dicer antibody or IgG (upper panel). 5% of the lysate input of exosomes extracted from MDA-MB231 cells was used as control Immunoblot of Dicer was used as control for immunoprecipitation (lower panel). (N) Immunoblot using anti-TRBP antibody in exosomal proteins extracted from MCF10A and MDA-MB231 cells immunoprecipitated with Dicer antibody or IgG (upper panel). Lysate input of exosomes (5%) extracted from MDA-MB231 cells was used as control. Immunoblot of Dicer was used as control (lower panel).
Figure 4A:
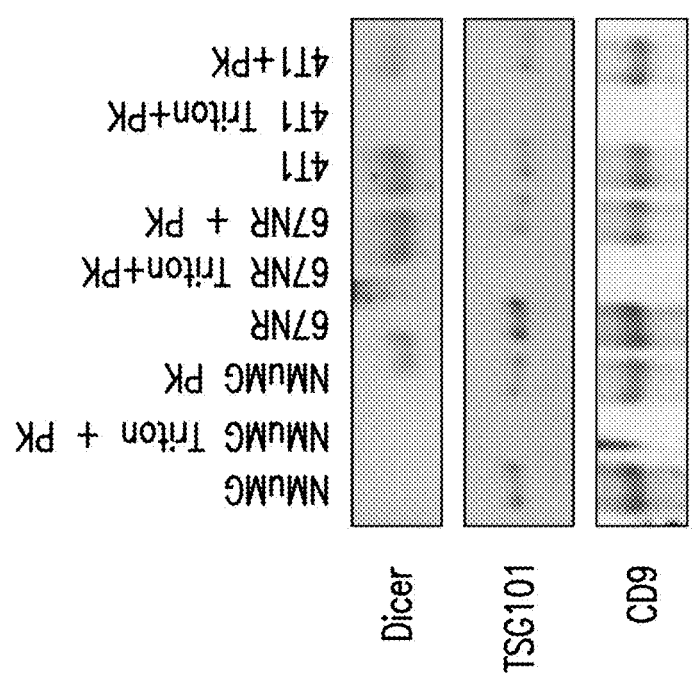
Figure 4B:
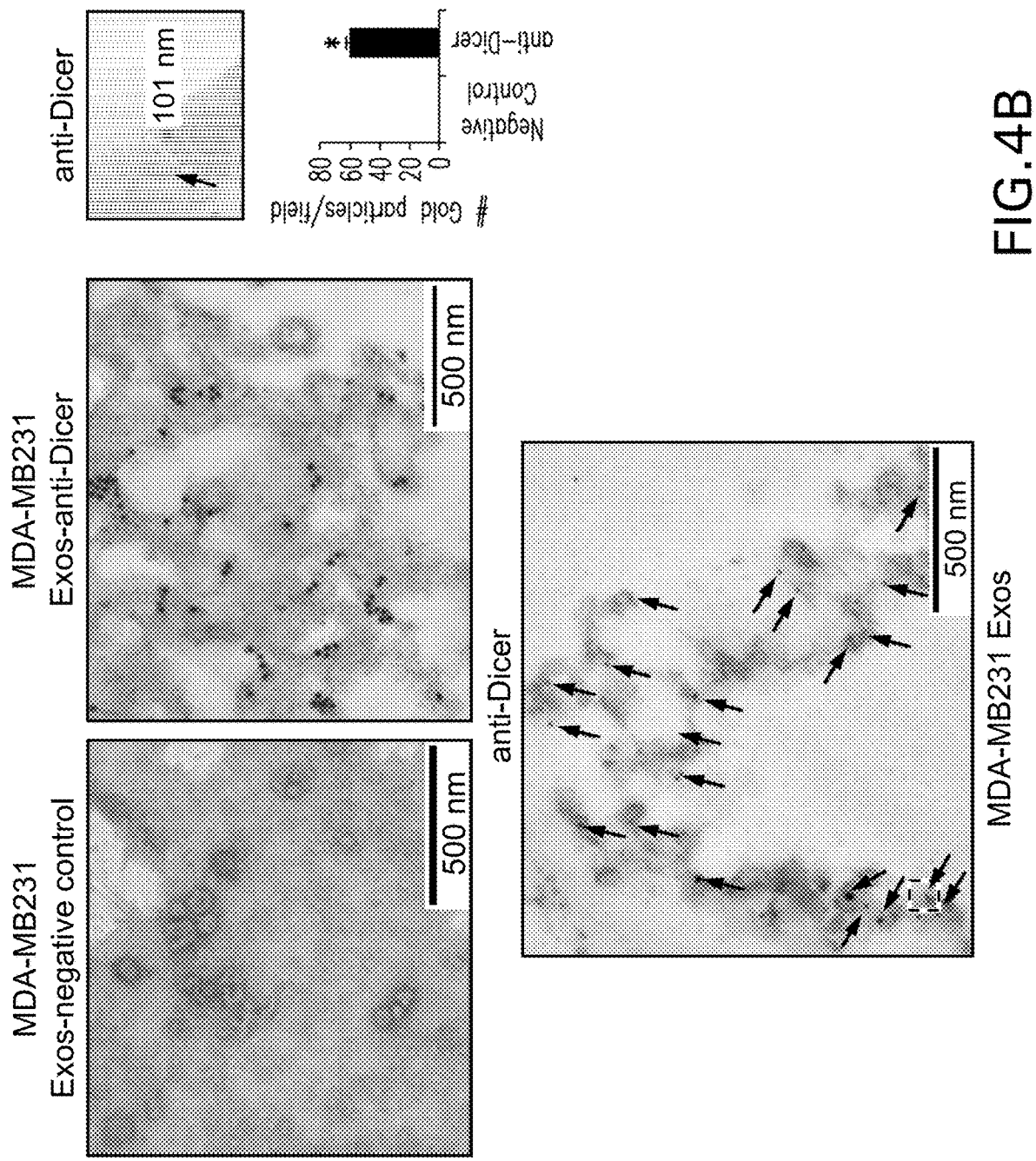
Figure 13A:
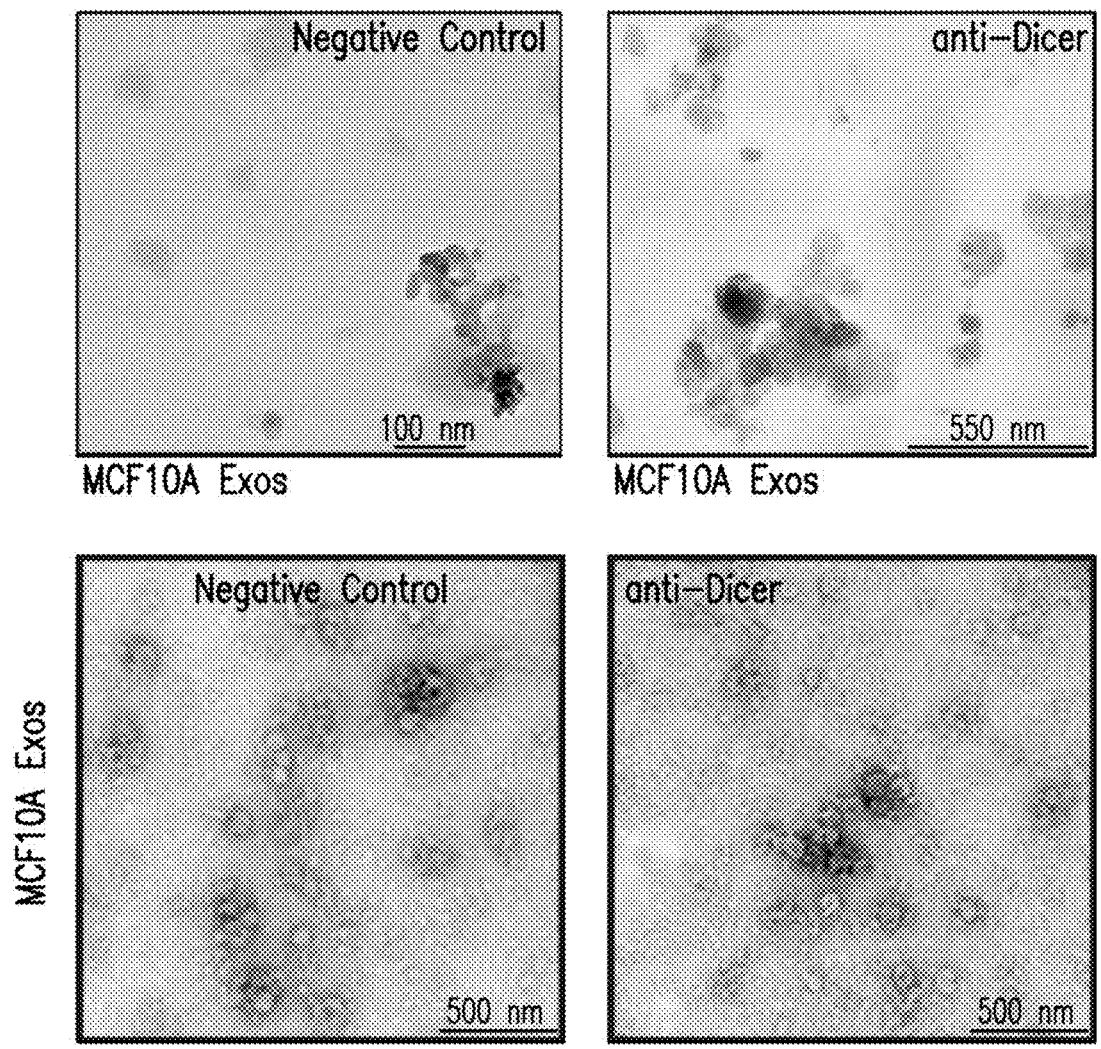
Figure 13B:
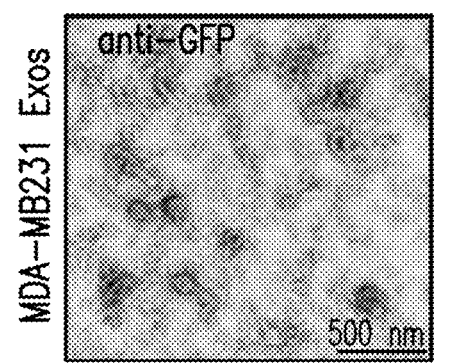
Figure 13C:
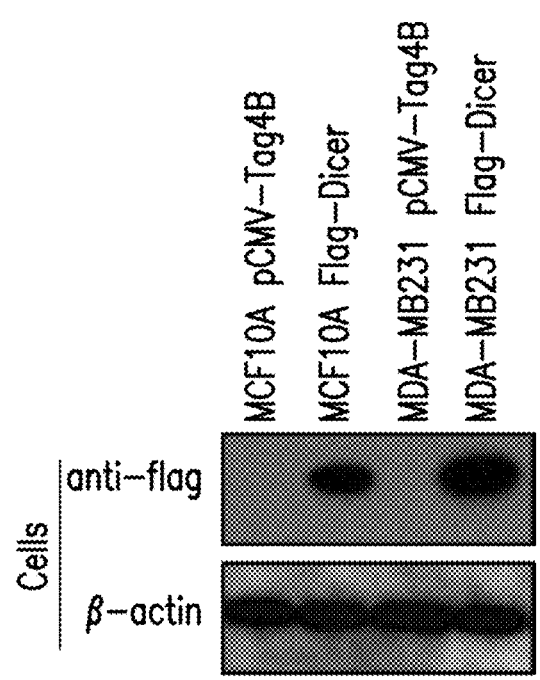
Figure 13D:
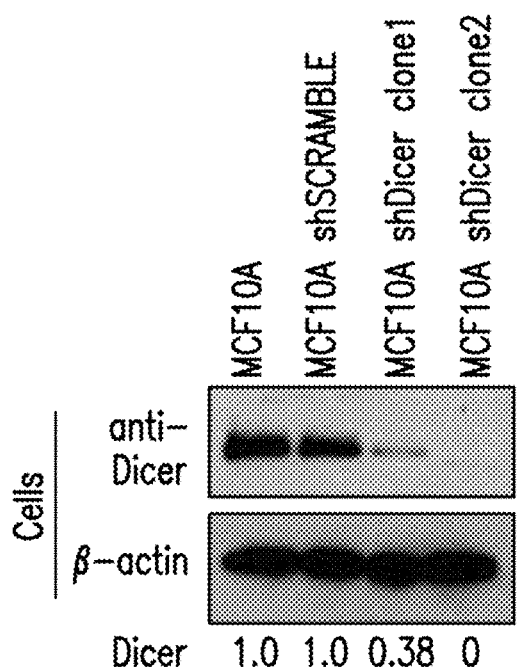
Figure 13E:
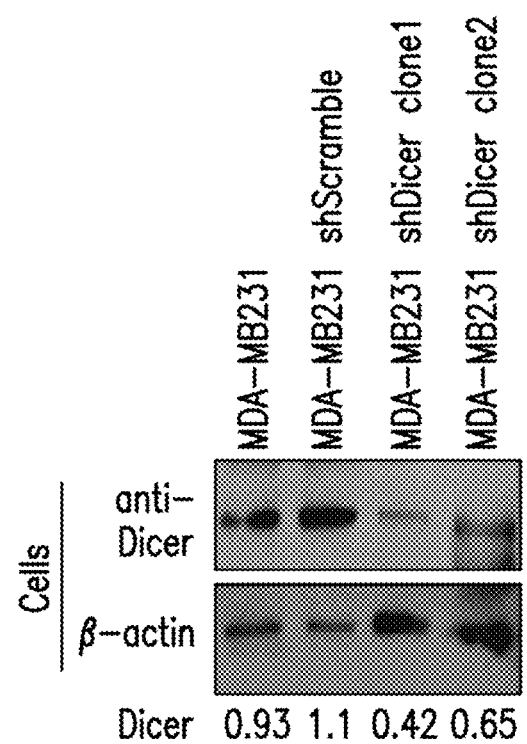

Oncosomes deplete their pre-miRNAs concentration with concomitant increase in their respective mature miRNAs with time. This led us to examine miRNA biogenesis and pre-miRNA processing capabilities in exosomes. MicroRNA biogenesis requires key protein components of the RLC, Dicer, TRBP and AGO2 (Chendrimada et al., 2005). It has been previously shown that Dicer and TRBP form a complex that provides stability to Dicer protein, while AGO2 is recruited later in the biogenesis pathway to help with strand selection and the RNA unwinding process (Chendrimada et al., 2005). Dicer protein was detected in oncosomes derived from MCF7, MDA-MB231, 67NR and 4T1 cancer cells (FIG. 1C and FIGS. 4A-B). The possibility of detecting contaminating extra-exosomal Dicer protein was removed by treating all exosomes preparations with proteinase K before exosomal protein extraction as previously described (Montecalvo et al., 2012) (FIG. 1C and FIGS. 4A-B). In addition, various cancer cell lines such as A549 (human lung cancer), SW480 (human colorectal cancer), HeLa (human cervical cancer) and 4T07 (mouse breast cancer) also produce Dicer-containing exosomes (FIG. 13H). Dicer protein was not detected in normosomes produced by MCF10A (human non-tumorigenic breast epithelial cells) and NMuMG (mouse non-tumorigenic breast epithelial cells) cell lines (FIG. 1C and FIG. 4A) Immunogold labeling of exosomes using transmission electron microscopy corroborated the presence of Dicer protein in oncosomes but not in normosomes (FIG. 4B and FIG. 13A). Additionally, anti-GFP antibody was used as another negative control in immunogold labeling experiments, and nothing was detected in the exosomes (FIG. 13B).

Figure 4C:
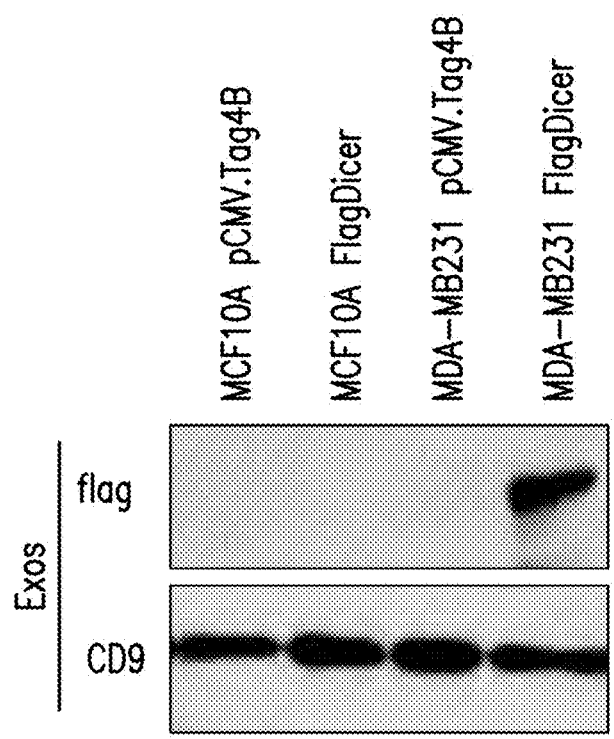
Figure 4D:
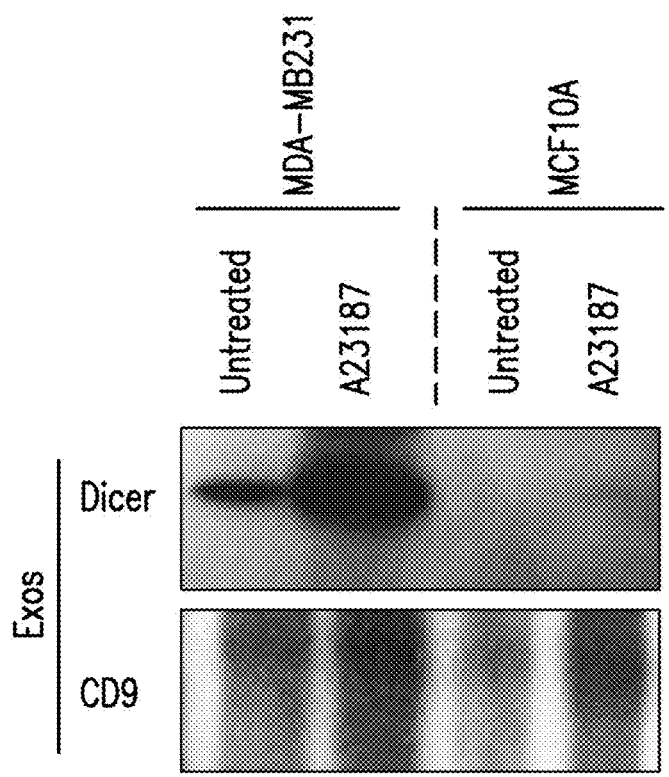
Figure 4E:
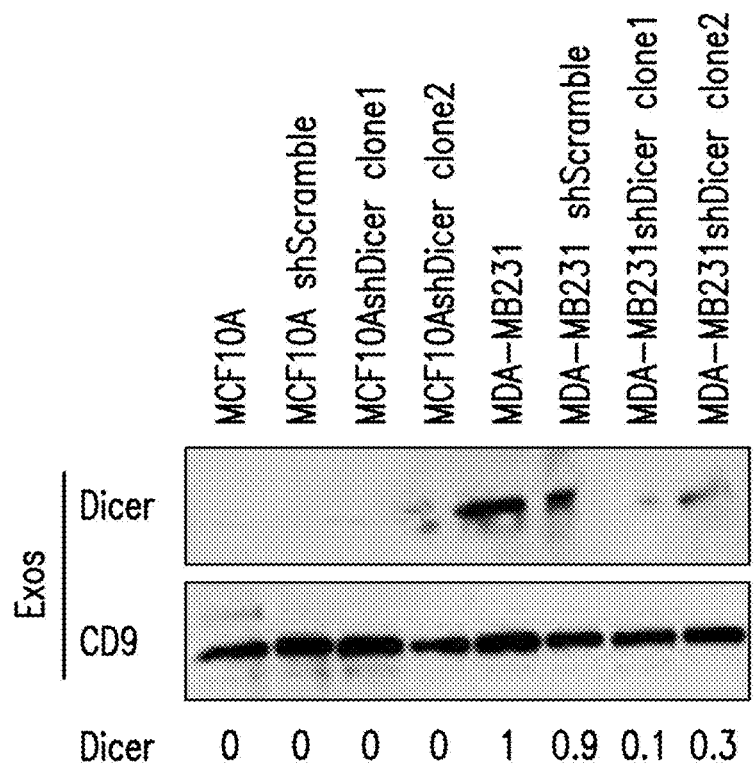
Figure 4F:
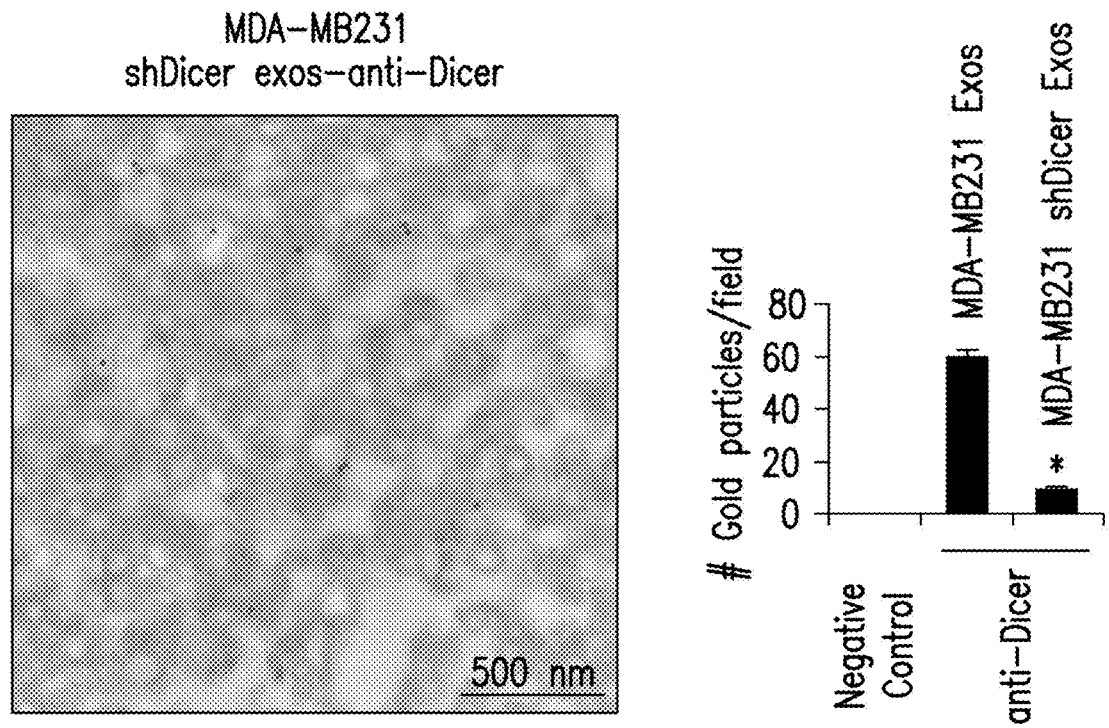

Dicer protein was further overexpressed with an N-terminal Flag tag in MCF10A and MDA-MB231 cells (FIG. 13C) Immunoblotting and confocal microscopy further confirmed the presence of the Flag-Dicer protein specifically in oncosomes and not normosomes (FIG. 4C). Increasing intracellular Ca2+ levels stimulates exosomes secretion (Savina et al., 2003). $Ca^{2+}$ ionophore A23187 was added to the culture media of MCF10A and MDA-MB231 cells and exosomes were collected. We observed a significant increase in exosomes production as judged by CD9 expression (FIG. 4D). Dicer protein was detected in oncosomes was but not in normosomes (FIG. 4D). These results further suggested that this is not the quantity of exosomes determining the content but rather a specific mechanism that leads to Dicer accumulation. In addition, Dicer expression was decreased via stable expression of two short-hairpin constructs in MCF10A and MDA-MB-231 cells (FIGS. 13D-E). The oncosomes derived from MDA-MB-231shDicer cells contained significantly less Dicer compared to shScramble or parental MDA-MB-231 cells detected by immunoblotting and immunogold labeling (FIGS. 4E-F). Dicer was also not detected in normosomes derived from MCF10AshDicer cells (FIG. 4E).

Figure 4G:
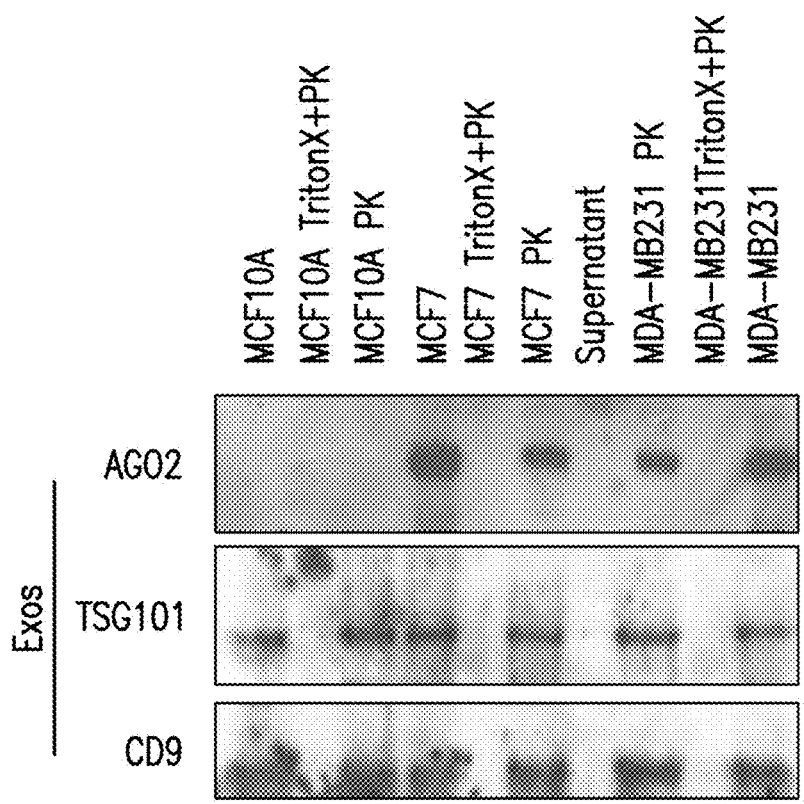
Figure 4H:
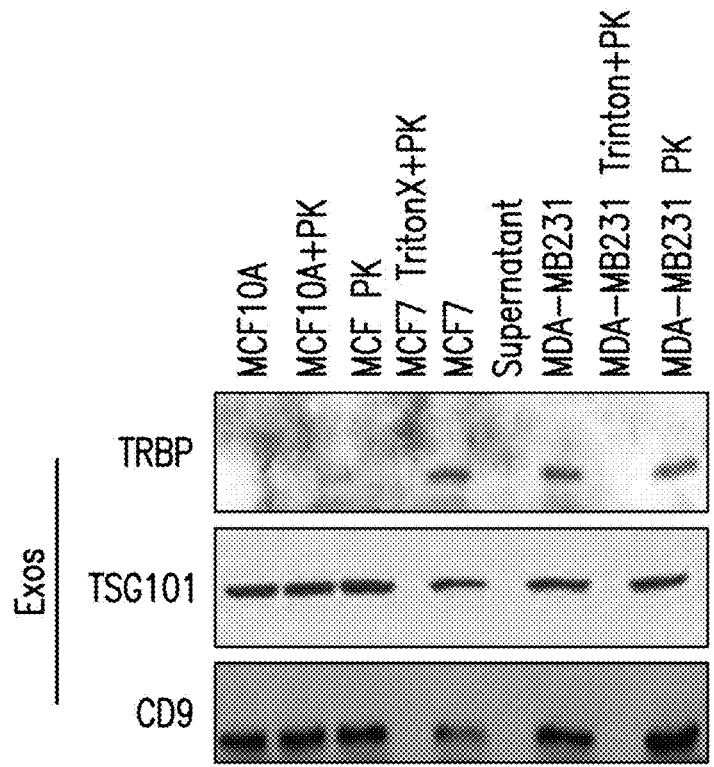
Figure 4I:
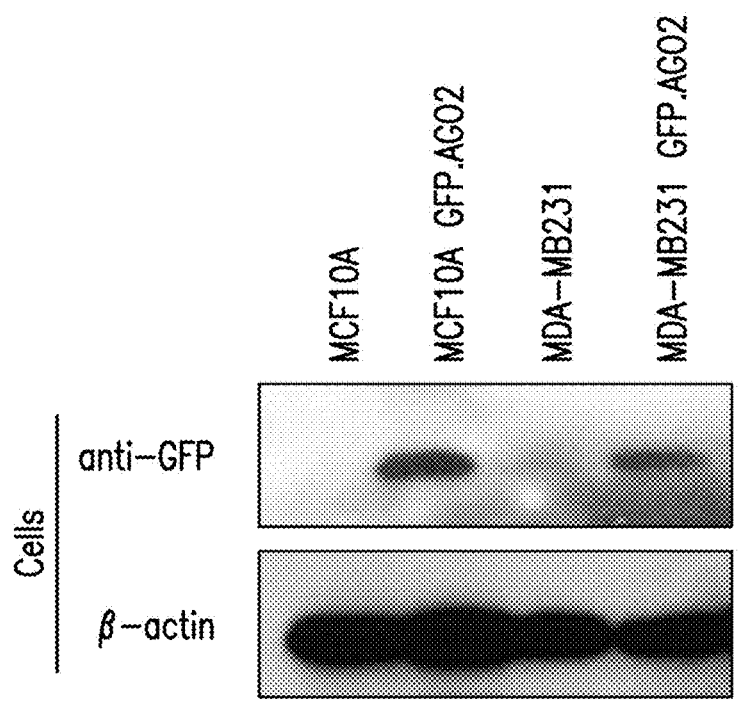
Figure 4J:
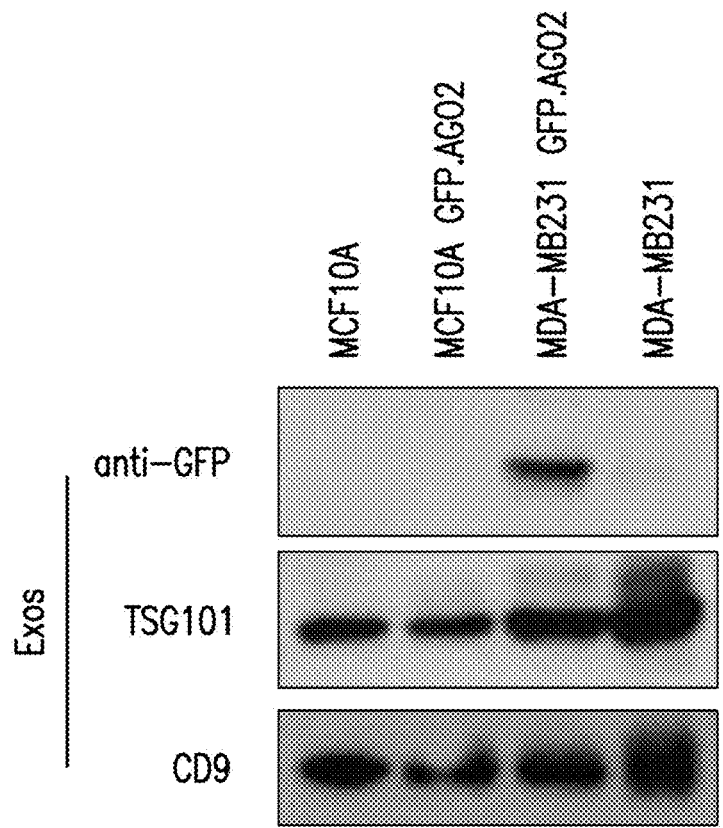
Figure 4K:
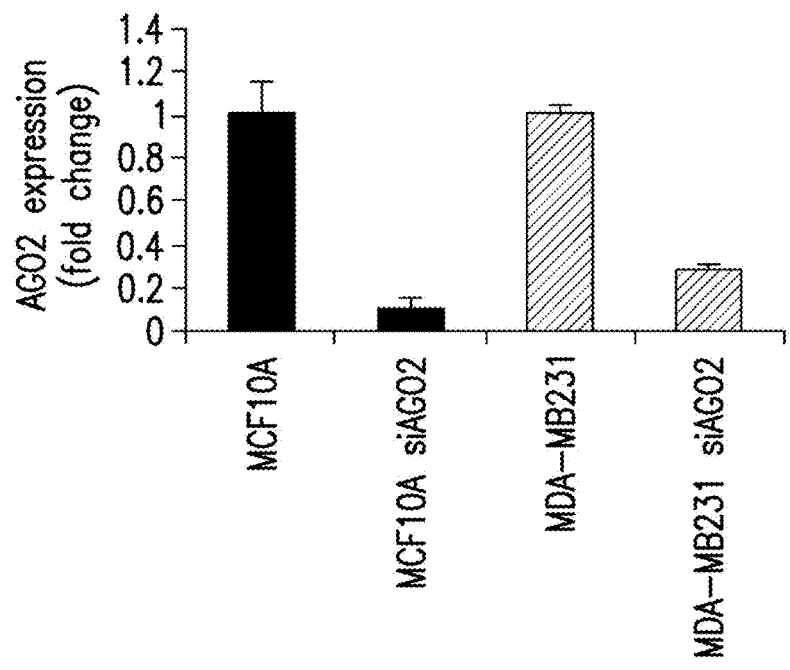
Figure 4L:
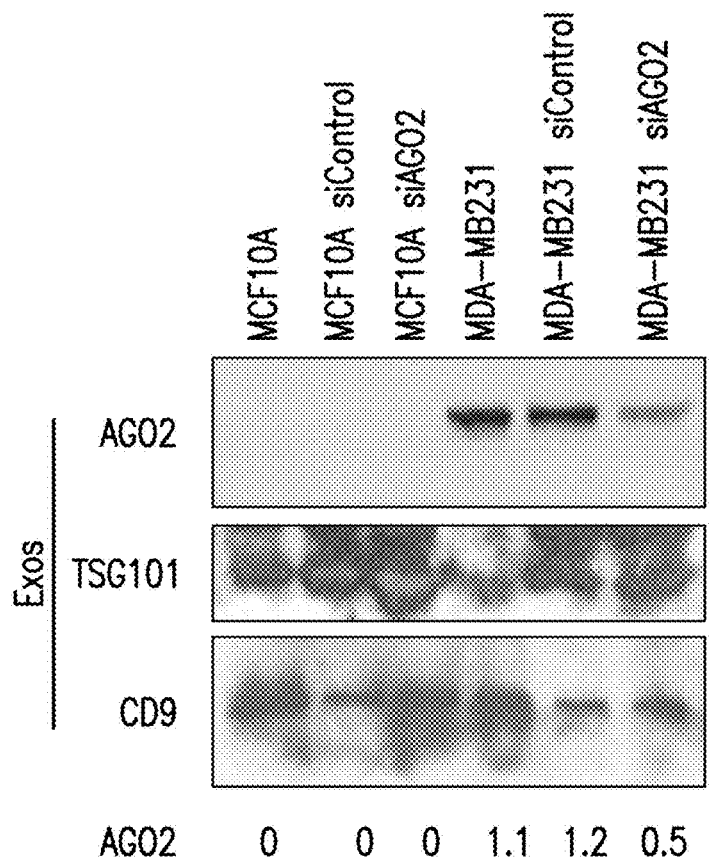
Figure 4M:
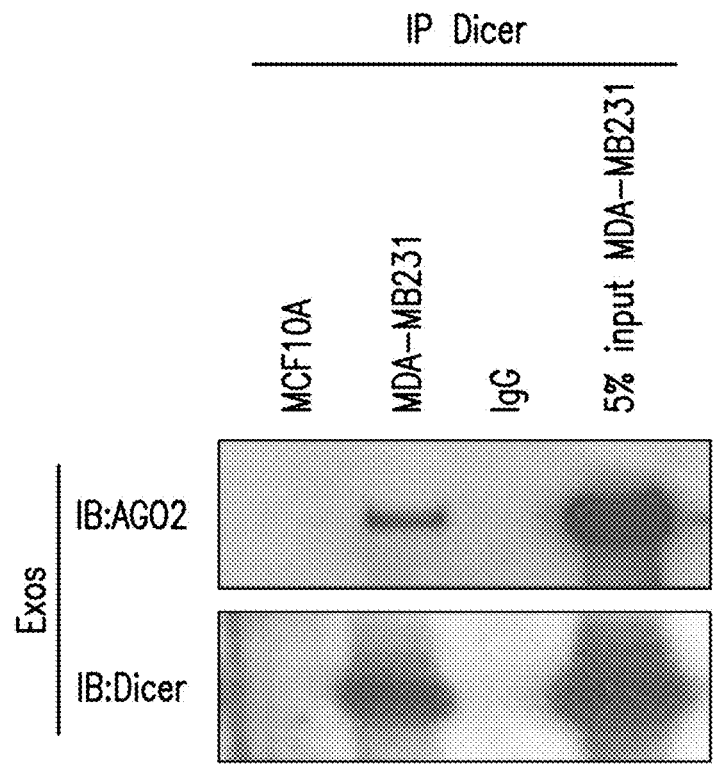
Figure 4N:
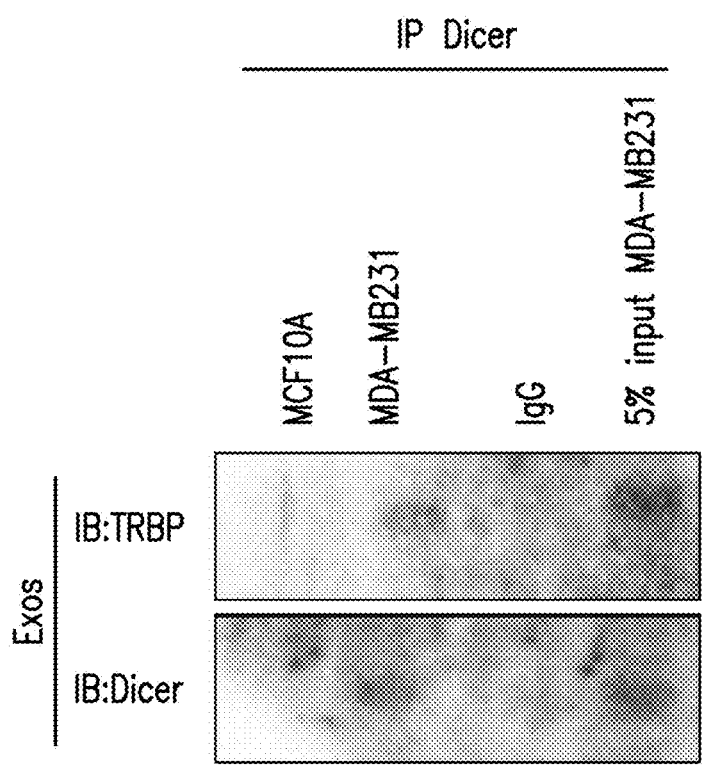

Additionally, RLC proteins, AGO2 and TRBP, were also detected in oncosomes but not in normosomes (FIGS. 4G-H). Exosomes were extracted from MCF10A and MDA-MB231 cells transfected with a GFP tagged AGO2 (FIG. 4I). Using an anti-GFP antibody, the presence of GFP-AGO2 was detected in exosomes extracted from MDA-MB231-GFP-AGO2 cells (FIG. 4J). Upon siRNA silencing of AGO2 in MCF10A and MDA-MB231 cells, a down regulation of AGO2 protein in MDA-MB231 derived oncosomes was observed (FIGS. 4K-L). We showed by immunoprecipitation that AGO2 binds Dicer in oncosomes while both are not detectable in normosomes (FIG. 4M). A fundamental partner that induces stability of Dicer and aids in its pre-miRNA cleavage activity is TRBP (Chendrimada et al., 2005; Melo et al., 2009) Immunoprecipitation revealed the presence of Dicer/TRBP complex in oncosomes but not in normosomes (FIG. 4N).

Figure 13F:
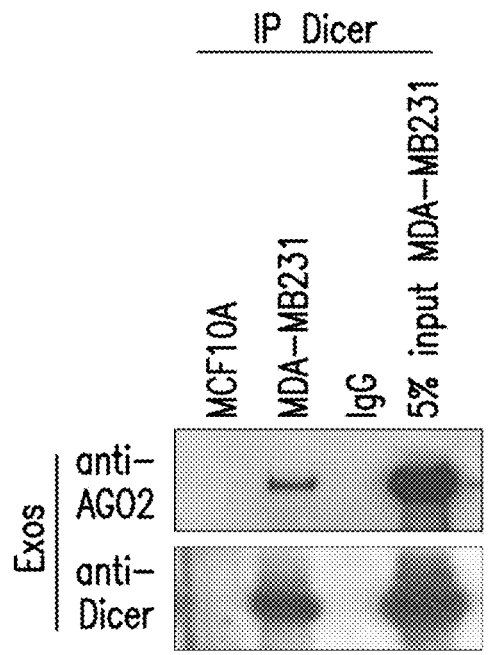
Figure 13G:
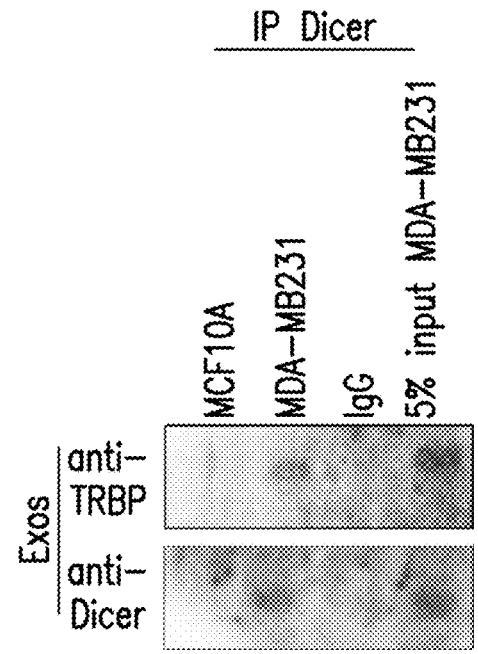
Figure 13H:
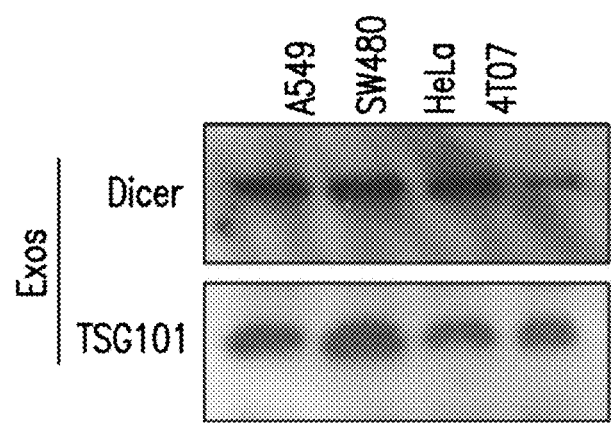

Immunoprecipitation using anti-Dicer antibody revealed that AGO2 binds to Dicer in oncosomes, while both are undetectable in normosomes (FIG. 13F). A fundamental partner that induces stability of Dicer and aids in its pre-miRNA cleavage activity is TRBP (Chendrimada et al., 2005; Melo et al., 2009) Immunoprecipitation with anti-Dicer antibody revealed the presence of Dicer/TRBP complex in oncosomes but not in normosomes (FIG. 13G).

Oncosomes Use RLC to Process Pre-miRNAs to Generate Mature miRNAs.

Figure 5A:
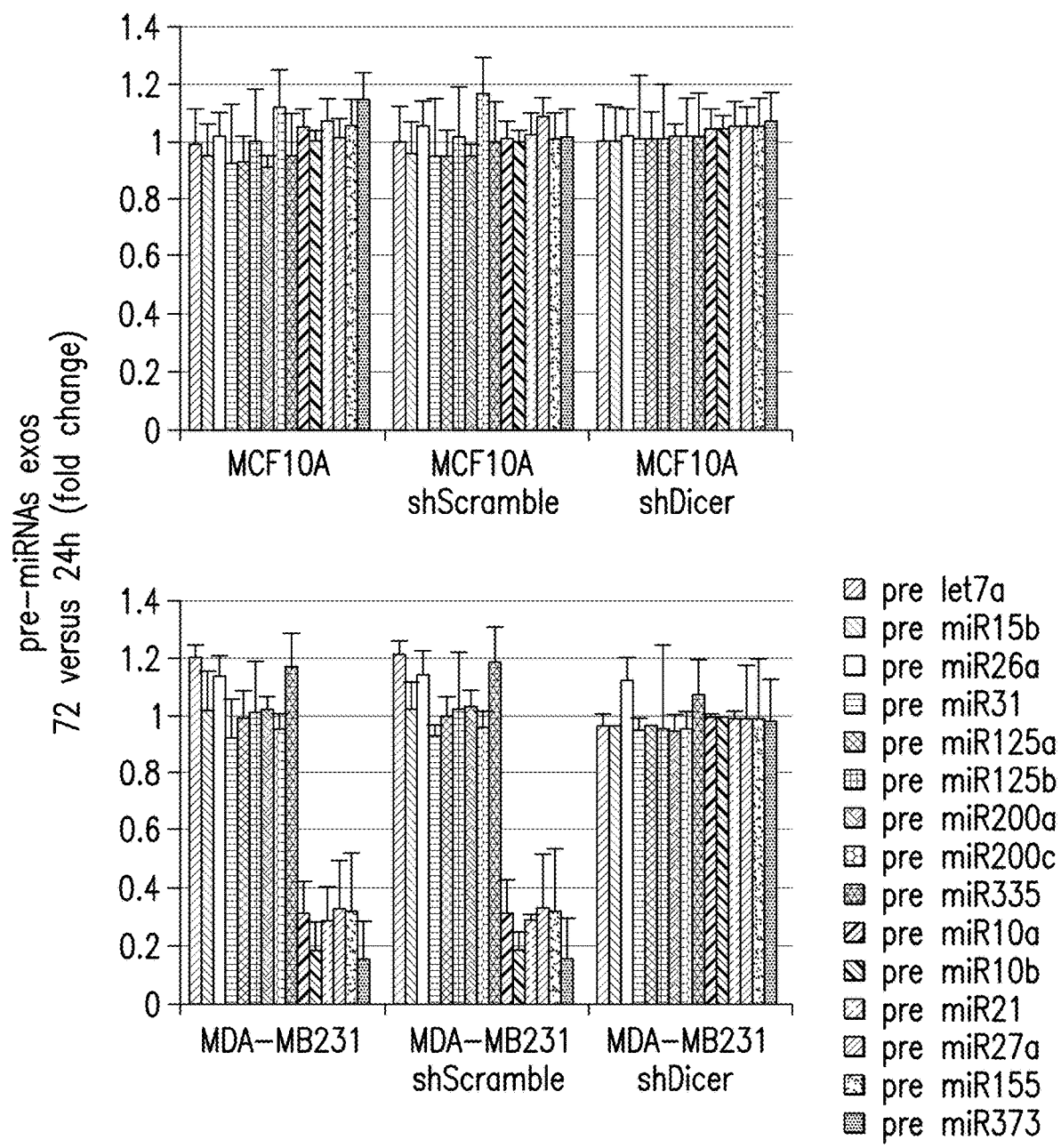
FIGS. 5A-E. Oncosomes process pre-miRNAs to generate mature miRNAs. (A) Exosomes were harvested from MCF10A, MCF10A shScramble, MCF10A shDicer cells (upper graph), MDA-MB231, MDA-MB231 shScramble and MDA-MB231 shDicer cells (lower graph) and maintained under cell-free culture conditions for 24 and 72 h. After 24 and 72 h exosomes were recovered and 15 pre-miRNAs were quantified by qPCR. Graphs show the fold-change of each pre-miRNA in the different exosomes after 72 h of cell-free culture relative to 24 h cell-free culture and are represented as ±s.d. (B) Exosomes were harvested from MCF10A, MCF10A shScramble, MCF10A shDicer cells (upper graph), MDA-MB231, MDA-MB231 shScramble and MDA-MB231 shDicer cells (lower graph) and maintained under cell-free culture conditions for 24 and 72 h. After 24 and 72 h exosomes were extracted once again and 15 miRNAs were quantified by qPCR. Graphs show the fold-change of each miRNA in the different exosomes after 72 h of cell-free culture relative to 24 h cell-free culture and are represented as ±s.d. (C) Immunoblot using antirabbit and anti-mouse secondary antibody to detect heavy chain (HC) and light chain (LC) primary Dicer antibody and primary Actin antibody electroporated in exosomes of MDA-MB231 cells. Electroporated exosomes without antibody derived from MDA-MB231 cells were used as negative control. Proteinase K treatments were performed after electroporation to ensure depletion of antibodies not included in exosomes. (D) Oncosomes (MDA-MB231) were harvested in duplicate (bottom graph) or quadruplicate (top graph). Samples were electroporated with anti-Dicer antibody, anti-actin antibody, or anti-TRBP antibody. The samples plus control were left in cell-free culture conditions for 24 and 72 h. After 24 and 72 h exosomes were extracted once again and the 6 oncogenic pre-miRNAs (top graph) or 15 pre-miRNAs (bottom graph) were quantified by qPCR. The fold-change of each pre-miRNA in exosomes after 72 h cell-free culture was quantified relative to the same pre-miRNA in exosomes after 24 h cell-free culture in each sample. The graphical plots represent an average fold-change for pre-miRNAs (in bottom graph–TS=tumor suppressor; ONC=oncogenic) in 72 h exosomes relative to 24 h exosomes and are represented as ±s.d. (E) Oncosomes (MDAMB231) were harvested in quadruplicate (top graph) or duplicate (bottom graph). Samples were electroporated with anti-Dicer antibody, anti-actin antibody, or anti-TRBP antibody. The samples plus control were left in cell-free culture conditions for 24 and 72 h. After 24 and 72 h exosomes were extracted once again and the 6 oncogenic miRNAs (top graph) or 15 miRNAs (bottom graph) were quantified by qPCR. The fold-change of each miRNA in exosomes after 72 h cell-free culture was quantified relative to the same miRNA in exosomes after 24 h cell-free culture in each sample. The graphical plots represent an average fold-change for the miRNAs (in bottom graph–TS=tumor suppressor; ONC=oncogenic) in 72 h exosomes relative to 24 h exosomes and are represented as ±s.d.
Figure 5B:
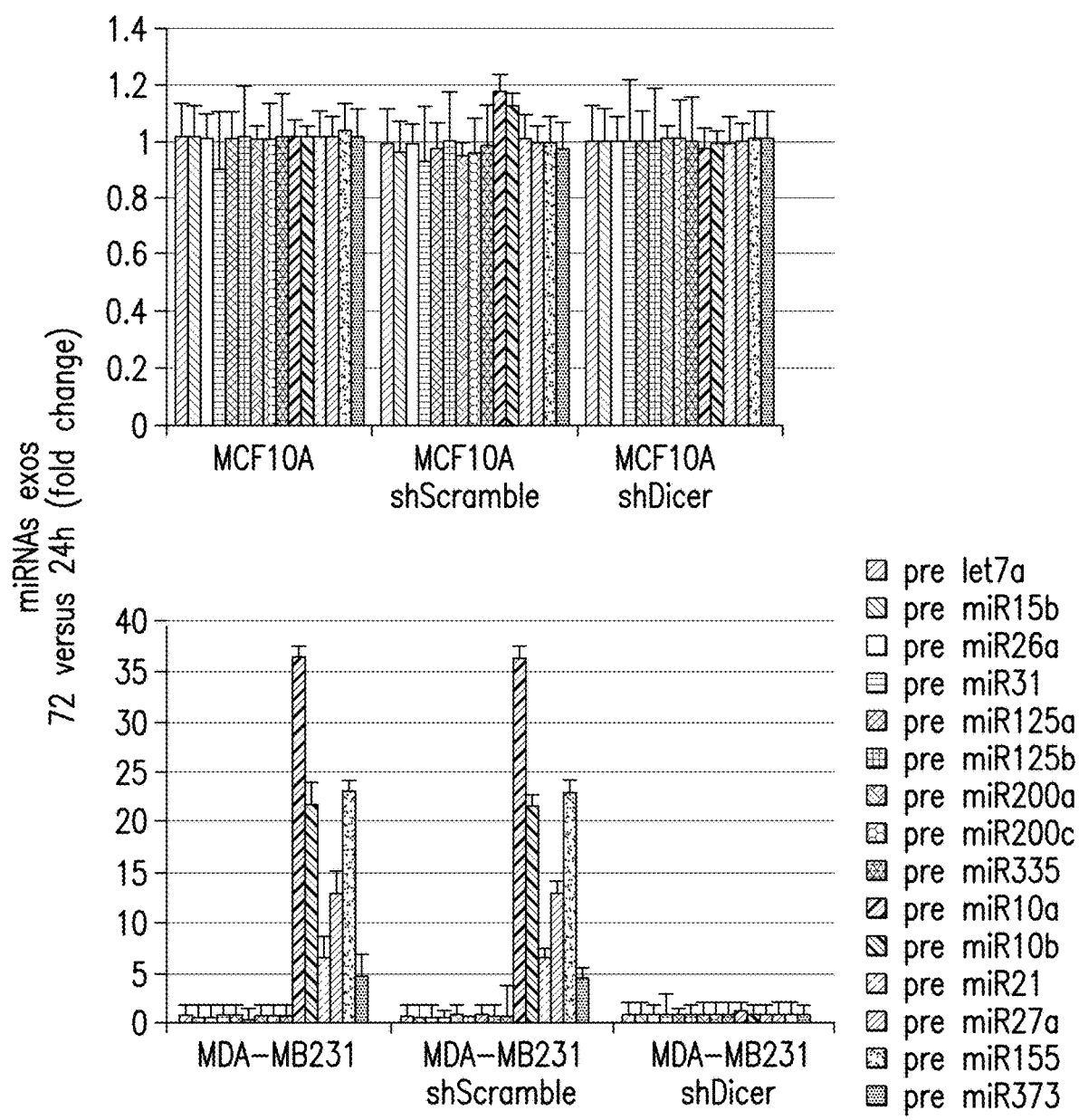
Figure 5C:
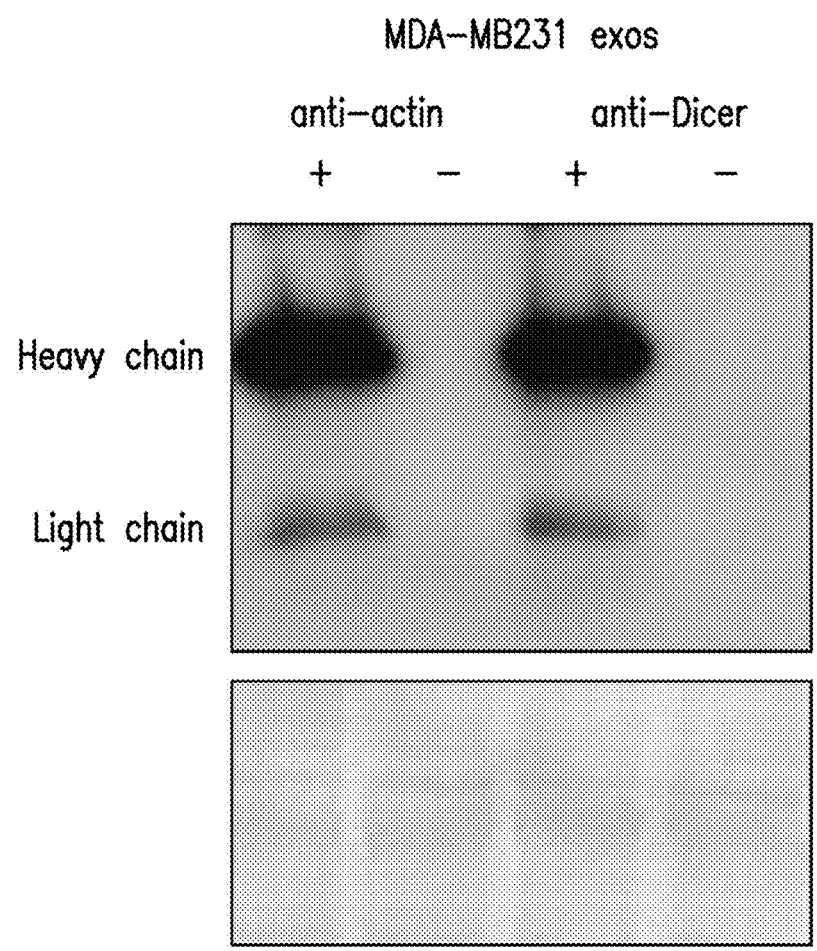
Figure 5D:
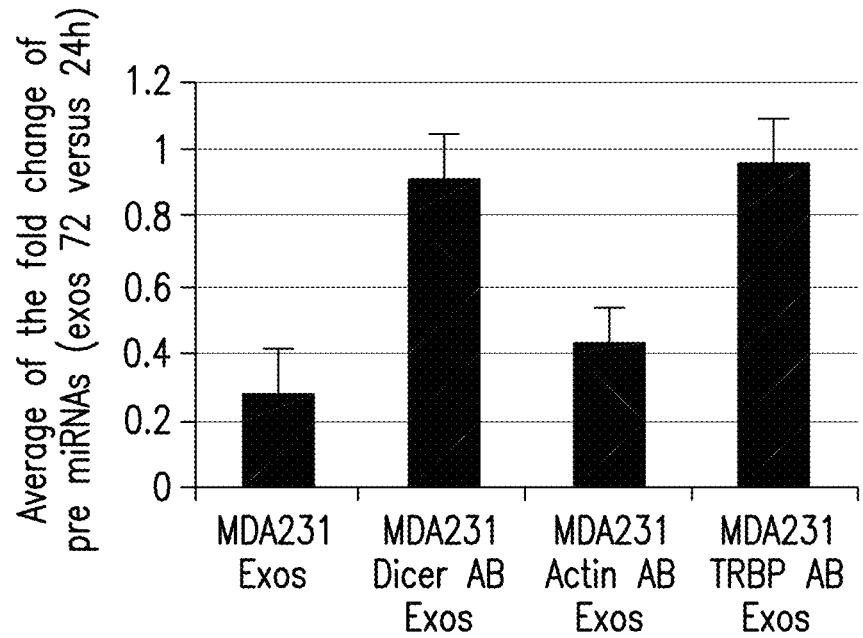
Figure 5D:
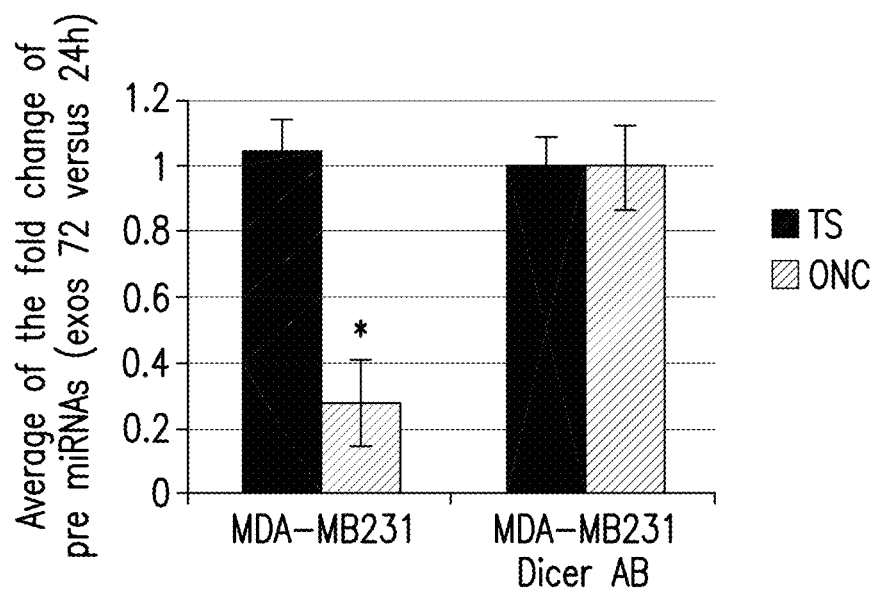
Figure 5E:
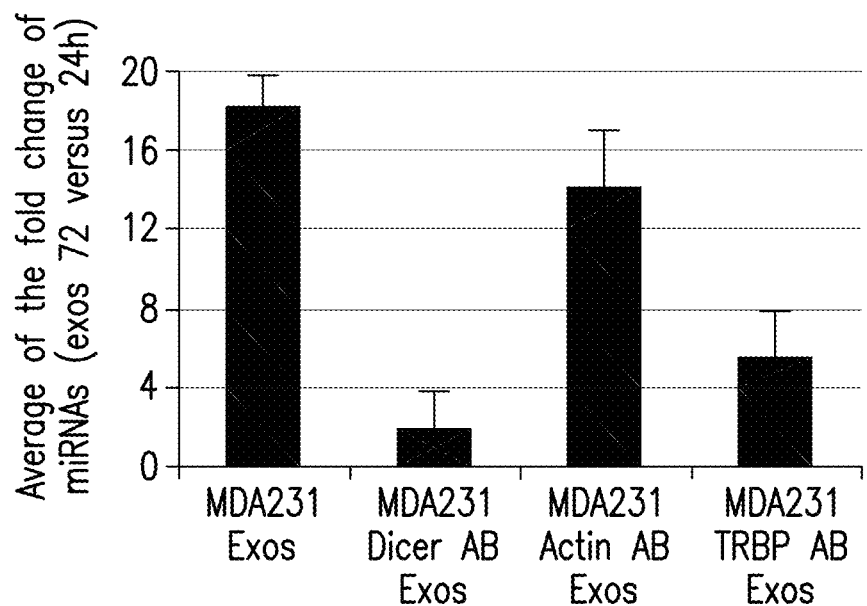
Figure 5E:
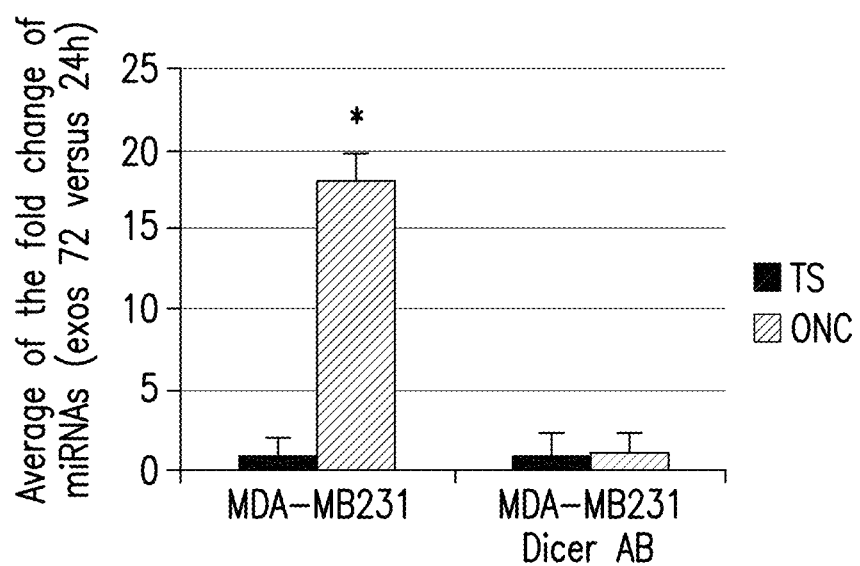
Figure 14A:
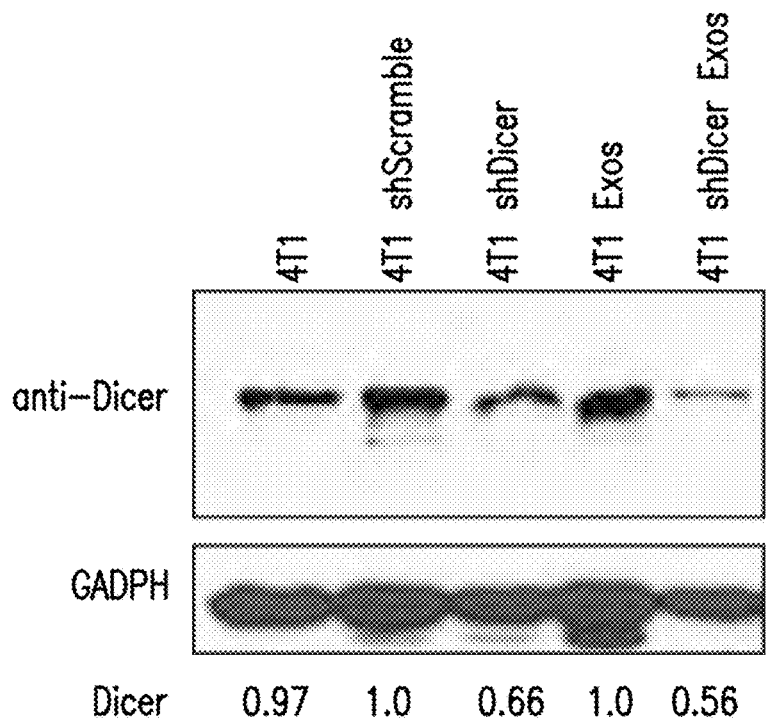
Figure 14B:
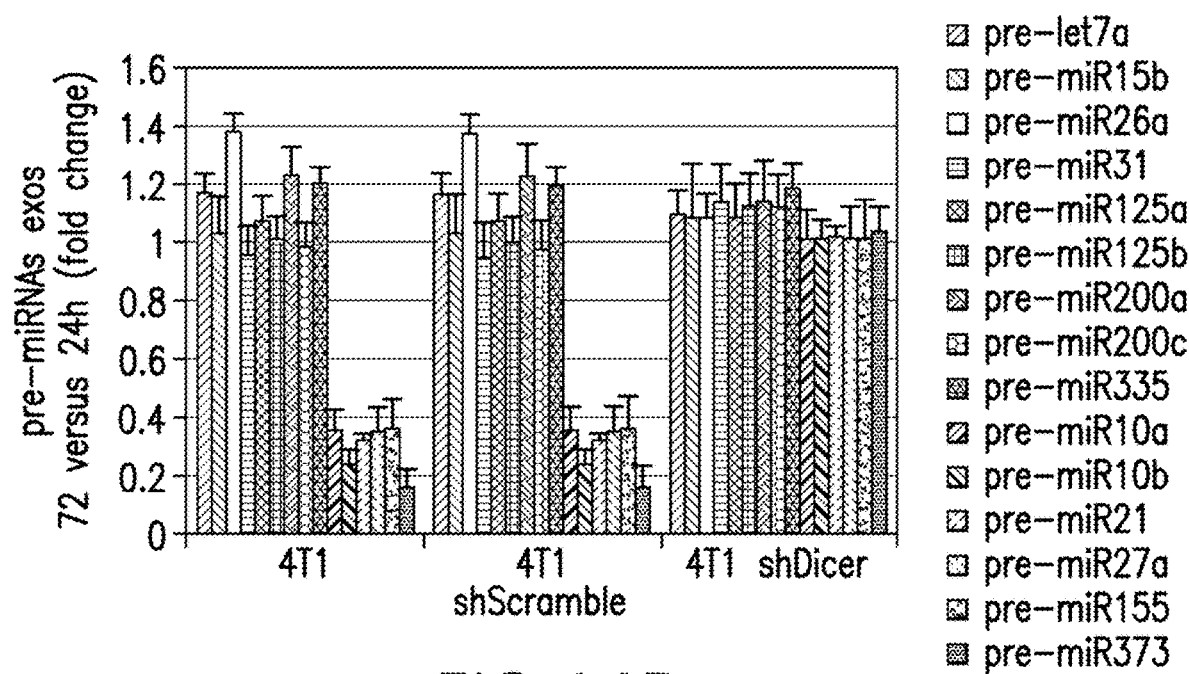
Figure 14C:
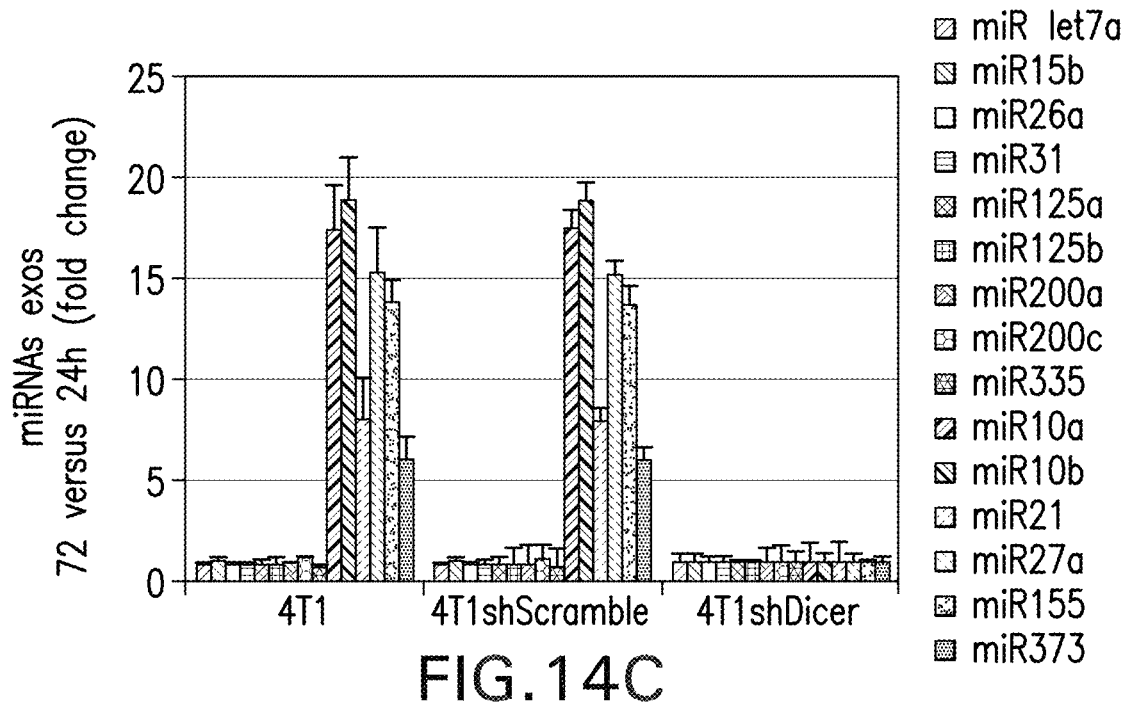
Figure 14D:
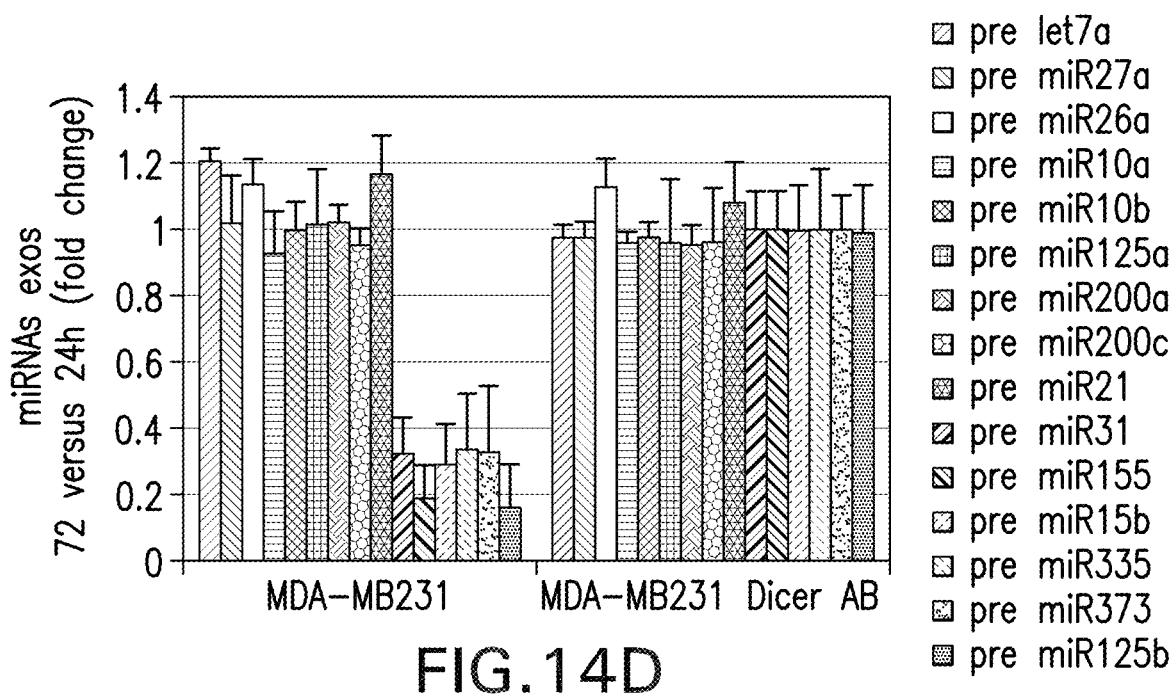
Figure 14E:
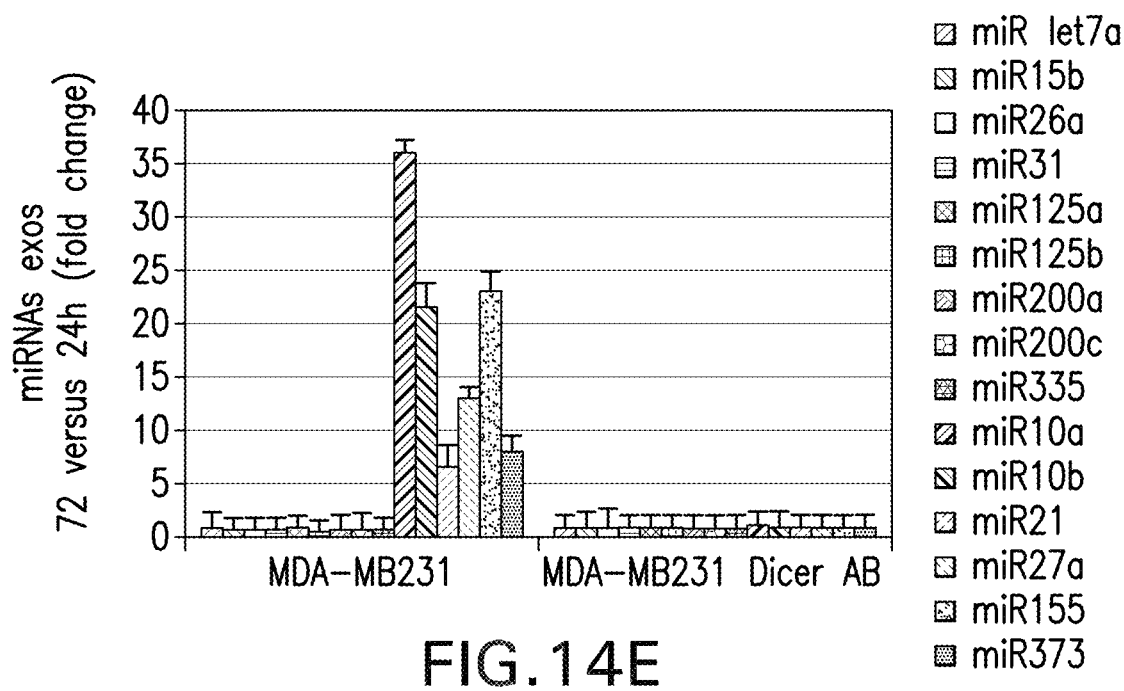
Figure 14F:
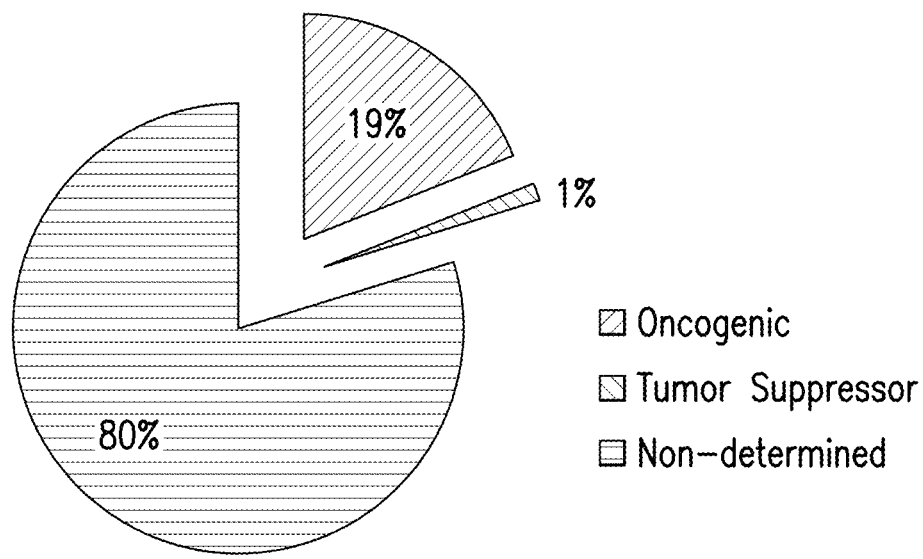

The functionality of RLC proteins (the dicing and silencing properties) in oncosomes was tested to generate mature miRNA from pre-miRNA. Exosomes that lacked Dicer were extracted from the MCF10AshDicer, MDA-MB231shDicer and 4T1shDicer cells (FIG. 14A). Pre-miRNAs and miRNAs content did not reveal any significant changes in the Dicer down regulated exosomes with time, indicating that the pre-miRNAs were not processed to generate miRNA in absence of Dicer in oncosomes (FIGS. 5A-B and FIGS. 14B-C). Next, anti-Dicer and anti-TRBP antibodies was inserted into exosomes by electroporation and compared to oncosomes and normosomes electroporated with an anti-actin control antibody treated with proteinase K after electroporation to avoid the presence of antibodies outside exosomes (FIG. 5C). Oncosomes electroporated with the control anti-actin antibody showed the same variations in pre-miRNA and mirNA levels as previously mentioned (FIGS. 5D-E and FIGS. 14D-E). In oncosomes with anti-Dicer and anti-TRBP antibodies, insignificant changes in levels of pre-miRNA and miRNA were observed with time, suggesting an inhibition of pre-miRNA processing (FIGS. 5D-e and FIGS. 14D-E). Total miRNA content was assessed by miRNA expression arrays of oncosomes (MDA-MB-231 derived), anti-Dicer antibody electroporated oncosomes (MDA-MB231 derived) and normosomes (MCF10A derived) after 72 h of cell-free culture. The total miRNA content of oncosomes with anti-Dicer antibody more closely resembled that of MCF10A normosomes ($R^2=0.79$) than MDA-MB231 derived oncosomes ($R^2=0.48$). When comparing oncosomes with oncosomes containing anti-Dicer antibody, 198 differentially expressed miRNAs were observed, 48% of which were significantly down regulated (Table 6). Of these, 19% are oncogenic while only 1% were reported to possess tumor suppressive properties based on previously published literature (FIG. 14F, Table 6).

Figure 6A:
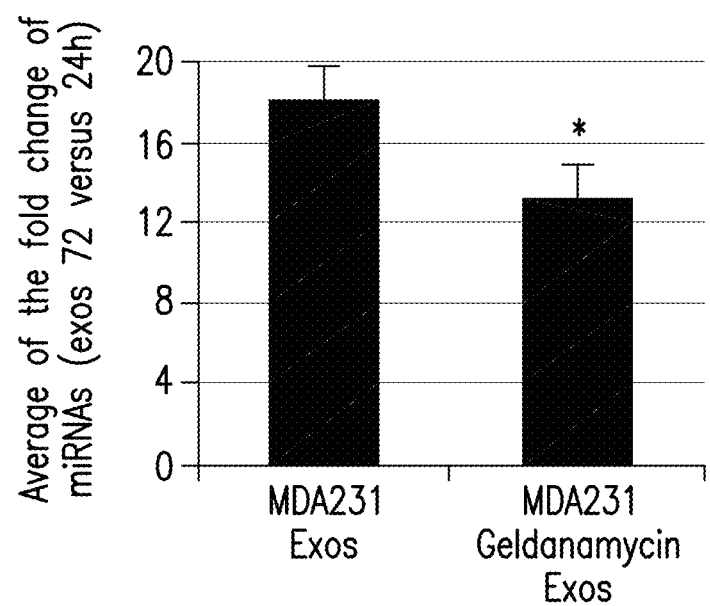

It is known that the enzymatic reaction that transforms a pre-miRNA into a mature miRNA is spontaneous and does not require any factors beyond the three RLC proteins, incorporated pre-miRNA, and Hsp90, a protein present in exosomes (Maniataki and Mourelatos, 2005; McCready et al., 2010). To further confirm this, oncosomes were electroporated with Geldanamycin, a drug that selectively inhibits Hsp90 activity (Miyata, 2005). A significant decrease in the amount of mature miRNAs synthesized in the presence of Geldanamycin was found when compared to controls (FIG. 6A). The effect of Hsp90 proteins on mature miRNA expression could be mediated via two potentially overlapping processes: an active role in aiding AGO2 activity in miRNA biogenesis and stabilization of mature miRNAs bound to AGO2 proteins in the RISC.

Figure 6B:
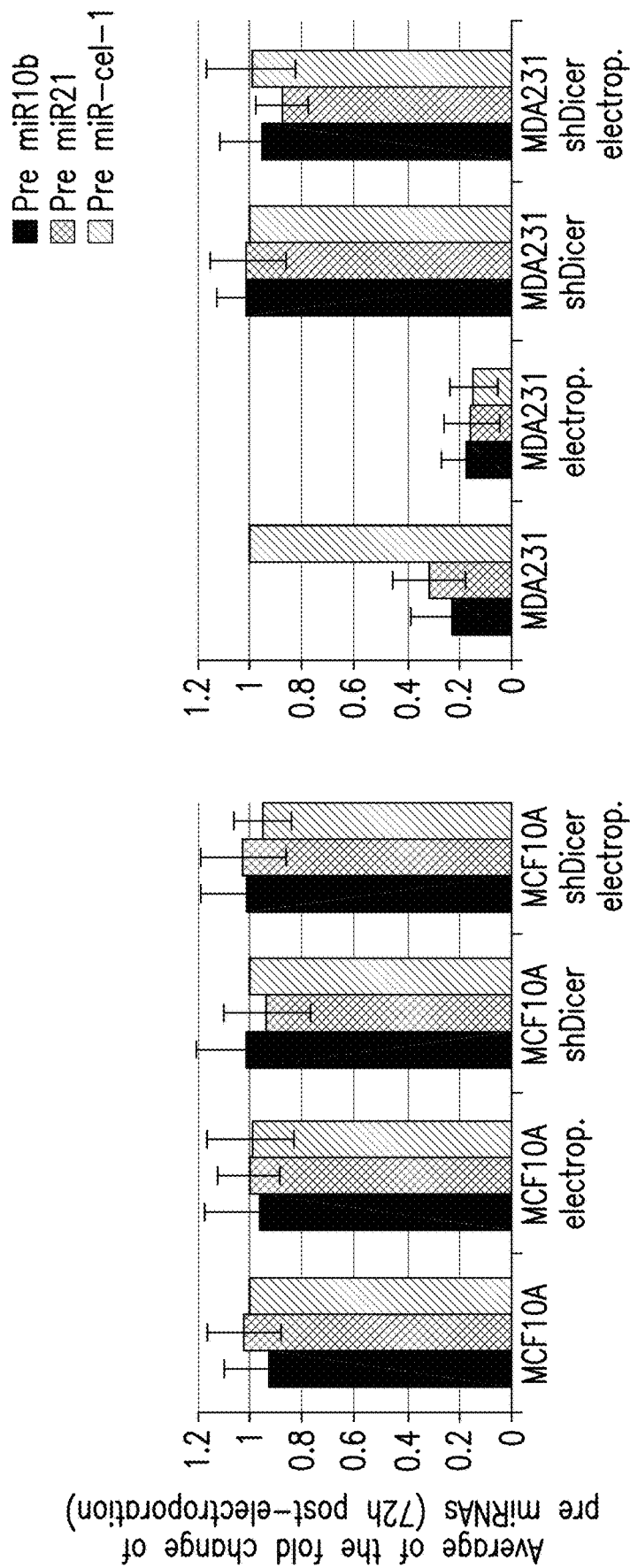
Figure 6C:
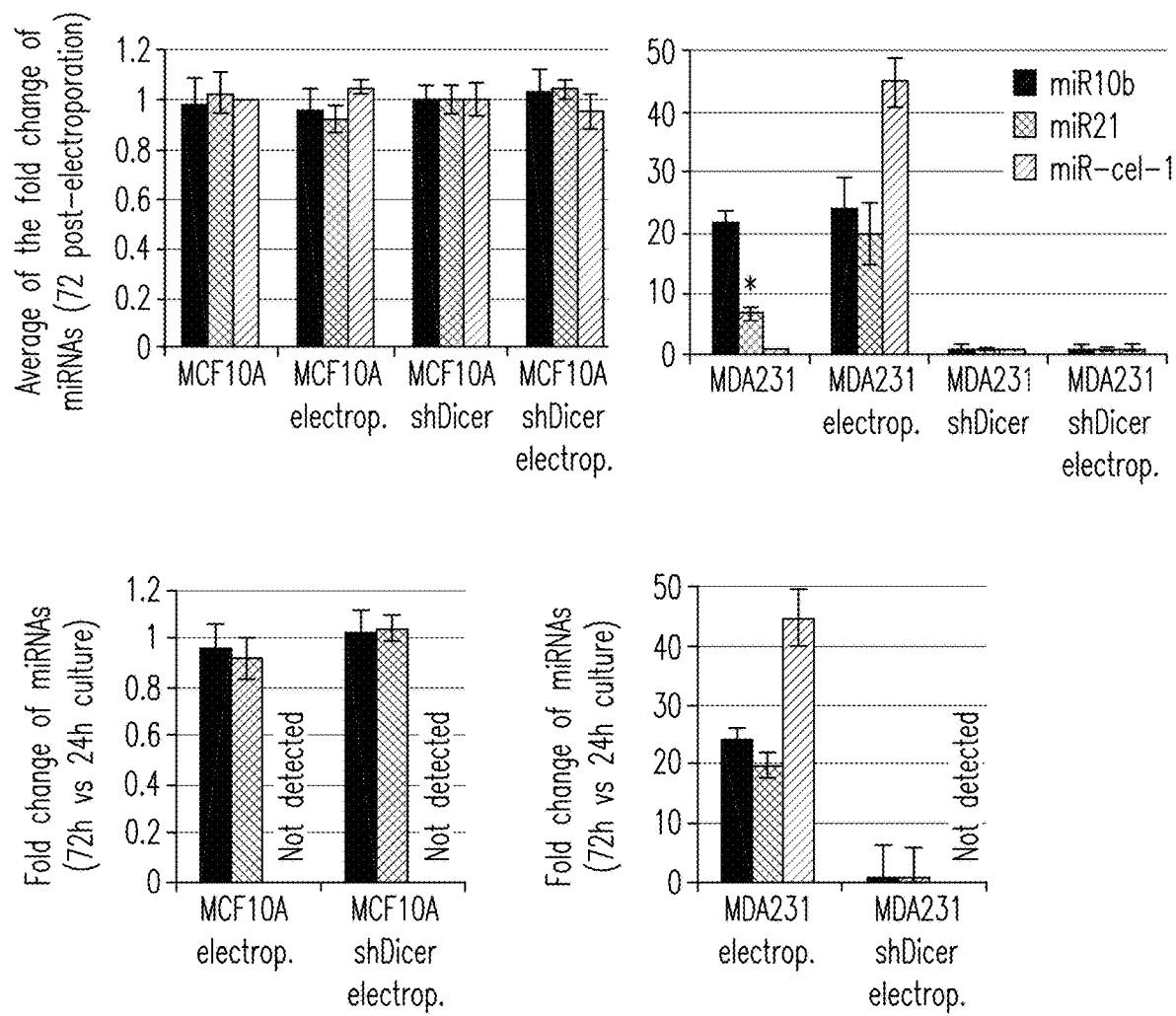

To further confirm the specific pre-miRNA processing capability of oncosomes, synthetic pre-miRNAs-10b and -21 as well as the C. elegans precursor pre-cel-1 pre-miRNA were electroporated into exosomes to study their processing (FIG. 15A). Significant down regulation of the pre-miRNAs and up-regulation of their respective miRNAs was observed in oncosomes after 72 h culture (FIGS. 6B-C). Oncosomes with Dicer antibody did not reveal a difference in pre-miRNA content after 72 h culture (FIGS. 6B-C). Oncosomes derived from shDicer cells did not reveal a difference in pre-miRNA content after 72 h culture (FIGS. 6B-C). Additionally, pre-miR-10b, -21 and -cel-1 were internally labeled with biotin-deoxythymidine (dT) and transfected them into MCF10A cells. The dT-modified pre-miRNAs were processed and resulted in the generation of mature miRNAs, confirmed the labeling did not alter their processing potential (FIGS. 15B-C). The modified pre-miRNAs were used in 'dicing' assays to show that Dicer containing exosomes were specifically capable of processing pre-miRNA and generate mature miRNAs (FIGS. 6D-F).

Cytoplasmic CD43 in Cancer Cells Contributes to Mobilization of Dicer.

Figure 16A:
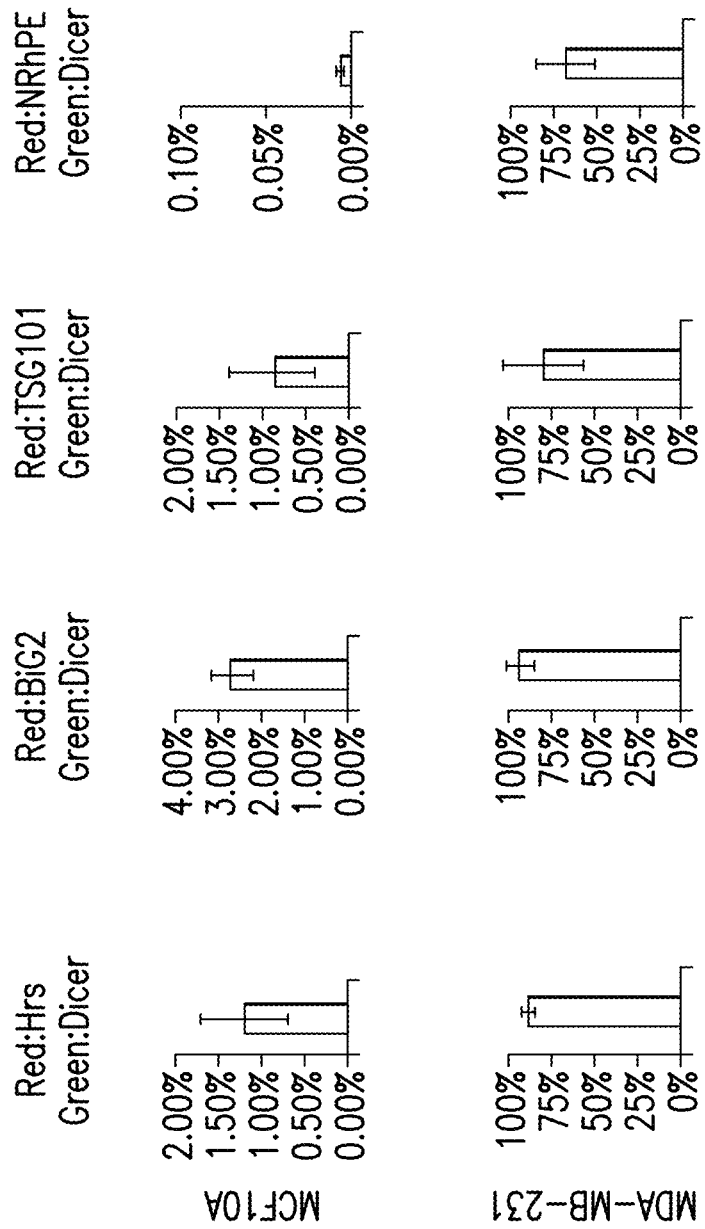
Figure 16B:
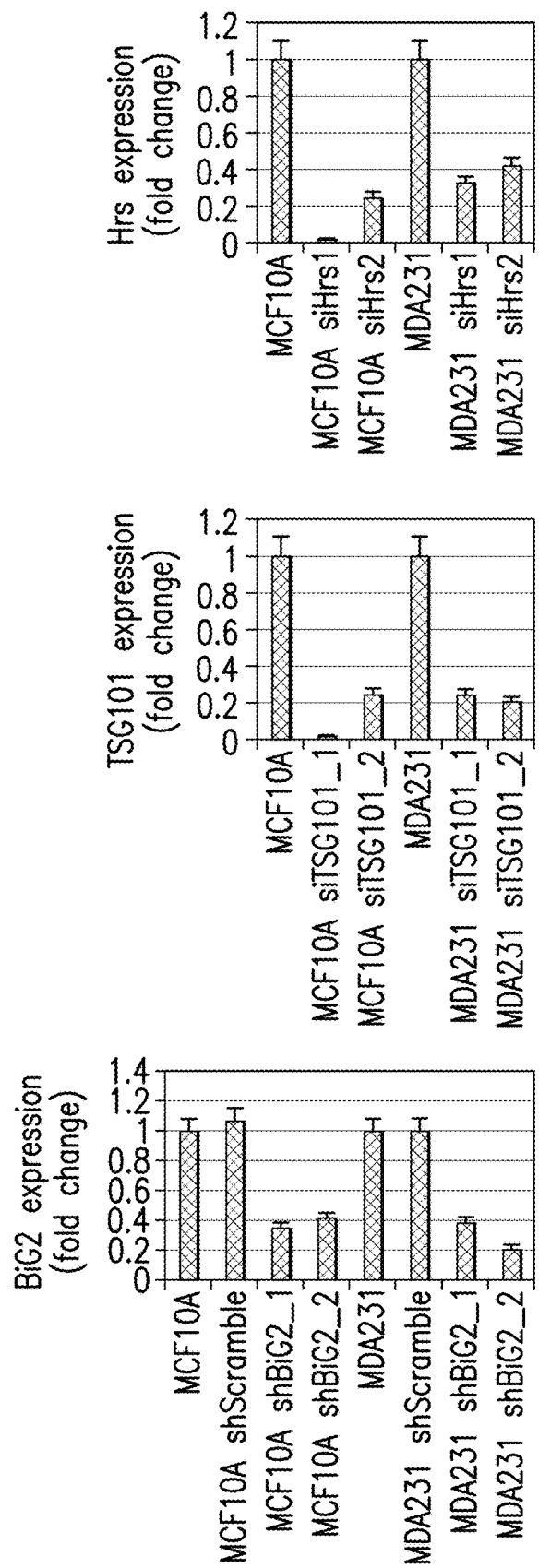
Figure 16C:
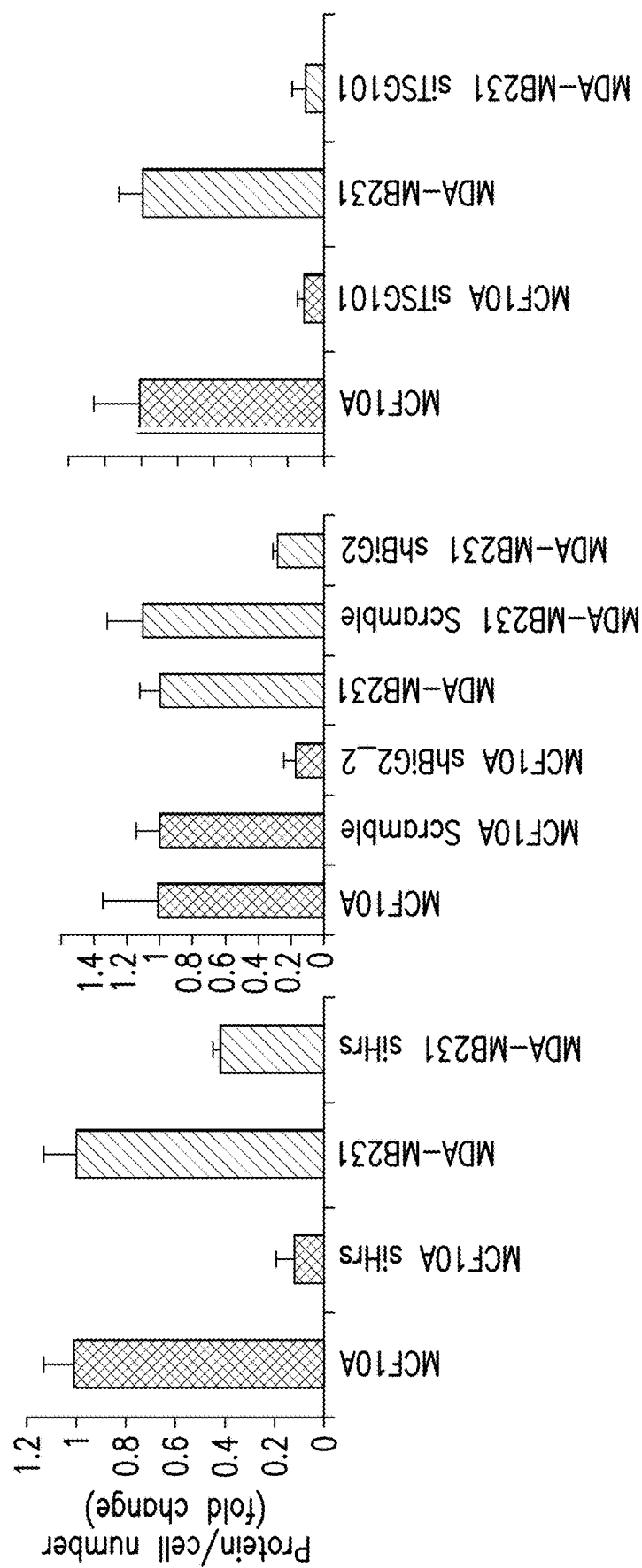
Figure 16D:
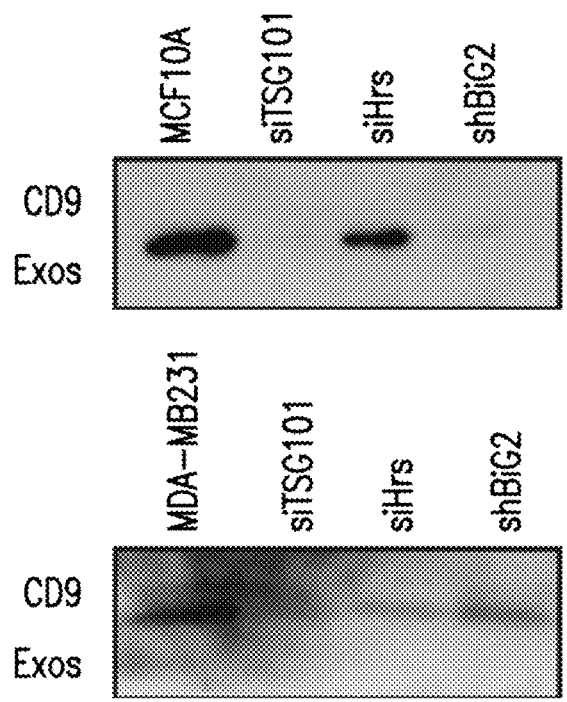
Figure 16E:
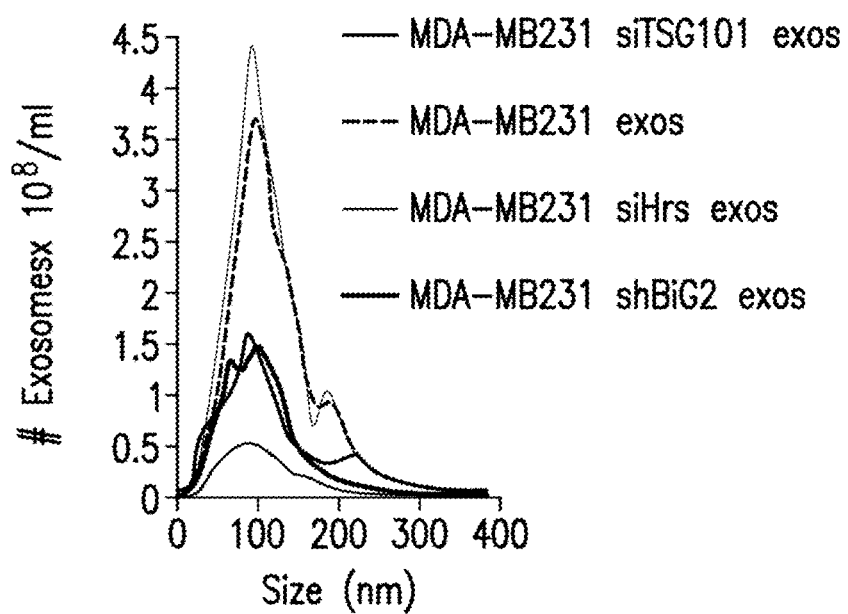
Figure 16F:
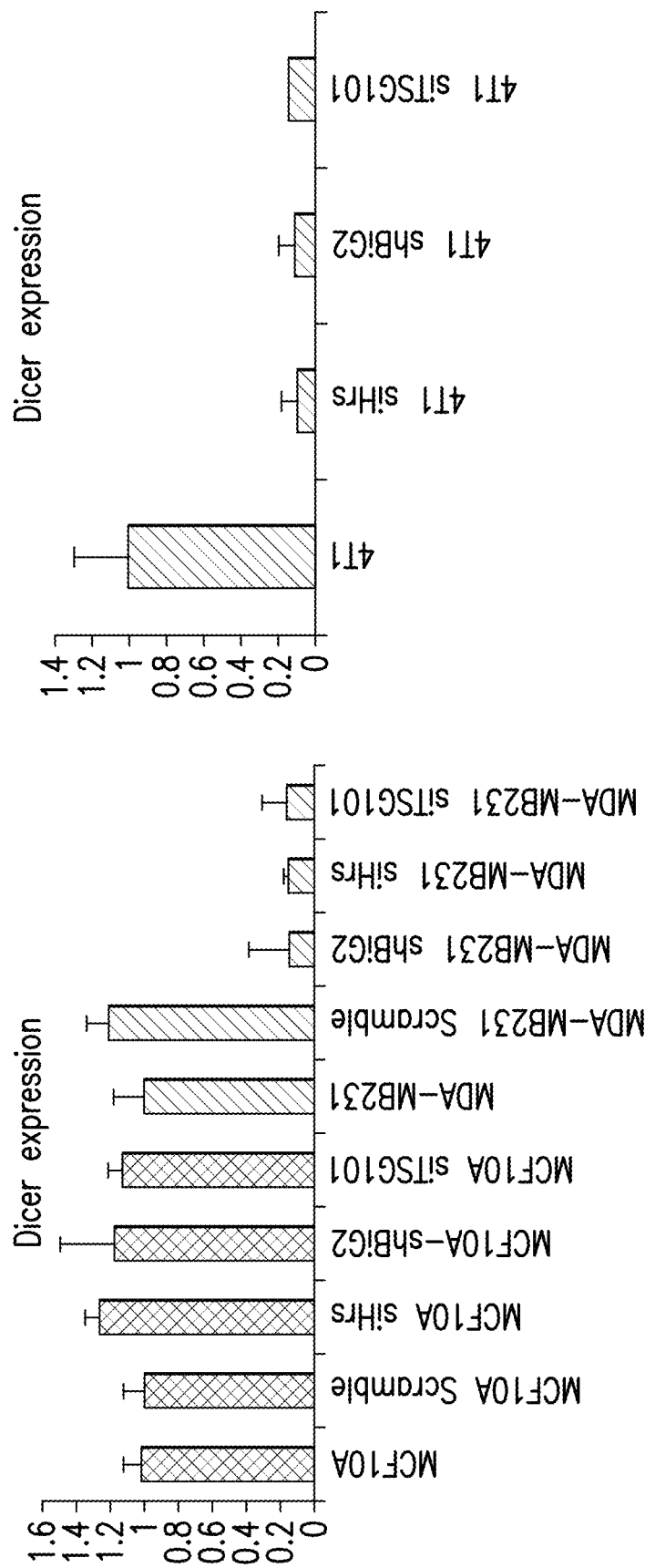

Multivesicular bodies (MVBs) are cellular organelles that contain endosomes that are released eventually as exosomes upon fusion with the plasma membrane (Pant et al., 2012). A possible mechanism that allows the recruitment of RISC proteins into endosomes and their subsequent release into exosomes was explored. First, whether Dicer associates with MVBs in cancer cells when compared to control cells was explored. The cellular distribution of Dicer in conjunction with markers of MVBs and exosomes biogenesis pathway was compared. Hrs and BiG2 are early endosome markers and TSG101 is a marker for MVBs (Razi and Futter, 2006; Shin et al., 2004). Dicer co-localized with Hrs, BiG2 and TSG101 in MDA-MB231 and 4T1 cells (FIG. 16A). Exogenously delivered N-rhodamine-labelled phosphotidylethanolamine (NRhPE) is taken up by cells and retained within MVBs (Sherer et al., 2003). Dicer staining in MDA-MB231 and 4T1 cells mostly co-localized with NRhPE in MVBs, which eventually generate exosomes. These data are in agreement with previous observations in co-fractionation studies were Dicer, TRBP and AGO2 appeared in late endosomes/MVB fractions (Shen et al., 2013). In contrast, there was no co-localization of Dicer with Hrs, BiG2, TSG101 or NRhPE in control cells (NMuMG and MCF10A) (FIG. 16A). Further, Hrs and TSG101 genes were silenced using two different siRNAs, as well as BiG2 using two different shRNAS, in MDA-MB231 and MCF10A cells, and Dicer protein expression was evaluated (FIG. 16B). Silencing of Hrs, BiG2 and TSG101 impairs MVBs formation and led to down regulation of exosomes production (FIGS. 16C-E). Increased Dicer protein was observed in the cytoplasm and nucleus of MDA-MB231 cells with siHrs, shBiG2 or siTSG101. Similar results were obtained when 4T1 cells were used instead of MDA-MB231 cells. When Hrs, BiG2 or TSG101 genes were silenced in MCF10A cells, altered Dicer protein expression and location (cytoplasm) was not observed. Interestingly, Dicer mRNA expression was decreased in siHrs, shBiG2 and siTSG101 MDA-MB231 and 4T1 cells (FIG. 16F). This could represent a negative feedback loop between the amount of Dicer protein in the cell and its transcription levels. These results suggest that exosomes-mediated export of Dicer protein is potentially a rate-limiting step for depletion of Dicer in cancer cells. Impaired MVB formation led to Dicer protein accumulation throughout the cytoplasm and nucleus, without increasing Dicer transcription levels.

Figure 16G:
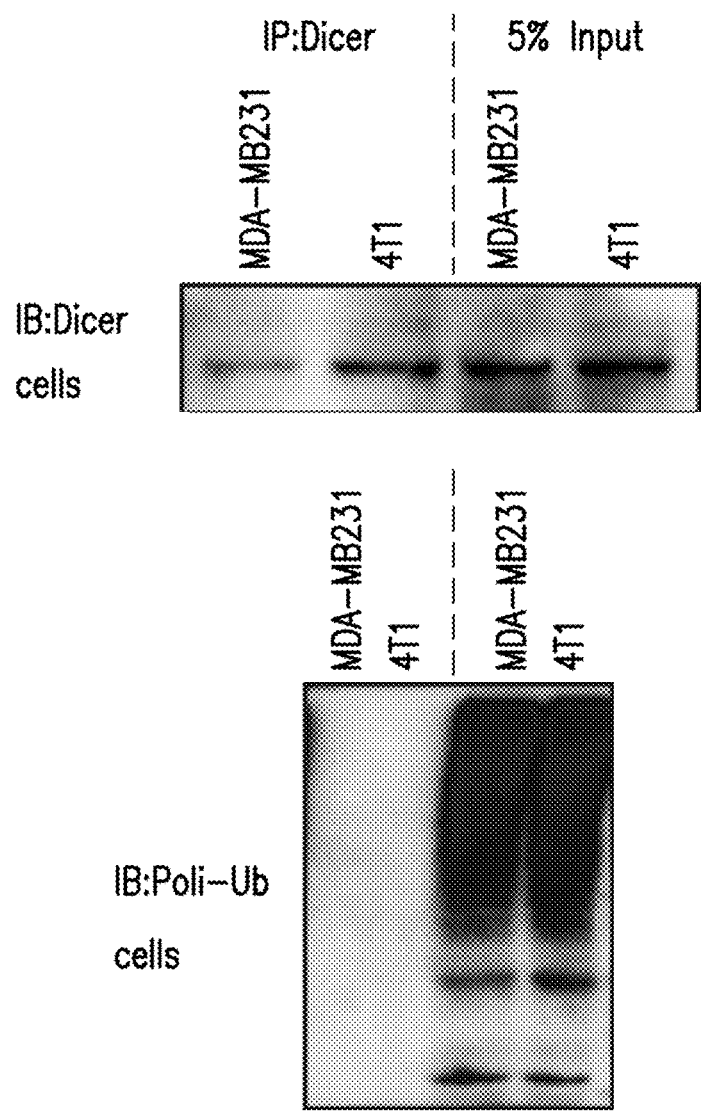
Figure 16H:
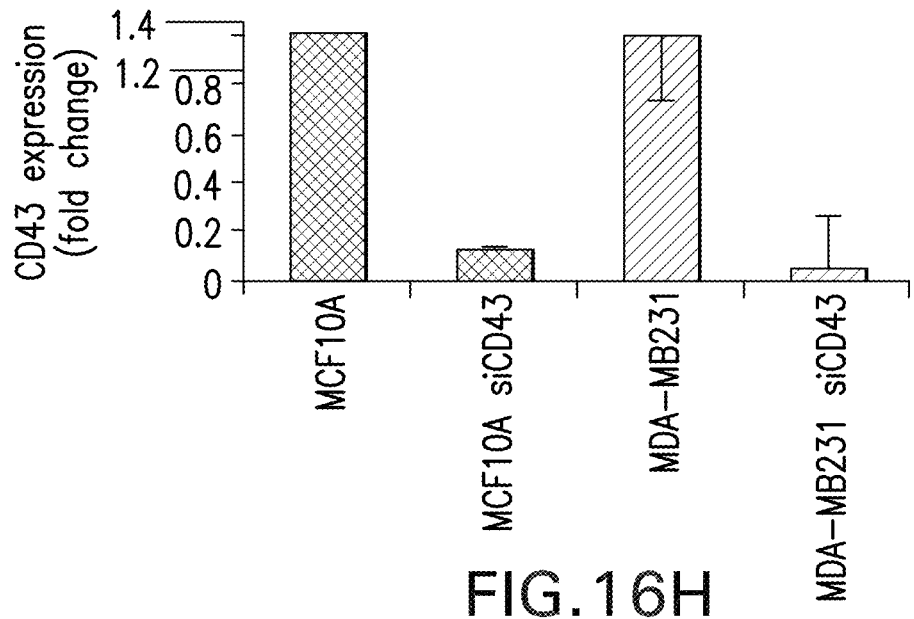

MVBs also sequester ubiquitinylated proteins for subsequent degradation by lysosomes (Luzio et al., 2009). We have shown that Dicer protein is not ubiquitinated and does not co-localize with LAMP-1, a widely used marker for lysosomes. These results suggest that Dicer is not targeted for degradation in cancer cells but rather secreted via exosomes (FIG. 16G).

Figure 9A:
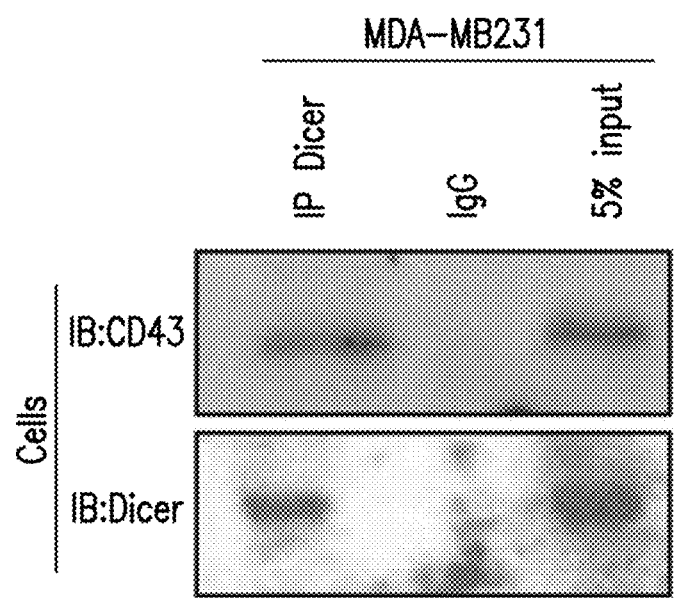
FIGS. 9A-B. Dicer is present in multivesicular bodies and cytoplasmic CD43 mobilizes Dicer into exosomes. (A) Immunoblot of CD43 in protein extracts of MDA-MB231 cells immunoprecipitated with Dicer antibody (IP Dicer) or with IgG (upper panel, right and middle lanes, respectively). Dicer alone immunoblot was used as control (lower panel). (B) Immunoblot of Dicer in protein extracts of MDA-MB231 derived exosomes and MDA-MB231 siCD43 derived exosomes. CD9 immunoblot was used as a loading control. Quantification was done using Image J software.
Figure 9B:
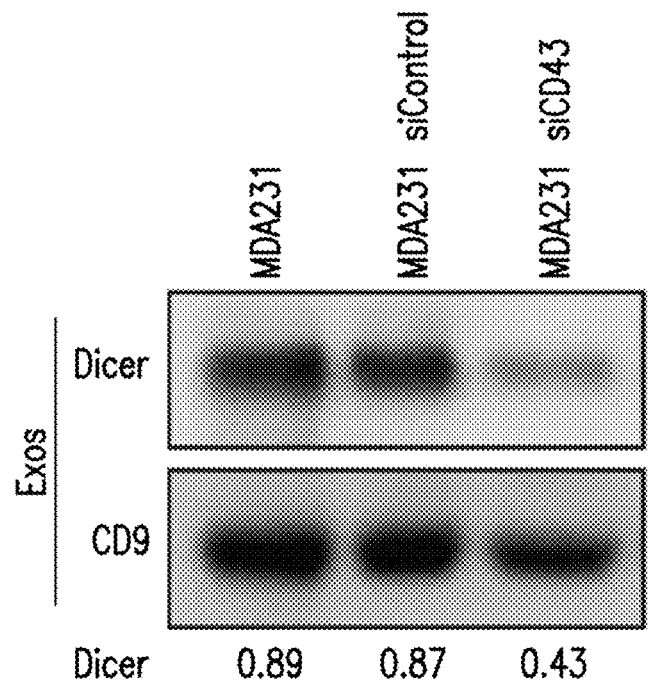
Figure 16I:
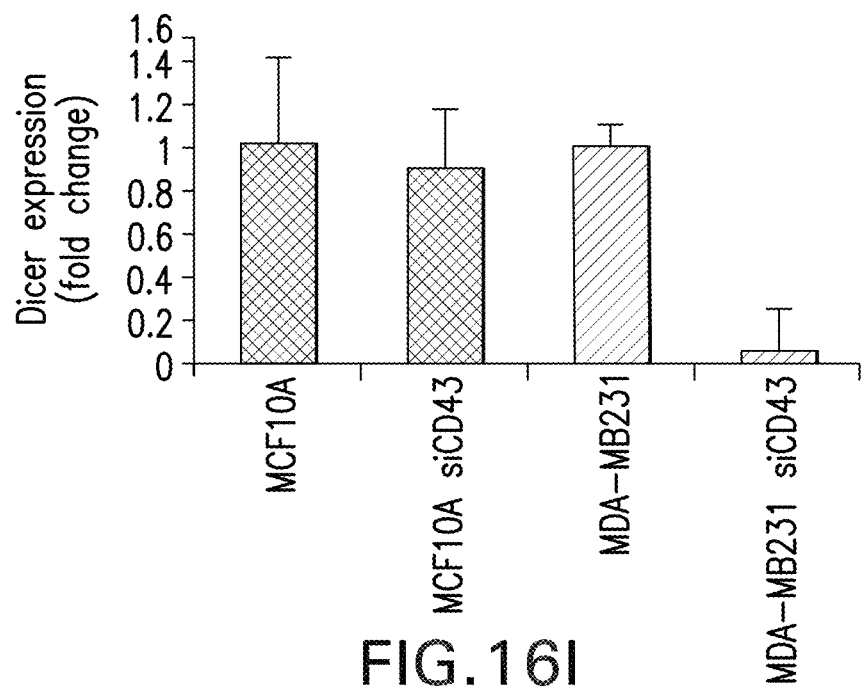

The signals that target proteins to MVBs and exosomes are largely unknown. Recently, a variety of plasma membrane anchor proteins, such as CD43, were speculated as likely mediators of protein transport into MVBs and exosomes (Shen et al., 2011b). CD43 is predominantly a leukocyte transmembrane sialoglycoprotein, which is expressed highly in cancer cells (in its truncated cytoplasmic form) and not in control cells (Shelley et al., 2012). CD43 is detected in many solid tumors including breast cancer, where it correlates with cancer progression and metastasis (Shelley et al., 2012). We explored whether CD43 might contribute to the transportation of RISC proteins to MVBs. We show that Dicer immunoprecipitates with CD43 protein in MDA-MB231 cells (FIG. 9A). When CD43 is down regulated using siRNA in MCF10A and MDA-MB231 cells, Dicer levels significantly decrease in oncosomes (FIGS. 9B and 16H), with a nuclear and cytoplasmic accumulation of Dicer protein. A down regulation of Dicer mRNA expression was observed in MDA-MB231siCD43 cancer cells but not in MCF10AsiCD43 non-tumorigenic cells, as also observed before with siHrs, shBiG2 and siTSG101 (FIG. 16I).

Oncosomes Alter the Transcriptome of Target Cells in a Dicer-Dependent Manner.

Figure 17A:
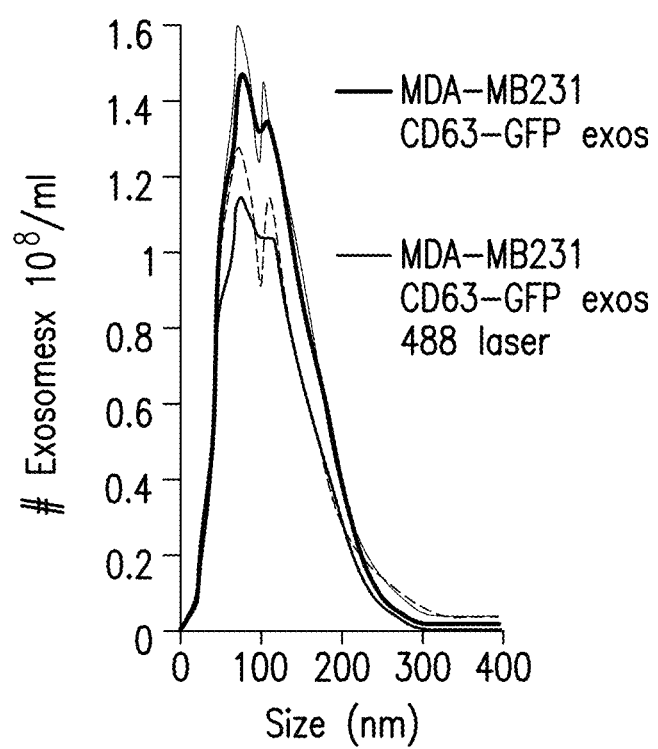

Cancer cells (MDA-MB231 cells) were transfected with CD63-GFP, a marker for exosomes (Escola et al., 1998). The CD63-GFP MDA-MB231 cells were used to isolate GFP+ exosomes, which were subsequently incubated with MCF10A cells. Exosomes from MDA-MB231-CD63-GFP were shown to be green by using NanoSight complemented with a laser beam that detects particles emitting green fluorescence (FIG. 17A). The CD63-GFP+ oncosomes were shown to enter MCF10A cells, where they appeared in the cytoplasm. Using miRNA expression arrays, it was shown that MCF10A cells exposed to MDA-MB231 derived oncosomes acquire a new miRNA expression profile distinct from the parental MCF10A cells and resembling MDA-MB231 cells. Using miRNA expression arrays, it was shown that MCF10A cells exposed to MDA-MB-231-derived oncosomes acquire a new miRNA expression profile distinct from the parental MCF10A cells. Global transcriptome profiling of MCF10A treated with oncosomes more closely resembles MDA-MB231 cells. Such significant alterations in the mRNA expression profile is reversed when MCF10A cells are exposed to MDA-MB231 oncosomes with Dicer antibody, and the expression pattern re-clusters with the parental MC10A cells.

Figure 7A:
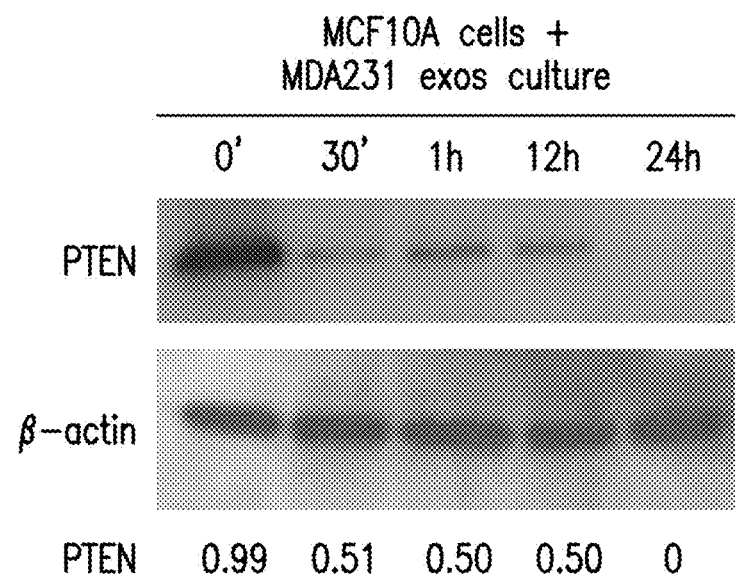
FIGS. 7A-H. Oncosomes induce transcriptome alterations in recipient cells and tumor formation in a Dicer-dependent manner (A) Immunoblot using anti-PTEN antibody and protein extracts of MCF10A cells treated for 0, 30 min, 1h, 12 h and 24 h with MDA-MB231 oncosomes after cell-free culture. Beta actin was used as a loading control. (B) Immunoblot using anti-HOXD10 antibody and protein extracts of MCF10A cells treated for 0, 30 min, 1h, 12 h and 24 h with MDA-MB231 oncosomes after cell-free culture conditions. Beta actin was used as a loading control. (C) Graph showing luciferase reporter activity in MCF10A cells transiently transfected with 3'UTR-PTEN-WT, 3'UTRPTEN-Mut, 3'UTR-HOXD10-WT and 3'UTR-HOXD10-Mut and treated with oncosomes derived from MDA-MB231 cells. (D) Immunoblot using anti-PTEN antibody (upper panel) and anti-HOXD10 antibody (middle panel) and protein extracts from MCF10A cells treated for 0, 30 min, 1 h, 12 h and 24 h with MDAMB231 oncosomes electroporated with Dicer antibody after cell-free culture conditions. Beta actin was used as a loading control. (E) Immunoblot using anti-Smad4 antibody (upper panel) and protein extracts of MCF10A cells and MCF10A cells treated with MDA-MB231 exosomes with anti-miR-182-5p and MDA-MB231 exosomes with no cell-free culture time. Beta actin was used as a loading control. (F) Cell viability measured by MTT assay during 5 days of culture of MCF10A cells, MCF10A cells treated with MDA-MB231 exosomes with no cell-free culture time (MCF10A+ MDA231 exos), MCF10A cells treated with MDA-MB231 exosomes with cell-free culture time (MCF10A cells+ MDA231 exos culture) and MCF10A cells treated with MDA-MB231 exosomes electroporated with Dicer antibody with cell-free culture time (MCF10A cells+MDA231 exos Dicer AB) and are represented as ±s.d. *p=0.0027. (G) The colony formation assay shows formation of colonies in culture plate and labeled with MTT reagent after 8 days MCF10A cells culture, MCF10A cells treated with MDA-MB231 exosomes with no cell-free culture time (MCF10A+ MDA231 exos), MCF10A cells treated with MDA-MB231 exosomes with cell-free culture time (MCF10A cells+ MDA231 exos culture) and MCF10A cells treated with MDA-MB231 exosomes electroporated with Dicer antibody with cell-free culture time (MCF10A cells+MDA231 exos Dicer AB). (H) Top graph: MCF10A cells, MCF10A cells exposed to MDA-MB-231 oncosomes (MCF10A cells+ MDA231 exos culture), MCF10A cells exposed to MDA-MB23 loncosomes electroporated with Dicer antibody (MCF10A cells+MDA231 exos Dicer AB) and MCF10A cells exposed to MDAMB23 loncosomes electroporated with Actin antibody (MCF10A cells+MDA231 exos Actin AB) were orthotopically injected into the mammary pads of athymic nude mice. Graph depicts tumor volume with respect to time and are represented as ±s.d. *p=0.005. Bottom graph: MCF10A cells, MDA-MB231 cells and MCF10A cells exposed to oncosomes (MDA-MB231) were orthotopically injected in the mammary pads of athymic nude mice. Graph depicts tumor volume with respect to time.
Figure 7B:
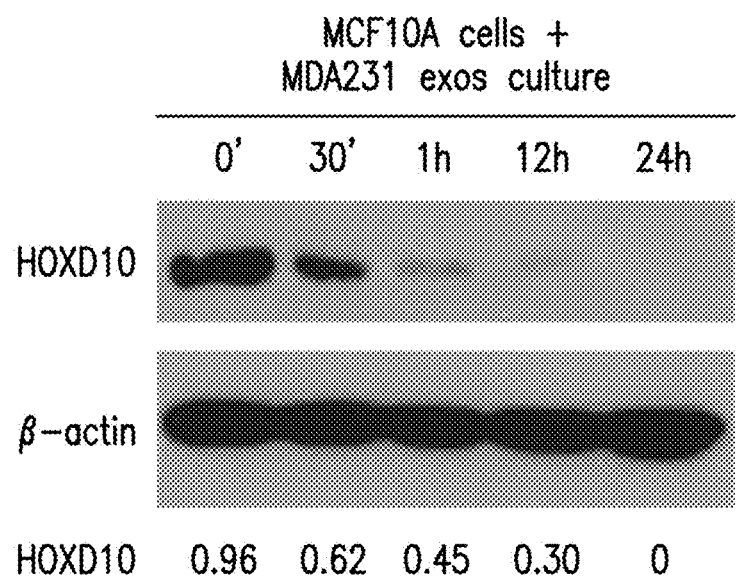
Figure 7C:
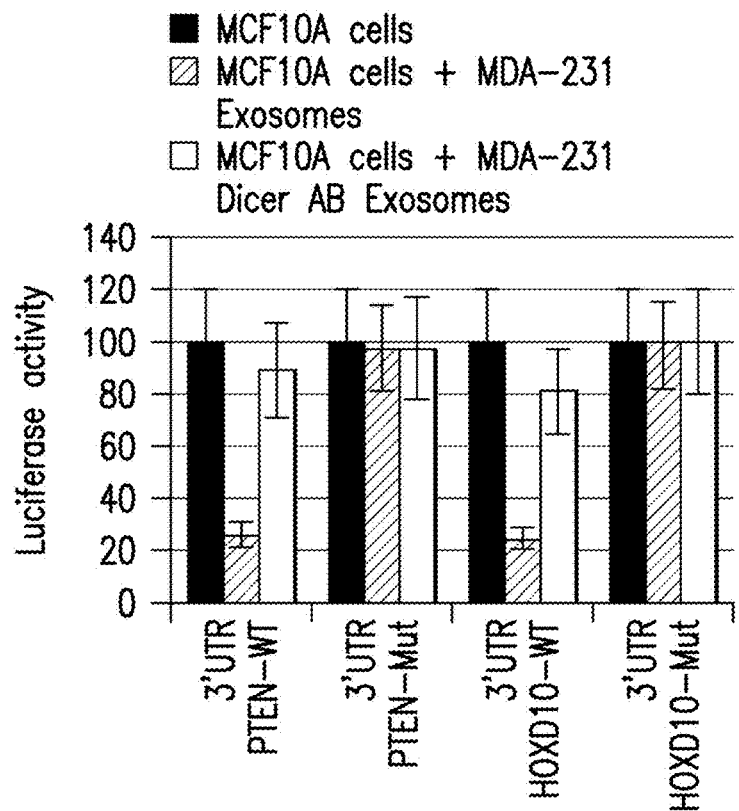
Figure 7D:
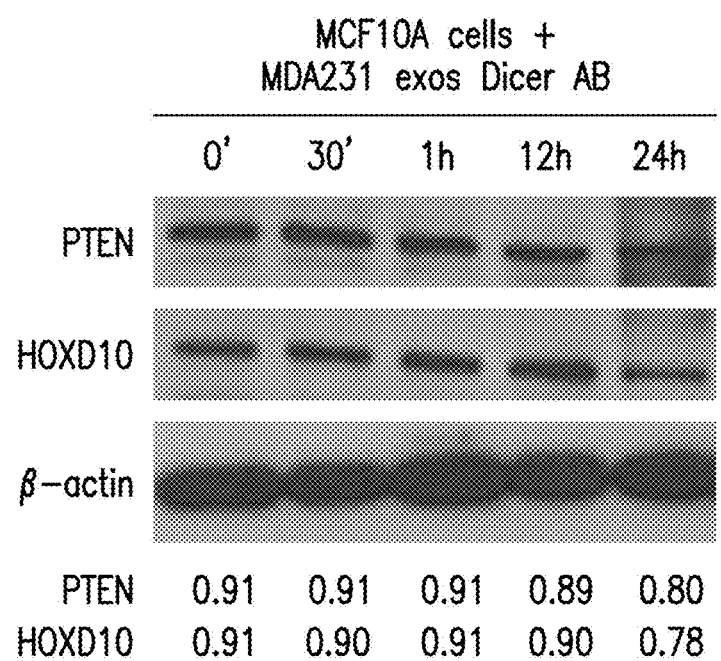
Figure 7E:
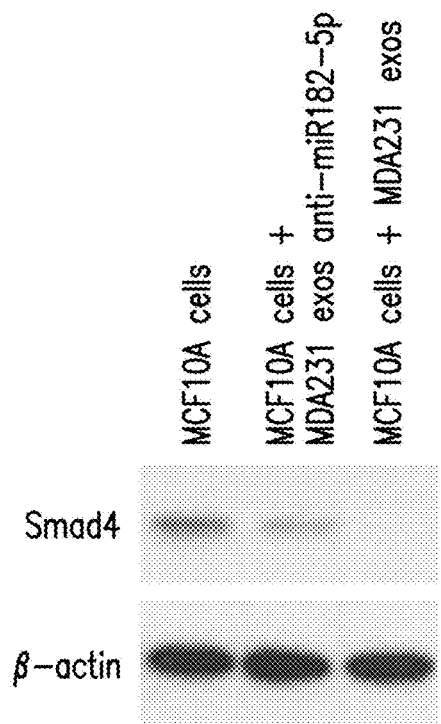
Figure 17B:
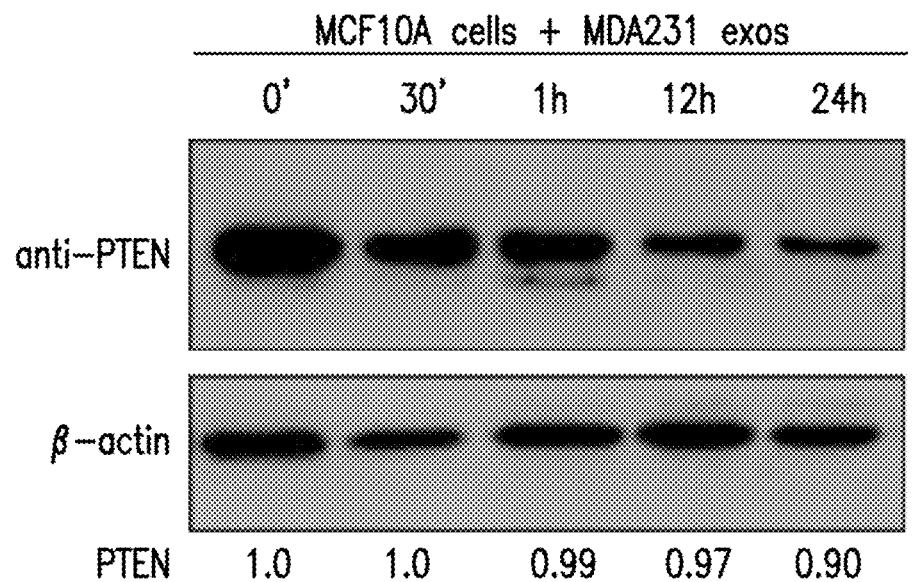
Figure 17C:
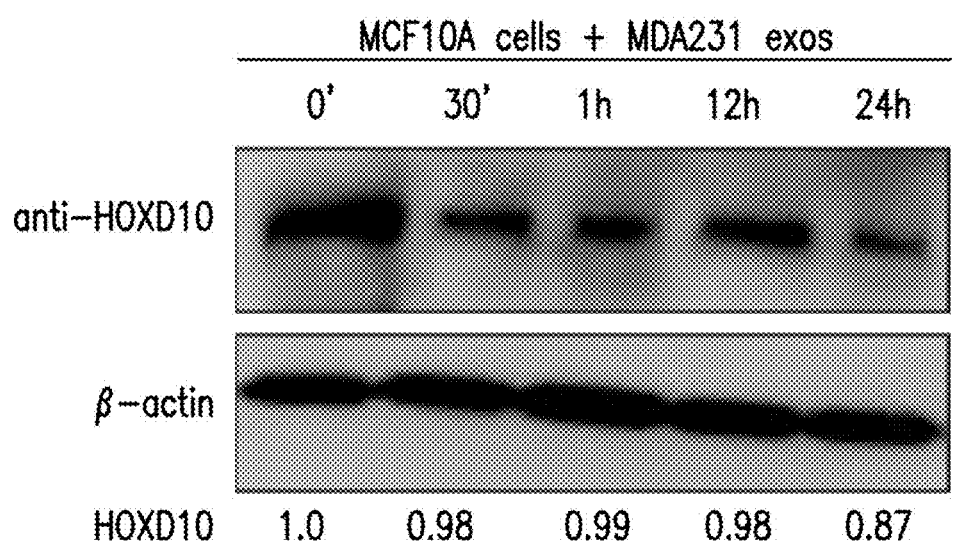
Figure 17D:
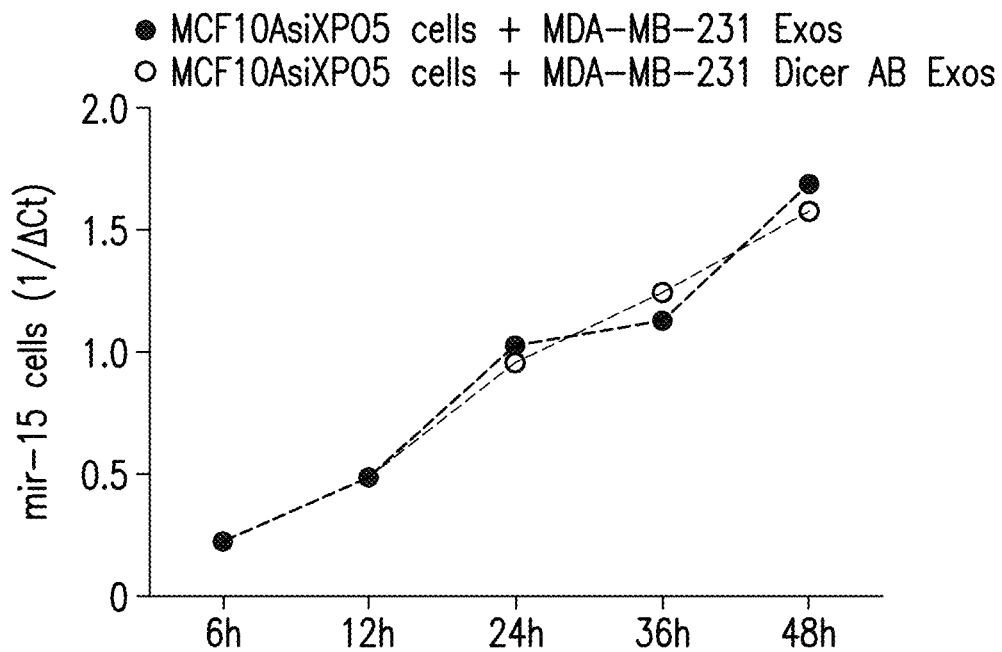
Figure 17E:
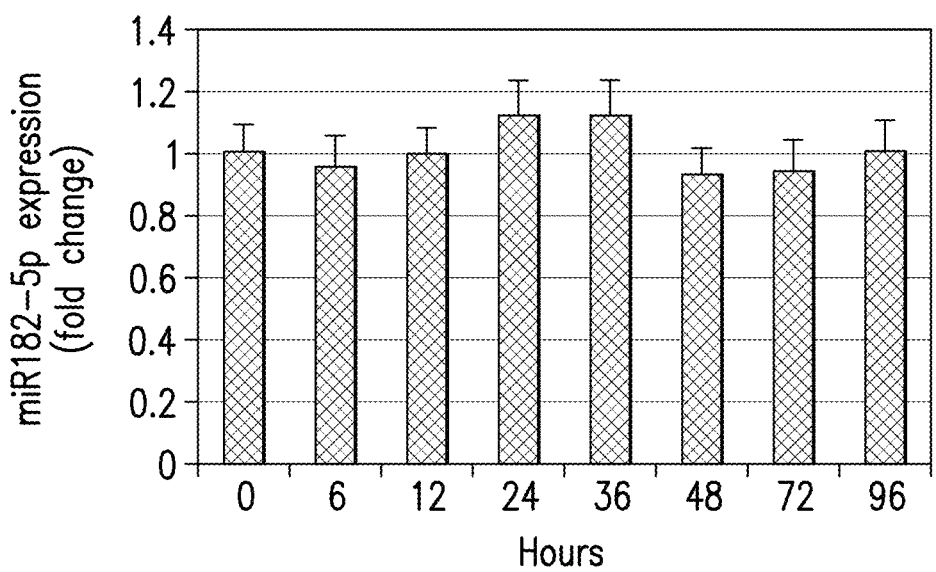
Figure 17F:
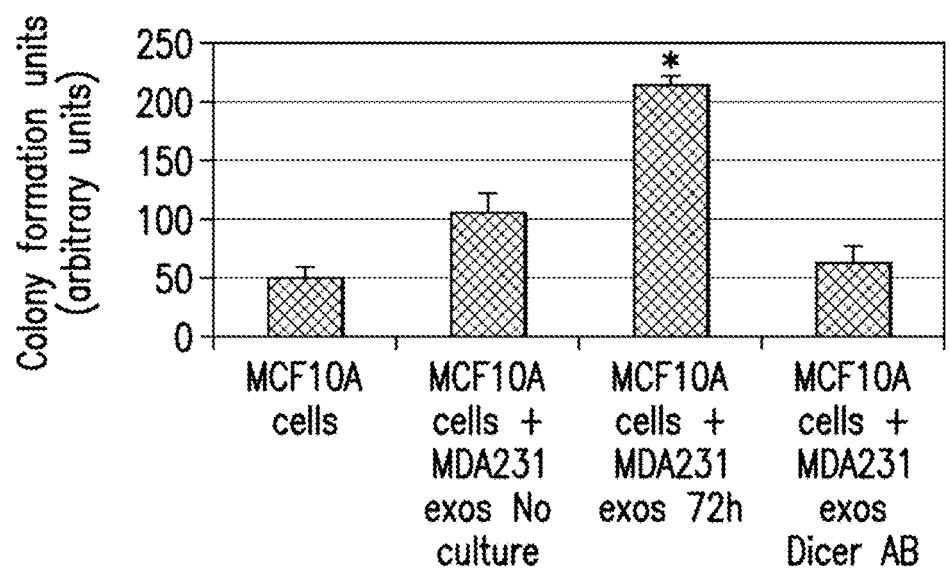
Figure 17G:
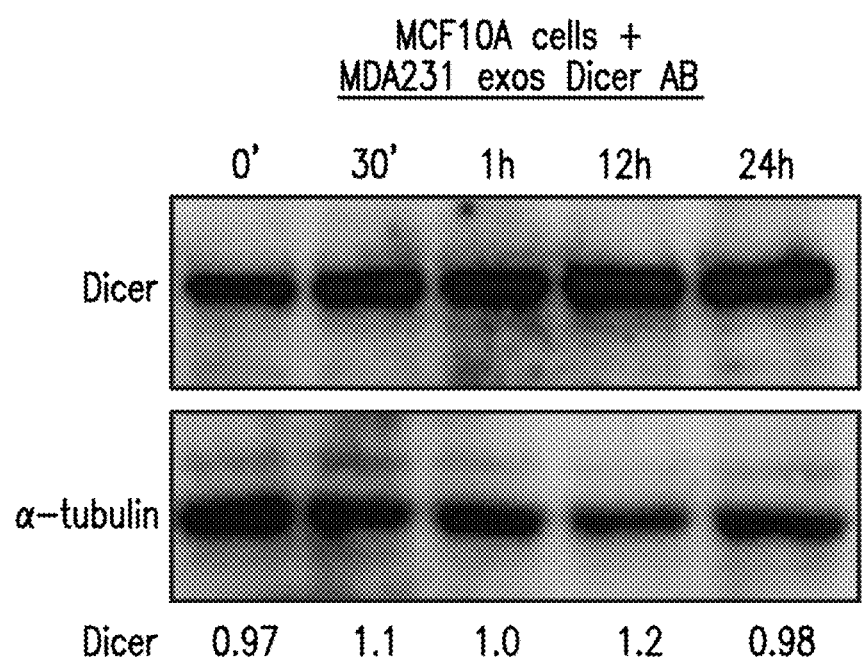

An in-depth analysis of the miRNA and mRNA expression profiles of MCF10A cells exposed to MDA-MB231 oncosomes compared to parental MCF10A cells revealed significant up-regulation of certain miRNAs and a down-regulation of their described mRNA targets in treated MCF10A cells. As an example, miRNA-21 and -10b were up-regulated (4.6 and 2.3 fold respectively) in treated MCF10A cells, among with other oncogenic miRNAs. MicroRNA-21 and -10b have been implicated in breast cancer progression, invasiveness and metastasis (Ma et al., 2007; Yan et al., 2011). As shown earlier, miR-21 and -10b were synthesized in oncosomes from their pre-miRNAs. PTEN and HOXD10 are described as miR-21 and miR-10b targets and were suppressed in the expression array analysis of MCF10A cells treated with oncosomes when compared to control MCF10A cells. Western blot analysis showed that PTEN and HOXD10 levels were suppressed in MCF10A cells exposed to oncosomes (FIGS. 7A-B). To examine whether miR-21 and miR-10b in oncosomes can silence PTEN and HOXD10 in MCF10A recipient cells, MCF10A cells were transiently transfected with luciferase reporters containing the wild-type 3'UTR of PTEN or HOXD10 genes that are capable of binding miR-21 and miR-10b. Mutant 3'UTR of PTEN or HOXD10 vectors were used as controls. A decrease in luciferase reporter activity was seen in MCF10A cells incubated with oncosomes, confirming functional delivery of miRNAs from oncosomes to recipient cells (FIG. 7C). In the oncosomes incubated MCF10A cells, PTEN and HOXD10 expression levels were evaluated at different time points. A significant decrease was detected in PTEN and HOXD10 expression immediately after treating the cells with 72 h cultured exosomes (FIGS. 7A-B). PTEN and HOXD10 expression levels changed minimally in MCF10A cells treated with freshly isolated exosomes, suggesting that sufficient concentration of the mature miRNAs may not have been present at this time point (FIGS. 17B-C). MCF10A cells treated with 72 h cultured oncosomes with anti-Dicer antibody revealed an insignificant down regulation of PTEN and HOXD10 (FIG. 7D and FIG. 17G). Additionally, processing of miR-15 in cells, a miRNA not detected in MDA-MB231-derived oncosomes, was not altered due to treatment of MCF10A cells with MDA-MB-231 exosomes containing Dicer antibody, showing an insignificant effect of Dicer antibody in treated cells (FIG. 17D). Some reports show down-regulation of miRNA targets in cells incubated with exosomes without a need for long culture periods (Kosaka et al., 2013; Narayanan et al., 2013; Pegtel et al., 2010). MiR-182-5p is one of the miRNAs up-regulated in MCF10A cells upon oncosomes treatment and Smad4, a miR-182-5p target (Hirata et al., 2012), is one of the genes down-regulated upon oncosomes treatment of these cells (FIG. 7E). Up-regulation of miR-182-5p in oncosomes during the culture period was not observed and pre-miR182-5p was not detected in oncosomes (FIG. 17E). Therefore, oncosomes also pack mature miRNAs without the need for processing pre-miRs. If such mature miRs are in relevant stoichiometric amounts, they may be able to regulate gene expression of recipient cells, as shown previously (Ismail et al., 2013; Kogure et al., 2011; Kosaka et al., 2013; Narayanan et al., 2013; Pegtel et al., 2010; Valadi et al., 2007; Zhang et al., 2010). However, if some mature miRNAs are not present in exosomes but their pre-miRNAs are, these can still have a biological effect on their targets since they will be processed into mature RLC associated miRNAs.

Figure 7F:
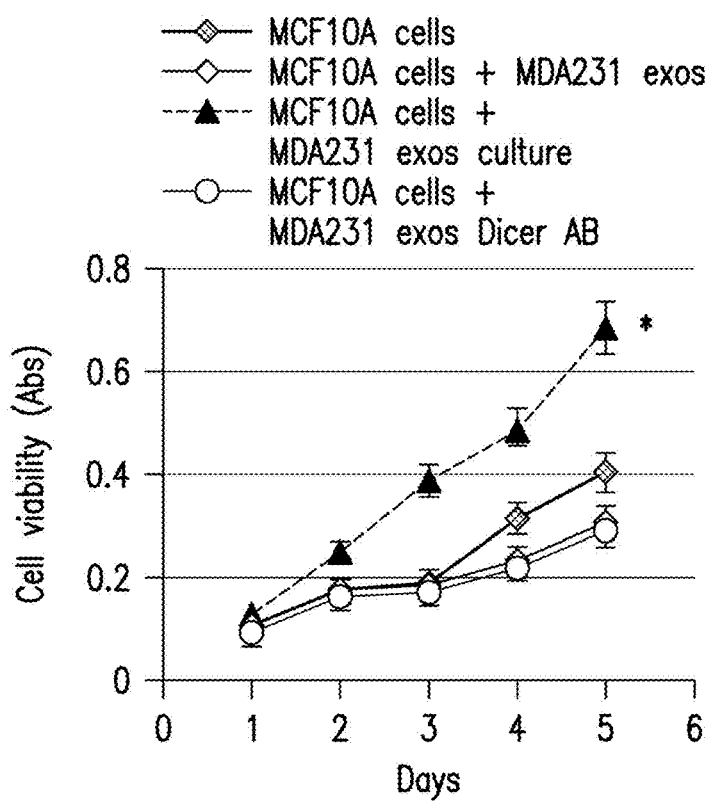
Figure 7G:
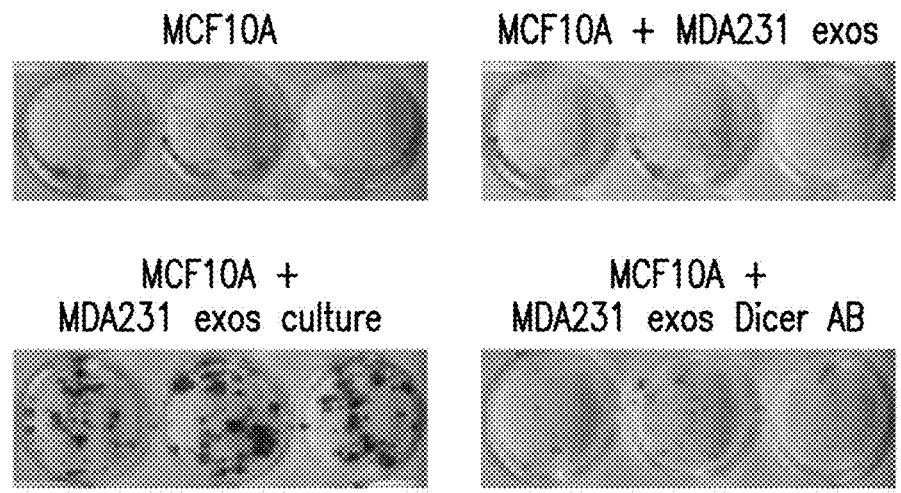

Cell viability and proliferation of MCF10A cells treated with 72 h cultured oncosomes was increased, which was not observed when freshly isolated oncosomes were used (FIG. 7F). A difference was not observed when MCF10A cells were treated with MDA-MB231 derived oncosomes containing anti-Dicer antibodies (FIG. 7F). The same pattern holds true for the colony formation capacity of MCF10A cells treated with oncosomes (FIGS. 7G and 17F). MCF10A cells treated with 72 h-cultured oncosomes form colonies when compared to non-treated cells (FIG. 7G). Such colony formation was not observed when freshly isolated oncosomes or AB Dicer oncosomes were used (FIG. 7G).

Oncosomes Induce Tumor Formation of Non-Tumorigenic Epithelial Cells and Activate Fibroblasts.

Figure 7H:
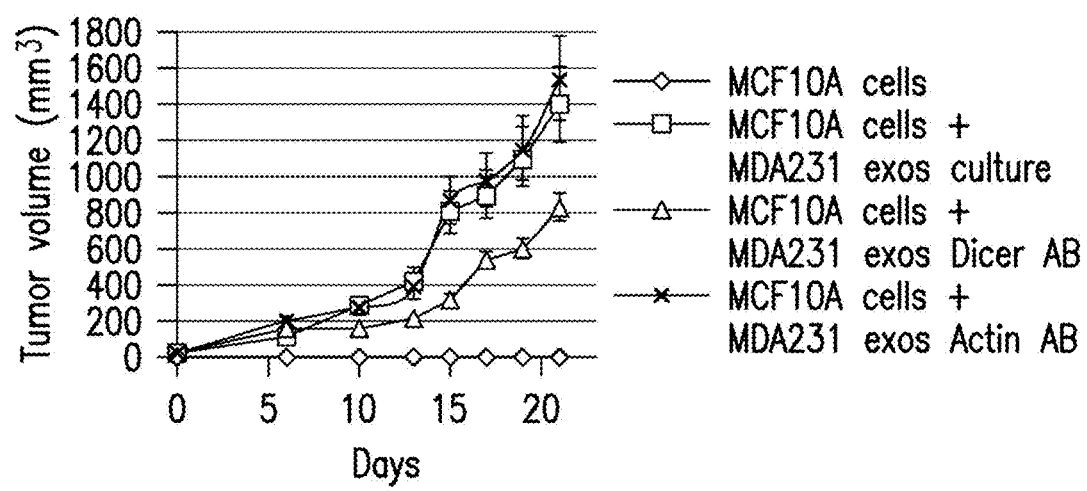
Figure 7H:
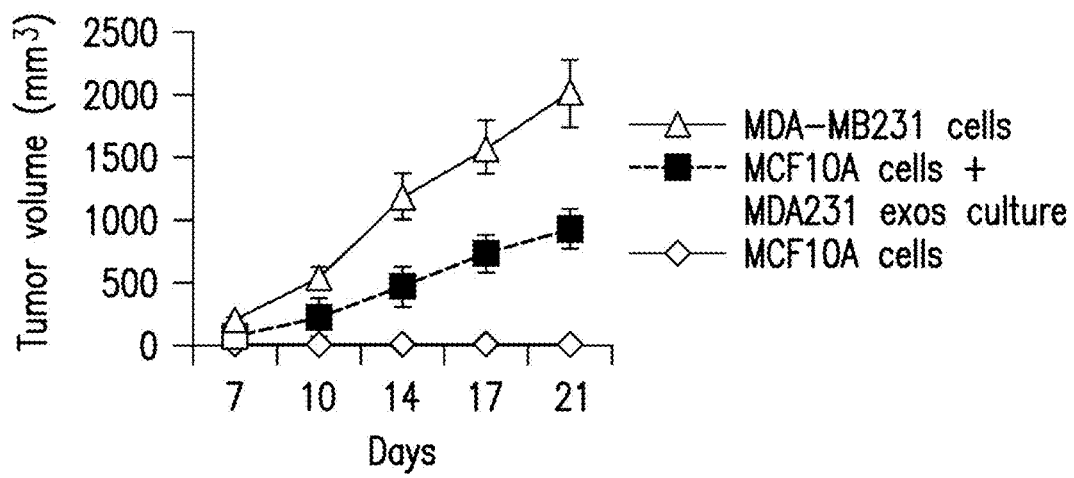

Recent studies suggest that exosomes derived from bone marrow mesenchymal stromal cells support multiple myeloma cell growth (Roccaro et al., 2013). To address the functional 'oncogenic potential' of MCF10A and MCF10A cells with prior exposure to oncosomes (MCF10A cells-oncosomes), these cells were injected orthotopically into the mammary fat pads of femail nu/nu mice, similar to the protocol described recently (Luga et al., 2012). MCF10A cells did not form tumors in these mice as also reported earlier (Mavel et al., 2002; Thery et al., 2002) (FIG. 7H). MCF10A cells-oncosomes formed tumors after 21 days, as well as the control MDA-MB231 cells (FIG. 7H). MCF10A cells incubated with oncosomes containing anti-Dicer antibody (but not control anti-actin antibodies) showed a significant reduction in tumor volume (FIG. 7H). These results support the oncogenic conversion of MCF10A cells when exposed to oncosomes containing Dicer protein (FIGS. 7F-H and FIG. 17F).

Serum Exosomes from Cancer Patients Contain Dicer and Process premiRNAs to Generate Mature miRNAs.

Figure 8A:
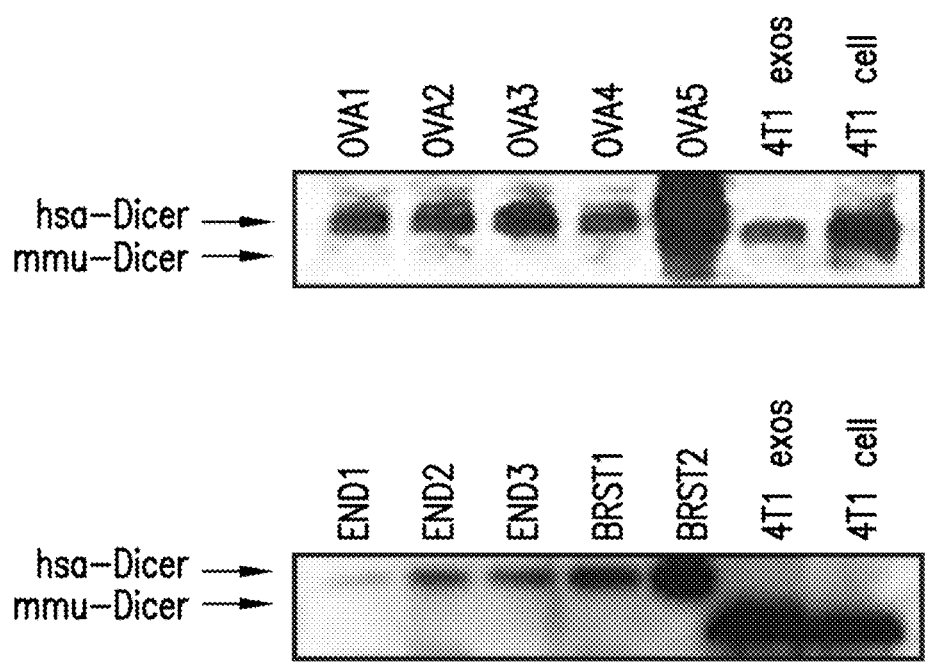
FIGS. 8A-I. Serum from breast cancer patients contain Dicer and process pre-miRNAs. (A) Immunoblot using anti-Dicer antibody, that recognizes human and mouse Dicer, and protein extracts from serum exosomes harvested from mice xenografted with human tumors (as shown in FIG. 18A). OVA1-5 represents human ovary xenografts; END1-3 represents human endometrial xenografts; and BRST1 and 2 represent human breast xenografts. 4T1 exosomes and cells were used as controls for murine Dicer. hsa-Dicer represents human Dicer molecular weight and mmu-Dicer represents murine Dicer molecular weight. See FIG. 18D for Comassie staining of membranes as loading control. (B) NanoSight particle tracking analysis showing size distribution of exosomes extracted from the serum of 8 healthy donors (left graph) and 11 breast cancer patients (right graph). Concentration of samples was standardized to better show size. (C) Transmission electron micrograph of exosomes harvested from the serum of breast cancer patients. (D) Concentration of exosomes from the serum of 8 healthy donors and 11 breast cancer patients assessed by NanoSight particle tracking analysis. *p=0.012 (E) Exosomes were harvested from fresh serum from 8 healthy donors and 11 breast cancer patients. The extracted samples were left in cell-free culture conditions for 24 and 72 h. After 24 and 72 h, exosomes were recovered and 6 pre-miRNAs were quantified by qPCR. The fold-change of each pre-miRNA in exosomes after 72 h cell-free culture was quantified relative to the same pre-miRNA in exosomes after 24 h cell-free culture in each sample. The graphical dot plots represent an average foldchange for the pre-miRNAs in 72 h exosomes relative to 24 h exosomes and are represented as ±s.d. (F) Exosomes were harvested from fresh serum from 8 healthy donors and 11 breast cancer patients. The extracted samples were left in cell-free culture conditions for 24 and 72 h. After 24 and 72 h, exosomes were recovered and 6 miRNAs were quantified by qPCR. The foldchange of each miRNA in exosomes after 72 h cell-free culture was quantified relative to the same miRNA in exosomes after 24 h cell-free culture in each sample. The graphical dot plots represent an average fold-change for the miRNAs in 72 h exosomes relative to 24 h exosomes. Both panels E and F are the result of three independent experiments each with three replicates and are represented as ±s.d. (G) MCF10A cells, MCF10A cells mixed with exosomes from healthy donors (H1-8) and MCF10A cells mixed with exosomes from breast cancer patients (BC1-11) were orthotopically injected into the mammary pads of athymic nude mice. The number of exosomes used was calculated per body weight reflecting the initial concentration collected from the serum. Samples that have not formed a tumor appear overlapped in the xaxis of the graph. This graph depicts tumor volume with respect to time and is represented as ±s.d. (H) Immunoblots using anti-Dicer antibody and protein extracts from serum exosomes harvested from 5 healthy individuals (C46, C45, C44, C43 and C41) and 4 metastatic breast carcinomas (Met219, Met354, Met299 and Met356) using CD9 blot as loading control. (I) Doubling time of HDF and HDF treated with oncosomes (MDA-MB231). *p=0.0114. Immunoblot quantification was done using Image J software.
Figure 18A:
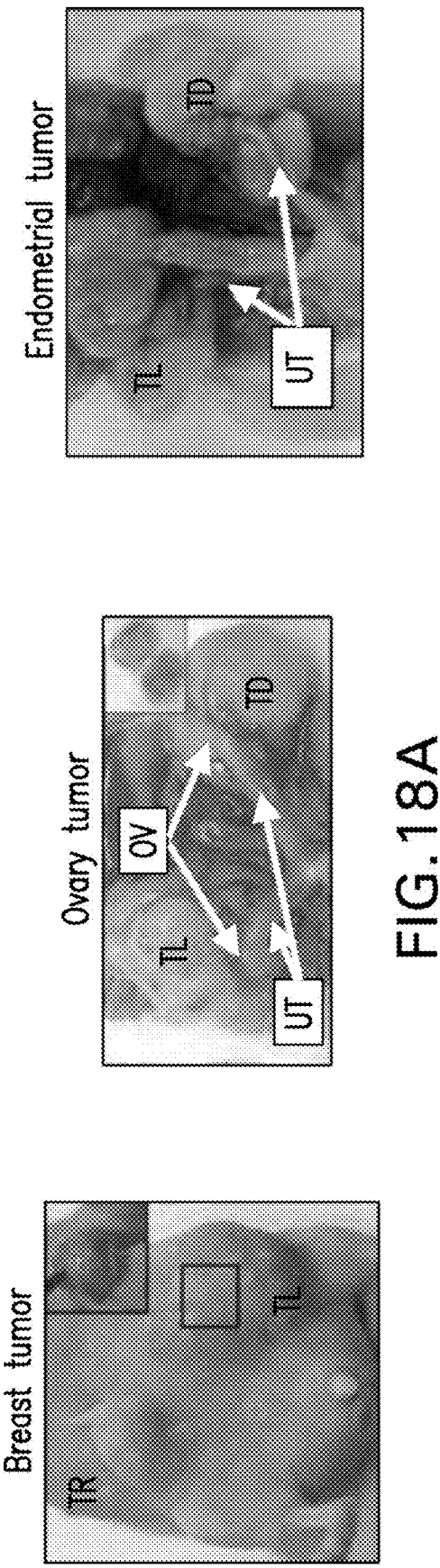
Figure 18B:
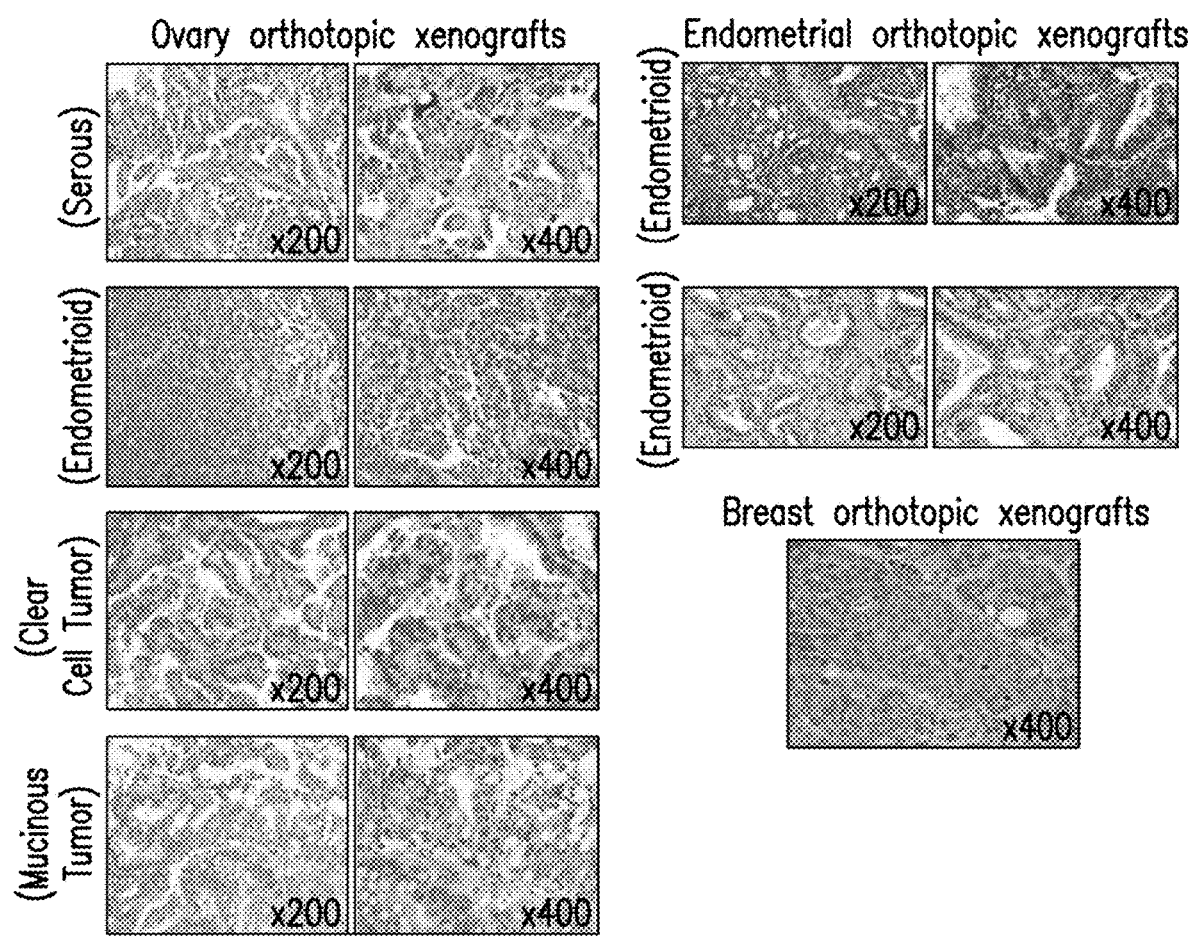
Figure 18D:
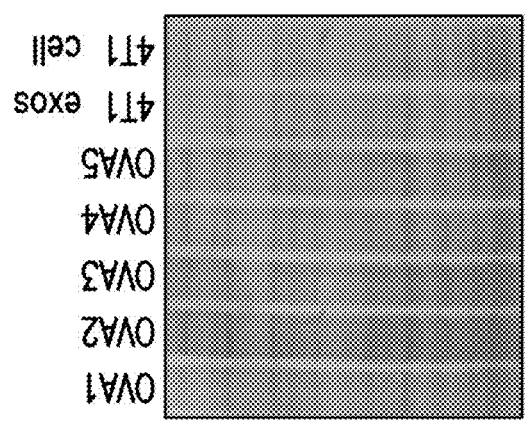
Figure 18C:
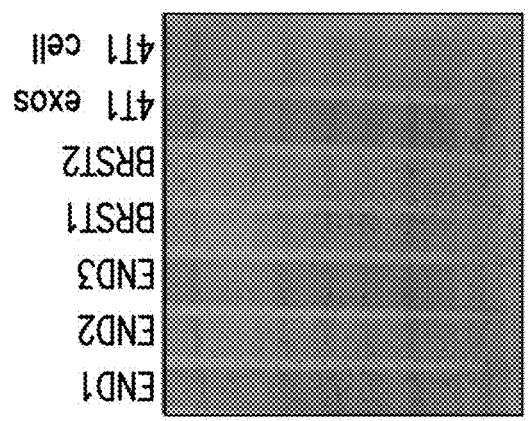
Figure 18C:
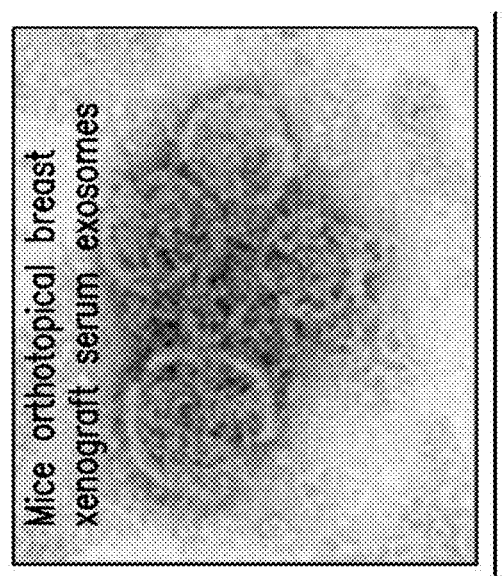

Exosomes of human tumors were examined for RISC proteins. To achieve cancer cell specificity, freshly isolated human primary ovarian, breast and endometrial tumor pieces were orthotopically grafted into appropriate organs of female athymic nu/nu mice (FIGS. 18A-B). Serum exosomes from these mice were evaluated by electron microscope (FIG. 18C). Size exclusion protein blotting of the content isolated from these exosomes demonstrated the existence of Dicer protein exclusively of human origin (hsa-Dicer) (FIG. 8A and FIG. 18D). Protein extracts from 4T1-derived exosomes and 4T1 cells were used as controls to show Dicer of mouse origin, which exhibits a different molecular weight (mmu-Dicer) (FIG. 8A).

Oncosomes from MDA-MB231 cells were incubated with human dermal fibroblasts (HDF). Global gene expression profiling of oncosomes incubated fibroblasts reveals a significant impact on their transcriptome, when compared to control cells. Up-regulation of aSMA (ACTA) (18 fold), COL1A1 (12 fold), TGF131 (15 fold), CTGF (8 fold), Ras (6 fold) and ERK (4 fold) was observed. Fibroblasts incubated with oncosomes proliferated at a higher rate (FIG. 8I). These results suggest that oncosomes can activate stromal fibroblasts to resemble a myofibroblast phenotype and display characteristic features associated with carcinoma-associated fibroblasts.

Figure 8B:
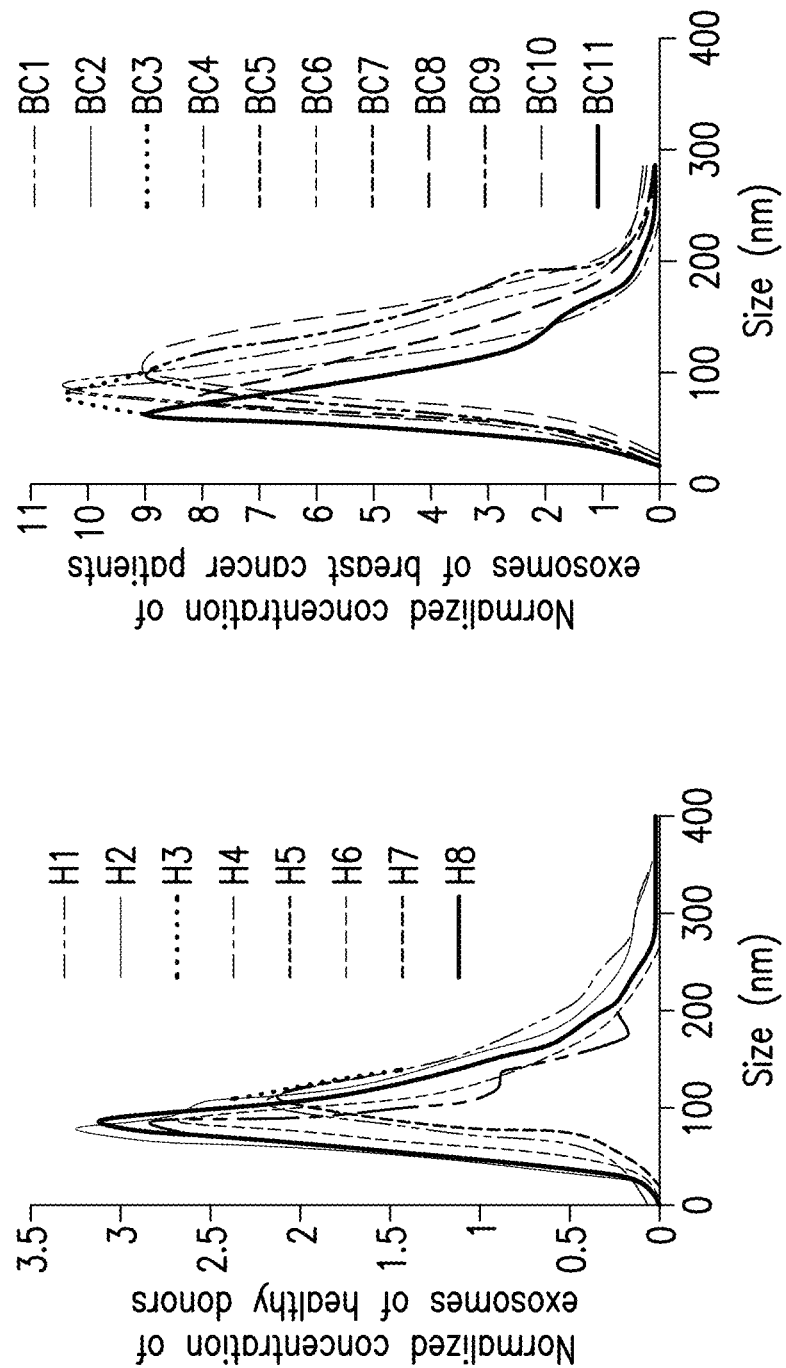
Figure 8C:
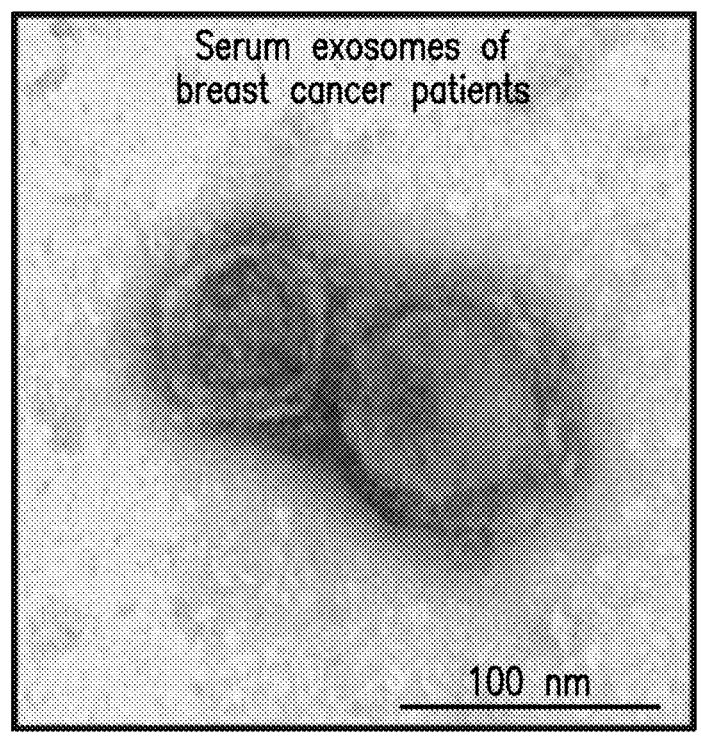
Figure 8D:
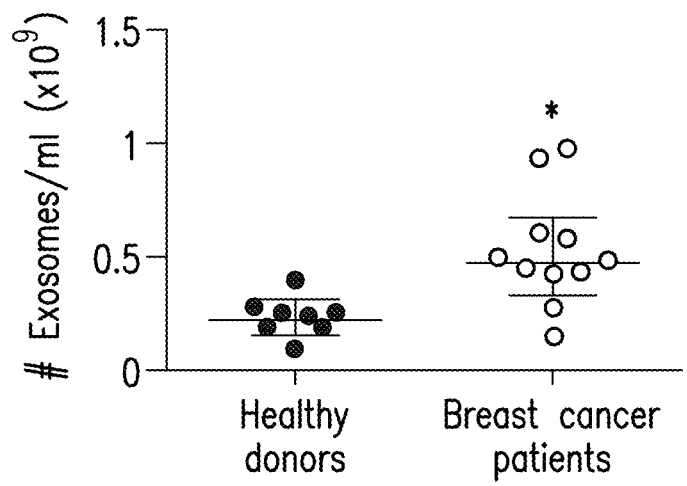
Figure 8E:
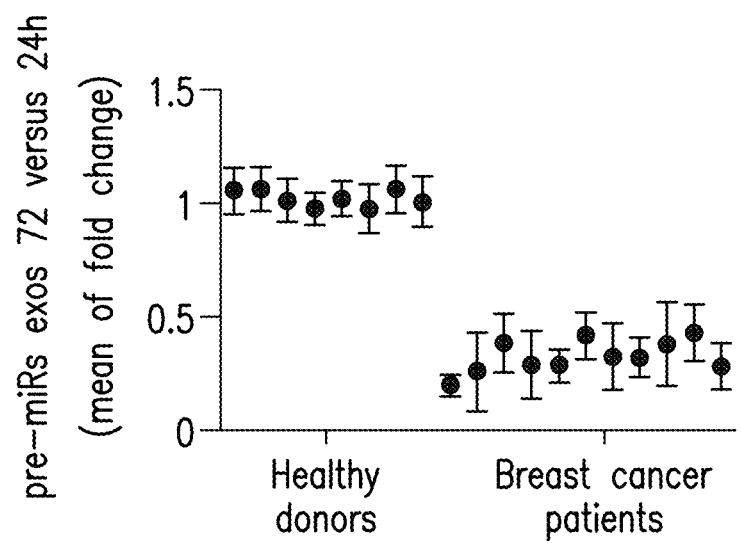
Figure 8F:
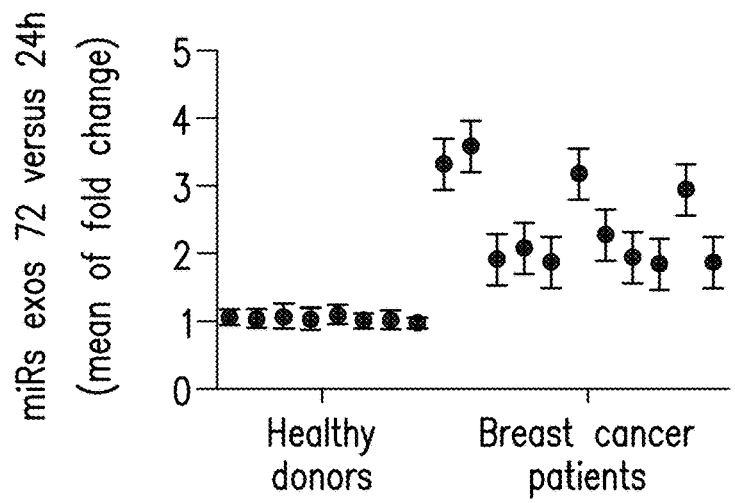
Figure 8G:
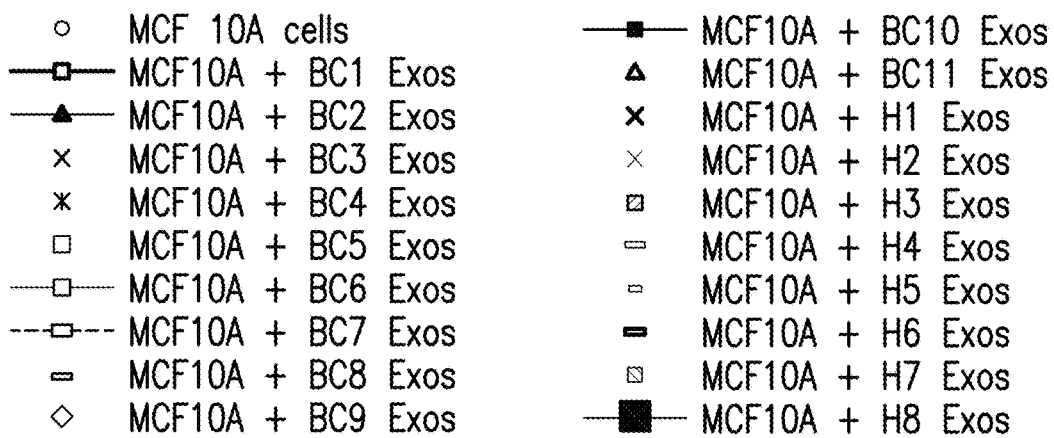
Figure 8G:
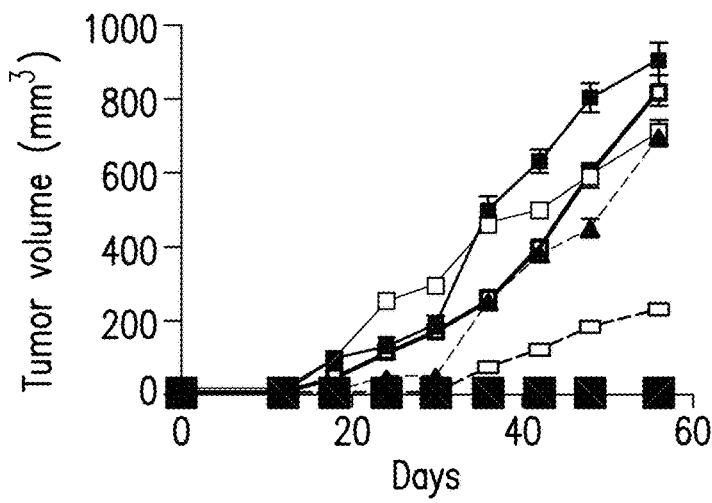

Next, exosomes were isolated from 100 µl of fresh serum samples from 8 healthy individuals (H) and 11 patients with breast carcinoma (BC) (FIG. 8B). Lipid bilayer membranes were distinguished by electron microscopy on exosomes (FIG. 8C). Serum of breast cancer patients contained significantly more exosomes when compared to serum of healthy donors (FIG. 8D). When equal number of exosomes were placed in culture for 24 and 72 h, the 6 pre-miRNAs were found to be downregulated exclusively in breast cancer patients and their respective mature miRNAs were upregulated after 72 h of culture, suggesting pre-miRNAs were processed into the mature form in the exosomes from fresh serum of breast cancer patients and not in the healthy controls (FIGS. 8E-F). Next, exosomes alone or combined with MCF10A cells, were injected orthotopically in the mammary fat pad of female nu/nu mice. Five out of 11 serum exosomes derived from breast cancer patients combined with MCF10A cells formed tumors while none of the healthy donor exosomes or exosomes alone, formed tumors (FIG. 8G). Interestingly, exosomes that formed tumors were also shown to have the highest fold-change increase in the amount of mature miRNAs after 72 h culture (FIGS. 8E-F).

Figure 8H:
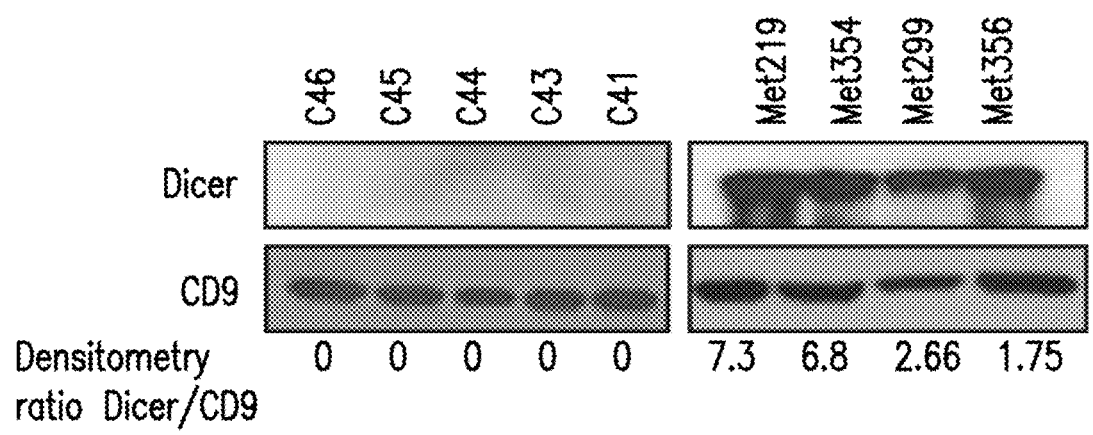
Figure 8I:
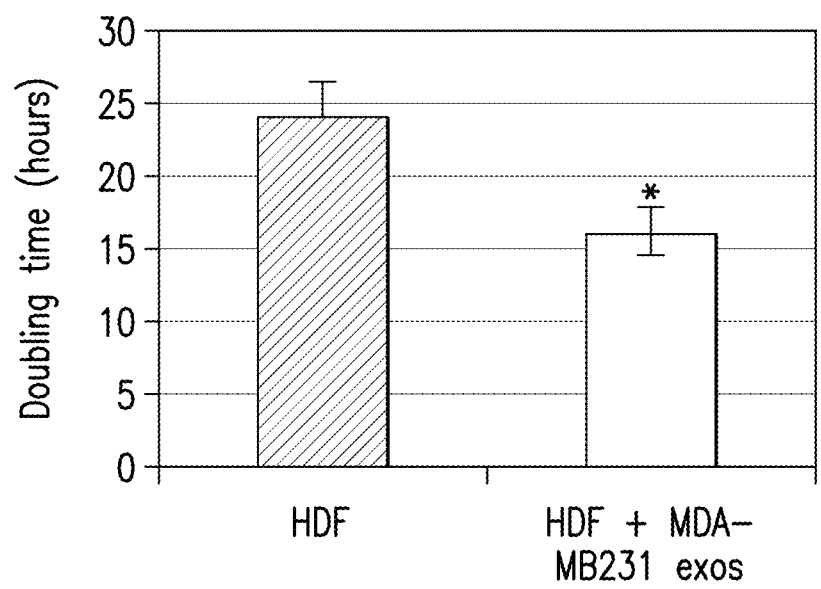

Exosomes were further isolated from a new set of serum samples obtained from 5 healthy individuals (C46, C45, C44, C43, and C41) and 4 patients with metastatic breast carcinoma (Met219, Met354, Met299 and Met356). Dicer expression in exosomes was observed only in metastatic breast carcinoma samples and not in exosomes from serum of healthy individuals (FIG. 8H).

TABLE 5

Differentially expressed miRNAs between oncosomes (MDA-MB231 derived) and normosomes (MCF10A derived).

| miRNA | p Value |
|---|---|
| mmu-miR-709 | 1.30E−06 |
| hsa-miR-1308 | 3.71E−06 |
| mmu-miR-615-3p | 9.08E−06 |
| hsa-miR-1260b | 1.06E−05 |
| mmu-miR-1937a | 1.36E−05 |
| mmu-mir-321-A | 1.54E−05 |
| hsa-miR-615-3p | 1.80E−05 |
| hsa-miR-1979 | 2.10E−05 |
| mmu-miR-1937b | 2.72E−05 |
| hsa-mir-373 | 3.15E−05 |
| mmu-miR-1937c | 3.28E−05 |
| hsa-miR-1273d-P | 3.68E−05 |
| mmu-miR-720 | 4.08E−05 |
| mmu-miR-1274a | 4.45E−05 |
| hsa-mir-565-A | 6.63E−05 |
| mmu-miR-1931 | 6.77E−05 |
| hsa-miR-1246 | 7.35E−05 |
| hsa-mir-594-P | 7.56E−05 |
| hsa-mir-321-A | 7.83E−05 |
| mmu-miR-2145-l-P | 9.36E−05 |
| hsa-mir-639-P | 9.54E−05 |
| hsa-miR-720 | 0.000112771 |
| hsa-miR-1280 | 0.000116 |
| mmu-miR-3473 | 0.000136388 |
| hsa-miR-1260 | 0.000178848 |
| hsa-miR-1281 | 0.000193167 |
| mmu-miR-1224-P | 0.00019941 |
| mmu-miR-690 | 0.000223064 |
| hsa-miR-375-P | 0.000242513 |
| hsa-miR-4301 | 0.000254614 |
| mmu-miR-700 | 0.000322167 |
| mmu-miR-125b-5p | 0.000333431 |
| mmu-miR-1191-P | 0.000412736 |
| hsa-miR-1274a | 0.000420621 |
| hsa-miR-3197 | 0.00042765 |
| mmu-miR-1935 | 0.000459256 |
| hsa-miR-1975-P | 0.000467699 |
| hsa-miR-4324 | 0.000595518 |
| hsa-miR-886-3p | 0.00060906 |
| hsa-miR-1274b | 0.000643024 |
| mmu-miR-1957 | 0.000679996 |
| hsa-miR-933 | 0.000752624 |
| hsa-mir-675 | 0.000775607 |
| hsa-miR-595 | 0.000835784 |

TABLE 5-continued

Differentially expressed miRNAs between oncosomes (MDA-MB231 derived) and normosomes (MCF10A derived).

| miRNA | p Value |
|---|---|
| mmu-miR-2137 | 0.000867405 |
| hsa-mir-572-P | 0.000935968 |
| mmu-miR-1195 | 0.000971222 |
| hsa-miR-4294-P | 0.001008217 |
| mmu-mir-1899-P | 0.00104201 |
| mmu-miR-689-P | 0.001048727 |
| hsa-miR-199b-3p | 0.001330193 |
| hsa-miR-3117-P | 0.001331776 |
| mmu-mir-321-P | 0.001407081 |
| mmu-miR-1961-P | 0.001479699 |
| hsa-mir-10a | 0.001756816 |
| mmu-miR-669d-P | 0.001842801 |
| mmu-miR-1937b-2-P | 0.001855411 |
| hsa-miR-3125-P | 0.00206976 |
| mmu-miR-1934-P | 0.002222993 |
| hsa-miR-574-3p | 0.002231887 |
| hsa-miR-718 | 0.002533178 |
| mmu-miR-1198 | 0.002640837 |
| mmu-miR-2182-P | 0.002722356 |
| hsa-miR-1273 | 0.002723198 |
| mmu-miR-2133-P | 0.002794947 |
| hsa-miR-92b* | 0.003046008 |
| hsa-miR-1290 | 0.003307286 |
| hsa-miR-448 | 0.003318093 |
| mmu-miR-689 | 0.003367203 |
| mmu-miR-449a | 0.003657703 |
| mmu-miR-1937b-4-P | 0.004021961 |
| hsa-miR-4286 | 0.004068181 |
| mmu-miR-1947 | 0.00408589 |
| mmu-miR-342-3p | 0.004178728 |
| hsa-miR-1303-P | 0.004771531 |
| mmu-miR-2132 | 0.004826438 |
| hsa-miR-4321-P | 0.004925885 |
| hsa-miR-4256-P | 0.004994658 |
| hsa-miR-4311 | 0.005120539 |
| mmu-miR-130a | 0.005138148 |
| mmu-miR-1939 | 0.005186979 |
| hsa-miR-1268-P | 0.005383176 |
| mmu-miR-31 | 0.005491579 |
| mmu-miR-99b | 0.005498217 |
| mmu-miR-2141 | 0.005742427 |
| hsa-miR-1202-P | 0.005825202 |
| mmu-miR-466b-3p | 0.005831681 |
| mmu-miR-2133 | 0.005962416 |
| hsa-miR-1268 | 0.006022349 |
| hsa-miR-466 | 0.006338384 |
| mmu-miR-494 | 0.006386665 |
| hsa-miR-1289 | 0.006571828 |
| hsa-miR-320b | 0.006612583 |
| hsa-miR-4254 | 0.006670963 |
| hsa-mir-7-3-P | 0.00673441 |
| hsa-miR-923 | 0.006748425 |
| hsa-miR-764 | 0.006790693 |
| mmu-miR-291a-3p | 0.007141562 |
| mmu-miR-883b-3p | 0.007204478 |
| hsa-mir-594-A | 0.00721747 |
| mmu-miR-1948-P | 0.007524668 |
| hsa-miR-206 | 0.007553353 |
| hsa-mir-565-P | 0.007700663 |
| mmu-miR-467e* | 0.00778865 |
| hsa-miR-1826 | 0.007812174 |
| mmu-miR-467a* | 0.007840082 |
| hsa-miR-1983 | 0.007889552 |
| hsa-miR-324-5p | 0.008058633 |
| mmu-let-7c | 0.008070282 |
| mmu-miR-1965 | 0.00810043 |
| hsa-mir-632-P | 0.008277449 |
| hsa-miR-181a*MM2GT/AC | 0.008292477 |
| hsa-miR-1265 | 0.008367622 |
| hsa-miR-323b-5p | 0.008373161 |
| hsa-mir-1914 | 0.008444953 |
| hsa-mir-1910 | 0.008458754 |
| hsa-miR-21 | 0.008557419 |
| hsa-miR-431* | 0.008595529 |
| hsa-miR-3135-P | 0.008851151 |
| mmu-miR-187-P | 0.009290275 |
| mmu-miR-126-3p | 0.009334952 |
| mmu-miR-669a-P | 0.00943601 |
| hsa-miR-367 | 0.009568574 |
| mmu-mir-320-P | 0.009788835 |
| hsa-miR-181a*MM1G/C | 0.009821714 |
| mmu-miR-484-P | 0.009847016 |
| mmu-miR-467c-P | 0.010318688 |
| hsa-miR-3154 | 0.010452692 |
| mmu-miR-466d-3p | 0.01047819 |
| hsa-miR-3162-P | 0.010642567 |
| mmu-miR-201 | 0.010827783 |
| mmu-miR-1946a | 0.010877863 |
| hsa-miR-937 | 0.011009279 |
| hsa-miR-3147 | 0.011883963 |
| hsa-mir-596-P | 0.012205467 |
| hsa-miR-3148 | 0.012245577 |
| hsa-miR-1304 | 0.012451991 |
| hsa-miR-222MM2GG/AC | 0.012512207 |
| mmu-miR-125a-5p | 0.012630083 |
| hsa-miR-1272-P | 0.012893462 |
| hsa-miR-638 | 0.012956727 |
| hsa-mir-320 | 0.013366703 |
| hsa-miR-545* | 0.013713081 |
| hsa-mir-1908-P | 0.01374103 |
| hsa-let-7d-v2-P | 0.013846844 |
| mmu-mir-30d-P | 0.014771375 |
| hsa-miR-4297 | 0.015365603 |
| mmu-miR-182 | 0.015432962 |
| hsa-miR-3166-P | 0.015893116 |
| hsa-miR-494 | 0.015960208 |
| mmu-miR-669o-P | 0.016133286 |
| hsa-miR-566 | 0.01616152 |
| mmu-miR-1188 | 0.016736136 |
| mmu-miR-2134-AP | 0.016811955 |
| hsa-miR-4259-P | 0.016856716 |
| mmu-miR-152 | 0.01715464 |
| mmu-miR-2134 | 0.017178929 |
| hsa-miR-3193-AP | 0.017496022 |
| hsa-miR-125b | 0.017917521 |
| hsa-miR-3124-P | 0.018466818 |
| hsa-miR-10b | 0.018671177 |
| hsa-miR-455-5p | 0.018771585 |
| mmu-miR-144 | 0.019121516 |
| hsa-miR-130a | 0.019424172 |
| hsa-miR-1285 | 0.019710834 |
| hsa-miR-516b* | 0.020003951 |
| hsa-miR-27a | 0.020049082 |
| hsa-miR-138-1* | 0.020302422 |
| mmu-miR-471 | 0.020513954 |
| hsa-miR-4298-P | 0.020520647 |
| hsa-miR-301b | 0.0205242 |
| hsa-mir-147-P | 0.020570657 |
| hsa-miR-362-5p | 0.020602873 |
| mmu-mir-471-P | 0.020639505 |
| mmu-miR-466a-3p | 0.020737186 |
| hsa-miR-561 | 0.020878532 |
| hsa-miR-486-5p | 0.021122352 |
| mmu-miR-2861 | 0.021313137 |
| hsa-miR-587 | 0.021396357 |
| mmu-miR-375 | 0.021423748 |
| hsa-mir-329-2-P | 0.021718025 |
| mmu-miR-2861-P | 0.022230123 |
| hsa-miR-144* | 0.022500042 |
| hsa-miR-1255a-P | 0.022928296 |
| hsa-miR-519a-2-P | 0.023328916 |
| hsa-miR-34c-5p | 0.023452529 |
| mmu-miR-466e-3p | 0.023486196 |
| mmu-miR-743b-5p | 0.023621503 |
| mmu-mir-350-P | 0.023797354 |
| mmu-miR-181d | 0.024929082 |
| hsa-miR-376a* | 0.025160569 |
| hsa-miR-1308-P | 0.025400926 |
| mmu-miR-467g | 0.025684158 |
| mmu-miR-1946a-P | 0.025903246 |

TABLE 5-continued

Differentially expressed miRNAs between oncosomes (MDA-MB231 derived) and normosomes (MCF10A derived).

| miRNA | p Value |
|---|---|
| hsa-miR-147-P | 0.025981647 |
| hsa-miR-923-P | 0.026407247 |
| mmu-miR-465c-5p | 0.026498492 |
| hsa-miR-891a | 0.026826475 |
| hsa-miR-28-5p | 0.026908406 |
| hsa-miR-4292 | 0.02699168 |
| mmu-miR-677-P | 0.027117156 |
| hsa-miR-4257 | 0.027412394 |
| hsa-miR-4326 | 0.027447003 |
| hsa-miR-17*MM2GG/AA | 0.02747134 |
| hsa-miR-939-P | 0.027590618 |
| mmu-miR-2182 | 0.027770773 |
| hsa-miR-220c-P | 0.027834269 |
| hsa-miR-3132-P | 0.027949304 |
| hsa-miR-532-5p | 0.028123552 |
| mmu-miR-1947-P | 0.028342198 |
| mmu-miR-29a | 0.028448253 |
| hsa-miR-3162 | 0.028472579 |
| hsa-miR-375MMlC/G | 0.028539316 |
| hsa-miR-768-3p | 0.028631264 |
| mmu-miR-182-P | 0.028668937 |
| mmu-miR-205-P | 0.029630816 |
| hsa-miR-505 | 0.029688956 |
| hsa-miR-3146-P | 0.02981021 |
| mmu-miR-721 | 0.029874269 |
| mmu-miR-376c | 0.030446032 |
| hsa-miR-1179-P | 0.030947356 |
| mmu-miR-1970 | 0.030975459 |
| hsa-miR-3133-P | 0.031120572 |
| hsa-miR-200c | 0.031203313 |
| hsa-miR-220a | 0.031358991 |
| mmu-miR-100 | 0.031556595 |
| hsa-miR-1255b | 0.031601448 |
| hsa-miR-222MMlG/A | 0.031650652 |
| hsa-miR-885-3p | 0.031822949 |
| hsa-miR-517b | 0.032138191 |
| hsa-miR-200a | 0.032181877 |
| hsa-miR-3141 | 0.032551657 |
| mmu-miR-669h-3p | 0.033076965 |
| hsa-miR-1301 | 0.033141515 |
| hsa-miR-877 | 0.033292052 |
| hsa-mir-941-2 | 0.033355824 |
| hsa-mir-487b-P | 0.033372231 |
| hsa-miR-4302 | 0.033621907 |
| hsa-miR-99b | 0.033827759 |
| hsa-miR-1253 | 0.034018422 |
| hsa-let-7a* | 0.034034943 |
| hsa-miR-34aMM2CT/TC | 0.034301895 |
| hsa-miR-3181-P | 0.034366501 |
| hsa-miR-3200 | 0.034397879 |
| hsa-miR-3129-P | 0.034538091 |
| hsa-miR-93* | 0.03464146 |
| hsa-miR-548q-P | 0.035140723 |
| mmu-miR-466g | 0.035388049 |
| hsa-miR-155 | 0.035624947 |
| hsa-miR-2278-P | 0.03584678 |
| hsa-miR-3065-5p | 0.035885091 |
| hsa-miR-633 | 0.035994294 |
| hsa-miR-4265 | 0.036055664 |
| mmu-miR-2135-P | 0.036119609 |
| hsa-miR-190 | 0.036305474 |
| mmu-miR-669f | 0.036533893 |
| hsa-miR-1323 | 0.036541729 |
| hsa-miR-588 | 0.036661363 |
| mmu-miR-183* | 0.037276389 |
| hsa-mir-941-4 | 0.037411697 |
| hsa-mir-1913 | 0.037527439 |
| hsa-miR-2116* | 0.037682483 |
| hsa-miR-1178 | 0.037847724 |
| mmu-miR-196a | 0.038163687 |
| mmu-miR-574-3p | 0.038418252 |
| hsa-miR-346 | 0.038809144 |
| mmu-miR-1199 | 0.039417628 |
| mmu-miR-681 | 0.039465517 |
| hsa-miR-4292-P | 0.039841449 |

TABLE 5-continued

Differentially expressed miRNAs between oncosomes (MDA-MB231 derived) and normosomes (MCF10A derived).

| miRNA | p Value |
|---|---|
| hsa-miR-522 | 0.040524939 |
| hsa-mir-611-P | 0.040860413 |
| hsa-miR-3171 | 0.040895673 |
| hsa-miR-635 | 0.041506047 |
| hsa-miR-1197-P | 0.041944121 |
| hsa-miR-604 | 0.04380685 |
| mmu-let-7a* | 0.043829675 |
| hsa-miR-335 | 0.043971349 |
| mmu-miR-466c-3p | 0.044407376 |
| mmu-miR-466i | 0.044504428 |
| hsa-miR-1297 | 0.04456723 |
| mmu-miR-338-5p | 0.044824503 |
| hsa-mir-526a-2-P | 0.044992512 |
| hsa-miR-181aMM2GC/AG | 0.045005369 |
| hsa-miR-15b* | 0.0452752 |
| hsa-miR-924-P | 0.045840226 |
| mmu-miR-190-P | 0.046060702 |
| hsa-miR-345 | 0.046092233 |
| mmu-miR-711 | 0.046378698 |
| hsa-miR-3116-2-P | 0.046593825 |
| hsa-miR-99a | 0.046936625 |
| mmu-miR-26a | 0.04716311 |
| hsa-miR-1248-P | 0.047256233 |
| mmu-miR-721-P | 0.047540414 |
| mmu-miR-801-P | 0.048152879 |
| hsa-miR-1826-P | 0.048243592 |
| hsa-miR-1236 | 0.048451235 |
| hsa-miR-339-5p | 0.048498093 |
| mmu-miR-804 | 0.04863614 |
| mmu-miR-467d* | 0.048653868 |
| mmu-miR-1191 | 0.048884442 |
| hsa-miR-148a | 0.048962197 |
| hsa-miR-141 | 0.049152638 |
| mmu-miR-1937a-P | 0.049351966 |
| mmu-miR-696 | 0.049529754 |
| hsa-miR-302a | 0.049722628 |

TABLE 6

Differentially expressed miRNAs between oncosomes (MDA-MB231 derived) and oncosomes with Dicer antibody (MDA-MB-231 derived).

| miRNAs | Fold Change |
|---|---|
| mmu-miR-3470a-P | −68.72008593 |
| mmu-miR-1186 | −37.7790082 |
| mmu-miR-3470b | −25.9441337 |
| mmu-miR-1935 | −21.29735527 |
| mmu-miR-3473-P | −17.73956758 |
| hsa-miR-665-P | −11.30652094 |
| mmu-miR-3470a | −21.53678167 |
| hsa-miR-1975-P | −8.378567946 |
| mmu-miR-1195 | −14.95080951 |
| mmu-miR-1196 | −41.418791 |
| mmu-miR-669h-3p | 7.716169349 |
| mmu-miR-4661 | 6.182505826 |
| mmu-miR-1954-P | −8.004541887 |
| mmu-miR-681-P | −5.576609952 |
| mmu-miR-467a* | 7.720120341 |
| hsa-miR-4294-P | −6.14881956 |
| hsa-miR-718 | −5.926179859 |
| hsa-mir-1910-P | −5.828360182 |
| hsa-miR-3188-P | −7.974527314 |
| hsa-miR-324-5p | −5.711776077 |
| mmu-miR-1937b-4-P | −5.520796704 |
| mmu-miR-669d-P | 6.842367137 |
| mmu-miR-3473 | −5.977639047 |
| hsa-miR-595 | −6.658387264 |
| hsa-miR-3197 | −6.118703616 |
| hsa-miR-4256-P | 4.894289461 |
| mmu-miR-201 | 5.429305446 |

TABLE 6-continued

Differentially expressed miRNAs between oncosomes (MDA-MB231 derived) and oncosomes with Dicer antibody (MDA-MB-231 derived).

| miRNAs | Fold Change |
|---|---|
| mmu-miR-2861-P | −5.546034309 |
| mmu-miR-3471-2-P | −5.968684885 |
| hsa-miR-3120-P | −5.809647124 |
| mmu-miR-494 | −5.460136383 |
| mmu-miR-690 | −6.785641527 |
| hsa-mir-591-P | −4.676566053 |
| hsa-miR-943 | −4.21472556 |
| hsa-miR-24-2* | −5.267717705 |
| hsa-miR-891a | 3.970259655 |
| mmu-miR-467e* | 4.371589059 |
| mmu-miR-196a | −4.673219124 |
| mmu-miR-763-P | −4.837159778 |
| mmu-miR-689-P | −4.006113822 |
| mmu-miR-1961-P | −4.02458343 |
| mmu-miR-709 | −43.11955582 |
| hsa-miR-3147 | −4.083582871 |
| hsa-miR-1323 | 3.866709935 |
| mmu-miR-761 | −4.758191473 |
| hsa-miR-1979 | −22.63130882 |
| hsa-miR-1255b | 3.856857003 |
| mmu-miR-3072 | −3.955191268 |
| hsa-miR-1248-P | 3.690795669 |
| hsa-mir-147-P | 4.119353729 |
| hsa-miR-3195 | −5.808376336 |
| hsa-miR-1273d-P | −7.045907865 |
| mmu-miR-207 | −4.467339352 |
| mmu-miR-689 | −3.348018214 |
| hsa-miR-4257 | −4.323649906 |
| mmu-miR-466d-3p | 3.585840199 |
| hsa-miR-923 | −3.344759672 |
| mmu-miR-1931 | −4.744652197 |
| hsa-mir-650-P | −6.161006285 |
| mmu-miR-466g | 3.874674458 |
| mmu-miR-1191-P | −4.045803649 |
| hsa-mir-1538 | −3.744109297 |
| hsa-miR-1246 | −3.337472797 |
| hsa-miR-124* | 3.31414605 |
| hsa-miR-4321-P | −7.691122096 |
| mmu-miR-1946a-P | −6.219634371 |
| hsa-miR-1972-2-P | −5.073720863 |
| hsa-miR-3200 | 3.335177401 |
| mmu-miR-1947 | −7.215369611 |
| mmu-miR-669o-P | 3.389226018 |
| mmu-miR-466e-3p | 3.534048216 |
| mmu-miR-707 | 3.877366764 |
| hsa-miR-4297 | −6.529597429 |
| hsa-miR-4313 | −4.609062464 |
| mmu-miR-1935-AP | −10.94537064 |
| mmu-miR-467g | 4.667383343 |
| mmu-miR-2133 | −4.243694889 |
| hsa-miR-923-P | −3.64025311 |
| hsa-miR-1236 | 3.197494004 |
| hsa-miR-1280 | −6.234163314 |
| mmu-miR-1937b-2-P | −5.358528363 |
| mmu-miR-499-P | 3.275110007 |
| hsa-miR-1263-P | 3.338653962 |
| hsa-miR-466 | 3.265124658 |
| hsa-mir-595-P | −3.780075724 |
| hsa-miR-1285-l-P | −3.392089631 |
| mmu-miR-338-5p | 3.139715849 |
| hsa-miR-3140 | 3.152896366 |
| mmu-miR-2182 | −4.235843782 |
| hsa-miR-23b* | −5.32306966 |
| hsa-mir-639-P | −7.052485203 |
| mmu-miR-1947-P | −5.939897094 |
| mmu-miR-22 | −3.74236459 |
| mmu-miR-1970 | −3.108998272 |
| mmu-miR-665-P | −3.597686151 |
| hsa-miR-3065-5p | 3.113930424 |
| mmu-miR-467c-P | 3.155074202 |
| mmu-miR-1268 | −2.922890303 |
| mmu-miR-24-2* | −3.48139554 |
| hsa-mir-1914 | −3.832959976 |
| hsa-miR-3118-5-P | 2.977569863 |
| mmu-miR-1306-P | −3.281316308 |
| mmu-miR-669f | 5.194629536 |
| mmu-miR-466b-3p | 3.438581421 |
| hsa-miR-1268-P | −3.678227949 |
| hsa-mir-1913 | −3.946642192 |
| mmu-miR-3470b-P | −4.037857355 |
| mmu-miR-32 | 2.989834039 |
| hsa-miR-1826-P | −4.872011411 |
| hsa-miR-147-P | 3.923947787 |
| hsa-miR-3172-P | 3.056599217 |
| hsa-miR-801 | −6.14009908 |
| hsa-miR-941-1 | −4.658601465 |
| mmu-miR-301a-P | 2.770796433 |
| mmu-miR-669a-P | 3.643950881 |
| hsa-miR-1289 | 3.559525037 |
| hsa-miR-548j | 2.858203465 |
| hsa-miR-877* | −3.015914917 |
| hsa-miR-10a | −5.70499997 |
| mmu-miR-181c | 2.79663413 |
| hsa-miR-3149-P | 3.067063437 |
| mmu-miR-3099* | −3.100792371 |
| mmu-miR-705-P | −4.314489552 |
| mmu-miR-2861 | −3.008526128 |
| hsa-miR-1976 | −2.80557125 |
| mmu-miR-1934-P | −6.614312993 |
| hsa-miR-138-1* | 2.769430194 |
| hsa-miR-1243 | 2.78669354 |
| hsa-miR-3160 | −3.16046745 |
| hsa-miR-500 | 2.766201976 |
| mmu-miR-1945 | −3.975181107 |
| hsa-mir-941-4 | −4.644133225 |
| hsa-miR-4301 | −16.10443714 |
| hsa-miR-1208 | −3.230411171 |
| hsa-mir-565-A | −8.232319234 |
| hsa-miR-1244 | 2.796864338 |
| mmu-miR-669j | 3.675114173 |
| hsa-miR-4314 | 2.810648214 |
| hsa-miR-502-5p | 2.743400714 |
| hsa-miR-371-5p | 2.607678279 |
| mmu-miR-10b | −3.034387515 |
| hsa-miR-26a | −3.497092003 |
| mmu-miR-483* | −2.743822775 |
| hsa-mir-487b-P | 4.073173842 |
| mmu-miR-1930-P | −3.656852693 |
| hsa-miR-1255a | 2.690838416 |
| hsa-miR-202 | −3.352756633 |
| hsa-miR-4311 | −2.706852207 |
| hsa-miR-1226* | 2.753774039 |
| mmu-miR-1943-P | 2.568476663 |
| hsa-mir-594-P | −7.693094002 |
| hsa-miR-21 | −3.331077571 |
| mmu-miR-466a-3p | 2.590518002 |
| hsa-miR-1301-P | 2.83454983 |
| hsa-miR-638 | −5.006318026 |
| hsa-mir-320 | −3.08053158 |
| mmu-miR-667 | −2.55941239 |
| mmu-miR-27a | 2.535988521 |
| hsa-miR-937 | −3.726272762 |
| hsa-miR-1255a-P | 3.247591046 |
| mmu-miR-505 | 2.610666762 |
| hsa-miR-1263 | 2.736571865 |
| mmu-miR-302b* | 2.945119065 |
| mmu-miR-721-P | 2.91504884 |
| hsa-miR-18b | 2.611682702 |
| hsa-mir-31 | −2.702014494 |
| mmu-miR-801-A | −6.683601538 |
| has-let-7f-l* | 3.908401267 |
| hsa-miR-1259-P | 2.644459942 |
| mmu-miR-320-P | −3.437080879 |
| mmu-miR-1939 | −4.465923575 |
| hsa-miR-1228 | −2.567882638 |
| hsa-miR-483-3p | −2.775662208 |
| hsa-miR-129-5p | 2.655425404 |
| mmu-miR-145* | 2.552327584 |

TABLE 6-continued

Differentially expressed miRNAs between oncosomes (MDA-MB231 derived) and oncosomes with Dicer antibody (MDA-MB-231 derived).

| miRNAs | Fold Change |
| --- | --- |
| hsa-miR-544 | 3.017286257 |
| hsa-miR-3124-P | 3.475660577 |
| hsa-let-7a* | 3.67482271 |
| hsa-miR-1308-P | −2.815549142 |
| hsa-miR-124 | 2.518148474 |
| mmu-miR-500-P | 2.439916722 |
| hsa-miR-589 | 2.619270955 |
| hsa-miR-155MM1G/T | −3.153648547 |
| hsa-miR-1254 | 3.039211354 |
| hsa-miR-1259 | 2.60142506 |
| mmu-mir-1904 | 2.553756257 |
| hsa-miR-320e | −3.6162361 |
| hsa-mir-373 | −9.005026193 |
| hsa-miR-3191-P | 2.777191568 |
| mmu-miR-700 | −4.536931094 |
| hsa-mir-539-P | 2.617416119 |
| hsa-miR-4259-P | 3.451286701 |
| hsa-miR-548h | 2.525655861 |
| mmu-miR-669e-P | 2.554714867 |
| mmu-miR-207-P | −3.619675577 |
| hsa-mir-1908-P | −3.739948569 |
| hsa-miR-4254 | −4.156361026 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Al-Nedawi, K., Meehan, B., Micallef, J., Lhotak, V., May, L., Guha, A., and Rak, J. (2008). Intercellular transfer of the oncogenic receptor EGFRvIII by microvesicles derived from tumour cells. Nature cell biology 10, 619-624.

Alvarez-Erviti, L., Seow, Y., Yin, H., Betts, C., Lakhal, S., and Wood, M. J. (2011). Delivery of siRNA to the mouse brain by systemic injection of targeted exosomes. Nature biotechnology 29, 341-345.

Ambros, V. (2004). The functions of animal microRNAs. Nature 431, 350-355.

Arroyo, J. D., Chevillet, J. R., Kroh, E. M., Ruf, I. K., Pritchard, C. C., Gibson, D. F., Mitchell, P. S., Bennett, C. F., Pogosova-Agadjanyan, E. L., Stirewalt, D. L., et al. (2011). Argonaute2 complexes carry a population of circulating microRNAs independent of vesicles in human plasma. Proceedings of the National Academy of Sciences of the United States of America 108, 5003-5008.

Ausubel et al., Current protocols in molecular biology, John Wiley & Sons Ltd, Wiley Interscience, 2003.

Bang, G. M., and Setabutr, P. (2010). Periocular capillary hemangiomas: indications and options for treatment. Middle East Afr J Ophthalmol 17, 121-128.

Bartel, D. P. (2009). MicroRNAs: target recognition and regulatory functions. Cell 136, 215-233.

Bartels, C. L., and Tsongalis, G. J. (2009). MicroRNAs: novel biomarkers for human cancer. Clinical chemistry 55, 623-631.

Benitez-vieyra, S., Medina, A. M., and Cocucci, A. A. (2009). Variable selection patterns on the labellum shape of Geoblasta pennicillata, a sexually deceptive orchid. J Evol Biol 22, 2354-2362.

Bernstein, E., Kim, S. Y., Carmell, M. A., Murchison, E. P., Alcorn, H., Li, M. Z., Mills, A. A., Elledge, S. J., Anderson, K. V., and Hannon, G. J. (2003). Dicer is essential for mouse development. Nature genetics 35, 215-217.

Chendrimada, T. P., Gregory, R. I., Kumaraswamy, E., Norman, J., Cooch, N., Nishikura, K., and Shiekhattar, R. (2005). TRBP recruits the Dicer complex to Ago2 for microRNA processing and gene silencing. Nature 436, 740-744.

Cocucci, E., Racchetti, G., and Meldolesi, J. (2009). Shedding microvesicles: artefacts no more. Trends Cell Biol 19, 43-51.

Cosacov, A. et al. New insights into the phylogenetic relationships, character evolution, and phytogeographic patterns of Calceolaria (Calceolariaceae). Am J Bot 96, 2240-2255, (2009).

de Laurentiis, A., Gaspari, M., Palmieri, C., Falcone, C., Iaccino, E., Fiume, G., Massa, O., Masullo, M., Tuccillo, F. M., Roveda, L., et al. (2011). Mass spectrometry-based identification of the tumor antigen UN1 as the transmembrane CD43 sialoglycoprotein. Mol Cell Proteomics 10, M111 007898.

Escola, J. M., Kleijmeer, M. J., Stoorvogel, W., Griffith, J. M., Yoshie, O., and Geuze, H. J. (1998). Selective enrichment of tetraspan proteins on the internal vesicles of multivesicular endosomes and on exosomes secreted by human B-lymphocytes. The Journal of biological chemistry 273, 20121-20127.

Fang, H., Qiu, L., Vitkin, E., Zaman, M. M., Andersson, C., Salahuddin, S., Kimerer, L. M., Cipolloni, P. B., Modell, M. D., Turner, B. S., et al. (2007). Confocal light absorption and scattering spectroscopic microscopy. Applied optics 46, 1760-1769.

Filipowicz, W. (2005). RNAi: the nuts and bolts of the RISC machine. Cell 122, 17-20.

Fukagawa, T., Nogami, M., Yoshikawa, M., Ikeno, M., Okazaki, T., Takami, Y., Nakayama, T., and Oshimura, M. (2004). Dicer is essential for formation of the heterochromatin structure in vertebrate cells. Nature cell biology 6, 784-791.

Gallo, A., Tandon, M., Alevizos, I., and Illei, G. G. (2012). The majority of microRNAs detectable in serum and saliva is concentrated in exosomes. PloS one 7, e30679.

Gibbings, D. J., Ciaudo, C., Erhardt, M., and Voinnet, 0. (2009). Multivesicular bodies associate with components of miRNA effector complexes and modulate miRNA activity. Nature cell biology 11, 1143-1149.

Gregory, R. I., Chendrimada, T. P., Cooch, N., and Shiekhattar, R. (2005). Human RISC couples microRNA biogenesis and posttranscriptional gene silencing. Cell 123, 631-640.

Grelier, G., Voirin, N., Ay, A. S., Cox, D. G., Chabaud, S., Treilleux, I., Leon-Goddard, S., Rimokh, R., Mikaelian, I., Venoux, C., et al. (2009). Prognostic value of Dicer expression in human breast cancers and association with the mesenchymal phenotype. British journal of cancer 101, 673-683.

Guermonprez, P., Valladeau, J., Zitvogel, L., Thery, C., and Amigorena, S. (2002). Antigen presentation and T cell stimulation by dendritic cells. Annu Rev Immunol 20, 621-667.

Guescini, M., Genedani, S., Stocchi, V., and Agnati, L. F. (2010). Astrocytes and Glioblastoma cells release exosomes carrying mtDNA. J Neural Transm 117, 1-4.

Gyorgy, B., Szabo, T. G., Pasztoi, M., Pal, Z., Misjak, P., Aradi, B., Laszlo, V., Pallinger, E., Pap, E., Kittel, A., et al. (2011). Membrane vesicles, current state-of-the-art: emerging role of extracellular vesicles. Cell Mol Life Sci 68, 2667-2688.

Haase, A. D., Jaskiewicz, L., Zhang, H., Laine, S., Sack, R., Gatignol, A., and Filipowicz, W. (2005). TRBP, a regulator of cellular PKR and HIV-1 virus expression, interacts with Dicer and functions in RNA silencing. EMBO reports 6, 961-967.

Hirata, H., Ueno, K., Shahryari, V., Tanaka, Y., Tabatabai, Z. L., Hinoda, Y., and Dahiya, R. (2012). Oncogenic miRNA-182-5p targets Smad4 and RECK in human bladder cancer. PloS one 7, e51056.

Hood, J. L., San, R. S., and Wickline, S. A. (2011). Exosomes released by melanoma cells prepare sentinel lymph nodes for tumor metastasis. Cancer research 71, 3792-3801.

Ismail, N., Wang, Y., Dakhlallah, D., Moldovan, L., Agarwal, K., Batte, K., Shah, P., Wisler, J., Eubank, T. D., Tridandapani, S., et al. (2013). Macrophage microvesicles induce macrophage differentiation and miR-223 transfer. Blood 121, 984-995.

Itzkan, I., Qiu, L., Fang, H., Zaman, M. M., Vitkin, E., Ghiran, I. C., Salahuddin, S., Modell, M., Andersson, C., Kimerer, L. M., et al. (2007). Confocal light absorption and scattering spectroscopic microscopy monitors organelles in live cells with no exogenous labels. Proceedings of the National Academy of Sciences of the United States of America 104, 17255-17260.

Kahlert, C., and Kalluri, R. (2013). Exosomes in tumor microenvironment influence cancer progression and metastasis. J Mol Med (Berl) 91, 431-437.

Karube, Y., Tanaka, H., Osada, H., Tomida, S., Tatematsu, Y., Yanagisawa, K., Yatabe, Y., Takamizawa, J., Miyoshi, S., Mitsudomi, T., et al. (2005). Reduced expression of Dicer associated with poor prognosis in lung cancer patients. Cancer science 96, 111-115.

Khairkar, P. H., Bang, G. M., Singh, A. B., and Tiple, P. G. (2010). Possible cross-sensitivity between sertraline and paroxetine in a panic disorder patient. Indian J Pharmacol 42, 110-111.

King, H. W., Michael, M. Z., and Gleadle, J. M. (2012). Hypoxic enhancement of exosome release by breast cancer cells. BMC Cancer 12, 421.

Kogure, T., Lin, W. L., Yan, I. K., Braconi, C., and Patel, T. (2011). Intercellular nanovesicle-mediated microRNA transfer: a mechanism of environmental modulation of hepatocellular cancer cell growth. Hepatology 54, 1237-1248.

Kosaka, N., Iguchi, H., Hagiwara, K., Yoshioka, Y., Takeshita, F., and Ochiya, T. (2013). Neutral sphingomyelinase 2 (nSMase2)-dependent exosomal transfer of angiogenic microRNAs regulate cancer cell metastasis. The Journal of biological chemistry 288, 10849-10859.

Kumar, M. S., Lu, J., Mercer, K. L., Golub, T. R., and Jacks, T. (2007). Impaired microRNA processing enhances cellular transformation and tumorigenesis. Nature genetics 39, 673-677.

Kumar, S., Ansari, F. A., and Scaria, V. (2009). Prediction of viral microRNA precursors based on human microRNA precursor sequence and structural features. Virol J 6, 129.

Lee, T. H., D'Asti, E., Magnus, N., Al-Nedawi, K., Meehan, B., and Rak, J. (2011). Microvesicles as mediators of intercellular communication in cancer—the emerging science of cellular 'debris'. Semin Immunopathol 33, 455-467.

Li, L., Zhu, D., Huang, L., Zhang, J., Bian, Z., Chen, X., Liu, Y., Zhang, C. Y., and Zen, K. (2012). Argonaute 2 complexes selectively protect the circulating microRNAs in cell-secreted microvesicles. PloS one 7, e46957.

Liu, C. G., Calin, G. A., Volinia, S. & Croce, C. M. MicroRNA expression profiling using microarrays. Nat Protoc 3, 563-578, (2008).

Livak, K. J., and Schmittgen, T. D. (2001). Analysis of relative gene expression data using real-time quantitative PCR and the 2(-Delta Delta C(T)) Method. Methods 25, 402-408.

Logozzi, M., De Milito, A., Lugini, L., Borghi, M., Calabro, L., Spada, M., Perdicchio, M., Marino, M. L., Federici, C., Iessi, E., et al. (2009). High levels of exosomes expressing CD63 and caveolin-1 in plasma of melanoma patients. PloS one 4, e5219.

Lu, J., Getz, G., Miska, E. A., Alvarez-Saavedra, E., Lamb, J., Peck, D., Sweet-Cordero, A., Ebert, B. L., Mak, R. H., Ferrando, A. A., et al. (2005). MicroRNA expression profiles classify human cancers. Nature 435, 834-838.

Luga, V., Zhang, L., Viloria-Petit, A. M., Ogunjimi, A. A., Inanlou, M. R., Chiu, E., Buchanan, M., Hosein, A. N., Basik, M., and Wrana, J. L. (2012). Exosomes Mediate Stromal Mobilization of Autocrine Wnt-PCP Signaling in Breast Cancer Cell Migration. Cell 151, 1542-1556.

Luzio, J. P., Parkinson, M. D., Gray, S. R., and Bright, N. A. (2009). The delivery of endocytosed cargo to lysosomes. Biochemical Society transactions 37, 1019-1021. Ma, L., Teruya-Feldstein, J., and Weinberg, R. A. (2007). Tumour invasion and metastasis initiated by microRNA-10b in breast cancer. Nature 449, 682-688.

MacRae, I. J., Ma, E., Zhou, M., Robinson, C. V., and Doudna, J. A. (2008). In vitro reconstitution of the human RISC-loading complex. Proceedings of the National Academy of Sciences of the United States of America 105, 512-517.

Maehama, T. (2007). PTEN: its deregulation and tumorigenesis. Biological & pharmaceutical bulletin 30, 1624-1627.

Maniataki, E., and Mourelatos, Z. (2005). A human, ATP-independent, RISC assembly machine fueled by pre-miRNA. Genes & development 19, 2979-2990.

Mao, X., Sun, Y., and Tang, J. (2013). Serum miR-21 is a diagnostic and prognostic marker of primary central nervous system lymphoma. Neurological sciences: official journal of the Italian Neurological Society and of the Italian Society of Clinical Neurophysiology.

Martello, G., Rosato, A., Ferrari, F., Manfrin, A., Cordenonsi, M., Dupont, S., Enzo, E., Guzzardo, V., Rondina, M., Spruce, T., et al. (2010). A MicroRNA targeting dicer for metastasis control. Cell 141, 1195-1207.

Mathivanan, S., Ji, H., and Simpson, R. J. (2010). Exosomes: extracellular organelles important in intercellular communication. Journal of proteomics 73, 1907-1920.

Mavel, S., Thery, I., and Gueiffier, A. (2002). Synthesis of imidazo[2,1-a]phthalazines, potential inhibitors of p38 MAP kinase. Prediction of binding affinities of protein ligands. Arch Pharm (Weinheim) 335, 7-14.

McCready, J., Sims, J. D., Chan, D., and Jay, D. G. (2010). Secretion of extracellular hsp90alpha via exosomes increases cancer cell motility: a role for plasminogen activation. BMC cancer 10, 294.

Melo, S., Villanueva, A., Moutinho, C., Davalos, V., Spizzo, R., Ivan, C., Rossi, S., Setien, F., Casanovas, O., Simo-Riudalbas, L., et al. (2011). Small molecule enoxacin is a cancer-specific growth inhibitor that acts by enhancing TAR RNA-binding protein 2-mediated microRNA processing. Proceedings of the National Academy of Sciences of the United States of America 108, 4394-4399.

Melo, S. A., Moutinho, C., Ropero, S., Calin, G. A., Rossi, S., Spizzo, R., Fernandez, A. F., Davalos, V., Villanueva, A., Montoya, G., et al. (2010). A genetic defect in exportin-5 traps precursor microRNAs in the nucleus of cancer cells. Cancer cell 18, 303-315.

Melo, S. A., Ropero, S., Moutinho, C., Aaltonen, L. A., Yamamoto, H., Calin, G. A., Rossi, S., Fernandez, A. F., Carneiro, F., Oliveira, C., et al. (2009). A TARBP2 mutation in human cancer impairs microRNA processing and DICER1 function. Nature genetics 41, 365-370.

Merritt, W. M., Lin, Y. G., Han, L. Y., Kamat, A. A., Spannuth, W. A., Schmandt, R., Urbauer, D., Pennacchio, L. A., Cheng, J. F., Nick, A. M., et al. (2008). Dicer, Drosha, and outcomes in patients with ovarian cancer. The New England journal of medicine 359, 2641-2650.

Min, M., Bang, G. S., Lee, H., and Yu, B. C. (2010). A photoswitchable methylene-spaced fluorinated aryl azobenzene monolayer grafted on silicon. Chem Commun (Camb) 46, 5232-5234.

Mittelbrunn, M., Gutierrez-Vazquez, C., Villarroya-Beltri, C., Gonzalez, S., Sanchez-Cabo, F., Gonzalez, M. A., Bernad, A., and Sanchez-Madrid, F. (2011). Unidirectional transfer of microRNA-loaded exosomes from T cells to antigen-presenting cells. Nature communications 2, 282.

Miyata, Y. (2005). Hsp90 inhibitor geldanamycin and its derivatives as novel cancer chemotherapeutic agents. Current pharmaceutical design 11, 1131-1138.

Montecalvo, A., Larregina, A. T., Shufesky, W. J., Stolz, D. B., Sullivan, M. L., Karlsson, J. M., Baty, C. J., Gibson, G. A., Erdos, G., Wang, Z., et al. (2012). Mechanism of transfer of functional microRNAs between mouse dendritic cells via exosomes. Blood 119, 756-766.

Narayanan, A., Iordanskiy, S., Das, R., Van Duyne, R., Santos, S., Jaworski, E., Guendel, I., Sampey, G., Dalby, E., Iglesias-Ussel, M., et al. (2013). Exosomes derived from HIV-1-infected cells contain trans-activation response element RNA. The Journal of biological chemistry 288, 20014-20033.

Nicoloso, M. S., Spizzo, R., Shimizu, M., Rossi, S., and Calin, G. A. (2009). MicroRNAs—the micro steering wheel of tumour metastases. Nature reviews Cancer 9, 293-302.

Ostrowski, M., Carmo, N. B., Krumeich, S., Fanget, I., Raposo, G., Savina, A., Moita, C. F., Schauer, K., Hume, A. N., Freitas, R. P., et al. (2010). Rab27a and Rab27b control different steps of the exosome secretion pathway. Nature cell biology 12, 19-30; sup pp 11-13.

Ozen, M., Creighton, C. J., Ozdemir, M., and Ittmann, M. (2008). Widespread deregulation of microRNA expression in human prostate cancer. Oncogene 27, 1788-1793.

Pant, S., Hilton, H., and Burczynski, M. E. (2012). The multifaceted exosome: biogenesis, role in normal and aberrant cellular function, and frontiers for pharmacological and biomarker opportunities. Biochemical pharmacology 83, 1484-1494.

Park, H. J., Bang, G., Lee, B. R., Kim, H. O., and Lee, P. H. (2011). Neuroprotective effect of human mesenchymal stem cells in an animal model of double toxin-induced multiple system atrophy parkinsonism. Cell Transplant 20, 827-835.

Pegtel, D. M., Cosmopoulos, K., Thorley-Lawson, D. A., van Eijndhoven, M. A., Hopmans, E. S., Lindenberg, J. L., de Gruijl, T. D., Wurdinger, T., and Middeldorp, J. M. (2010). Functional delivery of viral miRNAs via exosomes. Proceedings of the National Academy of Sciences of the United States of America 107, 6328-6333.

Peinado, H., Aleckovic, M., Lavotshkin, S., Matei, I., Costa-Silva, B., Moreno-Bueno, G., Hergueta-Redondo, M., Williams, C., Garcia-Santos, G., Ghajar, C., et al. (2012). Melanoma exosomes educate bone marrow progenitor cells toward a pro-metastatic phenotype through MET. Nat Med 18, 883-891.

Razi, M., and Futter, C. E. (2006). Distinct roles for Tsg101 and Hrs in multivesicular body formation and inward vesiculation. Molecular biology of the cell 17, 3469-3483.

Roccaro, A. M., Sacco, A., Maiso, P., Azab, A. K., Tai, Y. T., Reagan, M., Azab, F., Flores, L. M., Campigotto, F., Weller, E., et al. (2013). BM mesenchymal stromal cell-derived exosomes facilitate multiple myeloma progression. The Journal of clinical investigation.

Rothstein, D. M. et al. Targeting signal 1 through CD45RB synergizes with CD40 ligand blockade and promotes long term engraftment and tolerance in stringent transplant models. J Immunol 166, 322-329 (2001).

Sambrook et al., Molecular cloning: A laboratory manual, Cold Spring Harbor Laboratory Press, 1989.

Savina, A., Furlan, M., Vidal, M., and Colombo, M. I. (2003). Exosome release is regulated by a calcium-dependent mechanism in K562 cells. The Journal of biological chemistry 278, 20083-20090.

Schmittgen, T. D., Jiang, J., Liu, Q., and Yang, L. (2004). A high-throughput method to monitor the expression of microRNA precursors. Nucleic acids research 32, e43.

Shen, B., Fang, Y., Wu, N., and Gould, S. J. (2011a). Biogenesis of the posterior pole is mediated by the exosome/microvesicle protein-sorting pathway. The Journal of biological chemistry 286, 44162-44176.

Shen, B., Wu, N., Yang, J. M., and Gould, S. J. (2011b). Protein targeting to exosomes/microvesicles by plasma membrane anchors. The Journal of biological chemistry 286, 14383-14395.

Shen, J., Xia, W., Khotskaya, Y. B., Huo, L., Nakanishi, K., Lim, S. O., Du, Y., Wang, Y., Chang, W. C., Chen, C. H., et al. (2013). EGFR modulates microRNA maturation in response to hypoxia through phosphorylation of AGO2. Nature 497, 383-387.

Sherer, N. M., Lehmann, M. J., Jimenez-Soto, L. F., Ingmundson, A., Homer, S. M., Cicchetti, G., Allen, P. G., Pypaert, M., Cunningham, J. M., and Mothes, W. (2003). Visualization of retroviral replication in living cells reveals budding into multivesicular bodies. Traffic 4, 785-801.

Shi, W., Oshlack, A., and Smyth, G. K. (2010). Optimizing the noise versus bias trade-off for Illumina whole genome expression BeadChips. Nucleic acids research 38, e204.

Shin, H. W., Morinaga, N., Noda, M., and Nakayama, K. (2004). BIG2, a guanine nucleotide exchange factor for ADP-ribosylation factors: its localization to recycling endosomes and implication in the endosome integrity. Molecular biology of the cell 15, 5283-5294.

Simons, M., and Raposo, G. (2009). Exosomes—vesicular carriers for intercellular communication. Curr Opin Cell Biol 21, 575-581.

Simpson, R. J., Jensen, S. S., and Lim, J. W. (2008). Proteomic profiling of exosomes: current perspectives. Proteomics 8, 4083-4099.

Skog, J., Wurdinger, T., van Rijn, S., Meijer, D. H., Gainche, L., Sena-Esteves, M., Curry, W. T., Jr., Carter, B. S., Krichevsky, A. M., and Breakefield, X. O. (2008). Glioblastoma microvesicles transport RNA and proteins that promote tumour growth and provide diagnostic biomarkers. Nature cell biology 10, 1470-1476.

Tang, G. (2005). siRNA and miRNA: an insight into RISCs. Trends Biochem Sci 30, 106-114.

Taylor, D. D., and Gercel-Taylor, C. (2008). MicroRNA signatures of tumor-derived exosomes as diagnostic biomarkers of ovarian cancer. Gynecologic oncology 110, 13-21.

Taylor, D. D., and Gercel-Taylor, C. (2011). Exosomes/microvesicles: mediators of cancer-associated immunosuppressive microenvironments. Semin Immunopathol 33, 441-454.

Thery, C., Amigorena, S., Raposo, G., and Clayton, A. (2006). Isolation and characterization of exosomes from cell culture supernatants and biological fluids. Current protocols in cell biology/editorial board, Juan S Bonifacino [et al] Chapter 3, Unit 3 22.

Thery, C. et al. Indirect activation of naive CD4+ T cells by dendritic cell-derived exosomes. Nat Immunol 3, 1156-1162, (2002).

Thery, C., Zitvogel, L., and Amigorena, S. (2002). Exosomes: composition, biogenesis and function. Nat Rev Immunol 2, 569-579.

Thery, C. (2011). Exosomes: secreted vesicles and intercellular communications. F1000 biology reports 3, 15.

Thery, M., and Casas, J. (2002). Predator and prev views of spider camouflage. Nature 415, 133.

Thomson, D. W., Bracken, C. P., Szubert, J. M., and Goodall, G. J. (2013). On measuring miRNAs after transient transfection of mimics or antisense inhibitors. PloS one 8, e55214.

Tse, J. C., and Kalluri, R. (2011). Waking up dormant tumors. Breast cancer research: BCR 13, 310.

Turchinovich, A., Weiz, L., Langheinz, A., and Burwinkel, B. (2011). Characterization of extracellular circulating microRNA. Nucleic acids research 39, 7223-7233.

Valadi, H., Ekstrom, K., Bossios, A., Sjostrand, M., Lee, J. J., and Lotvall, J. O. (2007). Exosome-mediated transfer of mRNAs and microRNAs is a novel mechanism of genetic exchange between cells. Nature cell biology 9, 654-659.

van Balkom, B. W., de Jong, O. G., Smits, M., Brummelman, J., den Ouden, K., de Bree, P. M., van Eijndhoven, M. A., Pegtel, D. M., Stoorvogel, W., Wurdinger, T., and Verhaar, M. C. (2013). Endothelial cells require miR-214 to secrete exosomes that suppress senescence and induce angiogenesis in human and mouse endothelial cells. Blood 121, 3997-4006, 53991-3915.

Vickers, K. C., Palmisano, B. T., Shoucri, B. M., Shamburek, R. D., and Remaley, A. T. (2011). MicroRNAs are transported in plasma and delivered to recipient cells by high-density lipoproteins. Nature cell biology 13, 423-433.

Volinia, S., Calin, G. A., Liu, C. G., Ambs, S., Cimmino, A., Petrocca, F., Visone, R., Iorio, M., Roldo, C., Ferracin, M., et al. (2006). A microRNA expression signature of human solid tumors defines cancer gene targets. Proceedings of the National Academy of Sciences of the United States of America 103, 2257-2261.

Welch, D. R. (1997). Technical considerations for studying cancer metastasis in vivo. Clinical & experimental metastasis 15, 272-306.

Wiesen, J. L., and Tomasi, T. B. (2009). Dicer is regulated by cellular stresses and interferons. Mol Immunol 46, 1222-1228.

Yan, L. X., Huang, X. F., Shao, Q., Huang, M. Y., Deng, L., Wu, Q. L., Zeng, Y. X., and Shao, J. Y. (2008). MicroRNA miR-21 overexpression in human breast cancer is associated with advanced clinical stage, lymph node metastasis and patient poor prognosis. RNA 14, 2348-2360.

Yan, L. X., Wu, Q. N., Zhang, Y., Li, Y. Y., Liao, D. Z., Hou, J. H., Fu, J., Zeng, M. S., Yun, J. P., Wu, Q. L., et al. (2011). Knockdown of miR-21 in human breast cancer cell lines inhibits proliferation, in vitro migration and in vivo tumor growth. Breast cancer research: BCR 13, R2.

Yang, C., and Robbins, P. D. (2011). The roles of tumor-derived exosomes in cancer pathogenesis. Clin Dev Immunol 2011, 842849.

Yang, X., Meng, S., Jiang, H., Zhu, C., and Wu, W. (2011). Exosomes derived from immature bone marrow dendritic cells induce tolerogenicity of intestinal transplantation in rats. J Surg Res 171, 826-832.

Yi, R., Qin, Y., Macara, I. G., and Cullen, B. R. (2003). Exportin-5 mediates the nuclear export of pre-microRNAs and short hairpin RNAs. Genes & development 17, 3011-3016.

Zernecke, A., Bidzhekov, K., Noels, H., Shagdarsuren, E., Gan, L., Denecke, B., Hristov, M., Koppel, T., Jahantigh, M. N., Lutgens, E., et al. (2009). Delivery of microRNA-126 by apoptotic bodies induces CXCL12-dependent vascular protection. Science signaling 2, ra81.

Zhang, Y., Liu, D., Chen, X., Li, J., Li, L., Bian, Z., Sun, F., Lu, J., Yin, Y., Cai, X., et al. (2010). Secreted monocytic miR-150 enhances targeted endothelial cell migration. Molecular cell 39, 133-144.

The invention claimed is:

1. A method of treating a subject having breast cancer, the method comprising:
   (a) obtaining a biological sample from the subject;
   (b) measuring the level of Dicer in an exosomal fraction of the sample, wherein the exosomal fraction comprises exosomes that contain TSG101;
   (c) identifying the subject as having or not having a breast cancer biomarker based on the measured level of Dicer, wherein if the measured level of Dicer is increased relative to a reference level, then the patient is identified as having the breast cancer biomarker;
   (d) selecting a subject identified as having the breast cancer biomarker; and
   (e) administering an anti-breast cancer therapy to the selected subject, wherein the anti-breast cancer therapy is a chemotherapy, a radiation therapy, a hormonal therapy, a targeted therapy, an immunotherapy, or a surgical therapy.

2. The method of claim 1, wherein the sample is essentially free of cells.

3. The method of claim 1, wherein the sample is a lymph, saliva, urine, serum, or plasma sample.

4. The method of claim 1, wherein the reference sample is an exosomal fraction of a biological sample from a healthy subject.

5. The method of claim 1, further comprising purifying an exosomal fraction of the sample or increasing production of an exosomal fraction of the sample.

6. The method of claim 1, further comprising measuring the level of AGO2 protein and/or TRBP protein in the exosomal fraction of the sample.

7. The method of claim 1, wherein the level of Dicer is determined by measuring the level of Dicer protein in the exosomal fraction of the sample.

8. The method of claim 7, wherein the level of Dicer protein is determined by performing a Western blot, an ELISA, or by binding to an antibody array.

9. The method of claim 1, wherein the level of Dicer is determined by measuring the level of Dicer activity in the exosomal fraction of the sample.

10. The method of claim 9, wherein the level of Dicer activity is determined by performing an in vitro dicing assay.

* * * * *

SEQUENCE LISTING

<160> NUMBER OF SEQ ID NOS: 56

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
caggaggtgg tgaaggacat                                              20

<210> SEQ ID NO 2
<211> LENGTH: 19
<212> TYPE: DNA
<213> ORGANISM: Artificial sequence
<220> FEATURE:
<223> OTHER INFORMATION: Synthetic primer

<400> SEQUENCE: 2
cccgttggtc tgtgagttt                                               19

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
gataccctcc caatcccagt                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
gtcactgacc gcagagatga                                              20

<210> SEQ ID NO 5
<211> LENGTH: 21
<212> TYPE: DNA
<213> ORGANISM: Artificial sequence
<220> FEATURE:
<223> OTHER INFORMATION: Synthetic primer

<400> SEQUENCE: 5
agtggctgtc gggtattcat c                                            21

<210> SEQ ID NO 6
<211> LENGTH: 23
<212> TYPE: DNA
<213> ORGANISM: Artificial sequence
<220> FEATURE:
<223> OTHER INFORMATION: Synthetic primer

<400> SEQUENCE: 6
ccgtccatat cccttgaaga atc                                          23

<210> SEQ ID NO 7
<211> LENGTH: 19
<212> TYPE: DNA
<213> ORGANISM: Artificial sequence
<220> FEATURE:
<223> OTHER INFORMATION: Synthetic primer

<400> SEQUENCE: 7
gctggtggta agcccagac                                               19

-continued

<210> SEQ ID NO 8
<211> LENGTH: 21
<212> TYPE: DNA
<213> ORGANISM: Artificial sequence
<220> FEATURE:
<223> OTHER INFORMATION: Synthetic primer

<400> SEQUENCE: 8
ggctcgctag tagagaccaa a                                              21

<210> SEQ ID NO 9
<211> LENGTH: 21
<212> TYPE: DNA
<213> ORGANISM: Artificial sequence
<220> FEATURE:
<223> OTHER INFORMATION: Synthetic primer

<400> SEQUENCE: 9
catgtacgtt gctatccagg c                                              21

<210> SEQ ID NO 10
<211> LENGTH: 21
<212> TYPE: DNA
<213> ORGANISM: Artificial sequence
<220> FEATURE:
<223> OTHER INFORMATION: Synthetic primer

<400> SEQUENCE: 10
ctccttaatg tcacgcacga t                                              21

<210> SEQ ID NO 11
<211> LENGTH: 20
<212> TYPE: DNA
<213> ORGANISM: Artificial sequence
<220> FEATURE:
<223> OTHER INFORMATION: Synthetic primer

<400> SEQUENCE: 11
ggctgtattc ccctccatcg                                                20

<210> SEQ ID NO 12
<211> LENGTH: 22
<212> TYPE: DNA
<213> ORGANISM: Artificial sequence
<220> FEATURE:
<223> OTHER INFORMATION: Synthetic primer

<400> SEQUENCE: 12
ccagttggta acaatgccat gt                                             22

<210> SEQ ID NO 13
<211> LENGTH: 25
<212> TYPE: DNA
<213> ORGANISM: Artificial sequence
<220> FEATURE:
<223> OTHER INFORMATION: Synthetic primer

<400> SEQUENCE: 13
aggtagtagg ttgtatagtt ttagg                                          25

<210> SEQ ID NO 14
<211> LENGTH: 25
<212> TYPE: DNA
<213> ORGANISM: Artificial sequence
<220> FEATURE:
<223> OTHER INFORMATION: Synthetic primer

```
<400> SEQUENCE: 14
taggaaagac agtagattgt atagt                                        25

<210> SEQ ID NO 15
<211> LENGTH: 21
<212> TYPE: DNA
<213> ORGANISM: Artificial sequence
<220> FEATURE:
<223> OTHER INFORMATION: Synthetic primer

<400> SEQUENCE: 15
agcacatcat ggtttacatg c                                            21

<210> SEQ ID NO 16
<211> LENGTH: 23
<212> TYPE: DNA
<213> ORGANISM: Artificial sequence
<220> FEATURE:
<223> OTHER INFORMATION: Synthetic primer

<400> SEQUENCE: 16
ctagagcagc aaataatgat tgg                                          23

<210> SEQ ID NO 17
<211> LENGTH: 24
<212> TYPE: DNA
<213> ORGANISM: Artificial sequence
<220> FEATURE:
<223> OTHER INFORMATION: Synthetic primer

<400> SEQUENCE: 17
ttcaagtaat ccaggatagg ctgt                                         24

<210> SEQ ID NO 18
<211> LENGTH: 22
<212> TYPE: DNA
<213> ORGANISM: Artificial sequence
<220> FEATURE:
<223> OTHER INFORMATION: Synthetic primer

<400> SEQUENCE: 18
tgcaagtaac caagaatagg cc                                           22

<210> SEQ ID NO 19
<211> LENGTH: 20
<212> TYPE: DNA
<213> ORGANISM: Artificial sequence
<220> FEATURE:
<223> OTHER INFORMATION: Synthetic primer

<400> SEQUENCE: 19
tgagtgtgtt ttccctccct                                              20

<210> SEQ ID NO 20
<211> LENGTH: 17
<212> TYPE: DNA
<213> ORGANISM: Artificial sequence
<220> FEATURE:
<223> OTHER INFORMATION: Synthetic primer

<400> SEQUENCE: 20
gccatggctg ctgtcag                                                 17

<210> SEQ ID NO 21
```

```
<211> LENGTH: 20
<212> TYPE: DNA
<213> ORGANISM: Artificial sequence
<220> FEATURE:
<223> OTHER INFORMATION: Synthetic primer

<400> SEQUENCE: 21
gtccctgaga ccctttaacc                                              20

<210> SEQ ID NO 22
<211> LENGTH: 19
<212> TYPE: DNA
<213> ORGANISM: Artificial sequence
<220> FEATURE:
<223> OTHER INFORMATION: Synthetic primer

<400> SEQUENCE: 22
aacctcacct gtgaccctg                                               19

<210> SEQ ID NO 23
<211> LENGTH: 20
<212> TYPE: DNA
<213> ORGANISM: Artificial sequence
<220> FEATURE:
<223> OTHER INFORMATION: Synthetic primer

<400> SEQUENCE: 23
gtccctgaga ccctaacttg                                              20

<210> SEQ ID NO 24
<211> LENGTH: 18
<212> TYPE: DNA
<213> ORGANISM: Artificial sequence
<220> FEATURE:
<223> OTHER INFORMATION: Synthetic primer

<400> SEQUENCE: 24
agcctaaccc gtggattt                                                18

<210> SEQ ID NO 25
<211> LENGTH: 17
<212> TYPE: DNA
<213> ORGANISM: Artificial sequence
<220> FEATURE:
<223> OTHER INFORMATION: Synthetic primer

<400> SEQUENCE: 25
ttccacagca gccctg                                                  17

<210> SEQ ID NO 26
<211> LENGTH: 18
<212> TYPE: DNA
<213> ORGANISM: Artificial sequence
<220> FEATURE:
<223> OTHER INFORMATION: Synthetic primer

<400> SEQUENCE: 26
gatgtgcctc ggtggtgt                                                18

<210> SEQ ID NO 27
<211> LENGTH: 20
<212> TYPE: DNA
<213> ORGANISM: Artificial sequence
<220> FEATURE:
<223> OTHER INFORMATION: Synthetic primer

<400> SEQUENCE: 27
```
ctcgtcttac ccagcagtgt                                           20

<210> SEQ ID NO 28
<211> LENGTH: 24
<212> TYPE: DNA
<213> ORGANISM: Artificial sequence
<220> FEATURE:
<223> OTHER INFORMATION: Synthetic primer

<400> SEQUENCE: 28
gtcatcatta ccaggcagta ttag                                      24

<210> SEQ ID NO 29
<211> LENGTH: 23
<212> TYPE: DNA
<213> ORGANISM: Artificial sequence
<220> FEATURE:
<223> OTHER INFORMATION: Synthetic primer

<400> SEQUENCE: 29
gtcaagagca ataacgaaaa atg                                       23

<210> SEQ ID NO 30
<211> LENGTH: 21
<212> TYPE: DNA
<213> ORGANISM: Artificial sequence
<220> FEATURE:
<223> OTHER INFORMATION: Synthetic primer

<400> SEQUENCE: 30
gaggtcagga gcaataatga a                                         21

<210> SEQ ID NO 31
<211> LENGTH: 23
<212> TYPE: DNA
<213> ORGANISM: Artificial sequence
<220> FEATURE:
<223> OTHER INFORMATION: Synthetic primer

<400> SEQUENCE: 31
taccctgtag atccgaattt gtg                                       23

<210> SEQ ID NO 32
<211> LENGTH: 24
<212> TYPE: DNA
<213> ORGANISM: Artificial sequence
<220> FEATURE:
<223> OTHER INFORMATION: Synthetic primer

<400> SEQUENCE: 32
attcccctag atacgaattt gtga                                      24

<210> SEQ ID NO 33
<211> LENGTH: 23
<212> TYPE: DNA
<213> ORGANISM: Artificial sequence
<220> FEATURE:
<223> OTHER INFORMATION: Synthetic primer

<400> SEQUENCE: 33
gcttatcaga ctgatgttga ctg                                       23

<210> SEQ ID NO 34
<211> LENGTH: 17
<212> TYPE: DNA

```
<213> ORGANISM: Artificial sequence
<220> FEATURE:
<223> OTHER INFORMATION: Synthetic primer

<400> SEQUENCE: 34
cagcccatcg actggtg                                                    17

<210> SEQ ID NO 35
<211> LENGTH: 18
<212> TYPE: DNA
<213> ORGANISM: Artificial sequence
<220> FEATURE:
<223> OTHER INFORMATION: Synthetic primer

<400> SEQUENCE: 35
gcagggctta gctgcttg                                                   18

<210> SEQ ID NO 36
<211> LENGTH: 19
<212> TYPE: DNA
<213> ORGANISM: Artificial sequence
<220> FEATURE:
<223> OTHER INFORMATION: Synthetic primer

<400> SEQUENCE: 36
ggcggaactt agccactgt                                                  19

<210> SEQ ID NO 37
<211> LENGTH: 22
<212> TYPE: DNA
<213> ORGANISM: Artificial sequence
<220> FEATURE:
<223> OTHER INFORMATION: Synthetic primer

<400> SEQUENCE: 37
gttaatgcta atcgtgatag gg                                              22

<210> SEQ ID NO 38
<211> LENGTH: 24
<212> TYPE: DNA
<213> ORGANISM: Artificial sequence
<220> FEATURE:
<223> OTHER INFORMATION: Synthetic primer

<400> SEQUENCE: 38
gctaatatgt aggagtcagt tgga                                            24

<210> SEQ ID NO 39
<211> LENGTH: 18
<212> TYPE: DNA
<213> ORGANISM: Artificial sequence
<220> FEATURE:
<223> OTHER INFORMATION: Synthetic primer

<400> SEQUENCE: 39
ctcaaaatgg gggcgctt                                                   18

<210> SEQ ID NO 40
<211> LENGTH: 20
<212> TYPE: DNA
<213> ORGANISM: Artificial sequence
<220> FEATURE:
<223> OTHER INFORMATION: Synthetic primer

<400> SEQUENCE: 40
caccccaaaa tcgaagcact                                                 20
```

<210> SEQ ID NO 41
<211> LENGTH: 21
<212> TYPE: DNA
<213> ORGANISM: Artificial sequence
<220> FEATURE:
<223> OTHER INFORMATION: Synthetic primer

<400> SEQUENCE: 41
ccaccccgtt ctacatactt c                                                    21

<210> SEQ ID NO 42
<211> LENGTH: 20
<212> TYPE: DNA
<213> ORGANISM: Artificial sequence
<220> FEATURE:
<223> OTHER INFORMATION: Synthetic primer

<400> SEQUENCE: 42
accgtaccga gctgcatact                                                      20

<210> SEQ ID NO 43
<211> LENGTH: 21
<212> TYPE: DNA
<213> ORGANISM: Artificial Sequence
<220> FEATURE:
<223> OTHER INFORMATION: Synthetic probe

<400> SEQUENCE: 43
cacaaattcg gttctacagg g                                                    21

<210> SEQ ID NO 44
<211> LENGTH: 22
<212> TYPE: DNA
<213> ORGANISM: Artificial sequence
<220> FEATURE:
<223> OTHER INFORMATION: Synthetic probe

<400> SEQUENCE: 44
tcaacatcag tctgataagc ta                                                   22

<210> SEQ ID NO 45
<211> LENGTH: 20
<212> TYPE: DNA
<213> ORGANISM: Artificial sequence
<220> FEATURE:
<223> OTHER INFORMATION: Synthetic probe

<400> SEQUENCE: 45
agtatgcagc tcggtacggt                                                      20

<210> SEQ ID NO 46
<211> LENGTH: 40
<212> TYPE: DNA
<213> ORGANISM: Artificial sequence
<220> FEATURE:
<223> OTHER INFORMATION: Synthetic probe

<400> SEQUENCE: 46
tgaagttttt gcatcgacca tatattcccc tagaatcgaa                                40

<210> SEQ ID NO 47
<211> LENGTH: 36
<212> TYPE: DNA
<213> ORGANISM: Artificial sequence
<220> FEATURE:

<223> OTHER INFORMATION: Synthetic probe

<400> SEQUENCE: 47
tgtcagacag cccatcgact ggtgttgcca tgagat                                    36

<210> SEQ ID NO 48
<211> LENGTH: 25
<212> TYPE: DNA
<213> ORGANISM: Artificial sequence
<220> FEATURE:
<223> OTHER INFORMATION: Synthetic probe

<400> SEQUENCE: 48
cagcacgctt ccgctgcgcc actct                                                25

<210> SEQ ID NO 49
<211> LENGTH: 21
<212> TYPE: DNA
<213> ORGANISM: Artificial sequence
<220> FEATURE:
<223> OTHER INFORMATION: Synthetic oligo

<400> SEQUENCE: 49
ggaacgagcc caaguacaat t                                                    21

<210> SEQ ID NO 50
<211> LENGTH: 21
<212> TYPE: DNA
<213> ORGANISM: Artificial sequence
<220> FEATURE:
<223> OTHER INFORMATION: Synthetic oligo

<400> SEQUENCE: 50
uuguacuugg gcucguuccg g                                                    21

<210> SEQ ID NO 51
<211> LENGTH: 21
<212> TYPE: DNA
<213> ORGANISM: Artificial sequence
<220> FEATURE:
<223> OTHER INFORMATION: Synthetic oligo

<400> SEQUENCE: 51
guuuaucauu caaguguaat t                                                    21

<210> SEQ ID NO 52
<211> LENGTH: 21
<212> TYPE: DNA
<213> ORGANISM: Artificial sequence
<220> FEATURE:
<223> OTHER INFORMATION: Synthetic oligo

<400> SEQUENCE: 52
uuacacuuga augauaaact g                                                    21

<210> SEQ ID NO 53
<211> LENGTH: 21
<212> TYPE: DNA
<213> ORGANISM: Artificial sequence
<220> FEATURE:
<223> OTHER INFORMATION: Synthetic oligo

<400> SEQUENCE: 53
ggagagccuu uggucucuat t                                                    21

```
<210> SEQ ID NO 54
<211> LENGTH: 21
<212> TYPE: DNA
<213> ORGANISM: Artificial sequence
<220> FEATURE:
<223> OTHER INFORMATION: Synthetic oligo

<400> SEQUENCE: 54
uagagaccaa aggcucuccg g                                              21

<210> SEQ ID NO 55
<211> LENGTH: 21
<212> TYPE: DNA
<213> ORGANISM: Artificial sequence
<220> FEATURE:
<223> OTHER INFORMATION: Synthetic oligo

<400> SEQUENCE: 55
ggcguuacac gaugcacuut t                                              21

<210> SEQ ID NO 56
<211> LENGTH: 21
<212> TYPE: DNA
<213> ORGANISM: Artificial sequence
<220> FEATURE:
<223> OTHER INFORMATION: Synthetic oligo

<400> SEQUENCE: 56
aagugcaucg uguaacgcct g                                              21
```